US012097251B2

(12) United States Patent
Li et al.

(10) Patent No.: US 12,097,251 B2
(45) Date of Patent: Sep. 24, 2024

(54) HUMAN PAPILLOMA VIRUS TYPE 51 L1 PROTEIN MUTANTS

(71) Applicants: XIAMEN UNIVERSITY, Fujian (CN); XIAMEN INNOVAX BIOTECH CO., LTD., Fujian (CN)

(72) Inventors: Shaowei Li, Fujian (CN); Daning Wang, Fujian (CN); Jie Chen, Fujian (CN); Ying Gu, Fujian (CN); Jun Zhang, Fujian (CN); Ningshao Xia, Fujian (CN)

(73) Assignees: XIAMEN UNIVERSITY, Fujian (CN); XIAMEN INNOVAX BIOTECH CO., LTD., Fujian (CN)

(*) Notice: Subject to any disclaimer, the term of this patent is extended or adjusted under 35 U.S.C. 154(b) by 672 days.

(21) Appl. No.: 17/280,805

(22) PCT Filed: Sep. 26, 2019

(86) PCT No.: PCT/CN2019/108063
§ 371 (c)(1),
(2) Date: Mar. 26, 2021

(87) PCT Pub. No.: WO2020/063724
PCT Pub. Date: Apr. 2, 2020

(65) Prior Publication Data

US 2022/0001002 A1 Jan. 6, 2022

(30) Foreign Application Priority Data

Sep. 26, 2018 (CN) ......................... 201811122822.1

(51) Int. Cl.
*A61K 39/12* (2006.01)
*A61P 31/20* (2006.01)
*C07K 14/015* (2006.01)
*C12N 7/00* (2006.01)

(52) U.S. Cl.
CPC .............. *A61K 39/12* (2013.01); *A61P 31/20* (2018.01); *C07K 14/015* (2013.01); *C12N 7/00* (2013.01)

(58) Field of Classification Search
CPC ...................... A61K 39/12; C12N 2710/20022
See application file for complete search history.

(56) References Cited

FOREIGN PATENT DOCUMENTS

| | | | |
|---|---|---|---|
| CN | 1185810 | A | 6/1998 |
| CN | 1388253 | A | 1/2003 |
| CN | 101116745 | A | 2/2008 |
| CN | 101481407 | A | 7/2009 |
| CN | 101530614 | A | 9/2009 |
| CN | 102497880 | A | 6/2012 |
| CN | 106831960 | A | 6/2017 |
| WO | 1996/030520 | A2 | 10/1996 |
| WO | 2000/054730 | A2 | 9/2000 |
| WO | 2010/149752 | A2 | 12/2010 |
| WO | 2017/070616 | A2 | 4/2017 |
| WO | 2017/092710 | A1 | 6/2017 |
| WO | 2021/013060 | A1 | 1/2021 |

OTHER PUBLICATIONS

Burk, R. D., et al., 2013, Human papillomavirus genome variants, Virol. 445:232-243.*

Li, Z., et al., 2018, Rational design of a triple-type human papillomavirus vaccine by comprising viral-type specificity, Nat. Comm. 9: 5360, pp. 1-15 (published online Dec. 18, 2018).*

Bissett et al., "Pre-clinical immunogenicity of human papillomavirus alpha-7 andalpha-9 major capsid proteins," Vaccine 32(48):6548-6555 (2014).

Doorbar et al., "Identification of Proteins Encoded by the Li and L2 Open Reading Frames of Human Papillomavirus 1a," J Virol. 61(9):2793-2799 (1987).

Kirnbauer et al., "Papillomavirus L1 major capsid protein self-assembles into virus-like particles that are highly immunogenic," Proc Natl Acad Sci U S A. 89(24):12180-12184 (1992).

Li et al., "Rational design of a triple-type human papillomavirus vaccine by compromising viral-type specificity," *Nature Communications* 9(1):5360 (2018).

Wang et al., "Rational design of a multi-valent human papillomavirus vaccine by capsomere-hybrid co-assembly of virus-like particles," *Nature Communications* 11(1):2841 (2020).

* cited by examiner

*Primary Examiner* — Jeffrey S Parkin
(74) *Attorney, Agent, or Firm* — MEDLER FERRO WOODHOUSE & MILLS PLLC

(57) ABSTRACT

Provided are a mutated HPV51 L1 protein or a variant thereof, a coding sequence thereof, a preparation method therefor, and a virus-like particle containing same, wherein the protein or the variant and the virus-like particle thereof are capable of inducing neutralizing antibodies against at least two types of HPV (for example, HPV51 and HPV69, or HPV51, HPV69 and HPV26). Also provided is the use of the above-mentioned protein and the virus-like particle for preparing a pharmaceutical composition or a vaccine, wherein the pharmaceutical composition or the vaccine can be used to prevent infections of the at least two types of HPV and diseases caused by the infections, such as cervical cancer and condyloma acuminatum.

21 Claims, 12 Drawing Sheets

Specification includes a Sequence Listing.

SEQUENCE LISTING

```
<160> NUMBER OF SEQ ID NOS: 144

<210> SEQ ID NO 1
<211> LENGTH: 504
<212> TYPE: PRT
<213> ORGANISM: Human papillomavirus type 51

<400> SEQUENCE: 1

Met Ala Leu Trp Arg Thr Asn Asp Ser Lys Val Tyr Leu Pro Pro Ala
1               5                   10                  15

Pro Val Ser Arg Ile Val Asn Thr Glu Glu Tyr Ile Thr Arg Thr Gly
            20                  25                  30

Ile Tyr Tyr Tyr Ala Gly Ser Ser Arg Leu Ile Thr Leu Gly His Pro
        35                  40                  45

Tyr Phe Pro Leu Pro Lys Thr Ser Thr Arg Ala Ala Ile Pro Lys Val
    50                  55                  60
```

-continued

```
Ser Ala Phe Gln Tyr Arg Val Phe Arg Val Gln Leu Pro Asp Pro Asn
65                  70                  75                  80

Lys Phe Gly Leu Pro Asp Pro Asn Leu Tyr Asn Pro Asp Thr Asp Arg
                85                  90                  95

Leu Val Trp Gly Cys Val Gly Val Glu Val Gly Arg Gly Gln Pro Leu
            100                 105                 110

Gly Val Gly Leu Ser Gly His Pro Leu Phe Asn Lys Tyr Asp Asp Thr
        115                 120                 125

Glu Asn Ser Arg Ile Ala Asn Gly Asn Ala Gln Gln Asp Val Arg Asp
    130                 135                 140

Asn Thr Ser Val Asp Asn Lys Gln Thr Gln Leu Cys Ile Ile Gly Cys
145                 150                 155                 160

Ala Pro Pro Ile Gly Glu His Trp Gly Ile Gly Thr Thr Cys Lys Asn
                165                 170                 175

Thr Pro Val Pro Pro Gly Asp Cys Pro Pro Leu Glu Leu Val Ser Ser
            180                 185                 190

Val Ile Gln Asp Gly Asp Met Ile Asp Thr Gly Phe Gly Ala Met Asp
        195                 200                 205

Phe Ala Ala Leu Gln Ala Thr Lys Ser Asp Val Pro Leu Asp Ile Ser
    210                 215                 220

Gln Ser Val Cys Lys Tyr Pro Asp Tyr Leu Lys Met Ser Ala Asp Thr
225                 230                 235                 240

Tyr Gly Asn Ser Met Phe Phe His Leu Arg Arg Glu Gln Ile Phe Ala
                245                 250                 255

Arg His Tyr Tyr Asn Lys Leu Gly Ser Val Gly Glu Asp Ile Pro Thr
            260                 265                 270

Asp Tyr Tyr Ile Lys Gly Ser Gly Asn Gly Arg Asp Pro Ile Glu Ser
        275                 280                 285

Tyr Ile Tyr Ser Ala Thr Pro Ser Gly Ser Met Ile Thr Ser Asp Ser
    290                 295                 300

Gln Ile Phe Asn Lys Pro Tyr Trp Leu His Arg Ala Gln Gly His Asn
305                 310                 315                 320

Asn Gly Ile Cys Trp Asn Asn Gln Leu Phe Ile Thr Cys Val Asp Thr
                325                 330                 335

Thr Arg Ser Thr Asn Leu Thr Ile Ser Thr Ala Thr Ala Ala Val Ser
            340                 345                 350

Pro Thr Phe Thr Pro Ser Asn Phe Lys Gln Tyr Ile Arg His Gly Glu
        355                 360                 365

Glu Tyr Glu Leu Gln Phe Ile Phe Gln Leu Cys Lys Ile Thr Leu Thr
    370                 375                 380

Thr Glu Val Met Ala Tyr Leu His Thr Met Asp Pro Thr Ile Leu Glu
385                 390                 395                 400

Gln Trp Asn Phe Gly Leu Thr Leu Pro Pro Ser Ala Ser Leu Glu Asp
                405                 410                 415

Ala Tyr Arg Phe Val Arg Asn Ala Ala Thr Ser Cys Gln Lys Asp Thr
            420                 425                 430

Pro Pro Gln Ala Lys Pro Asp Pro Leu Ala Lys Tyr Lys Phe Trp Asp
        435                 440                 445

Val Asp Leu Lys Glu Arg Phe Ser Leu Asp Leu Asp Gln Phe Ala Leu
    450                 455                 460

Gly Arg Lys Phe Leu Leu Gln Val Gly Val Gln Arg Lys Pro Arg Pro
465                 470                 475                 480
```

Gly Leu Lys Arg Pro Ala Ser Ser Ala Ser Ser Ser Ser Ser Ser Ser
485 490 495

Ala Lys Arg Lys Arg Val Lys Lys
500

<210> SEQ ID NO 2
<211> LENGTH: 508
<212> TYPE: PRT
<213> ORGANISM: Human papillomavirus type 69

<400> SEQUENCE: 2

Met Ala Leu Trp Arg Thr Ser Asp Ser Lys Val Tyr Leu Pro Pro Thr
1 5 10 15

Pro Val Ser Arg Val Val Ser Thr Asp Glu Tyr Val Thr Arg Thr Gly
20 25 30

Ile Tyr Tyr Tyr Ala Gly Ser Ser Arg Leu Leu Thr Leu Gly His Pro
35 40 45

Tyr Phe Pro Ile Pro Lys Ser Gly Ser Thr Ala Glu Ile Pro Lys Val
50 55 60

Ser Ala Tyr Gln Tyr Arg Val Phe Arg Val His Leu Pro Asp Pro Asn
65 70 75 80

Lys Phe Gly Leu Pro Asp Pro Gln Leu Tyr Asn Pro Glu Thr Glu Arg
85 90 95

Leu Val Trp Ala Cys Val Gly Val Glu Val Gly Arg Gly Gln Pro Leu
100 105 110

Gly Val Gly Leu Ser Gly His Pro Leu Phe Asn Lys Leu Asp Asp Thr
115 120 125

Glu Asn Ser His Leu Ala Thr Ala Asn Ala Asp Thr Asp Asn Arg Asp
130 135 140

Asn Val Cys Val Asp Asn Lys Gln Thr Gln Leu Cys Ile Ile Gly Cys
145 150 155 160

Thr Pro Pro Leu Gly Glu His Trp Gly Val Gly Thr Val Cys Lys Asn
165 170 175

Ala Gln Ser Gln Val Gln Arg Gly Asp Cys Pro Pro Leu Glu Leu Ile
180 185 190

Ser Ser Val Ile Glu Asp Gly Asp Met Ile Asp Thr Gly Phe Gly Ala
195 200 205

Met Asp Phe Thr Ala Leu Gln Ala Thr Lys Cys Asp Val Pro Leu Asp
210 215 220

Ile Asn Gln Ser Ile Cys Lys Tyr Pro Asp Tyr Leu Lys Met Ser Ala
225 230 235 240

Asp Thr Tyr Gly Asn Ser Met Phe Phe Phe Leu Arg Arg Glu Gln Leu
245 250 255

Phe Ala Arg His Phe Phe Asn Lys Ala Gly Thr Ile Gly Asp Pro Val
260 265 270

Pro Val Ser Met Tyr Ile Lys Gly Ala Gly Gln Gly Arg Glu Pro Pro
275 280 285

Thr Thr Ser Ile Tyr Ser Ala Thr Pro Ser Gly Ser Met Val Thr Ser
290 295 300

Asp Ala Gln Leu Phe Asn Lys Pro Tyr Trp Leu Gln Arg Ala Gln Gly
305 310 315 320

His Asn Asn Gly Ile Cys Trp Gly Asn Gln Leu Phe Val Thr Cys Val
325 330 335

Asp Thr Thr Arg Ser Thr Asn Leu Thr Ile Ser Thr Val Ser Ala Gln
340 345 350

-continued

```
Ser Ala Ser Ala Thr Phe Lys Pro Ser Asp Tyr Lys Gln Phe Ile Arg
        355                 360                 365

His Gly Glu Glu Tyr Glu Leu Gln Phe Ile Phe Gln Leu Cys Lys Ile
    370                 375                 380

Thr Leu Thr Thr Asp Val Met Ala Tyr Ile His Thr Met Asn Ser Thr
385                 390                 395                 400

Ile Leu Glu Asn Trp Asn Phe Gly Leu Thr Leu Pro Pro Thr Ala Ser
                405                 410                 415

Leu Glu Asp Ala Tyr Arg Phe Ile Lys Asn Ser Ala Thr Thr Cys Gln
            420                 425                 430

Arg Asp Ala Pro Ala Gln Pro Lys Glu Asp Pro Phe Ser Lys Leu Lys
        435                 440                 445

Phe Trp Asp Val Asp Leu Lys Glu Lys Phe Ser Ile Asp Leu Asp Gln
    450                 455                 460

Phe Pro Leu Gly Arg Lys Phe Met Leu Gln Ala Gly Ile Gln Arg Arg
465                 470                 475                 480

Pro Lys Leu Gly Thr Lys Arg Pro Ala Ser Ser Leu Ser Ala Ser Ser
                485                 490                 495

Ser Ser Thr Thr Arg Lys Lys Arg Lys Leu Thr Lys
            500                 505


<210> SEQ ID NO 3
<211> LENGTH: 496
<212> TYPE: PRT
<213> ORGANISM: Human papillomavirus type 51

<400> SEQUENCE: 3

Met Lys Val Tyr Leu Pro Pro Ala Pro Val Ser Arg Ile Val Asn Thr
1               5                   10                  15

Glu Glu Tyr Ile Thr Arg Thr Gly Ile Tyr Tyr Tyr Ala Gly Ser Ser
            20                  25                  30

Arg Leu Ile Thr Leu Gly His Pro Tyr Phe Pro Leu Pro Lys Thr Ser
        35                  40                  45

Thr Arg Ala Ala Ile Pro Lys Val Ser Ala Phe Gln Tyr Arg Val Phe
    50                  55                  60

Arg Val Gln Leu Pro Asp Pro Asn Lys Phe Gly Leu Pro Asp Pro Asn
65                  70                  75                  80

Leu Tyr Asn Pro Asp Thr Asp Arg Leu Val Trp Gly Cys Val Gly Val
                85                  90                  95

Glu Val Gly Arg Gly Gln Pro Leu Gly Val Gly Leu Ser Gly His Pro
            100                 105                 110

Leu Phe Asn Lys Tyr Asp Asp Thr Glu Asn Ser Arg Ile Ala Asn Gly
        115                 120                 125

Asn Ala Gln Gln Asp Val Arg Asp Asn Thr Ser Val Asp Asn Lys Gln
    130                 135                 140

Thr Gln Leu Cys Ile Ile Gly Cys Ala Pro Pro Ile Gly Glu His Trp
145                 150                 155                 160

Gly Ile Gly Thr Thr Cys Lys Asn Thr Pro Val Pro Pro Gly Asp Cys
                165                 170                 175

Pro Pro Leu Glu Leu Val Ser Ser Val Ile Gln Asp Gly Asp Met Ile
            180                 185                 190

Asp Thr Gly Phe Gly Ala Met Asp Phe Ala Ala Leu Gln Ala Thr Lys
        195                 200                 205

Ser Asp Val Pro Leu Asp Ile Ser Gln Ser Val Cys Lys Tyr Pro Asp
```

-continued

```
    210                 215                 220

Tyr Leu Lys Met Ser Ala Asp Thr Tyr Gly Asn Ser Met Phe Phe His
225                 230                 235                 240

Leu Arg Arg Glu Gln Ile Phe Ala Arg His Tyr Tyr Asn Lys Leu Gly
                245                 250                 255

Ser Val Gly Glu Asp Ile Pro Thr Asp Tyr Tyr Ile Lys Gly Ser Gly
            260                 265                 270

Asn Gly Arg Asp Pro Ile Glu Ser Tyr Ile Tyr Ser Ala Thr Pro Ser
        275                 280                 285

Gly Ser Met Ile Thr Ser Asp Ser Gln Ile Phe Asn Lys Pro Tyr Trp
    290                 295                 300

Leu His Arg Ala Gln Gly His Asn Asn Gly Ile Cys Trp Asn Asn Gln
305                 310                 315                 320

Leu Phe Ile Thr Cys Val Asp Thr Thr Arg Ser Thr Asn Leu Thr Ile
                325                 330                 335

Ser Thr Ala Thr Ala Ala Val Ser Pro Thr Phe Thr Pro Ser Asn Phe
            340                 345                 350

Lys Gln Tyr Ile Arg His Gly Glu Glu Tyr Glu Leu Gln Phe Ile Phe
        355                 360                 365

Gln Leu Cys Lys Ile Thr Leu Thr Thr Glu Val Met Ala Tyr Leu His
    370                 375                 380

Thr Met Asp Pro Thr Ile Leu Glu Gln Trp Asn Phe Gly Leu Thr Leu
385                 390                 395                 400

Pro Pro Ser Ala Ser Leu Glu Asp Ala Tyr Arg Phe Val Arg Asn Ala
                405                 410                 415

Ala Thr Ser Cys Gln Lys Asp Thr Pro Pro Gln Ala Lys Pro Asp Pro
            420                 425                 430

Leu Ala Lys Tyr Lys Phe Trp Asp Val Asp Leu Lys Glu Arg Phe Ser
        435                 440                 445

Leu Asp Leu Asp Gln Phe Ala Leu Gly Arg Lys Phe Leu Leu Gln Val
    450                 455                 460

Gly Val Gln Arg Lys Pro Arg Pro Gly Leu Lys Arg Pro Ala Ser Ser
465                 470                 475                 480

Ala Ser Ser Ser Ser Ser Ser Ser Ala Lys Arg Lys Arg Val Lys Lys
                485                 490                 495


<210> SEQ ID NO 4
<211> LENGTH: 496
<212> TYPE: PRT
<213> ORGANISM: Artificial Sequence
<220> FEATURE:
<223> OTHER INFORMATION: H51N9-69T1

<400> SEQUENCE: 4

Met Lys Val Tyr Leu Pro Pro Ala Pro Val Ser Arg Ile Val Asn Thr
1               5                   10                  15

Glu Glu Tyr Ile Thr Arg Thr Gly Ile Tyr Tyr Tyr Ala Gly Ser Ser
            20                  25                  30

Arg Leu Ile Thr Leu Gly His Pro Tyr Phe Pro Ile Pro Lys Ser Gly
        35                  40                  45

Ser Thr Ala Glu Ile Pro Lys Val Ser Ala Phe Gln Tyr Arg Val Phe
    50                  55                  60

Arg Val Gln Leu Pro Asp Pro Asn Lys Phe Gly Leu Pro Asp Pro Asn
65                  70                  75                  80

Leu Tyr Asn Pro Asp Thr Asp Arg Leu Val Trp Gly Cys Val Gly Val
```

-continued

```
                85                  90                  95

Glu Val Gly Arg Gly Gln Pro Leu Gly Val Gly Leu Ser Gly His Pro
            100                 105                 110

Leu Phe Asn Lys Tyr Asp Asp Thr Glu Asn Ser Arg Ile Ala Asn Gly
        115                 120                 125

Asn Ala Gln Gln Asp Val Arg Asp Asn Thr Ser Val Asp Asn Lys Gln
    130                 135                 140

Thr Gln Leu Cys Ile Ile Gly Cys Ala Pro Pro Ile Gly Glu His Trp
145                 150                 155                 160

Gly Ile Gly Thr Thr Cys Lys Asn Thr Pro Val Pro Pro Gly Asp Cys
                165                 170                 175

Pro Pro Leu Glu Leu Val Ser Ser Val Ile Gln Asp Gly Asp Met Ile
            180                 185                 190

Asp Thr Gly Phe Gly Ala Met Asp Phe Ala Ala Leu Gln Ala Thr Lys
        195                 200                 205

Ser Asp Val Pro Leu Asp Ile Ser Gln Ser Val Cys Lys Tyr Pro Asp
    210                 215                 220

Tyr Leu Lys Met Ser Ala Asp Thr Tyr Gly Asn Ser Met Phe Phe His
225                 230                 235                 240

Leu Arg Arg Glu Gln Ile Phe Ala Arg His Tyr Tyr Asn Lys Leu Gly
                245                 250                 255

Ser Val Gly Glu Asp Ile Pro Thr Asp Tyr Tyr Ile Lys Gly Ser Gly
            260                 265                 270

Asn Gly Arg Asp Pro Ile Glu Ser Tyr Ile Tyr Ser Ala Thr Pro Ser
        275                 280                 285

Gly Ser Met Ile Thr Ser Asp Ser Gln Ile Phe Asn Lys Pro Tyr Trp
    290                 295                 300

Leu His Arg Ala Gln Gly His Asn Asn Gly Ile Cys Trp Asn Asn Gln
305                 310                 315                 320

Leu Phe Ile Thr Cys Val Asp Thr Thr Arg Ser Thr Asn Leu Thr Ile
                325                 330                 335

Ser Thr Ala Thr Ala Ala Val Ser Pro Thr Phe Thr Pro Ser Asn Phe
            340                 345                 350

Lys Gln Tyr Ile Arg His Gly Glu Glu Tyr Glu Leu Gln Phe Ile Phe
        355                 360                 365

Gln Leu Cys Lys Ile Thr Leu Thr Thr Glu Val Met Ala Tyr Leu His
    370                 375                 380

Thr Met Asp Pro Thr Ile Leu Glu Gln Trp Asn Phe Gly Leu Thr Leu
385                 390                 395                 400

Pro Pro Ser Ala Ser Leu Glu Asp Ala Tyr Arg Phe Val Arg Asn Ala
                405                 410                 415

Ala Thr Ser Cys Gln Lys Asp Thr Pro Pro Gln Ala Lys Pro Asp Pro
            420                 425                 430

Leu Ala Lys Tyr Lys Phe Trp Asp Val Asp Leu Lys Glu Arg Phe Ser
        435                 440                 445

Leu Asp Leu Asp Gln Phe Ala Leu Gly Arg Lys Phe Leu Leu Gln Val
    450                 455                 460

Gly Val Gln Arg Lys Pro Arg Pro Gly Leu Lys Arg Pro Ala Ser Ser
465                 470                 475                 480

Ala Ser Ser Ser Ser Ser Ser Ser Ala Lys Arg Lys Arg Val Lys Lys
                485                 490                 495
```

<210> SEQ ID NO 5

```
<211> LENGTH: 496
<212> TYPE: PRT
<213> ORGANISM: Artificial Sequence
<220> FEATURE:
<223> OTHER INFORMATION: H51N9-69T2

<400> SEQUENCE: 5

Met Lys Val Tyr Leu Pro Pro Ala Pro Val Ser Arg Ile Val Asn Thr
1               5                   10                  15

Glu Glu Tyr Ile Thr Arg Thr Gly Ile Tyr Tyr Tyr Ala Gly Ser Ser
            20                  25                  30

Arg Leu Ile Thr Leu Gly His Pro Tyr Phe Pro Leu Pro Lys Thr Ser
        35                  40                  45

Thr Arg Ala Ala Ile Pro Lys Val Ser Ala Phe Gln Tyr Arg Val Phe
    50                  55                  60

Arg Val Gln Leu Pro Asp Pro Asn Lys Phe Gly Leu Pro Asp Pro Asn
65                  70                  75                  80

Leu Tyr Asn Pro Asp Thr Asp Arg Leu Val Trp Gly Cys Val Gly Val
                85                  90                  95

Glu Val Gly Arg Gly Gln Pro Leu Gly Val Gly Leu Ser Gly His Pro
            100                 105                 110

Leu Phe Asn Lys Leu Asp Asp Thr Glu Asn Ser His Leu Ala Thr Ala
        115                 120                 125

Asn Ala Asp Thr Asp Asn Arg Asp Asn Val Cys Val Asp Asn Lys Gln
    130                 135                 140

Thr Gln Leu Cys Ile Ile Gly Cys Ala Pro Pro Ile Gly Glu His Trp
145                 150                 155                 160

Gly Ile Gly Thr Thr Cys Lys Asn Thr Pro Val Pro Pro Gly Asp Cys
                165                 170                 175

Pro Pro Leu Glu Leu Val Ser Ser Val Ile Gln Asp Gly Asp Met Ile
            180                 185                 190

Asp Thr Gly Phe Gly Ala Met Asp Phe Ala Ala Leu Gln Ala Thr Lys
        195                 200                 205

Ser Asp Val Pro Leu Asp Ile Ser Gln Ser Val Cys Lys Tyr Pro Asp
    210                 215                 220

Tyr Leu Lys Met Ser Ala Asp Thr Tyr Gly Asn Ser Met Phe Phe His
225                 230                 235                 240

Leu Arg Arg Glu Gln Ile Phe Ala Arg His Tyr Tyr Asn Lys Leu Gly
                245                 250                 255

Ser Val Gly Glu Asp Ile Pro Thr Asp Tyr Tyr Ile Lys Gly Ser Gly
            260                 265                 270

Asn Gly Arg Asp Pro Ile Glu Ser Tyr Ile Tyr Ser Ala Thr Pro Ser
        275                 280                 285

Gly Ser Met Ile Thr Ser Asp Ser Gln Ile Phe Asn Lys Pro Tyr Trp
    290                 295                 300

Leu His Arg Ala Gln Gly His Asn Asn Gly Ile Cys Trp Asn Asn Gln
305                 310                 315                 320

Leu Phe Ile Thr Cys Val Asp Thr Thr Arg Ser Thr Asn Leu Thr Ile
                325                 330                 335

Ser Thr Ala Thr Ala Ala Val Ser Pro Thr Phe Thr Pro Ser Asn Phe
            340                 345                 350

Lys Gln Tyr Ile Arg His Gly Glu Glu Tyr Glu Leu Gln Phe Ile Phe
        355                 360                 365

Gln Leu Cys Lys Ile Thr Leu Thr Thr Glu Val Met Ala Tyr Leu His
    370                 375                 380
```

```
Thr Met Asp Pro Thr Ile Leu Glu Gln Trp Asn Phe Gly Leu Thr Leu
385                 390                 395                 400

Pro Pro Ser Ala Ser Leu Glu Asp Ala Tyr Arg Phe Val Arg Asn Ala
                405                 410                 415

Ala Thr Ser Cys Gln Lys Asp Thr Pro Pro Gln Ala Lys Pro Asp Pro
            420                 425                 430

Leu Ala Lys Tyr Lys Phe Trp Asp Val Asp Leu Lys Glu Arg Phe Ser
        435                 440                 445

Leu Asp Leu Asp Gln Phe Ala Leu Gly Arg Lys Phe Leu Leu Gln Val
    450                 455                 460

Gly Val Gln Arg Lys Pro Arg Pro Gly Leu Lys Arg Pro Ala Ser Ser
465                 470                 475                 480

Ala Ser Ser Ser Ser Ser Ser Ser Ala Lys Arg Lys Arg Val Lys Lys
                485                 490                 495


<210> SEQ ID NO 6
<211> LENGTH: 498
<212> TYPE: PRT
<213> ORGANISM: Artificial Sequence
<220> FEATURE:
<223> OTHER INFORMATION: H51N9-69T3

<400> SEQUENCE: 6

Met Lys Val Tyr Leu Pro Pro Ala Pro Val Ser Arg Ile Val Asn Thr
1               5                   10                  15

Glu Glu Tyr Ile Thr Arg Thr Gly Ile Tyr Tyr Tyr Ala Gly Ser Ser
            20                  25                  30

Arg Leu Ile Thr Leu Gly His Pro Tyr Phe Pro Leu Pro Lys Thr Ser
        35                  40                  45

Thr Arg Ala Ala Ile Pro Lys Val Ser Ala Phe Gln Tyr Arg Val Phe
    50                  55                  60

Arg Val Gln Leu Pro Asp Pro Asn Lys Phe Gly Leu Pro Asp Pro Asn
65                  70                  75                  80

Leu Tyr Asn Pro Asp Thr Asp Arg Leu Val Trp Gly Cys Val Gly Val
                85                  90                  95

Glu Val Gly Arg Gly Gln Pro Leu Gly Val Gly Leu Ser Gly His Pro
            100                 105                 110

Leu Phe Asn Lys Tyr Asp Asp Thr Glu Asn Ser Arg Ile Ala Asn Gly
        115                 120                 125

Asn Ala Gln Gln Asp Val Arg Asp Asn Thr Ser Val Asp Asn Lys Gln
    130                 135                 140

Thr Gln Leu Cys Ile Ile Gly Cys Ala Pro Pro Ile Gly Glu His Trp
145                 150                 155                 160

Gly Val Gly Thr Val Cys Lys Asn Ala Gln Ser Gln Val Gln Arg Gly
                165                 170                 175

Asp Cys Pro Pro Leu Glu Leu Val Ser Ser Val Ile Gln Asp Gly Asp
            180                 185                 190

Met Ile Asp Thr Gly Phe Gly Ala Met Asp Phe Ala Ala Leu Gln Ala
        195                 200                 205

Thr Lys Ser Asp Val Pro Leu Asp Ile Ser Gln Ser Val Cys Lys Tyr
    210                 215                 220

Pro Asp Tyr Leu Lys Met Ser Ala Asp Thr Tyr Gly Asn Ser Met Phe
225                 230                 235                 240

Phe His Leu Arg Arg Glu Gln Ile Phe Ala Arg His Tyr Tyr Asn Lys
                245                 250                 255
```

```
Leu Gly Ser Val Gly Glu Asp Ile Pro Thr Asp Tyr Tyr Ile Lys Gly
            260                 265                 270

Ser Gly Asn Gly Arg Asp Pro Ile Glu Ser Tyr Ile Tyr Ser Ala Thr
        275                 280                 285

Pro Ser Gly Ser Met Ile Thr Ser Asp Ser Gln Ile Phe Asn Lys Pro
    290                 295                 300

Tyr Trp Leu His Arg Ala Gln Gly His Asn Asn Gly Ile Cys Trp Asn
305                 310                 315                 320

Asn Gln Leu Phe Ile Thr Cys Val Asp Thr Thr Arg Ser Thr Asn Leu
                325                 330                 335

Thr Ile Ser Thr Ala Thr Ala Ala Val Ser Pro Thr Phe Thr Pro Ser
            340                 345                 350

Asn Phe Lys Gln Tyr Ile Arg His Gly Glu Glu Tyr Glu Leu Gln Phe
        355                 360                 365

Ile Phe Gln Leu Cys Lys Ile Thr Leu Thr Thr Glu Val Met Ala Tyr
    370                 375                 380

Leu His Thr Met Asp Pro Thr Ile Leu Glu Gln Trp Asn Phe Gly Leu
385                 390                 395                 400

Thr Leu Pro Pro Ser Ala Ser Leu Glu Asp Ala Tyr Arg Phe Val Arg
                405                 410                 415

Asn Ala Ala Thr Ser Cys Gln Lys Asp Thr Pro Pro Gln Ala Lys Pro
            420                 425                 430

Asp Pro Leu Ala Lys Tyr Lys Phe Trp Asp Val Asp Leu Lys Glu Arg
        435                 440                 445

Phe Ser Leu Asp Leu Asp Gln Phe Ala Leu Gly Arg Lys Phe Leu Leu
    450                 455                 460

Gln Val Gly Val Gln Arg Lys Pro Arg Pro Gly Leu Lys Arg Pro Ala
465                 470                 475                 480

Ser Ser Ala Ser Ser Ser Ser Ser Ser Ser Ala Lys Arg Lys Arg Val
                485                 490                 495

Lys Lys


<210> SEQ ID NO 7
<211> LENGTH: 496
<212> TYPE: PRT
<213> ORGANISM: Artificial Sequence
<220> FEATURE:
<223> OTHER INFORMATION: H51N9-69T4

<400> SEQUENCE: 7

Met Lys Val Tyr Leu Pro Pro Ala Pro Val Ser Arg Ile Val Asn Thr
1               5                   10                  15

Glu Glu Tyr Ile Thr Arg Thr Gly Ile Tyr Tyr Tyr Ala Gly Ser Ser
            20                  25                  30

Arg Leu Ile Thr Leu Gly His Pro Tyr Phe Pro Leu Pro Lys Thr Ser
        35                  40                  45

Thr Arg Ala Ala Ile Pro Lys Val Ser Ala Phe Gln Tyr Arg Val Phe
    50                  55                  60

Arg Val Gln Leu Pro Asp Pro Asn Lys Phe Gly Leu Pro Asp Pro Asn
65                  70                  75                  80

Leu Tyr Asn Pro Asp Thr Asp Arg Leu Val Trp Gly Cys Val Gly Val
                85                  90                  95

Glu Val Gly Arg Gly Gln Pro Leu Gly Val Gly Leu Ser Gly His Pro
            100                 105                 110
```

-continued

```
Leu Phe Asn Lys Tyr Asp Asp Thr Glu Asn Ser Arg Ile Ala Asn Gly
        115                 120                 125

Asn Ala Gln Gln Asp Val Arg Asp Asn Thr Ser Val Asp Asn Lys Gln
    130                 135                 140

Thr Gln Leu Cys Ile Ile Gly Cys Ala Pro Pro Ile Gly Glu His Trp
145                 150                 155                 160

Gly Ile Gly Thr Thr Cys Lys Asn Thr Pro Val Pro Pro Gly Asp Cys
                165                 170                 175

Pro Pro Leu Glu Leu Val Ser Ser Val Ile Gln Asp Gly Asp Met Ile
            180                 185                 190

Asp Thr Gly Phe Gly Ala Met Asp Phe Ala Ala Leu Gln Ala Thr Lys
        195                 200                 205

Ser Asp Val Pro Leu Asp Ile Ser Gln Ser Val Cys Lys Tyr Pro Asp
    210                 215                 220

Tyr Leu Lys Met Ser Ala Asp Thr Tyr Gly Asn Ser Met Phe Phe His
225                 230                 235                 240

Leu Arg Arg Glu Gln Ile Phe Ala Arg His Phe Phe Asn Lys Ala Gly
                245                 250                 255

Thr Ile Gly Asp Pro Val Pro Val Ser Met Tyr Ile Lys Gly Ala Gly
            260                 265                 270

Gln Gly Arg Glu Pro Pro Thr Thr Ser Ile Tyr Ser Ala Thr Pro Ser
        275                 280                 285

Gly Ser Met Ile Thr Ser Asp Ser Gln Ile Phe Asn Lys Pro Tyr Trp
    290                 295                 300

Leu His Arg Ala Gln Gly His Asn Asn Gly Ile Cys Trp Asn Asn Gln
305                 310                 315                 320

Leu Phe Ile Thr Cys Val Asp Thr Thr Arg Ser Thr Asn Leu Thr Ile
                325                 330                 335

Ser Thr Ala Thr Ala Ala Val Ser Pro Thr Phe Thr Pro Ser Asn Phe
            340                 345                 350

Lys Gln Tyr Ile Arg His Gly Glu Glu Tyr Glu Leu Gln Phe Ile Phe
        355                 360                 365

Gln Leu Cys Lys Ile Thr Leu Thr Thr Glu Val Met Ala Tyr Leu His
    370                 375                 380

Thr Met Asp Pro Thr Ile Leu Glu Gln Trp Asn Phe Gly Leu Thr Leu
385                 390                 395                 400

Pro Pro Ser Ala Ser Leu Glu Asp Ala Tyr Arg Phe Val Arg Asn Ala
                405                 410                 415

Ala Thr Ser Cys Gln Lys Asp Thr Pro Pro Gln Ala Lys Pro Asp Pro
            420                 425                 430

Leu Ala Lys Tyr Lys Phe Trp Asp Val Asp Leu Lys Glu Arg Phe Ser
        435                 440                 445

Leu Asp Leu Asp Gln Phe Ala Leu Gly Arg Lys Phe Leu Leu Gln Val
    450                 455                 460

Gly Val Gln Arg Lys Pro Arg Pro Gly Leu Lys Arg Pro Ala Ser Ser
465                 470                 475                 480

Ala Ser Ser Ser Ser Ser Ser Ser Ala Lys Arg Lys Arg Val Lys Lys
                485                 490                 495
```

<210> SEQ ID NO 8
<211> LENGTH: 497
<212> TYPE: PRT
<213> ORGANISM: Artificial Sequence
<220> FEATURE:
<223> OTHER INFORMATION: H51N9-69T5

<400> SEQUENCE: 8

```
Met Lys Val Tyr Leu Pro Pro Ala Pro Val Ser Arg Ile Val Asn Thr
1               5                   10                  15

Glu Glu Tyr Ile Thr Arg Thr Gly Ile Tyr Tyr Tyr Ala Gly Ser Ser
            20                  25                  30

Arg Leu Ile Thr Leu Gly His Pro Tyr Phe Pro Leu Pro Lys Thr Ser
        35                  40                  45

Thr Arg Ala Ala Ile Pro Lys Val Ser Ala Phe Gln Tyr Arg Val Phe
    50                  55                  60

Arg Val Gln Leu Pro Asp Pro Asn Lys Phe Gly Leu Pro Asp Pro Asn
65                  70                  75                  80

Leu Tyr Asn Pro Asp Thr Asp Arg Leu Val Trp Gly Cys Val Gly Val
                85                  90                  95

Glu Val Gly Arg Gly Gln Pro Leu Gly Val Gly Leu Ser Gly His Pro
            100                 105                 110

Leu Phe Asn Lys Tyr Asp Asp Thr Glu Asn Ser Arg Ile Ala Asn Gly
        115                 120                 125

Asn Ala Gln Gln Asp Val Arg Asp Asn Thr Ser Val Asp Asn Lys Gln
    130                 135                 140

Thr Gln Leu Cys Ile Ile Gly Cys Ala Pro Pro Ile Gly Glu His Trp
145                 150                 155                 160

Gly Ile Gly Thr Thr Cys Lys Asn Thr Pro Val Pro Pro Gly Asp Cys
                165                 170                 175

Pro Pro Leu Glu Leu Val Ser Ser Val Ile Gln Asp Gly Asp Met Ile
            180                 185                 190

Asp Thr Gly Phe Gly Ala Met Asp Phe Ala Ala Leu Gln Ala Thr Lys
        195                 200                 205

Ser Asp Val Pro Leu Asp Ile Ser Gln Ser Val Cys Lys Tyr Pro Asp
    210                 215                 220

Tyr Leu Lys Met Ser Ala Asp Thr Tyr Gly Asn Ser Met Phe Phe His
225                 230                 235                 240

Leu Arg Arg Glu Gln Ile Phe Ala Arg His Tyr Tyr Asn Lys Leu Gly
                245                 250                 255

Ser Val Gly Glu Asp Ile Pro Thr Asp Tyr Tyr Ile Lys Gly Ser Gly
            260                 265                 270

Asn Gly Arg Asp Pro Ile Glu Ser Tyr Ile Tyr Ser Ala Thr Pro Ser
        275                 280                 285

Gly Ser Met Ile Thr Ser Asp Ser Gln Ile Phe Asn Lys Pro Tyr Trp
    290                 295                 300

Leu His Arg Ala Gln Gly His Asn Asn Gly Ile Cys Trp Asn Asn Gln
305                 310                 315                 320

Leu Phe Ile Thr Cys Val Asp Thr Thr Arg Ser Thr Asn Leu Thr Ile
                325                 330                 335

Ser Thr Ala Ser Ala Gln Ser Ala Ser Ala Thr Phe Lys Pro Ser Asp
            340                 345                 350

Phe Lys Gln Tyr Ile Arg His Gly Glu Glu Tyr Glu Leu Gln Phe Ile
        355                 360                 365

Phe Gln Leu Cys Lys Ile Thr Leu Thr Thr Glu Val Met Ala Tyr Leu
    370                 375                 380

His Thr Met Asp Pro Thr Ile Leu Glu Gln Trp Asn Phe Gly Leu Thr
385                 390                 395                 400

Leu Pro Pro Ser Ala Ser Leu Glu Asp Ala Tyr Arg Phe Val Arg Asn
```

```
                405                 410                 415

Ala Ala Thr Ser Cys Gln Lys Asp Thr Pro Pro Gln Ala Lys Pro Asp
            420                 425                 430

Pro Leu Ala Lys Tyr Lys Phe Trp Asp Val Asp Leu Lys Glu Arg Phe
        435                 440                 445

Ser Leu Asp Leu Asp Gln Phe Ala Leu Gly Arg Lys Phe Leu Leu Gln
    450                 455                 460

Val Gly Val Gln Arg Lys Pro Arg Pro Gly Leu Lys Arg Pro Ala Ser
465                 470                 475                 480

Ser Ala Ser Ser Ser Ser Ser Ser Ser Ala Lys Arg Lys Arg Val Lys
                485                 490                 495

Lys


<210> SEQ ID NO 9
<211> LENGTH: 1515
<212> TYPE: DNA
<213> ORGANISM: Human papillomavirus type 51

<400> SEQUENCE: 9

atggccctgt ggaggaccaa cgacagcaag gtgtacctgc cccccgcccc cgtgagcagg     60

atcgtgaaca ccgaggagta catcaccagg accggcatct actactacgc cggcagcagc    120

aggctgatca ccctgggcca cccctacttc cccctgccca agaccagcac cagggccgcc    180

atccccaagg tgagcgcctt ccagtacagg gtgttcaggg tgcagctccc cgaccccaac    240

aagttcggcc tgcccgaccc caacctgtac aaccccgaca ccgacaggct ggtgtggggc    300

tgcgtgggcg tggaggtggg caggggccag cccctgggcg tgggcctgag cggccacccc    360

ctgttcaaca agtacgacga caccgagaac agcaggatcg ccaacggcaa cgcccagcag    420

gacgtgaggg acaacaccag cgtggacaac aagcagaccc agctgtgcat catcggctgc    480

gcccccccca tcggcgagca ctggggcatc ggcaccacct gcaagaacac ccccgtgccc    540

cccggcgact gcccccccct ggagctggtg agcagcgtga tccaggacgg cgacatgatc    600

gacaccggct tcggcgccat ggacttcgcc gccctgcagg ccaccaagag cgacgtgccc    660

ctggacatca gccagagcgt gtgcaagtac cccgactacc tgaagatgag cgccgacacc    720

tacggcaaca gcatgttctt ccacctgagg agggagcaga tcttcgccag gcactactac    780

aacaagctgg gcagcgtggg cgaggacatc cccaccgact actacatcaa gggcagcggc    840

aacggcaggg accccatcga gagctacatc tacagcgcca cccccagcgg cagcatgatc    900

accagcgaca gccagatctt caacaagccc tactggctgc acagggccca gggccacaac    960

aacggcatct gctggaacaa ccagctgttc atcacctgcg tggacaccac caggagcacc   1020

aacctgacca tcagcaccgc caccgccgcc gtgagcccca ccttcacccc cagcaacttc   1080

aagcagtaca tcaggcacgg cgaggagtac gagctgcagt tcatcttcca gctgtgcaag   1140

atcaccctga ccaccgaggt gatggcctac ctgcacacca tggaccccac catcctggag   1200

cagtggaact tcggcctgac cctgccccc agcgccagcc tggaggacgc ctacaggttc   1260

gtgaggaacg ccgccaccag ctgccagaag gacaccccc cccaggccaa gcccgacccc   1320

ctggccaagt acaagttctg ggacgtggac ctgaaggaga ggttcagcct ggacctggac   1380

cagttcgccc tgggcaggaa gttcctgctg caggtgggcg tgcagaggaa gcccaggccc   1440

ggcctgaaga ggcccgctag cagcgccagc tccagcagct ccagcagcgc caagaggaag   1500

agggtgaaga agtaa                                                    1515
```

<210> SEQ ID NO 10
<211> LENGTH: 1527
<212> TYPE: DNA
<213> ORGANISM: Human papillomavirus type 69

<400> SEQUENCE: 10
atggctctgt ggcgtacctc tgactctaaa gtttacctgc cgccgacccc ggtttctcgt 60
gttgtttcta ccgacgaata cgttacccgt accggtatct actactacgc tggttcttct 120
cgtctgctga ccctgggtca cccgtacttc ccgatcccga aatctggttc taccgctgaa 180
atcccgaagg tctctgctta ccagtaccgg gtattccgtg tccacctgcc ggacccgaac 240
aaattcggtc tgccggaccc gcagctgtac aatccagaaa ccgaacgtct ggtttgggct 300
tgcgttggtg tcgaggtcgg tcgtggtcag ccgctgggtg tcggtctgtc tggtcacccg 360
ctgttcaaca aactggacga caccgaaaac tctcacctgg ctaccgctaa cgctgacacc 420
gacaaccgtg acaacgtttg cgttgacaac aaacagaccc agctgtgcat catcggttgc 480
accccgccgc tgggtgaaca ctggggtgtc ggtaccgttt gcaaaaacgc tcagtctcag 540
gttcagcgtg gtgactgccc gccgctggaa ctgatctctt ctgttatcga agacggtgac 600
atgatcgaca ccggtttcgg tgctatggac ttcaccgctc tgcaggctac caaatgcgac 660
gttccgctgg acatcaacca gtctatctgc aaataccccg actacctgaa aatgtctgct 720
gacacctacg gtaactctat gttcttcttc ctgcgtcgtg aacagctgtt cgctcgtcac 780
ttcttcaaca aagctggtac catcggtgac cctgttccgg tttctatgta catcaaaggt 840
gctggtcagg gtcgtgaacc gccgaccaca tccatctact ctgctacccc gtctggttct 900
atggttacat ccgacgctca gctgttcaac aaaccgtact ggctgcagcg tgctcagggt 960
cacaacaacg gtatctgctg ggtaaccag ctgttcgtta cctgcgttga caccacccgt 1020
tctaccaacc tgaccatctc taccgtttct gctcagtctg cttctgctac cttcaaaccg 1080
tctgactaca aacaatttat ccgtcacggt gaagaatacg aactgcagtt catcttccag 1140
ctgtgcaaaa tcaccctgac caccgacgtt atggcttaca tccacaccat gaactctacc 1200
atcctggaaa actggaactt cggtctgacc ctgccgccga ccgcttctct ggaagacgct 1260
taccgtttca tcaaaaactc tgctaccacc tgccagcgtg acgctccggc tcagccgaaa 1320
gaagacccgt tctctaaact gaaattctgg gacgttgacc tgaaagaaaa attctctatc 1380
gacctggacc agttcccgct gggtcgtaaa ttcatgctgc aggctggtat ccagcgtcgt 1440
ccgaaactgg gtaccaaacg tccggcttct tctctgtctg cttcttcttc ttctaccacc 1500
cgtaaaaaac gtaaactgac caaataa 1527

<210> SEQ ID NO 11
<211> LENGTH: 1491
<212> TYPE: DNA
<213> ORGANISM: Human papillomavirus type 51

<400> SEQUENCE: 11
atgaaggtgt acctgccccc cgccccgtg agcaggatcg tgaacaccga ggagtacatc 60
accaggaccg gcatctacta ctacgccggc agcagcaggc tgatcaccct gggccacccc 120
tacttccccc tgcccaagac cagcaccagg gccgccatcc ccaaggtgag cgccttccag 180
tacagggtgt tcagggtgca gctccccgac cccaacaagt tcggcctgcc cgaccccaac 240
ctgtacaacc ccgacaccga caggctggtg tggggctgcg tgggcgtgga ggtgggcagg 300
ggccagcccc tgggcgtggg cctgagcggc cacccccctgt tcaacaagta cgacgacacc 360
gagaacagca ggatcgccaa cggcaacgcc cagcaggacg tgagggacaa caccagcgtg 420
gacaacaagc agacccagct gtgcatcatc ggctgcgccc cccccatcgg cgagcactgg 480
ggcatcggca ccacctgcaa gaacaccccc gtgccccccg gcgactgccc ccccctggag 540
ctggtgagca gcgtgatcca ggacggcgac atgatcgaca ccggcttcgg cgccatggac 600
ttcgccgccc tgcaggccac caagagcgac gtgcccctgg acatcagcca gagcgtgtgc 660
aagtaccccg actacctgaa gatgagcgcc gacacctacg gcaacagcat gttcttccac 720
ctgaggaggg agcagatctt cgccaggcac tactacaaca agctgggcag cgtgggcgag 780
gacatcccca ccgactacta catcaagggc agcggcaacg gcagggaccc catcgagagc 840
tacatctaca gcgccacccc cagcggcagc atgatcacca gcgacagcca gatcttcaac 900
aagccctact ggctgcacag ggcccagggc cacaacaacg gcatctgctg gaacaaccag 960
ctgttcatca cctgcgtgga caccaccagg agcaccaacc tgaccatcag caccgccacc 1020
gccgccgtga gccccacctt cacccccagc aacttcaagc agtacatcag gcacggcgag 1080
gagtacgagc tgcagttcat cttccagctg tgcaagatca ccctgaccac cgaggtgatg 1140
gcctacctgc acaccatgga ccccaccatc ctggagcagt ggaacttcgg cctgaccctg 1200
ccccccagcg ccagcctgga ggacgcctac aggttcgtga ggaacgccgc caccagctgc 1260
cagaaggaca cccccccccca ggccaagccc gacccccctgg ccaagtacaa gttctgggac 1320
gtggacctga aggagaggtt cagcctggac ctggaccagt tcgccctggg caggaagttc 1380
ctgctgcagg tgggcgtgca gaggaagccc aggcccggcc tgaagaggcc cgctagcagc 1440
gccagctcca gcagctccag cagcgccaag aggaagaggg tgaagaagta a 1491

<210> SEQ ID NO 12
<211> LENGTH: 1491
<212> TYPE: DNA
<213> ORGANISM: Artificial Sequence
<220> FEATURE:
<223> OTHER INFORMATION: The DNA sequence encoding H51N9-69T1

<400> SEQUENCE: 12
atgaaggtgt acctgccccc cgcccccgtg agcaggatcg tgaacaccga ggagtacatc 60
accaggaccg gcatctacta ctacgccggc agcagcaggc tgatcaccct gggccacccc 120
tacttcccga tcccgaaatc tggttctacc gctgaaatcc cgaaggtctc tgccttccag 180
tacagggtgt tcagggtgca gctccccgac cccaacaagt tcggcctgcc cgaccccaac 240
ctgtacaacc ccgacaccga caggctggtg tggggctgcg tgggcgtgga ggtgggcagg 300
ggccagcccc tgggcgtggg cctgagcggc cacccccctgt tcaacaagta cgacgacacc 360
gagaacagca ggatcgccaa cggcaacgcc cagcaggacg tgagggacaa caccagcgtg 420
gacaacaagc agacccagct gtgcatcatc ggctgcgccc cccccatcgg cgagcactgg 480
ggcatcggca ccacctgcaa gaacaccccc gtgccccccg gcgactgccc ccccctggag 540
ctggtgagca gcgtgatcca ggacggcgac atgatcgaca ccggcttcgg cgccatggac 600
ttcgccgccc tgcaggccac caagagcgac gtgcccctgg acatcagcca gagcgtgtgc 660
aagtaccccg actacctgaa gatgagcgcc gacacctacg gcaacagcat gttcttccac 720
ctgaggaggg agcagatctt cgccaggcac tactacaaca agctgggcag cgtgggcgag 780
gacatcccca ccgactacta catcaagggc agcggcaacg gcagggaccc catcgagagc 840
tacatctaca gcgccacccc cagcggcagc atgatcacca gcgacagcca gatcttcaac 900

-continued

```
aagccctact ggctgcacag ggcccagggc cacaacaacg gcatctgctg gaacaaccag    960
ctgttcatca cctgcgtgga caccaccagg agcaccaacc tgaccatcag caccgccacc   1020
gccgccgtga gccccacctt cacccccagc aacttcaagc agtacatcag gcacggcgag   1080
gagtacgagc tgcagttcat cttccagctg tgcaagatca ccctgaccac cgaggtgatg   1140
gcctacctgc acaccatgga ccccaccatc ctggagcagt ggaacttcgg cctgaccctg   1200
ccccccagcg ccagcctgga ggacgcctac aggttcgtga ggaacgccgc caccagctgc   1260
cagaaggaca cccccccccca ggccaagccc gacccccctgg ccaagtacaa gttctgggac   1320
gtggacctga aggagaggtt cagcctggac ctggaccagt tcgccctggg caggaagttc   1380
ctgctgcagg tgggcgtgca gaggaagccc aggcccggcc tgaagaggcc cgctagcagc   1440
gccagctcca gcagctccag cagcgccaag aggaagaggg tgaagaagta a            1491
```

<210> SEQ ID NO 13
<211> LENGTH: 1491
<212> TYPE: DNA
<213> ORGANISM: Artificial Sequence
<220> FEATURE:
<223> OTHER INFORMATION: The DNA sequence encoding H51N9-69T2

<400> SEQUENCE: 13

```
atgaaggtgt acctgccccc cgcccccgtg agcaggatcg tgaacaccga ggagtacatc     60
accaggaccg gcatctacta ctacgccggc agcagcaggc tgatcaccct gggccacccc    120
tacttccccc tgcccaagac cagcaccagg gccgccatcc ccaaggtgag cgccttccag    180
tacagggtgt tcagggtgca gctccccgac cccaacaagt tcggcctgcc cgaccccaac    240
ctgtacaacc ccgacaccga caggctggtg tggggctgcg tgggcgtgga ggtgggtcgt    300
ggtcagccgc tgggtgtcgg tctgtctggt cacccgctgt tcaacaaact ggacgacacc    360
gaaaactctc acctggctac cgctaacgct gacaccgaca accgtgacaa cgtttgcgtt    420
gacaacaagc agacccagct gtgcatcatc ggctgcgccc cccccatcgg cgagcactgg    480
ggcatcggca ccacctgcaa gaacaccccc gtgcccccccg gcgactgccc cccccctggag    540
ctggtgagca gcgtgatcca ggacggcgac atgatcgaca ccggcttcgg cgccatggac    600
ttcgccgccc tgcaggccac caagagcgac gtgcccctgg acatcagcca gagcgtgtgc    660
aagtaccccg actacctgaa gatgagcgcc gacacctacg gcaacagcat gttcttccac    720
ctgaggaggg agcagatctt cgccaggcac tactacaaca agctgggcag cgtgggcgag    780
gacatcccca ccgactacta catcaagggc agcggcaacg gcagggaccc catcgagagc    840
tacatctaca gcgccacccc cagcggcagc atgatcacca gcgacagcca gatcttcaac    900
aagccctact ggctgcacag ggcccagggc cacaacaacg gcatctgctg gaacaaccag    960
ctgttcatca cctgcgtgga caccaccagg agcaccaacc tgaccatcag caccgccacc   1020
gccgccgtga gccccacctt cacccccagc aacttcaagc agtacatcag gcacggcgag   1080
gagtacgagc tgcagttcat cttccagctg tgcaagatca ccctgaccac cgaggtgatg   1140
gcctacctgc acaccatgga ccccaccatc ctggagcagt ggaacttcgg cctgaccctg   1200
ccccccagcg ccagcctgga ggacgcctac aggttcgtga ggaacgccgc caccagctgc   1260
cagaaggaca cccccccccca ggccaagccc gacccccctgg ccaagtacaa gttctgggac   1320
gtggacctga aggagaggtt cagcctggac ctggaccagt tcgccctggg caggaagttc   1380
ctgctgcagg tgggcgtgca gaggaagccc aggcccggcc tgaagaggcc cgctagcagc   1440
gccagctcca gcagctccag cagcgccaag aggaagaggg tgaagaagta a            1491
```

<210> SEQ ID NO 14
<211> LENGTH: 1497
<212> TYPE: DNA
<213> ORGANISM: Artificial Sequence
<220> FEATURE:
<223> OTHER INFORMATION: The DNA sequence encoding H51N9-69T3

<400> SEQUENCE: 14
atgaaggtgt acctgccccc cgcccccgtg agcaggatcg tgaacaccga ggagtacatc 60
accaggaccg gcatctacta ctacgccggc agcagcaggc tgatcaccct gggccacccc 120
tacttccccc tgcccaagac cagcaccagg gccgccatcc ccaaggtgag cgccttccag 180
tacagggtgt tcagggtgca gctccccgac cccaacaagt tcggcctgcc cgaccccaac 240
ctgtacaacc ccgacaccga caggctggtg tggggctgcg tgggcgtgga ggtgggcagg 300
ggccagcccc tgggcgtggg cctgagcggc cacccccctgt tcaacaagta cgacgacacc 360
gagaacagca ggatcgccaa cggcaacgcc cagcaggacg tgagggacaa caccagcgtg 420
gacaacaagc agacccagct gtgcatcatc ggctgcgccc cccccatcgg cgagcactgg 480
ggtgtcggta ccgtttgcaa aaacgctcag tctcaggttc agcgtggtga ctgcccgccg 540
ctggagctgg tgagcagcgt gatccaggac ggcgacatga tcgacaccgg cttcggcgcc 600
atggacttcg ccgccctgca ggccaccaag agcgacgtgc ccctggacat cagccagagc 660
gtgtgcaagt accccgacta cctgaagatg agcgccgaca cctacggcaa cagcatgttc 720
ttccacctga ggagggagca gatcttcgcc aggcactact acaacaagct gggcagcgtg 780
ggcgaggaca tccccaccga ctactacatc aagggcagcg gcaacggcag ggaccccatc 840
gagagctaca tctacagcgc cacccccagc ggcagcatga tcaccagcga cagccagatc 900
ttcaacaagc cctactggct gcacagggcc cagggccaca acaacggcat ctgctggaac 960
aaccagctgt tcatcacctg cgtggacacc accaggagca ccaacctgac catcagcacc 1020
gccaccgccg ccgtgagccc caccttcacc cccagcaact tcaagcagta catcaggcac 1080
ggcgaggagt acgagctgca gttcatcttc cagctgtgca agatcaccct gaccaccgag 1140
gtgatggcct acctgcacac catggacccc accatcctgg agcagtggaa cttcggcctg 1200
accctgcccc ccagcgccag cctggaggac gcctacaggt tcgtgaggaa cgccgccacc 1260
agctgccaga aggacacccc cccccaggcc aagcccgacc ccctggccaa gtacaagttc 1320
tgggacgtgg acctgaagga gaggttcagc ctggacctgg accagttcgc cctgggcagg 1380
aagttcctgc tgcaggtggg cgtgcagagg aagcccaggc ccggcctgaa gaggcccgct 1440
agcagcgcca gctccagcag ctccagcagc gccaagagga agagggtgaa gaagtaa 1497

<210> SEQ ID NO 15
<211> LENGTH: 1491
<212> TYPE: DNA
<213> ORGANISM: Artificial Sequence
<220> FEATURE:
<223> OTHER INFORMATION: The DNA sequence encoding H51N9-69T4

<400> SEQUENCE: 15
atgaaggtgt acctgccccc cgcccccgtg agcaggatcg tgaacaccga ggagtacatc 60
accaggaccg gcatctacta ctacgccggc agcagcaggc tgatcaccct gggccacccc 120
tacttccccc tgcccaagac cagcaccagg gccgccatcc ccaaggtgag cgccttccag 180
tacagggtgt tcagggtgca gctccccgac cccaacaagt tcggcctgcc cgaccccaac 240

-continued

```
ctgtacaacc ccgacaccga caggctggtg tggggctgcg tgggcgtgga ggtgggcagg    300
ggccagcccc tgggcgtggg cctgagcggc cacccccctgt tcaacaagta cgacgacacc    360
gagaacagca ggatcgccaa cggcaacgcc cagcaggacg tgagggacaa caccagcgtg    420
gacaacaagc agacccagct gtgcatcatc ggctgcgccc cccccatcgg cgagcactgg    480
ggcatcggca ccacctgcaa gaacaccccc gtgccccccg gcgactgccc ccccctggag    540
ctggtgagca gcgtgatcca ggacggcgac atgatcgaca ccggcttcgg cgccatggac    600
ttcgccgccc tgcaggccac caagagcgac gtgcccctgg acatcagcca gagcgtgtgc    660
aagtaccccg actacctgaa gatgagcgcc gacacctacg gcaacagcat gttcttccac    720
ctgaggaggg agcagatctt cgccaggcac ttcttcaaca aagctggtac catcggtgac    780
cctgttccgg tttctatgta catcaaaggt gctggtcagg gtcgtgaacc gccgaccaca    840
tccatctact ctgccacccc cagcggcagc atgatcacca gcgacagcca gatcttcaac    900
aagccctact ggctgcacag ggcccagggc cacaacaacg gcatctgctg gaacaaccag    960
ctgttcatca cctgcgtgga caccaccagg agcaccaacc tgaccatcag caccgccacc   1020
gccgccgtga gccccacctt caccccccagc aacttcaagc agtacatcag gcacggcgag   1080
gagtacgagc tgcagttcat cttccagctg tgcaagatca ccctgaccac cgaggtgatg   1140
gcctacctgc acaccatgga ccccaccatc ctggagcagt ggaacttcgg cctgaccctg   1200
ccccccagcg ccagcctgga ggacgcctac aggttcgtga ggaacgccgc caccagctgc   1260
cagaaggaca cccccccccca ggccaagccc gaccccctgg ccaagtacaa gttctgggac   1320
gtggacctga aggagaggtt cagcctggac ctggaccagt tcgccctggg caggaagttc   1380
ctgctgcagg tgggcgtgca gaggaagccc aggcccggcc tgaagaggcc cgctagcagc   1440
gccagctcca gcagctccag cagcgccaag aggaagaggg tgaagaagta a             1491
```

<210> SEQ ID NO 16
<211> LENGTH: 1494
<212> TYPE: DNA
<213> ORGANISM: Artificial Sequence
<220> FEATURE:
<223> OTHER INFORMATION: The DNA sequence encoding H51N9-69T5

<400> SEQUENCE: 16

```
atgaaggtgt acctgccccc cgcccccgtg agcaggatcg tgaacaccga ggagtacatc     60
accaggaccg gcatctacta ctacgccggc agcagcaggc tgatcaccct gggccacccc    120
tacttccccc tgcccaagac cagcaccagg gccgccatcc ccaaggtgag cgccttccag    180
tacagggtgt tcagggtgca gctccccgac cccaacaagt tcggcctgcc cgaccccaac    240
ctgtacaacc ccgacaccga caggctggtg tggggctgcg tgggcgtgga ggtgggcagg    300
ggccagcccc tgggcgtggg cctgagcggc cacccccctgt tcaacaagta cgacgacacc    360
gagaacagca ggatcgccaa cggcaacgcc cagcaggacg tgagggacaa caccagcgtg    420
gacaacaagc agacccagct gtgcatcatc ggctgcgccc cccccatcgg cgagcactgg    480
ggcatcggca ccacctgcaa gaacaccccc gtgccccccg gcgactgccc ccccctggag    540
ctggtgagca gcgtgatcca ggacggcgac atgatcgaca ccggcttcgg cgccatggac    600
ttcgccgccc tgcaggccac caagagcgac gtgcccctgg acatcagcca gagcgtgtgc    660
aagtaccccg actacctgaa gatgagcgcc gacacctacg gcaacagcat gttcttccac    720
ctgaggaggg agcagatctt cgccaggcac tactacaaca agctgggcag cgtgggcgag    780
gacatcccca ccgactacta catcaagggc agcggcaacg gcagggaccc catcgagagc    840
```

```
tacatctaca gcgccacccc cagcggcagc atgatcacca gcgacagcca gatcttcaac    900

aagccctact ggctgcacag ggcccagggc cacaacaacg gcatctgctg gaacaaccag    960

ctgttcatca cctgcgtgga caccaccagg agcaccaacc tgaccatcag caccgcctct   1020

gctcagtctg cttctgctac cttcaaaccg tctgacttca agcagtacat caggcacggc   1080

gaggagtacg agctgcagtt catcttccag ctgtgcaaga tcaccctgac caccgaggtg   1140

atggcctacc tgcacaccat ggaccccacc atcctggagc agtggaactt cggcctgacc   1200

ctgcccccca gcgccagcct ggaggacgcc tacaggttcg tgaggaacgc cgccaccagc   1260

tgccagaagg acaccccccc ccaggccaag cccgaccccc tggccaagta caagttctgg   1320

gacgtggacc tgaaggagag gttcagcctg gacctggacc agttcgccct gggcaggaag   1380

ttcctgctgc aggtgggcgt gcagaggaag cccaggcccg gcctgaagag gcccgctagc   1440

agcgccagct ccagcagctc cagcagcgcc aagaggaaga gggtgaagaa gtaa         1494


<210> SEQ ID NO 17
<211> LENGTH: 9
<212> TYPE: PRT
<213> ORGANISM: Human papillomavirus type 69

<400> SEQUENCE: 17

Ile Pro Lys Ser Gly Ser Thr Ala Glu
1               5


<210> SEQ ID NO 18
<211> LENGTH: 23
<212> TYPE: PRT
<213> ORGANISM: Human papillomavirus type 69

<400> SEQUENCE: 18

Leu Asp Asp Thr Glu Asn Ser His Leu Ala Thr Ala Asn Ala Asp Thr
1               5                   10                  15

Asp Asn Arg Asp Asn Val Cys
            20


<210> SEQ ID NO 19
<211> LENGTH: 14
<212> TYPE: PRT
<213> ORGANISM: Human papillomavirus type 69

<400> SEQUENCE: 19

Val Gly Thr Val Cys Lys Asn Ala Gln Ser Gln Val Gln Arg
1               5                   10


<210> SEQ ID NO 20
<211> LENGTH: 31
<212> TYPE: PRT
<213> ORGANISM: Human papillomavirus type 69

<400> SEQUENCE: 20

Phe Phe Asn Lys Ala Gly Thr Ile Gly Asp Pro Val Pro Val Ser Met
1               5                   10                  15

Tyr Ile Lys Gly Ala Gly Gln Gly Arg Glu Pro Pro Thr Thr Ser
            20                  25                  30


<210> SEQ ID NO 21
<211> LENGTH: 13
<212> TYPE: PRT
<213> ORGANISM: Human papillomavirus type 69
```

<400> SEQUENCE: 21

```
Ser Ala Gln Ser Ala Ser Ala Thr Phe Lys Pro Ser Asp
1               5                   10
```

<210> SEQ ID NO 22
<211> LENGTH: 503
<212> TYPE: PRT
<213> ORGANISM: Human papillomavirus type 26

<400> SEQUENCE: 22

```
Met Ala Leu Trp Arg Thr Ser Asp Ser Lys Val Tyr Leu Pro Pro Thr
1               5                   10                  15

Pro Val Ser Arg Val Val Asn Thr Asp Glu Tyr Val Thr Arg Thr Gly
            20                  25                  30

Ile Tyr Tyr Tyr Ala Gly Ser Ser Arg Leu Leu Thr Leu Gly His Pro
        35                  40                  45

Tyr Phe Ser Ile Pro Lys Thr Gly Gln Lys Ala Glu Ile Pro Lys Val
    50                  55                  60

Ser Ala Tyr Gln Tyr Arg Val Phe Arg Val His Leu Pro Asp Pro Asn
65                  70                  75                  80

Lys Phe Gly Leu Pro Asp Pro Gln Leu Tyr Asn Pro Asp Thr Glu Arg
                85                  90                  95

Leu Val Trp Ala Cys Val Gly Val Glu Val Gly Arg Gly Gln Pro Leu
            100                 105                 110

Gly Ile Gly Leu Ser Gly His Pro Leu Phe Asn Lys Leu Asp Asp Thr
        115                 120                 125

Glu Asn Ser His Leu Ala Thr Val Asn Ala Asp Thr Asp Asn Arg Asp
    130                 135                 140

Asn Val Ser Val Asp Asn Lys Gln Thr Gln Leu Cys Ile Ile Gly Cys
145                 150                 155                 160

Thr Pro Pro Leu Gly Glu His Trp Gly Ile Gly Thr Ile Cys Lys Asn
                165                 170                 175

Thr Gln Thr Gln Arg Gly Asp Cys Pro Pro Leu Glu Leu Ile Ser Ser
            180                 185                 190

Ile Ile Glu Asp Gly Asp Met Ile Asp Thr Gly Phe Gly Ala Met Asp
        195                 200                 205

Phe Thr Ala Leu Gln Ala Thr Lys Ser Asp Val Pro Ile Asp Ile Ser
    210                 215                 220

Gln Ser Thr Cys Lys Tyr Pro Asp Tyr Leu Lys Met Ser Ala Asp Thr
225                 230                 235                 240

Tyr Gly Asn Ser Met Phe Phe Phe Leu Arg Arg Glu Gln Leu Phe Ala
                245                 250                 255

Arg His Phe Tyr Asn Lys Ala Gly Ala Val Gly Asp Ala Ile Pro Thr
            260                 265                 270

Thr Leu Tyr Ile Lys Gly Ala Glu Ser Gly Arg Glu Pro Pro Thr Ser
        275                 280                 285

Ser Ile Tyr Ser Ala Thr Pro Ser Gly Ser Met Val Thr Ser Asp Ala
    290                 295                 300

Gln Leu Phe Asn Lys Pro Tyr Trp Leu Gln Arg Ala Gln Gly His Asn
305                 310                 315                 320

Asn Gly Ile Cys Trp Gly Asn Gln Leu Phe Val Thr Cys Val Asp Thr
                325                 330                 335

Thr Arg Ser Thr Asn Leu Thr Ile Ser Thr Leu Ser Ala Ala Ser Ala
            340                 345                 350
```

-continued

```
Ser Thr Pro Phe Lys Pro Ser Asp Tyr Lys Gln Phe Ile Arg His Gly
        355                 360                 365

Glu Glu Tyr Glu Leu Gln Phe Ile Phe Gln Leu Cys Lys Ile Thr Leu
    370                 375                 380

Thr Thr Asp Val Met Ala Tyr Ile His Leu Met Asn Ala Ser Ile Leu
385                 390                 395                 400

Glu Asp Trp Asn Phe Gly Leu Thr Leu Pro Pro Thr Ala Ser Leu Glu
                405                 410                 415

Asp Ala Tyr Arg Phe Ile Lys Asn Ser Ala Thr Thr Cys Gln Arg Asn
            420                 425                 430

Ala Pro Pro Val Pro Lys Glu Asp Pro Phe Gln Lys Phe Lys Phe Trp
        435                 440                 445

Asp Val Asp Leu Lys Glu Lys Phe Ser Ile Asp Leu Asp Gln Phe Pro
    450                 455                 460

Leu Gly Arg Lys Phe Met Leu Gln Ala Gly Ile Gln Arg Arg Pro Lys
465                 470                 475                 480

Leu Gly Thr Lys Arg Pro Leu Ser Ser Thr Ser Ser Ser Thr Lys Arg
                485                 490                 495

Lys Lys Arg Lys Leu Thr Lys
            500


<210> SEQ ID NO 23
<211> LENGTH: 496
<212> TYPE: PRT
<213> ORGANISM: Artificial Sequence
<220> FEATURE:
<223> OTHER INFORMATION: H51N9-69T1-26S2

<400> SEQUENCE: 23

Met Lys Val Tyr Leu Pro Pro Ala Pro Val Ser Arg Ile Val Asn Thr
1               5                   10                  15

Glu Glu Tyr Ile Thr Arg Thr Gly Ile Tyr Tyr Tyr Ala Gly Ser Ser
            20                  25                  30

Arg Leu Ile Thr Leu Gly His Pro Tyr Phe Pro Ile Pro Lys Ser Gly
        35                  40                  45

Ser Thr Ala Glu Ile Pro Lys Val Ser Ala Phe Gln Tyr Arg Val Phe
    50                  55                  60

Arg Val Gln Leu Pro Asp Pro Asn Lys Phe Gly Leu Pro Asp Pro Asn
65                  70                  75                  80

Leu Tyr Asn Pro Asp Thr Asp Arg Leu Val Trp Gly Cys Val Gly Val
                85                  90                  95

Glu Val Gly Arg Gly Gln Pro Leu Gly Ile Gly Leu Ser Gly His Pro
            100                 105                 110

Leu Phe Asn Lys Leu Asp Asp Thr Glu Asn Ser His Leu Ala Thr Val
        115                 120                 125

Asn Ala Asp Thr Asp Asn Arg Asp Asn Val Ser Val Asp Asn Lys Gln
    130                 135                 140

Thr Gln Leu Cys Ile Ile Gly Cys Ala Pro Pro Ile Gly Glu His Trp
145                 150                 155                 160

Gly Ile Gly Thr Thr Cys Lys Asn Thr Pro Val Pro Pro Gly Asp Cys
                165                 170                 175

Pro Pro Leu Glu Leu Val Ser Ser Val Ile Gln Asp Gly Asp Met Ile
            180                 185                 190

Asp Thr Gly Phe Gly Ala Met Asp Phe Ala Ala Leu Gln Ala Thr Lys
        195                 200                 205
```

```
Ser Asp Val Pro Leu Asp Ile Ser Gln Ser Val Cys Lys Tyr Pro Asp
    210                 215                 220

Tyr Leu Lys Met Ser Ala Asp Thr Tyr Gly Asn Ser Met Phe Phe His
225                 230                 235                 240

Leu Arg Arg Glu Gln Ile Phe Ala Arg His Tyr Tyr Asn Lys Leu Gly
                245                 250                 255

Ser Val Gly Glu Asp Ile Pro Thr Asp Tyr Tyr Ile Lys Gly Ser Gly
            260                 265                 270

Asn Gly Arg Asp Pro Ile Glu Ser Tyr Ile Tyr Ser Ala Thr Pro Ser
        275                 280                 285

Gly Ser Met Ile Thr Ser Asp Ser Gln Ile Phe Asn Lys Pro Tyr Trp
    290                 295                 300

Leu His Arg Ala Gln Gly His Asn Asn Gly Ile Cys Trp Asn Asn Gln
305                 310                 315                 320

Leu Phe Ile Thr Cys Val Asp Thr Thr Arg Ser Thr Asn Leu Thr Ile
                325                 330                 335

Ser Thr Ala Thr Ala Ala Val Ser Pro Thr Phe Thr Pro Ser Asn Phe
            340                 345                 350

Lys Gln Tyr Ile Arg His Gly Glu Glu Tyr Glu Leu Gln Phe Ile Phe
        355                 360                 365

Gln Leu Cys Lys Ile Thr Leu Thr Thr Glu Val Met Ala Tyr Leu His
    370                 375                 380

Thr Met Asp Pro Thr Ile Leu Glu Gln Trp Asn Phe Gly Leu Thr Leu
385                 390                 395                 400

Pro Pro Ser Ala Ser Leu Glu Asp Ala Tyr Arg Phe Val Arg Asn Ala
                405                 410                 415

Ala Thr Ser Cys Gln Lys Asp Thr Pro Pro Gln Ala Lys Pro Asp Pro
            420                 425                 430

Leu Ala Lys Tyr Lys Phe Trp Asp Val Asp Leu Lys Glu Arg Phe Ser
        435                 440                 445

Leu Asp Leu Asp Gln Phe Ala Leu Gly Arg Lys Phe Leu Leu Gln Val
    450                 455                 460

Gly Val Gln Arg Lys Pro Arg Pro Gly Leu Lys Arg Pro Ala Ser Ser
465                 470                 475                 480

Ala Ser Ser Ser Ser Ser Ser Ser Ala Lys Arg Lys Arg Val Lys Lys
                485                 490                 495


<210> SEQ ID NO 24
<211> LENGTH: 496
<212> TYPE: PRT
<213> ORGANISM: Artificial Sequence
<220> FEATURE:
<223> OTHER INFORMATION: H51N9-69T1-26S3

<400> SEQUENCE: 24

Met Lys Val Tyr Leu Pro Pro Ala Pro Val Ser Arg Ile Val Asn Thr
1               5                   10                  15

Glu Glu Tyr Ile Thr Arg Thr Gly Ile Tyr Tyr Tyr Ala Gly Ser Ser
            20                  25                  30

Arg Leu Ile Thr Leu Gly His Pro Tyr Phe Pro Ile Pro Lys Ser Gly
        35                  40                  45

Ser Thr Ala Glu Ile Pro Lys Val Ser Ala Phe Gln Tyr Arg Val Phe
    50                  55                  60

Arg Val Gln Leu Pro Asp Pro Asn Lys Phe Gly Leu Pro Asp Pro Asn
65                  70                  75                  80
```

-continued

```
Leu Tyr Asn Pro Asp Thr Asp Arg Leu Val Trp Gly Cys Val Gly Val
                85                  90                  95

Glu Val Gly Arg Gly Gln Pro Leu Gly Val Gly Leu Ser Gly His Pro
            100                 105                 110

Leu Phe Asn Lys Tyr Asp Asp Thr Glu Asn Ser Arg Ile Ala Asn Gly
        115                 120                 125

Asn Ala Gln Gln Asp Val Arg Asp Asn Thr Ser Val Asp Asn Lys Gln
    130                 135                 140

Thr Gln Leu Cys Ile Ile Gly Cys Ala Pro Pro Ile Gly Glu His Trp
145                 150                 155                 160

Gly Ile Gly Thr Ile Cys Lys Asn Thr Gln Thr Gln Arg Gly Asp Cys
                165                 170                 175

Pro Pro Leu Glu Leu Val Ser Ser Val Ile Gln Asp Gly Asp Met Ile
            180                 185                 190

Asp Thr Gly Phe Gly Ala Met Asp Phe Ala Ala Leu Gln Ala Thr Lys
        195                 200                 205

Ser Asp Val Pro Leu Asp Ile Ser Gln Ser Val Cys Lys Tyr Pro Asp
    210                 215                 220

Tyr Leu Lys Met Ser Ala Asp Thr Tyr Gly Asn Ser Met Phe Phe His
225                 230                 235                 240

Leu Arg Arg Glu Gln Ile Phe Ala Arg His Tyr Tyr Asn Lys Leu Gly
                245                 250                 255

Ser Val Gly Glu Asp Ile Pro Thr Asp Tyr Tyr Ile Lys Gly Ser Gly
            260                 265                 270

Asn Gly Arg Asp Pro Ile Glu Ser Tyr Ile Tyr Ser Ala Thr Pro Ser
        275                 280                 285

Gly Ser Met Ile Thr Ser Asp Ser Gln Ile Phe Asn Lys Pro Tyr Trp
    290                 295                 300

Leu His Arg Ala Gln Gly His Asn Asn Gly Ile Cys Trp Asn Asn Gln
305                 310                 315                 320

Leu Phe Ile Thr Cys Val Asp Thr Thr Arg Ser Thr Asn Leu Thr Ile
                325                 330                 335

Ser Thr Ala Thr Ala Ala Val Ser Pro Thr Phe Thr Pro Ser Asn Phe
            340                 345                 350

Lys Gln Tyr Ile Arg His Gly Glu Glu Tyr Glu Leu Gln Phe Ile Phe
        355                 360                 365

Gln Leu Cys Lys Ile Thr Leu Thr Thr Glu Val Met Ala Tyr Leu His
    370                 375                 380

Thr Met Asp Pro Thr Ile Leu Glu Gln Trp Asn Phe Gly Leu Thr Leu
385                 390                 395                 400

Pro Pro Ser Ala Ser Leu Glu Asp Ala Tyr Arg Phe Val Arg Asn Ala
                405                 410                 415

Ala Thr Ser Cys Gln Lys Asp Thr Pro Pro Gln Ala Lys Pro Asp Pro
            420                 425                 430

Leu Ala Lys Tyr Lys Phe Trp Asp Val Asp Leu Lys Glu Arg Phe Ser
        435                 440                 445

Leu Asp Leu Asp Gln Phe Ala Leu Gly Arg Lys Phe Leu Leu Gln Val
    450                 455                 460

Gly Val Gln Arg Lys Pro Arg Pro Gly Leu Lys Arg Pro Ala Ser Ser
465                 470                 475                 480

Ala Ser Ser Ser Ser Ser Ser Ser Ala Lys Arg Lys Arg Val Lys Lys
                485                 490                 495
```

```
<210> SEQ ID NO 25
<211> LENGTH: 496
<212> TYPE: PRT
<213> ORGANISM: Artificial Sequence
<220> FEATURE:
<223> OTHER INFORMATION: H51N9-69T1-26S4

<400> SEQUENCE: 25

Met Lys Val Tyr Leu Pro Pro Ala Pro Val Ser Arg Ile Val Asn Thr
1               5                   10                  15

Glu Glu Tyr Ile Thr Arg Thr Gly Ile Tyr Tyr Tyr Ala Gly Ser Ser
            20                  25                  30

Arg Leu Ile Thr Leu Gly His Pro Tyr Phe Pro Ile Pro Lys Ser Gly
        35                  40                  45

Ser Thr Ala Glu Ile Pro Lys Val Ser Ala Phe Gln Tyr Arg Val Phe
    50                  55                  60

Arg Val Gln Leu Pro Asp Pro Asn Lys Phe Gly Leu Pro Asp Pro Asn
65                  70                  75                  80

Leu Tyr Asn Pro Asp Thr Asp Arg Leu Val Trp Gly Cys Val Gly Val
                85                  90                  95

Glu Val Gly Arg Gly Gln Pro Leu Gly Val Gly Leu Ser Gly His Pro
            100                 105                 110

Leu Phe Asn Lys Tyr Asp Asp Thr Glu Asn Ser Arg Ile Ala Asn Gly
        115                 120                 125

Asn Ala Gln Gln Asp Val Arg Asp Asn Thr Ser Val Asp Asn Lys Gln
    130                 135                 140

Thr Gln Leu Cys Ile Ile Gly Cys Ala Pro Pro Ile Gly Glu His Trp
145                 150                 155                 160

Gly Ile Gly Thr Thr Cys Lys Asn Thr Pro Val Pro Pro Gly Asp Cys
                165                 170                 175

Pro Pro Leu Glu Leu Val Ser Ser Val Ile Gln Asp Gly Asp Met Ile
            180                 185                 190

Asp Thr Gly Phe Gly Ala Met Asp Phe Ala Ala Leu Gln Ala Thr Lys
        195                 200                 205

Ser Asp Val Pro Leu Asp Ile Ser Gln Ser Val Cys Lys Tyr Pro Asp
    210                 215                 220

Tyr Leu Lys Met Ser Ala Asp Thr Tyr Gly Asn Ser Met Phe Phe His
225                 230                 235                 240

Leu Arg Arg Glu Gln Ile Phe Ala Arg His Phe Tyr Asn Lys Ala Gly
                245                 250                 255

Ala Val Gly Asp Ala Ile Pro Thr Thr Leu Tyr Ile Lys Gly Ala Glu
            260                 265                 270

Ser Gly Arg Glu Pro Pro Thr Ser Ser Ile Tyr Ser Ala Thr Pro Ser
        275                 280                 285

Gly Ser Met Ile Thr Ser Asp Ser Gln Ile Phe Asn Lys Pro Tyr Trp
    290                 295                 300

Leu His Arg Ala Gln Gly His Asn Asn Gly Ile Cys Trp Asn Asn Gln
305                 310                 315                 320

Leu Phe Ile Thr Cys Val Asp Thr Thr Arg Ser Thr Asn Leu Thr Ile
                325                 330                 335

Ser Thr Ala Thr Ala Ala Val Ser Pro Thr Phe Thr Pro Ser Asn Phe
            340                 345                 350

Lys Gln Tyr Ile Arg His Gly Glu Glu Tyr Glu Leu Gln Phe Ile Phe
        355                 360                 365

Gln Leu Cys Lys Ile Thr Leu Thr Thr Glu Val Met Ala Tyr Leu His
```

```
    370                 375                 380

Thr Met Asp Pro Thr Ile Leu Glu Gln Trp Asn Phe Gly Leu Thr Leu
385                 390                 395                 400

Pro Pro Ser Ala Ser Leu Glu Asp Ala Tyr Arg Phe Val Arg Asn Ala
                405                 410                 415

Ala Thr Ser Cys Gln Lys Asp Thr Pro Pro Gln Ala Lys Pro Asp Pro
            420                 425                 430

Leu Ala Lys Tyr Lys Phe Trp Asp Val Asp Leu Lys Glu Arg Phe Ser
        435                 440                 445

Leu Asp Leu Asp Gln Phe Ala Leu Gly Arg Lys Phe Leu Leu Gln Val
    450                 455                 460

Gly Val Gln Arg Lys Pro Arg Pro Gly Leu Lys Arg Pro Ala Ser Ser
465                 470                 475                 480

Ala Ser Ser Ser Ser Ser Ser Ser Ala Lys Arg Lys Arg Val Lys Lys
                485                 490                 495


<210> SEQ ID NO 26
<211> LENGTH: 497
<212> TYPE: PRT
<213> ORGANISM: Artificial Sequence
<220> FEATURE:
<223> OTHER INFORMATION: H51N9-69T1-26S5

<400> SEQUENCE: 26

Met Lys Val Tyr Leu Pro Pro Ala Pro Val Ser Arg Ile Val Asn Thr
1               5                   10                  15

Glu Glu Tyr Ile Thr Arg Thr Gly Ile Tyr Tyr Tyr Ala Gly Ser Ser
            20                  25                  30

Arg Leu Ile Thr Leu Gly His Pro Tyr Phe Pro Ile Pro Lys Ser Gly
        35                  40                  45

Ser Thr Ala Glu Ile Pro Lys Val Ser Ala Phe Gln Tyr Arg Val Phe
    50                  55                  60

Arg Val Gln Leu Pro Asp Pro Asn Lys Phe Gly Leu Pro Asp Pro Asn
65                  70                  75                  80

Leu Tyr Asn Pro Asp Thr Asp Arg Leu Val Trp Gly Cys Val Gly Val
                85                  90                  95

Glu Val Gly Arg Gly Gln Pro Leu Gly Val Gly Leu Ser Gly His Pro
            100                 105                 110

Leu Phe Asn Lys Tyr Asp Asp Thr Glu Asn Ser Arg Ile Ala Asn Gly
        115                 120                 125

Asn Ala Gln Gln Asp Val Arg Asp Asn Thr Ser Val Asp Asn Lys Gln
    130                 135                 140

Thr Gln Leu Cys Ile Ile Gly Cys Ala Pro Pro Ile Gly Glu His Trp
145                 150                 155                 160

Gly Ile Gly Thr Thr Cys Lys Asn Thr Pro Val Pro Pro Gly Asp Cys
                165                 170                 175

Pro Pro Leu Glu Leu Val Ser Ser Val Ile Gln Asp Gly Asp Met Ile
            180                 185                 190

Asp Thr Gly Phe Gly Ala Met Asp Phe Ala Ala Leu Gln Ala Thr Lys
        195                 200                 205

Ser Asp Val Pro Leu Asp Ile Ser Gln Ser Val Cys Lys Tyr Pro Asp
    210                 215                 220

Tyr Leu Lys Met Ser Ala Asp Thr Tyr Gly Asn Ser Met Phe Phe His
225                 230                 235                 240

Leu Arg Arg Glu Gln Ile Phe Ala Arg His Tyr Tyr Asn Lys Leu Gly
```

-continued

```
                245                 250                 255

Ser Val Gly Glu Asp Ile Pro Thr Asp Tyr Tyr Ile Lys Gly Ser Gly
            260                 265                 270

Asn Gly Arg Asp Pro Ile Glu Ser Tyr Ile Tyr Ser Ala Thr Pro Ser
        275                 280                 285

Gly Ser Met Ile Thr Ser Asp Ser Gln Ile Phe Asn Lys Pro Tyr Trp
    290                 295                 300

Leu His Arg Ala Gln Gly His Asn Asn Gly Ile Cys Trp Asn Asn Gln
305                 310                 315                 320

Leu Phe Ile Thr Cys Val Asp Thr Thr Arg Ser Thr Asn Leu Thr Ile
                325                 330                 335

Ser Thr Ala Ser Ala Ala Ser Ala Ser Thr Pro Phe Lys Pro Ser Asp
            340                 345                 350

Phe Lys Gln Tyr Ile Arg His Gly Glu Glu Tyr Glu Leu Gln Phe Ile
        355                 360                 365

Phe Gln Leu Cys Lys Ile Thr Leu Thr Thr Glu Val Met Ala Tyr Leu
    370                 375                 380

His Thr Met Asp Pro Thr Ile Leu Glu Gln Trp Asn Phe Gly Leu Thr
385                 390                 395                 400

Leu Pro Pro Ser Ala Ser Leu Glu Asp Ala Tyr Arg Phe Val Arg Asn
                405                 410                 415

Ala Ala Thr Ser Cys Gln Lys Asp Thr Pro Pro Gln Ala Lys Pro Asp
            420                 425                 430

Pro Leu Ala Lys Tyr Lys Phe Trp Asp Val Asp Leu Lys Glu Arg Phe
        435                 440                 445

Ser Leu Asp Leu Asp Gln Phe Ala Leu Gly Arg Lys Phe Leu Leu Gln
    450                 455                 460

Val Gly Val Gln Arg Lys Pro Arg Pro Gly Leu Lys Arg Pro Ala Ser
465                 470                 475                 480

Ser Ala Ser Ser Ser Ser Ser Ser Ser Ala Lys Arg Lys Arg Val Lys
                485                 490                 495

Lys


<210> SEQ ID NO 27
<211> LENGTH: 498
<212> TYPE: PRT
<213> ORGANISM: Artificial Sequence
<220> FEATURE:
<223> OTHER INFORMATION: H51N9-69T3-26S1

<400> SEQUENCE: 27

Met Lys Val Tyr Leu Pro Pro Ala Pro Val Ser Arg Ile Val Asn Thr
1               5                   10                  15

Glu Glu Tyr Ile Thr Arg Thr Gly Ile Tyr Tyr Tyr Ala Gly Ser Ser
            20                  25                  30

Arg Leu Ile Thr Leu Gly His Pro Tyr Phe Ser Ile Pro Lys Thr Gly
        35                  40                  45

Gln Lys Ala Glu Ile Pro Lys Val Ser Ala Phe Gln Tyr Arg Val Phe
    50                  55                  60

Arg Val Gln Leu Pro Asp Pro Asn Lys Phe Gly Leu Pro Asp Pro Asn
65                  70                  75                  80

Leu Tyr Asn Pro Asp Thr Asp Arg Leu Val Trp Gly Cys Val Gly Val
                85                  90                  95

Glu Val Gly Arg Gly Gln Pro Leu Gly Val Gly Leu Ser Gly His Pro
            100                 105                 110
```

```
Leu Phe Asn Lys Tyr Asp Asp Thr Glu Asn Ser Arg Ile Ala Asn Gly
        115                 120                 125

Asn Ala Gln Gln Asp Val Arg Asp Asn Thr Ser Val Asp Asn Lys Gln
    130                 135                 140

Thr Gln Leu Cys Ile Ile Gly Cys Ala Pro Pro Ile Gly Glu His Trp
145                 150                 155                 160

Gly Val Gly Thr Val Cys Lys Asn Ala Gln Ser Gln Val Gln Arg Gly
                165                 170                 175

Asp Cys Pro Pro Leu Glu Leu Val Ser Ser Val Ile Gln Asp Gly Asp
            180                 185                 190

Met Ile Asp Thr Gly Phe Gly Ala Met Asp Phe Ala Ala Leu Gln Ala
        195                 200                 205

Thr Lys Ser Asp Val Pro Leu Asp Ile Ser Gln Ser Val Cys Lys Tyr
    210                 215                 220

Pro Asp Tyr Leu Lys Met Ser Ala Asp Thr Tyr Gly Asn Ser Met Phe
225                 230                 235                 240

Phe His Leu Arg Arg Glu Gln Ile Phe Ala Arg His Tyr Tyr Asn Lys
                245                 250                 255

Leu Gly Ser Val Gly Glu Asp Ile Pro Thr Asp Tyr Tyr Ile Lys Gly
            260                 265                 270

Ser Gly Asn Gly Arg Asp Pro Ile Glu Ser Tyr Ile Tyr Ser Ala Thr
        275                 280                 285

Pro Ser Gly Ser Met Ile Thr Ser Asp Ser Gln Ile Phe Asn Lys Pro
    290                 295                 300

Tyr Trp Leu His Arg Ala Gln Gly His Asn Asn Gly Ile Cys Trp Asn
305                 310                 315                 320

Asn Gln Leu Phe Ile Thr Cys Val Asp Thr Thr Arg Ser Thr Asn Leu
                325                 330                 335

Thr Ile Ser Thr Ala Thr Ala Ala Val Ser Pro Thr Phe Thr Pro Ser
            340                 345                 350

Asn Phe Lys Gln Tyr Ile Arg His Gly Glu Glu Tyr Glu Leu Gln Phe
        355                 360                 365

Ile Phe Gln Leu Cys Lys Ile Thr Leu Thr Thr Glu Val Met Ala Tyr
    370                 375                 380

Leu His Thr Met Asp Pro Thr Ile Leu Glu Gln Trp Asn Phe Gly Leu
385                 390                 395                 400

Thr Leu Pro Pro Ser Ala Ser Leu Glu Asp Ala Tyr Arg Phe Val Arg
                405                 410                 415

Asn Ala Ala Thr Ser Cys Gln Lys Asp Thr Pro Pro Gln Ala Lys Pro
            420                 425                 430

Asp Pro Leu Ala Lys Tyr Lys Phe Trp Asp Val Asp Leu Lys Glu Arg
        435                 440                 445

Phe Ser Leu Asp Leu Asp Gln Phe Ala Leu Gly Arg Lys Phe Leu Leu
    450                 455                 460

Gln Val Gly Val Gln Arg Lys Pro Arg Pro Gly Leu Lys Arg Pro Ala
465                 470                 475                 480

Ser Ser Ala Ser Ser Ser Ser Ser Ser Ser Ala Lys Arg Lys Arg Val
                485                 490                 495

Lys Lys
```

<210> SEQ ID NO 28
<211> LENGTH: 498
<212> TYPE: PRT

```
<213> ORGANISM: Artificial Sequence
<220> FEATURE:
<223> OTHER INFORMATION: H51N9-69T3-26S2

<400> SEQUENCE: 28

Met Lys Val Tyr Leu Pro Pro Ala Pro Val Ser Arg Ile Val Asn Thr
1               5                   10                  15

Glu Glu Tyr Ile Thr Arg Thr Gly Ile Tyr Tyr Tyr Ala Gly Ser Ser
            20                  25                  30

Arg Leu Ile Thr Leu Gly His Pro Tyr Phe Pro Leu Pro Lys Thr Ser
        35                  40                  45

Thr Arg Ala Ala Ile Pro Lys Val Ser Ala Phe Gln Tyr Arg Val Phe
    50                  55                  60

Arg Val Gln Leu Pro Asp Pro Asn Lys Phe Gly Leu Pro Asp Pro Asn
65                  70                  75                  80

Leu Tyr Asn Pro Asp Thr Asp Arg Leu Val Trp Gly Cys Val Gly Val
                85                  90                  95

Glu Val Gly Arg Gly Gln Pro Leu Gly Ile Gly Leu Ser Gly His Pro
            100                 105                 110

Leu Phe Asn Lys Leu Asp Asp Thr Glu Asn Ser His Leu Ala Thr Val
        115                 120                 125

Asn Ala Asp Thr Asp Asn Arg Asp Asn Val Ser Val Asp Asn Lys Gln
    130                 135                 140

Thr Gln Leu Cys Ile Ile Gly Cys Ala Pro Pro Ile Gly Glu His Trp
145                 150                 155                 160

Gly Val Gly Thr Val Cys Lys Asn Ala Gln Ser Gln Val Gln Arg Gly
                165                 170                 175

Asp Cys Pro Pro Leu Glu Leu Val Ser Ser Val Ile Gln Asp Gly Asp
            180                 185                 190

Met Ile Asp Thr Gly Phe Gly Ala Met Asp Phe Ala Ala Leu Gln Ala
        195                 200                 205

Thr Lys Ser Asp Val Pro Leu Asp Ile Ser Gln Ser Val Cys Lys Tyr
    210                 215                 220

Pro Asp Tyr Leu Lys Met Ser Ala Asp Thr Tyr Gly Asn Ser Met Phe
225                 230                 235                 240

Phe His Leu Arg Arg Glu Gln Ile Phe Ala Arg His Tyr Tyr Asn Lys
                245                 250                 255

Leu Gly Ser Val Gly Glu Asp Ile Pro Thr Asp Tyr Tyr Ile Lys Gly
            260                 265                 270

Ser Gly Asn Gly Arg Asp Pro Ile Glu Ser Tyr Ile Tyr Ser Ala Thr
        275                 280                 285

Pro Ser Gly Ser Met Ile Thr Ser Asp Ser Gln Ile Phe Asn Lys Pro
    290                 295                 300

Tyr Trp Leu His Arg Ala Gln Gly His Asn Asn Gly Ile Cys Trp Asn
305                 310                 315                 320

Asn Gln Leu Phe Ile Thr Cys Val Asp Thr Thr Arg Ser Thr Asn Leu
                325                 330                 335

Thr Ile Ser Thr Ala Thr Ala Ala Val Ser Pro Thr Phe Thr Pro Ser
            340                 345                 350

Asn Phe Lys Gln Tyr Ile Arg His Gly Glu Glu Tyr Glu Leu Gln Phe
        355                 360                 365

Ile Phe Gln Leu Cys Lys Ile Thr Leu Thr Thr Glu Val Met Ala Tyr
    370                 375                 380

Leu His Thr Met Asp Pro Thr Ile Leu Glu Gln Trp Asn Phe Gly Leu
```

385 390 395 400

Thr Leu Pro Pro Ser Ala Ser Leu Glu Asp Ala Tyr Arg Phe Val Arg
405 410 415

Asn Ala Ala Thr Ser Cys Gln Lys Asp Thr Pro Pro Gln Ala Lys Pro
420 425 430

Asp Pro Leu Ala Lys Tyr Lys Phe Trp Asp Val Asp Leu Lys Glu Arg
435 440 445

Phe Ser Leu Asp Leu Asp Gln Phe Ala Leu Gly Arg Lys Phe Leu Leu
450 455 460

Gln Val Gly Val Gln Arg Lys Pro Arg Pro Gly Leu Lys Arg Pro Ala
465 470 475 480

Ser Ser Ala Ser Ser Ser Ser Ser Ser Ser Ala Lys Arg Lys Arg Val
485 490 495

Lys Lys

<210> SEQ ID NO 29
<211> LENGTH: 498
<212> TYPE: PRT
<213> ORGANISM: Artificial Sequence
<220> FEATURE:
<223> OTHER INFORMATION: H51N9-69T3-26S4

<400> SEQUENCE: 29

Met Lys Val Tyr Leu Pro Pro Ala Pro Val Ser Arg Ile Val Asn Thr
1 5 10 15

Glu Glu Tyr Ile Thr Arg Thr Gly Ile Tyr Tyr Tyr Ala Gly Ser Ser
20 25 30

Arg Leu Ile Thr Leu Gly His Pro Tyr Phe Pro Leu Pro Lys Thr Ser
35 40 45

Thr Arg Ala Ala Ile Pro Lys Val Ser Ala Phe Gln Tyr Arg Val Phe
50 55 60

Arg Val Gln Leu Pro Asp Pro Asn Lys Phe Gly Leu Pro Asp Pro Asn
65 70 75 80

Leu Tyr Asn Pro Asp Thr Asp Arg Leu Val Trp Gly Cys Val Gly Val
85 90 95

Glu Val Gly Arg Gly Gln Pro Leu Gly Val Gly Leu Ser Gly His Pro
100 105 110

Leu Phe Asn Lys Tyr Asp Asp Thr Glu Asn Ser Arg Ile Ala Asn Gly
115 120 125

Asn Ala Gln Gln Asp Val Arg Asp Asn Thr Ser Val Asp Asn Lys Gln
130 135 140

Thr Gln Leu Cys Ile Ile Gly Cys Ala Pro Pro Ile Gly Glu His Trp
145 150 155 160

Gly Val Gly Thr Val Cys Lys Asn Ala Gln Ser Gln Val Gln Arg Gly
165 170 175

Asp Cys Pro Pro Leu Glu Leu Val Ser Ser Val Ile Gln Asp Gly Asp
180 185 190

Met Ile Asp Thr Gly Phe Gly Ala Met Asp Phe Ala Ala Leu Gln Ala
195 200 205

Thr Lys Ser Asp Val Pro Leu Asp Ile Ser Gln Ser Val Cys Lys Tyr
210 215 220

Pro Asp Tyr Leu Lys Met Ser Ala Asp Thr Tyr Gly Asn Ser Met Phe
225 230 235 240

Phe His Leu Arg Arg Glu Gln Ile Phe Ala Arg His Phe Tyr Asn Lys
245 250 255

```
Ala Gly Ala Val Gly Asp Ala Ile Pro Thr Thr Leu Tyr Ile Lys Gly
            260                 265                 270

Ala Glu Ser Gly Arg Glu Pro Pro Thr Ser Ser Ile Tyr Ser Ala Thr
        275                 280                 285

Pro Ser Gly Ser Met Ile Thr Ser Asp Ser Gln Ile Phe Asn Lys Pro
    290                 295                 300

Tyr Trp Leu His Arg Ala Gln Gly His Asn Asn Gly Ile Cys Trp Asn
305                 310                 315                 320

Asn Gln Leu Phe Ile Thr Cys Val Asp Thr Thr Arg Ser Thr Asn Leu
                325                 330                 335

Thr Ile Ser Thr Ala Thr Ala Ala Val Ser Pro Thr Phe Thr Pro Ser
            340                 345                 350

Asn Phe Lys Gln Tyr Ile Arg His Gly Glu Glu Tyr Glu Leu Gln Phe
        355                 360                 365

Ile Phe Gln Leu Cys Lys Ile Thr Leu Thr Thr Glu Val Met Ala Tyr
    370                 375                 380

Leu His Thr Met Asp Pro Thr Ile Leu Glu Gln Trp Asn Phe Gly Leu
385                 390                 395                 400

Thr Leu Pro Pro Ser Ala Ser Leu Glu Asp Ala Tyr Arg Phe Val Arg
                405                 410                 415

Asn Ala Ala Thr Ser Cys Gln Lys Asp Thr Pro Pro Gln Ala Lys Pro
            420                 425                 430

Asp Pro Leu Ala Lys Tyr Lys Phe Trp Asp Val Asp Leu Lys Glu Arg
        435                 440                 445

Phe Ser Leu Asp Leu Asp Gln Phe Ala Leu Gly Arg Lys Phe Leu Leu
    450                 455                 460

Gln Val Gly Val Gln Arg Lys Pro Arg Pro Gly Leu Lys Arg Pro Ala
465                 470                 475                 480

Ser Ser Ala Ser Ser Ser Ser Ser Ser Ser Ala Lys Arg Lys Arg Val
                485                 490                 495

Lys Lys


<210> SEQ ID NO 30
<211> LENGTH: 499
<212> TYPE: PRT
<213> ORGANISM: Artificial Sequence
<220> FEATURE:
<223> OTHER INFORMATION: H51N9-69T3-26S5

<400> SEQUENCE: 30

Met Lys Val Tyr Leu Pro Pro Ala Pro Val Ser Arg Ile Val Asn Thr
1               5                   10                  15

Glu Glu Tyr Ile Thr Arg Thr Gly Ile Tyr Tyr Tyr Ala Gly Ser Ser
            20                  25                  30

Arg Leu Ile Thr Leu Gly His Pro Tyr Phe Pro Leu Pro Lys Thr Ser
        35                  40                  45

Thr Arg Ala Ala Ile Pro Lys Val Ser Ala Phe Gln Tyr Arg Val Phe
    50                  55                  60

Arg Val Gln Leu Pro Asp Pro Asn Lys Phe Gly Leu Pro Asp Pro Asn
65                  70                  75                  80

Leu Tyr Asn Pro Asp Thr Asp Arg Leu Val Trp Gly Cys Val Gly Val
                85                  90                  95

Glu Val Gly Arg Gly Gln Pro Leu Gly Val Gly Leu Ser Gly His Pro
            100                 105                 110
```

-continued

```
Leu Phe Asn Lys Tyr Asp Asp Thr Glu Asn Ser Arg Ile Ala Asn Gly
        115                 120                 125

Asn Ala Gln Gln Asp Val Arg Asp Asn Thr Ser Val Asp Asn Lys Gln
    130                 135                 140

Thr Gln Leu Cys Ile Ile Gly Cys Ala Pro Pro Ile Gly Glu His Trp
145                 150                 155                 160

Gly Val Gly Thr Val Cys Lys Asn Ala Gln Ser Gln Val Gln Arg Gly
                165                 170                 175

Asp Cys Pro Pro Leu Glu Leu Val Ser Ser Val Ile Gln Asp Gly Asp
            180                 185                 190

Met Ile Asp Thr Gly Phe Gly Ala Met Asp Phe Ala Ala Leu Gln Ala
        195                 200                 205

Thr Lys Ser Asp Val Pro Leu Asp Ile Ser Gln Ser Val Cys Lys Tyr
    210                 215                 220

Pro Asp Tyr Leu Lys Met Ser Ala Asp Thr Tyr Gly Asn Ser Met Phe
225                 230                 235                 240

Phe His Leu Arg Arg Glu Gln Ile Phe Ala Arg His Tyr Tyr Asn Lys
                245                 250                 255

Leu Gly Ser Val Gly Glu Asp Ile Pro Thr Asp Tyr Tyr Ile Lys Gly
            260                 265                 270

Ser Gly Asn Gly Arg Asp Pro Ile Glu Ser Tyr Ile Tyr Ser Ala Thr
        275                 280                 285

Pro Ser Gly Ser Met Ile Thr Ser Asp Ser Gln Ile Phe Asn Lys Pro
    290                 295                 300

Tyr Trp Leu His Arg Ala Gln Gly His Asn Asn Gly Ile Cys Trp Asn
305                 310                 315                 320

Asn Gln Leu Phe Ile Thr Cys Val Asp Thr Thr Arg Ser Thr Asn Leu
                325                 330                 335

Thr Ile Ser Thr Ala Ser Ala Ala Ser Ala Ser Thr Pro Phe Lys Pro
            340                 345                 350

Ser Asp Phe Lys Gln Tyr Ile Arg His Gly Glu Glu Tyr Glu Leu Gln
        355                 360                 365

Phe Ile Phe Gln Leu Cys Lys Ile Thr Leu Thr Thr Glu Val Met Ala
    370                 375                 380

Tyr Leu His Thr Met Asp Pro Thr Ile Leu Glu Gln Trp Asn Phe Gly
385                 390                 395                 400

Leu Thr Leu Pro Pro Ser Ala Ser Leu Glu Asp Ala Tyr Arg Phe Val
                405                 410                 415

Arg Asn Ala Ala Thr Ser Cys Gln Lys Asp Thr Pro Pro Gln Ala Lys
            420                 425                 430

Pro Asp Pro Leu Ala Lys Tyr Lys Phe Trp Asp Val Asp Leu Lys Glu
        435                 440                 445

Arg Phe Ser Leu Asp Leu Asp Gln Phe Ala Leu Gly Arg Lys Phe Leu
    450                 455                 460

Leu Gln Val Gly Val Gln Arg Lys Pro Arg Pro Gly Leu Lys Arg Pro
465                 470                 475                 480

Ala Ser Ser Ala Ser Ser Ser Ser Ser Ser Ser Ala Lys Arg Lys Arg
                485                 490                 495

Val Lys Lys
```

<210> SEQ ID NO 31
<211> LENGTH: 1512
<212> TYPE: DNA
<213> ORGANISM: Human papillomavirus type 26

<400> SEQUENCE: 31
atggctctgt ggcgtacctc tgactctaaa gtttacctgc cgccgacccc ggtttctcgt 60
gttgttaaca ccgacgaata cgttacccgt accggtatct actactacgc tggttcttct 120
cgtctgctga ccctgggtca cccgtacttc tctatcccga aaaccggtca gaaagctgaa 180
atcccgaaag tttctgctta ccagtaccgt gttttccgtg ttcacctgcc ggacccgaac 240
aaattcggtc tgccggaccc gcagctgtac aacccggaca ccgaacgtct ggtttgggct 300
tgcgttggtg ttgaagttgg tcgtggtcag ccgctgggta tcggtctgtc tggtcacccg 360
ctgttcaaca aactggacga caccgaaaac tctcacctgg ctaccgttaa cgctgacacc 420
gacaaccgtg acaacgtttc tgttgacaac aaacagaccc agctgtgcat catcggttgc 480
accccgccgc tgggtgaaca ctggggtatc ggtaccatct gcaaaaacac ccagacccag 540
cgtggtgact gcccgccgct ggaactgatc tcttctatca tcgaagacgg tgacatgatc 600
gacaccggtt tcggtgctat ggacttcacc gctctgcagg ctaccaaatc tgacgttccg 660
atcgacatct ctcagtctac ctgcaaatac ccggactacc tgaaaatgtc tgctgacacc 720
tacggtaact ctatgttctt cttcctgcgt cgtgaacagc tgttcgctcg tcacttctac 780
aacaaagctg gtgctgttgg tgacgctatc ccgaccaccc tgtacatcaa aggtgctgaa 840
tctggtcgtg aaccgccgac ctcttctatc tactctgcta ccccgtctgg ttctatggtt 900
acctctgacg ctcagctgtt caacaaaccg tactggctgc agcgtgctca gggtcacaac 960
aacggtatct gctggggtaa ccagctgttc gttacctgcg ttgacaccac ccgttctacc 1020
aacctgacca tctctaccct gtctgctgct tctgcttcta ccccgttcaa accgtctgac 1080
tacaaacagt tcatccgtca cggtgaagaa tacgaactgc agttcatctt ccagctgtgc 1140
aaaatcaccc tgaccaccga cgttatggct tacatccacc tgatgaacgc ttctatcctg 1200
gaagactgga acttcggtct gaccctgccg ccgaccgctt ctctggaaga cgcttaccgt 1260
ttcatcaaaa actctgctac cacctgccag cgtaacgctc cgccggttcc gaaagaagac 1320
ccgttccaga aattcaaatt ctgggacgtt gacctgaaag aaaaattctc tatcgacctg 1380
gaccagttcc cgctgggtcg taaattcatg ctgcaggctg gtatccagcg tcgtccgaaa 1440
ctgggtacca aacgtccgct gtcttctacc tcttcttcta ccaaacgtaa aaaacgtaaa 1500
ctgaccaaat aa 1512

<210> SEQ ID NO 32
<211> LENGTH: 1491
<212> TYPE: DNA
<213> ORGANISM: Artificial Sequence
<220> FEATURE:
<223> OTHER INFORMATION: The DNA sequence encoding H51N9-69T1-26S2

<400> SEQUENCE: 32
atgaaggtgt acctgccccc cgcccccgtg agcaggatcg tgaacaccga ggagtacatc 60
accaggaccg gcatctacta ctacgccggc agcagcaggc tgatcaccct gggccacccc 120
tacttcccga tcccgaaatc tggttctacc gctgaaatcc cgaaggtctc tgccttccag 180
tacagggtgt tcagggtgca gctccccgac cccaacaagt tcggcctgcc cgaccccaac 240
ctgtacaacc ccgacaccga caggctggtg tggggctgcg tgggcgtgga ggtgggtcgt 300
ggtcagccgc tgggtatcgg tctgtctggt cacccgctgt tcaacaaact ggacgacacc 360
gaaaactctc acctggctac cgttaacgct gacaccgaca accgtgacaa cgtttctgtt 420
gacaacaagc agacccagct gtgcatcatc ggctgcgccc cccccatcgg cgagcactgg 480
ggcatcggca ccacctgcaa gaacaccccc gtgccccccg gcgactgccc ccccctggag 540
ctggtgagca gcgtgatcca ggacggcgac atgatcgaca ccggcttcgg cgccatggac 600
ttcgccgccc tgcaggccac caagagcgac gtgcccctgg acatcagcca gagcgtgtgc 660
aagtaccccg actacctgaa gatgagcgcc gacacctacg gcaacagcat gttcttccac 720
ctgaggaggg agcagatctt cgccaggcac tactacaaca agctgggcag cgtgggcgag 780
gacatcccca ccgactacta catcaagggc agcggcaacg gcagggaccc catcgagagc 840
tacatctaca gcgccacccc cagcggcagc atgatcacca gcgacagcca gatcttcaac 900
aagccctact ggctgcacag ggcccagggc cacaacaacg gcatctgctg gaacaaccag 960
ctgttcatca cctgcgtgga caccaccagg agcaccaacc tgaccatcag caccgccacc 1020
gccgccgtga gccccacctt cacccccagc aacttcaagc agtacatcag gcacggcgag 1080
gagtacgagc tgcagttcat cttccagctg tgcaagatca ccctgaccac cgaggtgatg 1140
gcctacctgc acaccatgga ccccaccatc ctggagcagt ggaacttcgg cctgaccctg 1200
ccccccagcg ccagcctgga ggacgcctac aggttcgtga ggaacgccgc caccagctgc 1260
cagaaggaca cccccccccca ggccaagccc gacccccctgg ccaagtacaa gttctgggac 1320
gtggacctga aggagaggtt cagcctggac ctggaccagt tcgccctggg caggaagttc 1380
ctgctgcagg tgggcgtgca gaggaagccc aggcccggcc tgaagaggcc cgctagcagc 1440
gccagctcca gcagctccag cagcgccaag aggaagaggg tgaagaagta a 1491

<210> SEQ ID NO 33
<211> LENGTH: 1491
<212> TYPE: DNA
<213> ORGANISM: Artificial Sequence
<220> FEATURE:
<223> OTHER INFORMATION: The DNA sequence encoding H51N9-69T1-26S3

<400> SEQUENCE: 33
atgaaggtgt acctgccccc cgcccccgtg agcaggatcg tgaacaccga ggagtacatc 60
accaggaccg gcatctacta ctacgccggc agcagcaggc tgatcaccct gggccacccc 120
tacttcccga tcccgaaatc tggttctacc gctgaaatcc cgaaggtctc tgccttccag 180
tacagggtgt tcagggtgca gctccccgac cccaacaagt tcggcctgcc cgaccccaac 240
ctgtacaacc ccgacaccga caggctggtg tggggctgcg tgggcgtgga ggtgggcagg 300
ggccagcccc tgggcgtggg cctgagcggc cacccccctgt tcaacaagta cgacgacacc 360
gagaacagca ggatcgccaa cggcaacgcc cagcaggacg tgagggacaa caccagcgtg 420
gacaacaagc agacccagct gtgcatcatc ggctgcgccc cccccatcgg cgagcactgg 480
ggtatcggta ccatctgcaa aaacacccag acccagcgtg gtgactgccc gccgctggag 540
ctggtgagca gcgtgatcca ggacggcgac atgatcgaca ccggcttcgg cgccatggac 600
ttcgccgccc tgcaggccac caagagcgac gtgcccctgg acatcagcca gagcgtgtgc 660
aagtaccccg actacctgaa gatgagcgcc gacacctacg gcaacagcat gttcttccac 720
ctgaggaggg agcagatctt cgccaggcac tactacaaca agctgggcag cgtgggcgag 780
gacatcccca ccgactacta catcaagggc agcggcaacg gcagggaccc catcgagagc 840
tacatctaca gcgccacccc cagcggcagc atgatcacca gcgacagcca gatcttcaac 900
aagccctact ggctgcacag ggcccagggc cacaacaacg gcatctgctg gaacaaccag 960
ctgttcatca cctgcgtgga caccaccagg agcaccaacc tgaccatcag caccgccacc 1020
gccgccgtga gccccacctt cacccccagc aacttcaagc agtacatcag gcacggcgag 1080
gagtacgagc tgcagttcat cttccagctg tgcaagatca ccctgaccac cgaggtgatg 1140
gcctacctgc acaccatgga ccccaccatc ctggagcagt ggaacttcgg cctgaccctg 1200
ccccccagcg ccagcctgga ggacgcctac aggttcgtga ggaacgccgc caccagctgc 1260
cagaaggaca cccccccccca ggccaagccc gacccccctgg ccaagtacaa gttctgggac 1320
gtggacctga aggagaggtt cagcctggac ctggaccagt tcgccctggg caggaagttc 1380
ctgctgcagg tgggcgtgca gaggaagccc aggcccggcc tgaagaggcc cgctagcagc 1440
gccagctcca gcagctccag cagcgccaag aggaagaggg tgaagaagta a 1491

<210> SEQ ID NO 34
<211> LENGTH: 1491
<212> TYPE: DNA
<213> ORGANISM: Artificial Sequence
<220> FEATURE:
<223> OTHER INFORMATION: The DNA sequence encoding H51N9-69T1-26S4

<400> SEQUENCE: 34
atgaaggtgt acctgccccc cgcccccgtg agcaggatcg tgaacaccga ggagtacatc 60
accaggaccg gcatctacta ctacgccggc agcagcaggc tgatcaccct gggccacccc 120
tacttcccga tcccgaaatc tggttctacc gctgaaatcc cgaaggtctc tgccttccag 180
tacagggtgt tcagggtgca gctccccgac cccaacaagt tcggcctgcc cgaccccaac 240
ctgtacaacc ccgacaccga caggctggtg tggggctgcg tgggcgtgga ggtgggcagg 300
ggccagcccc tgggcgtggg cctgagcggc cacccccctgt tcaacaagta cgacgacacc 360
gagaacagca ggatcgccaa cggcaacgcc cagcaggacg tgagggacaa caccagcgtg 420
gacaacaagc agacccagct gtgcatcatc ggctgcgccc cccccatcgg cgagcactgg 480
ggcatcggca ccacctgcaa gaacaccccc gtgccccccg gcgactgccc cccccctggag 540 ctggtgagca gcgtgatcca ggacggcgac atgatcgaca ccggcttcgg cgccatggac 600
ttcgccgccc tgcaggccac caagagcgac gtgcccctgg acatcagcca gagcgtgtgc 660
aagtaccccg actacctgaa gatgagcgcc gacacctacg gcaacagcat gttcttccac 720
ctgaggaggg agcagatctt cgccaggcac ttctacaaca aagctggtgc tgttggtgac 780
gctatcccga ccaccctgta catcaaaggt gctgaatctg gtcgtgaacc gccgacctct 840
tctatctact ctgccacccc cagcggcagc atgatcacca gcgacagcca gatcttcaac 900
aagccctact ggctgcacag ggcccagggc cacaacaacg gcatctgctg gaacaaccag 960
ctgttcatca cctgcgtgga caccaccagg agcaccaacc tgaccatcag caccgccacc 1020
gccgccgtga gccccacctt cacccccagc aacttcaagc agtacatcag gcacggcgag 1080
gagtacgagc tgcagttcat cttccagctg tgcaagatca ccctgaccac cgaggtgatg 1140
gcctacctgc acaccatgga ccccaccatc ctggagcagt ggaacttcgg cctgaccctg 1200
ccccccagcg ccagcctgga ggacgcctac aggttcgtga ggaacgccgc caccagctgc 1260
cagaaggaca cccccccccca ggccaagccc gacccccctgg ccaagtacaa gttctgggac 1320
gtggacctga aggagaggtt cagcctggac ctggaccagt tcgccctggg caggaagttc 1380
ctgctgcagg tgggcgtgca gaggaagccc aggcccggcc tgaagaggcc cgctagcagc 1440
gccagctcca gcagctccag cagcgccaag aggaagaggg tgaagaagta a 1491

<210> SEQ ID NO 35

<211> LENGTH: 1494
<212> TYPE: DNA
<213> ORGANISM: Artificial Sequence
<220> FEATURE:
<223> OTHER INFORMATION: The DNA sequence encoding H51N9-69T1-26S5

<400> SEQUENCE: 35
atgaaggtgt acctgccccc cgcccccgtg agcaggatcg tgaacaccga ggagtacatc 60
accaggaccg gcatctacta ctacgccggc agcagcaggc tgatcaccct gggccacccc 120
tacttcccga tcccgaaatc tggttctacc gctgaaatcc cgaaggtctc tgccttccag 180
tacagggtgt tcagggtgca gctccccgac cccaacaagt tcggcctgcc cgaccccaac 240
ctgtacaacc ccgacaccga caggctggtg tggggctgcg tgggcgtgga ggtgggcagg 300
ggccagcccc tgggcgtggg cctgagcggc cacccccctgt tcaacaagta cgacgacacc 360
gagaacagca ggatcgccaa cggcaacgcc cagcaggacg tgagggacaa caccagcgtg 420
gacaacaagc agacccagct gtgcatcatc ggctgcgccc cccccatcgg cgagcactgg 480
ggcatcggca ccacctgcaa gaacaccccc gtgccccccg gcgactgccc ccccctggag 540
ctggtgagca gcgtgatcca ggacggcgac atgatcgaca ccggcttcgg cgccatggac 600
ttcgccgccc tgcaggccac caagagcgac gtgcccctgg acatcagcca gagcgtgtgc 660
aagtaccccg actacctgaa gatgagcgcc gacacctacg gcaacagcat gttcttccac 720
ctgaggaggg agcagatctt cgccaggcac tactacaaca agctgggcag cgtgggcgag 780
gacatcccca ccgactacta catcaagggc agcggcaacg gcagggaccc catcgagagc 840
tacatctaca gcgccacccc cagcggcagc atgatcacca gcgacagcca gatcttcaac 900
aagccctact ggctgcacag ggcccagggc cacaacaacg gcatctgctg gaacaaccag 960
ctgttcatca cctgcgtgga caccaccagg agcaccaacc tgaccatcag caccgcctct 1020
gctgcttctg cttctacccc gttcaaaccg tctgacttca agcagtacat caggcacggc 1080
gaggagtacg agctgcagtt catcttccag ctgtgcaaga tcaccctgac caccgaggtg 1140
atggcctacc tgcacaccat ggaccccacc atcctggagc agtggaactt cggcctgacc 1200
ctgcccccca gcgccagcct ggaggacgcc tacaggttcg tgaggaacgc cgccaccagc 1260
tgccagaagg acaccccccc ccaggccaag cccgaccccc tggccaagta caagttctgg 1320
gacgtggacc tgaaggagag gttcagcctg gacctggacc agttcgccct gggcaggaag 1380
ttcctgctgc aggtgggcgt gcagaggaag cccaggcccg gcctgaagag gcccgctagc 1440
agcgccagct ccagcagctc cagcagcgcc aagaggaaga gggtgaagaa gtaa 1494

<210> SEQ ID NO 36
<211> LENGTH: 1497
<212> TYPE: DNA
<213> ORGANISM: Artificial Sequence
<220> FEATURE:
<223> OTHER INFORMATION: The DNA sequence encoding H51N9-69T3-26S1

<400> SEQUENCE: 36
atgaaggtgt acctgccccc cgcccccgtg agcaggatcg tgaacaccga ggagtacatc 60
accaggaccg gcatctacta ctacgccggc agcagcaggc tgatcaccct gggccacccc 120
tacttctcta tcccgaaaac cggtcagaaa gctgaaatcc cgaaagtttc tgccttccag 180
tacagggtgt tcagggtgca gctccccgac cccaacaagt tcggcctgcc cgaccccaac 240
ctgtacaacc ccgacaccga caggctggtg tggggctgcg tgggcgtgga ggtgggcagg 300
ggccagcccc tgggcgtggg cctgagcggc cacccccctgt tcaacaagta cgacgacacc 360

```
gagaacagca ggatcgccaa cggcaacgcc cagcaggacg tgagggacaa caccagcgtg    420
gacaacaagc agacccagct gtgcatcatc ggctgcgccc cccccatcgg cgagcactgg    480
ggtgtcggta ccgtttgcaa aaacgctcag tctcaggttc agcgtggtga ctgcccgccg    540
ctggagctgg tgagcagcgt gatccaggac ggcgacatga tcgacaccgg cttcggcgcc    600
atggacttcg ccgccctgca ggccaccaag agcgacgtgc ccctggacat cagccagagc    660
gtgtgcaagt accccgacta cctgaagatg agcgccgaca cctacggcaa cagcatgttc    720
ttccacctga ggagggagca gatcttcgcc aggcactact acaacaagct gggcagcgtg    780
ggcgaggaca tccccaccga ctactacatc aagggcagcg gcaacggcag ggaccccatc    840
gagagctaca tctacagcgc cacccccagc ggcagcatga tcaccagcga cagccagatc    900
ttcaacaagc cctactggct gcacagggcc cagggccaca acaacggcat ctgctggaac    960
aaccagctgt tcatcacctg cgtggacacc accaggagca ccaacctgac catcagcacc   1020
gccaccgccg ccgtgagccc caccttcacc cccagcaact tcaagcagta catcaggcac   1080
ggcgaggagt acgagctgca gttcatcttc cagctgtgca agatcaccct gaccaccgag   1140
gtgatggcct acctgcacac catggacccc accatcctgg agcagtggaa cttcggcctg   1200
accctgcccc ccagcgccag cctggaggac gcctacaggt tcgtgaggaa cgccgccacc   1260
agctgccaga aggacacccc cccccaggcc aagcccgacc ccctggccaa gtacaagttc   1320
tgggacgtgg acctgaagga gaggttcagc ctggacctgg accagttcgc cctgggcagg   1380
aagttcctgc tgcaggtggg cgtgcagagg aagcccaggc ccggcctgaa gaggcccgct   1440
agcagcgcca gctccagcag ctccagcagc gccaagagga agagggtgaa gaagtaa      1497
```

```
<210> SEQ ID NO 37
<211> LENGTH: 1497
<212> TYPE: DNA
<213> ORGANISM: Artificial Sequence
<220> FEATURE:
<223> OTHER INFORMATION: The DNA sequence encoding H51N9-69T3-26S2

<400> SEQUENCE: 37
```

```
atgaaggtgt acctgccccc cgcccccgtg agcaggatcg tgaacaccga ggagtacatc     60
accaggaccg gcatctacta ctacgccggc agcagcaggc tgatcaccct gggccacccc    120
tacttccccc tgcccaagac cagcaccagg gccgccatcc ccaaggtgag cgccttccag    180
tacagggtgt tcagggtgca gctccccgac cccaacaagt tcggcctgcc cgaccccaac    240
ctgtacaacc ccgacaccga caggctggtg tggggctgcg tgggcgtgga ggtgggtcgt    300
ggtcagccgc tgggtatcgg tctgtctggt cacccgctgt tcaacaaact ggacgacacc    360
gaaaactctc acctggctac cgttaacgct gacaccgaca accgtgacaa cgtttctgtt    420
gacaacaagc agacccagct gtgcatcatc ggctgcgccc cccccatcgg cgagcactgg    480
ggtgtcggta ccgtttgcaa aaacgctcag tctcaggttc agcgtggtga ctgcccgccg    540
ctggagctgg tgagcagcgt gatccaggac ggcgacatga tcgacaccgg cttcggcgcc    600
atggacttcg ccgccctgca ggccaccaag agcgacgtgc ccctggacat cagccagagc    660
gtgtgcaagt accccgacta cctgaagatg agcgccgaca cctacggcaa cagcatgttc    720
ttccacctga ggagggagca gatcttcgcc aggcactact acaacaagct gggcagcgtg    780
ggcgaggaca tccccaccga ctactacatc aagggcagcg gcaacggcag ggaccccatc    840
gagagctaca tctacagcgc cacccccagc ggcagcatga tcaccagcga cagccagatc    900
```

```
ttcaacaagc cctactggct gcacagggcc cagggccaca acaacggcat ctgctggaac    960

aaccagctgt tcatcacctg cgtggacacc accaggagca ccaacctgac catcagcacc   1020

gccaccgccg ccgtgagccc caccttcacc cccagcaact tcaagcagta catcaggcac   1080

ggcgaggagt acgagctgca gttcatcttc cagctgtgca agatcaccct gaccaccgag   1140

gtgatggcct acctgcacac catggacccc accatcctgg agcagtggaa cttcggcctg   1200

accctgcccc ccagcgccag cctggaggac gcctacaggt tcgtgaggaa cgccgccacc   1260

agctgccaga aggacacccc cccccaggcc aagcccgacc ccctggccaa gtacaagttc   1320

tgggacgtgg acctgaagga gaggttcagc ctggacctgg accagttcgc cctgggcagg   1380

aagttcctgc tgcaggtggg cgtgcagagg aagcccaggc ccggcctgaa gaggcccgct   1440

agcagcgcca gctccagcag ctccagcagc gccaagagga agagggtgaa gaagtaa      1497
```

<210> SEQ ID NO 38
<211> LENGTH: 1497
<212> TYPE: DNA
<213> ORGANISM: Artificial Sequence
<220> FEATURE:
<223> OTHER INFORMATION: The DNA sequence encoding H51N9-69T3-26S4

<400> SEQUENCE: 38

```
atgaaggtgt acctgccccc cgcccccgtg agcaggatcg tgaacaccga ggagtacatc     60

accaggaccg gcatctacta ctacgccggc agcagcaggc tgatcaccct gggccacccc    120

tacttccccc tgcccaagac cagcaccagg gccgccatcc ccaaggtgag cgccttccag    180

tacagggtgt tcagggtgca gctccccgac cccaacaagt tcggcctgcc cgaccccaac    240

ctgtacaacc ccgacaccga caggctggtg tggggctgcg tgggcgtgga ggtgggcagg    300

ggccagcccc tgggcgtggg cctgagcggc cacccccctgt tcaacaagta cgacgacacc    360

gagaacagca ggatcgccaa cggcaacgcc cagcaggacg tgagggacaa caccagcgtg    420

gacaacaagc agacccagct gtgcatcatc ggctgcgccc cccccatcgg cgagcactgg    480

ggtgtcggta ccgtttgcaa aaacgctcag tctcaggttc agcgtggtga ctgcccgccg    540

ctggagctgg tgagcagcgt gatccaggac ggcgacatga tcgacaccgg cttcggcgcc    600

atggacttcg ccgccctgca ggccaccaag agcgacgtgc ccctggacat cagccagagc    660

gtgtgcaagt accccgacta cctgaagatg agcgccgaca cctacggcaa cagcatgttc    720

ttccacctga ggagggagca gatcttcgcc aggcacttct acaacaaagc tggtgctgtt    780

ggtgacgcta tcccgaccac cctgtacatc aaaggtgctg aatctggtcg tgaaccgccg    840

acctcttcta tctactctgc cacccccagc ggcagcatga tcaccagcga cagccagatc    900

ttcaacaagc cctactggct gcacagggcc cagggccaca acaacggcat ctgctggaac    960

aaccagctgt tcatcacctg cgtggacacc accaggagca ccaacctgac catcagcacc   1020

gccaccgccg ccgtgagccc caccttcacc cccagcaact tcaagcagta catcaggcac   1080

ggcgaggagt acgagctgca gttcatcttc cagctgtgca agatcaccct gaccaccgag   1140

gtgatggcct acctgcacac catggacccc accatcctgg agcagtggaa cttcggcctg   1200

accctgcccc ccagcgccag cctggaggac gcctacaggt tcgtgaggaa cgccgccacc   1260

agctgccaga aggacacccc cccccaggcc aagcccgacc ccctggccaa gtacaagttc   1320

tgggacgtgg acctgaagga gaggttcagc ctggacctgg accagttcgc cctgggcagg   1380

aagttcctgc tgcaggtggg cgtgcagagg aagcccaggc ccggcctgaa gaggcccgct   1440

agcagcgcca gctccagcag ctccagcagc gccaagagga agagggtgaa gaagtaa      1497
```

<210> SEQ ID NO 39
<211> LENGTH: 1500
<212> TYPE: DNA
<213> ORGANISM: Artificial Sequence
<220> FEATURE:
<223> OTHER INFORMATION: The DNA sequence encoding H51N9-69T3-26S5

<400> SEQUENCE: 39

```
atgaaggtgt acctgccccc cgcccccgtg agcaggatcg tgaacaccga ggagtacatc     60

accaggaccg gcatctacta ctacgccggc agcagcaggc tgatcaccct gggccacccc    120

tacttccccc tgcccaagac cagcaccagg gccgccatcc ccaaggtgag cgccttccag    180

tacagggtgt tcagggtgca gctccccgac cccaacaagt tcggcctgcc cgaccccaac    240

ctgtacaacc ccgacaccga caggctggtg tggggctgcg tgggcgtgga ggtgggcagg    300

ggccagcccc tgggcgtggg cctgagcggc cacccccctgt tcaacaagta cgacgacacc    360

gagaacagca ggatcgccaa cggcaacgcc cagcaggacg tgagggacaa caccagcgtg    420

gacaacaagc agacccagct gtgcatcatc ggctgcgccc cccccatcgg cgagcactgg    480

ggtgtcggta ccgtttgcaa aaacgctcag tctcaggttc agcgtggtga ctgcccgccg    540

ctggagctgg tgagcagcgt gatccaggac ggcgacatga tcgacaccgg cttcggcgcc    600

atggacttcg ccgccctgca ggccaccaag agcgacgtgc ccctggacat cagccagagc    660

gtgtgcaagt accccgacta cctgaagatg agcgccgaca cctacggcaa cagcatgttc    720

ttccacctga ggagggagca gatcttcgcc aggcactact acaacaagct gggcagcgtg    780

ggcgaggaca tccccaccga ctactacatc aagggcagcg gcaacggcag ggaccccatc    840

gagagctaca tctacagcgc cacccccagc ggcagcatga tcaccagcga cagccagatc    900

ttcaacaagc cctactggct gcacagggcc cagggccaca acaacggcat ctgctggaac    960

aaccagctgt tcatcacctg cgtggacacc accaggagca ccaacctgac catcagcacc   1020

gcctctgctg cttctgcttc taccccgttc aaaccgtctg acttcaagca gtacatcagg   1080

cacggcgagg agtacgagct gcagttcatc ttccagctgt gcaagatcac cctgaccacc   1140

gaggtgatgg cctacctgca caccatggac ccccaccatcc tggagcagtg gaacttcggc   1200

ctgaccctgc cccccagcgc cagcctggag gacgcctaca ggttcgtgag gaacgccgcc   1260

accagctgcc agaaggacac cccccccccag gccaagcccg acccccctggc caagtacaag   1320

ttctgggacg tggacctgaa ggagaggttc agcctggacc tggaccagtt cgccctgggc   1380

aggaagttcc tgctgcaggt gggcgtgcag aggaagccca ggcccggcct gaagaggccc   1440

gctagcagcg ccagctccag cagctccagc agcgccaaga ggaagagggt gaagaagtaa   1500
```

<210> SEQ ID NO 40
<211> LENGTH: 496
<212> TYPE: PRT
<213> ORGANISM: Artificial Sequence
<220> FEATURE:
<223> OTHER INFORMATION: H51N9-69T2-26S1

<400> SEQUENCE: 40

```
Met Lys Val Tyr Leu Pro Pro Ala Pro Val Ser Arg Ile Val Asn Thr
1               5                   10                  15

Glu Glu Tyr Ile Thr Arg Thr Gly Ile Tyr Tyr Tyr Ala Gly Ser Ser
            20                  25                  30

Arg Leu Ile Thr Leu Gly His Pro Tyr Phe Ser Ile Pro Lys Thr Gly
        35                  40                  45
```

-continued

```
Gln Lys Ala Glu Ile Pro Lys Val Ser Ala Phe Gln Tyr Arg Val Phe
    50                  55                  60

Arg Val Gln Leu Pro Asp Pro Asn Lys Phe Gly Leu Pro Asp Pro Asn
65                  70                  75                  80

Leu Tyr Asn Pro Asp Thr Asp Arg Leu Val Trp Gly Cys Val Gly Val
                85                  90                  95

Glu Val Gly Arg Gly Gln Pro Leu Gly Val Gly Leu Ser Gly His Pro
            100                 105                 110

Leu Phe Asn Lys Leu Asp Asp Thr Glu Asn Ser His Leu Ala Thr Ala
        115                 120                 125

Asn Ala Asp Thr Asp Asn Arg Asp Asn Val Cys Val Asp Asn Lys Gln
    130                 135                 140

Thr Gln Leu Cys Ile Ile Gly Cys Ala Pro Pro Ile Gly Glu His Trp
145                 150                 155                 160

Gly Ile Gly Thr Thr Cys Lys Asn Thr Pro Val Pro Pro Gly Asp Cys
                165                 170                 175

Pro Pro Leu Glu Leu Val Ser Ser Val Ile Gln Asp Gly Asp Met Ile
            180                 185                 190

Asp Thr Gly Phe Gly Ala Met Asp Phe Ala Ala Leu Gln Ala Thr Lys
        195                 200                 205

Ser Asp Val Pro Leu Asp Ile Ser Gln Ser Val Cys Lys Tyr Pro Asp
    210                 215                 220

Tyr Leu Lys Met Ser Ala Asp Thr Tyr Gly Asn Ser Met Phe Phe His
225                 230                 235                 240

Leu Arg Arg Glu Gln Ile Phe Ala Arg His Tyr Tyr Asn Lys Leu Gly
                245                 250                 255

Ser Val Gly Glu Asp Ile Pro Thr Asp Tyr Tyr Ile Lys Gly Ser Gly
            260                 265                 270

Asn Gly Arg Asp Pro Ile Glu Ser Tyr Ile Tyr Ser Ala Thr Pro Ser
        275                 280                 285

Gly Ser Met Ile Thr Ser Asp Ser Gln Ile Phe Asn Lys Pro Tyr Trp
    290                 295                 300

Leu His Arg Ala Gln Gly His Asn Asn Gly Ile Cys Trp Asn Asn Gln
305                 310                 315                 320

Leu Phe Ile Thr Cys Val Asp Thr Thr Arg Ser Thr Asn Leu Thr Ile
                325                 330                 335

Ser Thr Ala Thr Ala Ala Val Ser Pro Thr Phe Thr Pro Ser Asn Phe
            340                 345                 350

Lys Gln Tyr Ile Arg His Gly Glu Glu Tyr Glu Leu Gln Phe Ile Phe
        355                 360                 365

Gln Leu Cys Lys Ile Thr Leu Thr Thr Glu Val Met Ala Tyr Leu His
    370                 375                 380

Thr Met Asp Pro Thr Ile Leu Glu Gln Trp Asn Phe Gly Leu Thr Leu
385                 390                 395                 400

Pro Pro Ser Ala Ser Leu Glu Asp Ala Tyr Arg Phe Val Arg Asn Ala
                405                 410                 415

Ala Thr Ser Cys Gln Lys Asp Thr Pro Pro Gln Ala Lys Pro Asp Pro
            420                 425                 430

Leu Ala Lys Tyr Lys Phe Trp Asp Val Asp Leu Lys Glu Arg Phe Ser
        435                 440                 445

Leu Asp Leu Asp Gln Phe Ala Leu Gly Arg Lys Phe Leu Leu Gln Val
    450                 455                 460
```

```
Gly Val Gln Arg Lys Pro Arg Pro Gly Leu Lys Arg Pro Ala Ser Ser
465                 470                 475                 480

Ala Ser Ser Ser Ser Ser Ser Ser Ala Lys Arg Lys Arg Val Lys Lys
                485                 490                 495


<210> SEQ ID NO 41
<211> LENGTH: 496
<212> TYPE: PRT
<213> ORGANISM: Artificial Sequence
<220> FEATURE:
<223> OTHER INFORMATION: H51N9-69T2-26S3

<400> SEQUENCE: 41

Met Lys Val Tyr Leu Pro Pro Ala Pro Val Ser Arg Ile Val Asn Thr
1               5                   10                  15

Glu Glu Tyr Ile Thr Arg Thr Gly Ile Tyr Tyr Tyr Ala Gly Ser Ser
            20                  25                  30

Arg Leu Ile Thr Leu Gly His Pro Tyr Phe Pro Leu Pro Lys Thr Ser
        35                  40                  45

Thr Arg Ala Ala Ile Pro Lys Val Ser Ala Phe Gln Tyr Arg Val Phe
    50                  55                  60

Arg Val Gln Leu Pro Asp Pro Asn Lys Phe Gly Leu Pro Asp Pro Asn
65                  70                  75                  80

Leu Tyr Asn Pro Asp Thr Asp Arg Leu Val Trp Gly Cys Val Gly Val
                85                  90                  95

Glu Val Gly Arg Gly Gln Pro Leu Gly Val Gly Leu Ser Gly His Pro
            100                 105                 110

Leu Phe Asn Lys Leu Asp Asp Thr Glu Asn Ser His Leu Ala Thr Ala
        115                 120                 125

Asn Ala Asp Thr Asp Asn Arg Asp Asn Val Cys Val Asp Asn Lys Gln
    130                 135                 140

Thr Gln Leu Cys Ile Ile Gly Cys Ala Pro Pro Ile Gly Glu His Trp
145                 150                 155                 160

Gly Ile Gly Thr Ile Cys Lys Asn Thr Gln Thr Gln Arg Gly Asp Cys
                165                 170                 175

Pro Pro Leu Glu Leu Val Ser Ser Val Ile Gln Asp Gly Asp Met Ile
            180                 185                 190

Asp Thr Gly Phe Gly Ala Met Asp Phe Ala Ala Leu Gln Ala Thr Lys
        195                 200                 205

Ser Asp Val Pro Leu Asp Ile Ser Gln Ser Val Cys Lys Tyr Pro Asp
    210                 215                 220

Tyr Leu Lys Met Ser Ala Asp Thr Tyr Gly Asn Ser Met Phe Phe His
225                 230                 235                 240

Leu Arg Arg Glu Gln Ile Phe Ala Arg His Tyr Tyr Asn Lys Leu Gly
                245                 250                 255

Ser Val Gly Glu Asp Ile Pro Thr Asp Tyr Tyr Ile Lys Gly Ser Gly
            260                 265                 270

Asn Gly Arg Asp Pro Ile Glu Ser Tyr Ile Tyr Ser Ala Thr Pro Ser
        275                 280                 285

Gly Ser Met Ile Thr Ser Asp Ser Gln Ile Phe Asn Lys Pro Tyr Trp
    290                 295                 300

Leu His Arg Ala Gln Gly His Asn Asn Gly Ile Cys Trp Asn Asn Gln
305                 310                 315                 320

Leu Phe Ile Thr Cys Val Asp Thr Thr Arg Ser Thr Asn Leu Thr Ile
                325                 330                 335
```

```
Ser Thr Ala Thr Ala Ala Val Ser Pro Thr Phe Thr Pro Ser Asn Phe
            340                 345                 350

Lys Gln Tyr Ile Arg His Gly Glu Glu Tyr Glu Leu Gln Phe Ile Phe
        355                 360                 365

Gln Leu Cys Lys Ile Thr Leu Thr Thr Glu Val Met Ala Tyr Leu His
    370                 375                 380

Thr Met Asp Pro Thr Ile Leu Glu Gln Trp Asn Phe Gly Leu Thr Leu
385                 390                 395                 400

Pro Pro Ser Ala Ser Leu Glu Asp Ala Tyr Arg Phe Val Arg Asn Ala
                405                 410                 415

Ala Thr Ser Cys Gln Lys Asp Thr Pro Pro Gln Ala Lys Pro Asp Pro
            420                 425                 430

Leu Ala Lys Tyr Lys Phe Trp Asp Val Asp Leu Lys Glu Arg Phe Ser
        435                 440                 445

Leu Asp Leu Asp Gln Phe Ala Leu Gly Arg Lys Phe Leu Leu Gln Val
    450                 455                 460

Gly Val Gln Arg Lys Pro Arg Pro Gly Leu Lys Arg Pro Ala Ser Ser
465                 470                 475                 480

Ala Ser Ser Ser Ser Ser Ser Ser Ala Lys Arg Lys Arg Val Lys Lys
                485                 490                 495


<210> SEQ ID NO 42
<211> LENGTH: 496
<212> TYPE: PRT
<213> ORGANISM: Artificial Sequence
<220> FEATURE:
<223> OTHER INFORMATION: H51N9-69T2-26S4

<400> SEQUENCE: 42

Met Lys Val Tyr Leu Pro Pro Ala Pro Val Ser Arg Ile Val Asn Thr
1               5                   10                  15

Glu Glu Tyr Ile Thr Arg Thr Gly Ile Tyr Tyr Tyr Ala Gly Ser Ser
            20                  25                  30

Arg Leu Ile Thr Leu Gly His Pro Tyr Phe Pro Leu Pro Lys Thr Ser
        35                  40                  45

Thr Arg Ala Ala Ile Pro Lys Val Ser Ala Phe Gln Tyr Arg Val Phe
    50                  55                  60

Arg Val Gln Leu Pro Asp Pro Asn Lys Phe Gly Leu Pro Asp Pro Asn
65                  70                  75                  80

Leu Tyr Asn Pro Asp Thr Asp Arg Leu Val Trp Gly Cys Val Gly Val
                85                  90                  95

Glu Val Gly Arg Gly Gln Pro Leu Gly Val Gly Leu Ser Gly His Pro
            100                 105                 110

Leu Phe Asn Lys Leu Asp Asp Thr Glu Asn Ser His Leu Ala Thr Ala
        115                 120                 125

Asn Ala Asp Thr Asp Asn Arg Asp Asn Val Cys Val Asp Asn Lys Gln
    130                 135                 140

Thr Gln Leu Cys Ile Ile Gly Cys Ala Pro Pro Ile Gly Glu His Trp
145                 150                 155                 160

Gly Ile Gly Thr Thr Cys Lys Asn Thr Pro Val Pro Pro Gly Asp Cys
                165                 170                 175

Pro Pro Leu Glu Leu Val Ser Ser Val Ile Gln Asp Gly Asp Met Ile
            180                 185                 190

Asp Thr Gly Phe Gly Ala Met Asp Phe Ala Ala Leu Gln Ala Thr Lys
        195                 200                 205
```

Ser Asp Val Pro Leu Asp Ile Ser Gln Ser Val Cys Lys Tyr Pro Asp
    210                 215                 220

Tyr Leu Lys Met Ser Ala Asp Thr Tyr Gly Asn Ser Met Phe Phe His
225                 230                 235                 240

Leu Arg Arg Glu Gln Ile Phe Ala Arg His Phe Tyr Asn Lys Ala Gly
                245                 250                 255

Ala Val Gly Asp Ala Ile Pro Thr Thr Leu Tyr Ile Lys Gly Ala Glu
            260                 265                 270

Ser Gly Arg Glu Pro Pro Thr Ser Ser Ile Tyr Ser Ala Thr Pro Ser
        275                 280                 285

Gly Ser Met Ile Thr Ser Asp Ser Gln Ile Phe Asn Lys Pro Tyr Trp
    290                 295                 300

Leu His Arg Ala Gln Gly His Asn Asn Gly Ile Cys Trp Asn Asn Gln
305                 310                 315                 320

Leu Phe Ile Thr Cys Val Asp Thr Thr Arg Ser Thr Asn Leu Thr Ile
                325                 330                 335

Ser Thr Ala Thr Ala Ala Val Ser Pro Thr Phe Thr Pro Ser Asn Phe
            340                 345                 350

Lys Gln Tyr Ile Arg His Gly Glu Glu Tyr Glu Leu Gln Phe Ile Phe
        355                 360                 365

Gln Leu Cys Lys Ile Thr Leu Thr Thr Glu Val Met Ala Tyr Leu His
    370                 375                 380

Thr Met Asp Pro Thr Ile Leu Glu Gln Trp Asn Phe Gly Leu Thr Leu
385                 390                 395                 400

Pro Pro Ser Ala Ser Leu Glu Asp Ala Tyr Arg Phe Val Arg Asn Ala
                405                 410                 415

Ala Thr Ser Cys Gln Lys Asp Thr Pro Pro Gln Ala Lys Pro Asp Pro
            420                 425                 430

Leu Ala Lys Tyr Lys Phe Trp Asp Val Asp Leu Lys Glu Arg Phe Ser
        435                 440                 445

Leu Asp Leu Asp Gln Phe Ala Leu Gly Arg Lys Phe Leu Leu Gln Val
    450                 455                 460

Gly Val Gln Arg Lys Pro Arg Pro Gly Leu Lys Arg Pro Ala Ser Ser
465                 470                 475                 480

Ala Ser Ser Ser Ser Ser Ser Ser Ala Lys Arg Lys Arg Val Lys Lys
                485                 490                 495

<210> SEQ ID NO 43
<211> LENGTH: 497
<212> TYPE: PRT
<213> ORGANISM: Artificial Sequence
<220> FEATURE:
<223> OTHER INFORMATION: H51N9-69T2-26S5

<400> SEQUENCE: 43

Met Lys Val Tyr Leu Pro Pro Ala Pro Val Ser Arg Ile Val Asn Thr
1               5                   10                  15

Glu Glu Tyr Ile Thr Arg Thr Gly Ile Tyr Tyr Tyr Ala Gly Ser Ser
            20                  25                  30

Arg Leu Ile Thr Leu Gly His Pro Tyr Phe Pro Leu Pro Lys Thr Ser
        35                  40                  45

Thr Arg Ala Ala Ile Pro Lys Val Ser Ala Phe Gln Tyr Arg Val Phe
    50                  55                  60

Arg Val Gln Leu Pro Asp Pro Asn Lys Phe Gly Leu Pro Asp Pro Asn
65                  70                  75                  80

```
Leu Tyr Asn Pro Asp Thr Asp Arg Leu Val Trp Gly Cys Val Gly Val
                85                  90                  95

Glu Val Gly Arg Gly Gln Pro Leu Gly Val Gly Leu Ser Gly His Pro
            100                 105                 110

Leu Phe Asn Lys Leu Asp Asp Thr Glu Asn Ser His Leu Ala Thr Ala
        115                 120                 125

Asn Ala Asp Thr Asp Asn Arg Asp Asn Val Cys Val Asp Asn Lys Gln
    130                 135                 140

Thr Gln Leu Cys Ile Ile Gly Cys Ala Pro Pro Ile Gly Glu His Trp
145                 150                 155                 160

Gly Ile Gly Thr Thr Cys Lys Asn Thr Pro Val Pro Pro Gly Asp Cys
                165                 170                 175

Pro Pro Leu Glu Leu Val Ser Ser Val Ile Gln Asp Gly Asp Met Ile
            180                 185                 190

Asp Thr Gly Phe Gly Ala Met Asp Phe Ala Ala Leu Gln Ala Thr Lys
        195                 200                 205

Ser Asp Val Pro Leu Asp Ile Ser Gln Ser Val Cys Lys Tyr Pro Asp
    210                 215                 220

Tyr Leu Lys Met Ser Ala Asp Thr Tyr Gly Asn Ser Met Phe Phe His
225                 230                 235                 240

Leu Arg Arg Glu Gln Ile Phe Ala Arg His Tyr Tyr Asn Lys Leu Gly
                245                 250                 255

Ser Val Gly Glu Asp Ile Pro Thr Asp Tyr Tyr Ile Lys Gly Ser Gly
            260                 265                 270

Asn Gly Arg Asp Pro Ile Glu Ser Tyr Ile Tyr Ser Ala Thr Pro Ser
        275                 280                 285

Gly Ser Met Ile Thr Ser Asp Ser Gln Ile Phe Asn Lys Pro Tyr Trp
    290                 295                 300

Leu His Arg Ala Gln Gly His Asn Asn Gly Ile Cys Trp Asn Asn Gln
305                 310                 315                 320

Leu Phe Ile Thr Cys Val Asp Thr Thr Arg Ser Thr Asn Leu Thr Ile
                325                 330                 335

Ser Thr Ala Ser Ala Ala Ser Ala Ser Thr Pro Phe Lys Pro Ser Asp
            340                 345                 350

Phe Lys Gln Tyr Ile Arg His Gly Glu Glu Tyr Glu Leu Gln Phe Ile
        355                 360                 365

Phe Gln Leu Cys Lys Ile Thr Leu Thr Thr Glu Val Met Ala Tyr Leu
    370                 375                 380

His Thr Met Asp Pro Thr Ile Leu Glu Gln Trp Asn Phe Gly Leu Thr
385                 390                 395                 400

Leu Pro Pro Ser Ala Ser Leu Glu Asp Ala Tyr Arg Phe Val Arg Asn
                405                 410                 415

Ala Ala Thr Ser Cys Gln Lys Asp Thr Pro Pro Gln Ala Lys Pro Asp
            420                 425                 430

Pro Leu Ala Lys Tyr Lys Phe Trp Asp Val Asp Leu Lys Glu Arg Phe
        435                 440                 445

Ser Leu Asp Leu Asp Gln Phe Ala Leu Gly Arg Lys Phe Leu Leu Gln
    450                 455                 460

Val Gly Val Gln Arg Lys Pro Arg Pro Gly Leu Lys Arg Pro Ala Ser
465                 470                 475                 480

Ser Ala Ser Ser Ser Ser Ser Ser Ser Ala Lys Arg Lys Arg Val Lys
                485                 490                 495

Lys
```

-continued

<210> SEQ ID NO 44
<211> LENGTH: 496
<212> TYPE: PRT
<213> ORGANISM: Artificial Sequence
<220> FEATURE:
<223> OTHER INFORMATION: H51N9-69T4-26S1

<400> SEQUENCE: 44

```
Met Lys Val Tyr Leu Pro Pro Ala Pro Val Ser Arg Ile Val Asn Thr
1               5                   10                  15

Glu Glu Tyr Ile Thr Arg Thr Gly Ile Tyr Tyr Tyr Ala Gly Ser Ser
            20                  25                  30

Arg Leu Ile Thr Leu Gly His Pro Tyr Phe Ser Ile Pro Lys Thr Gly
        35                  40                  45

Gln Lys Ala Glu Ile Pro Lys Val Ser Ala Phe Gln Tyr Arg Val Phe
    50                  55                  60

Arg Val Gln Leu Pro Asp Pro Asn Lys Phe Gly Leu Pro Asp Pro Asn
65                  70                  75                  80

Leu Tyr Asn Pro Asp Thr Asp Arg Leu Val Trp Gly Cys Val Gly Val
                85                  90                  95

Glu Val Gly Arg Gly Gln Pro Leu Gly Val Gly Leu Ser Gly His Pro
            100                 105                 110

Leu Phe Asn Lys Tyr Asp Asp Thr Glu Asn Ser Arg Ile Ala Asn Gly
        115                 120                 125

Asn Ala Gln Gln Asp Val Arg Asp Asn Thr Ser Val Asp Asn Lys Gln
    130                 135                 140

Thr Gln Leu Cys Ile Ile Gly Cys Ala Pro Pro Ile Gly Glu His Trp
145                 150                 155                 160

Gly Ile Gly Thr Thr Cys Lys Asn Thr Pro Val Pro Pro Gly Asp Cys
                165                 170                 175

Pro Pro Leu Glu Leu Val Ser Ser Val Ile Gln Asp Gly Asp Met Ile
            180                 185                 190

Asp Thr Gly Phe Gly Ala Met Asp Phe Ala Ala Leu Gln Ala Thr Lys
        195                 200                 205

Ser Asp Val Pro Leu Asp Ile Ser Gln Ser Val Cys Lys Tyr Pro Asp
    210                 215                 220

Tyr Leu Lys Met Ser Ala Asp Thr Tyr Gly Asn Ser Met Phe Phe His
225                 230                 235                 240

Leu Arg Arg Glu Gln Ile Phe Ala Arg His Phe Phe Asn Lys Ala Gly
                245                 250                 255

Thr Ile Gly Asp Pro Val Pro Val Ser Met Tyr Ile Lys Gly Ala Gly
            260                 265                 270

Gln Gly Arg Glu Pro Pro Thr Thr Ser Ile Tyr Ser Ala Thr Pro Ser
        275                 280                 285

Gly Ser Met Ile Thr Ser Asp Ser Gln Ile Phe Asn Lys Pro Tyr Trp
    290                 295                 300

Leu His Arg Ala Gln Gly His Asn Asn Gly Ile Cys Trp Asn Asn Gln
305                 310                 315                 320

Leu Phe Ile Thr Cys Val Asp Thr Thr Arg Ser Thr Asn Leu Thr Ile
                325                 330                 335

Ser Thr Ala Thr Ala Ala Val Ser Pro Thr Phe Thr Pro Ser Asn Phe
            340                 345                 350

Lys Gln Tyr Ile Arg His Gly Glu Glu Tyr Glu Leu Gln Phe Ile Phe
        355                 360                 365
```

```
Gln Leu Cys Lys Ile Thr Leu Thr Thr Glu Val Met Ala Tyr Leu His
    370                 375                 380

Thr Met Asp Pro Thr Ile Leu Glu Gln Trp Asn Phe Gly Leu Thr Leu
385                 390                 395                 400

Pro Pro Ser Ala Ser Leu Glu Asp Ala Tyr Arg Phe Val Arg Asn Ala
                405                 410                 415

Ala Thr Ser Cys Gln Lys Asp Thr Pro Pro Gln Ala Lys Pro Asp Pro
            420                 425                 430

Leu Ala Lys Tyr Lys Phe Trp Asp Val Asp Leu Lys Glu Arg Phe Ser
        435                 440                 445

Leu Asp Leu Asp Gln Phe Ala Leu Gly Arg Lys Phe Leu Leu Gln Val
    450                 455                 460

Gly Val Gln Arg Lys Pro Arg Pro Gly Leu Lys Arg Pro Ala Ser Ser
465                 470                 475                 480

Ala Ser Ser Ser Ser Ser Ser Ser Ala Lys Arg Lys Arg Val Lys Lys
                485                 490                 495


<210> SEQ ID NO 45
<211> LENGTH: 496
<212> TYPE: PRT
<213> ORGANISM: Artificial Sequence
<220> FEATURE:
<223> OTHER INFORMATION: H51N9-69T4-26S2

<400> SEQUENCE: 45

Met Lys Val Tyr Leu Pro Pro Ala Pro Val Ser Arg Ile Val Asn Thr
1               5                   10                  15

Glu Glu Tyr Ile Thr Arg Thr Gly Ile Tyr Tyr Tyr Ala Gly Ser Ser
            20                  25                  30

Arg Leu Ile Thr Leu Gly His Pro Tyr Phe Pro Leu Pro Lys Thr Ser
        35                  40                  45

Thr Arg Ala Ala Ile Pro Lys Val Ser Ala Phe Gln Tyr Arg Val Phe
    50                  55                  60

Arg Val Gln Leu Pro Asp Pro Asn Lys Phe Gly Leu Pro Asp Pro Asn
65                  70                  75                  80

Leu Tyr Asn Pro Asp Thr Asp Arg Leu Val Trp Gly Cys Val Gly Val
                85                  90                  95

Glu Val Gly Arg Gly Gln Pro Leu Gly Ile Gly Leu Ser Gly His Pro
            100                 105                 110

Leu Phe Asn Lys Leu Asp Asp Thr Glu Asn Ser His Leu Ala Thr Val
        115                 120                 125

Asn Ala Asp Thr Asp Asn Arg Asp Asn Val Ser Val Asp Asn Lys Gln
    130                 135                 140

Thr Gln Leu Cys Ile Ile Gly Cys Ala Pro Pro Ile Gly Glu His Trp
145                 150                 155                 160

Gly Ile Gly Thr Thr Cys Lys Asn Thr Pro Val Pro Pro Gly Asp Cys
                165                 170                 175

Pro Pro Leu Glu Leu Val Ser Ser Val Ile Gln Asp Gly Asp Met Ile
            180                 185                 190

Asp Thr Gly Phe Gly Ala Met Asp Phe Ala Ala Leu Gln Ala Thr Lys
        195                 200                 205

Ser Asp Val Pro Leu Asp Ile Ser Gln Ser Val Cys Lys Tyr Pro Asp
    210                 215                 220

Tyr Leu Lys Met Ser Ala Asp Thr Tyr Gly Asn Ser Met Phe Phe His
225                 230                 235                 240
```

```
Leu Arg Arg Glu Gln Ile Phe Ala Arg His Phe Phe Asn Lys Ala Gly
                245                 250                 255

Thr Ile Gly Asp Pro Val Pro Val Ser Met Tyr Ile Lys Gly Ala Gly
            260                 265                 270

Gln Gly Arg Glu Pro Pro Thr Thr Ser Ile Tyr Ser Ala Thr Pro Ser
        275                 280                 285

Gly Ser Met Ile Thr Ser Asp Ser Gln Ile Phe Asn Lys Pro Tyr Trp
    290                 295                 300

Leu His Arg Ala Gln Gly His Asn Asn Gly Ile Cys Trp Asn Asn Gln
305                 310                 315                 320

Leu Phe Ile Thr Cys Val Asp Thr Thr Arg Ser Thr Asn Leu Thr Ile
                325                 330                 335

Ser Thr Ala Thr Ala Ala Val Ser Pro Thr Phe Thr Pro Ser Asn Phe
            340                 345                 350

Lys Gln Tyr Ile Arg His Gly Glu Glu Tyr Glu Leu Gln Phe Ile Phe
        355                 360                 365

Gln Leu Cys Lys Ile Thr Leu Thr Thr Glu Val Met Ala Tyr Leu His
    370                 375                 380

Thr Met Asp Pro Thr Ile Leu Glu Gln Trp Asn Phe Gly Leu Thr Leu
385                 390                 395                 400

Pro Pro Ser Ala Ser Leu Glu Asp Ala Tyr Arg Phe Val Arg Asn Ala
                405                 410                 415

Ala Thr Ser Cys Gln Lys Asp Thr Pro Pro Gln Ala Lys Pro Asp Pro
            420                 425                 430

Leu Ala Lys Tyr Lys Phe Trp Asp Val Asp Leu Lys Glu Arg Phe Ser
        435                 440                 445

Leu Asp Leu Asp Gln Phe Ala Leu Gly Arg Lys Phe Leu Leu Gln Val
    450                 455                 460

Gly Val Gln Arg Lys Pro Arg Pro Gly Leu Lys Arg Pro Ala Ser Ser
465                 470                 475                 480

Ala Ser Ser Ser Ser Ser Ser Ser Ala Lys Arg Lys Arg Val Lys Lys
                485                 490                 495


<210> SEQ ID NO 46
<211> LENGTH: 496
<212> TYPE: PRT
<213> ORGANISM: Artificial Sequence
<220> FEATURE:
<223> OTHER INFORMATION: H51N9-69T4-26S3

<400> SEQUENCE: 46

Met Lys Val Tyr Leu Pro Pro Ala Pro Val Ser Arg Ile Val Asn Thr
1               5                   10                  15

Glu Glu Tyr Ile Thr Arg Thr Gly Ile Tyr Tyr Tyr Ala Gly Ser Ser
            20                  25                  30

Arg Leu Ile Thr Leu Gly His Pro Tyr Phe Pro Leu Pro Lys Thr Ser
        35                  40                  45

Thr Arg Ala Ala Ile Pro Lys Val Ser Ala Phe Gln Tyr Arg Val Phe
    50                  55                  60

Arg Val Gln Leu Pro Asp Pro Asn Lys Phe Gly Leu Pro Asp Pro Asn
65                  70                  75                  80

Leu Tyr Asn Pro Asp Thr Asp Arg Leu Val Trp Gly Cys Val Gly Val
                85                  90                  95

Glu Val Gly Arg Gly Gln Pro Leu Gly Val Gly Leu Ser Gly His Pro
            100                 105                 110
```

-continued

```
Leu Phe Asn Lys Tyr Asp Asp Thr Glu Asn Ser Arg Ile Ala Asn Gly
        115                 120                 125

Asn Ala Gln Gln Asp Val Arg Asp Asn Thr Ser Val Asp Asn Lys Gln
    130                 135                 140

Thr Gln Leu Cys Ile Ile Gly Cys Ala Pro Pro Ile Gly Glu His Trp
145                 150                 155                 160

Gly Ile Gly Thr Ile Cys Lys Asn Thr Gln Thr Gln Arg Gly Asp Cys
                165                 170                 175

Pro Pro Leu Glu Leu Val Ser Ser Val Ile Gln Asp Gly Asp Met Ile
            180                 185                 190

Asp Thr Gly Phe Gly Ala Met Asp Phe Ala Ala Leu Gln Ala Thr Lys
        195                 200                 205

Ser Asp Val Pro Leu Asp Ile Ser Gln Ser Val Cys Lys Tyr Pro Asp
    210                 215                 220

Tyr Leu Lys Met Ser Ala Asp Thr Tyr Gly Asn Ser Met Phe Phe His
225                 230                 235                 240

Leu Arg Arg Glu Gln Ile Phe Ala Arg His Phe Phe Asn Lys Ala Gly
                245                 250                 255

Thr Ile Gly Asp Pro Val Pro Val Ser Met Tyr Ile Lys Gly Ala Gly
            260                 265                 270

Gln Gly Arg Glu Pro Pro Thr Thr Ser Ile Tyr Ser Ala Thr Pro Ser
        275                 280                 285

Gly Ser Met Ile Thr Ser Asp Ser Gln Ile Phe Asn Lys Pro Tyr Trp
    290                 295                 300

Leu His Arg Ala Gln Gly His Asn Asn Gly Ile Cys Trp Asn Asn Gln
305                 310                 315                 320

Leu Phe Ile Thr Cys Val Asp Thr Thr Arg Ser Thr Asn Leu Thr Ile
                325                 330                 335

Ser Thr Ala Thr Ala Ala Val Ser Pro Thr Phe Thr Pro Ser Asn Phe
            340                 345                 350

Lys Gln Tyr Ile Arg His Gly Glu Glu Tyr Glu Leu Gln Phe Ile Phe
        355                 360                 365

Gln Leu Cys Lys Ile Thr Leu Thr Thr Glu Val Met Ala Tyr Leu His
    370                 375                 380

Thr Met Asp Pro Thr Ile Leu Glu Gln Trp Asn Phe Gly Leu Thr Leu
385                 390                 395                 400

Pro Pro Ser Ala Ser Leu Glu Asp Ala Tyr Arg Phe Val Arg Asn Ala
                405                 410                 415

Ala Thr Ser Cys Gln Lys Asp Thr Pro Pro Gln Ala Lys Pro Asp Pro
            420                 425                 430

Leu Ala Lys Tyr Lys Phe Trp Asp Val Asp Leu Lys Glu Arg Phe Ser
        435                 440                 445

Leu Asp Leu Asp Gln Phe Ala Leu Gly Arg Lys Phe Leu Leu Gln Val
    450                 455                 460

Gly Val Gln Arg Lys Pro Arg Pro Gly Leu Lys Arg Pro Ala Ser Ser
465                 470                 475                 480

Ala Ser Ser Ser Ser Ser Ser Ser Ala Lys Arg Lys Arg Val Lys Lys
                485                 490                 495
```

<210> SEQ ID NO 47
<211> LENGTH: 497
<212> TYPE: PRT
<213> ORGANISM: Artificial Sequence
<220> FEATURE:

<223> OTHER INFORMATION: H51N9-69T4-26S5

<400> SEQUENCE: 47

```
Met Lys Val Tyr Leu Pro Pro Ala Pro Val Ser Arg Ile Val Asn Thr
1               5                   10                  15

Glu Glu Tyr Ile Thr Arg Thr Gly Ile Tyr Tyr Tyr Ala Gly Ser Ser
            20                  25                  30

Arg Leu Ile Thr Leu Gly His Pro Tyr Phe Pro Leu Pro Lys Thr Ser
        35                  40                  45

Thr Arg Ala Ala Ile Pro Lys Val Ser Ala Phe Gln Tyr Arg Val Phe
    50                  55                  60

Arg Val Gln Leu Pro Asp Pro Asn Lys Phe Gly Leu Pro Asp Pro Asn
65                  70                  75                  80

Leu Tyr Asn Pro Asp Thr Asp Arg Leu Val Trp Gly Cys Val Gly Val
                85                  90                  95

Glu Val Gly Arg Gly Gln Pro Leu Gly Val Gly Leu Ser Gly His Pro
            100                 105                 110

Leu Phe Asn Lys Tyr Asp Asp Thr Glu Asn Ser Arg Ile Ala Asn Gly
        115                 120                 125

Asn Ala Gln Gln Asp Val Arg Asp Asn Thr Ser Val Asp Asn Lys Gln
    130                 135                 140

Thr Gln Leu Cys Ile Ile Gly Cys Ala Pro Pro Ile Gly Glu His Trp
145                 150                 155                 160

Gly Ile Gly Thr Thr Cys Lys Asn Thr Pro Val Pro Pro Gly Asp Cys
                165                 170                 175

Pro Pro Leu Glu Leu Val Ser Ser Val Ile Gln Asp Gly Asp Met Ile
            180                 185                 190

Asp Thr Gly Phe Gly Ala Met Asp Phe Ala Ala Leu Gln Ala Thr Lys
        195                 200                 205

Ser Asp Val Pro Leu Asp Ile Ser Gln Ser Val Cys Lys Tyr Pro Asp
    210                 215                 220

Tyr Leu Lys Met Ser Ala Asp Thr Tyr Gly Asn Ser Met Phe Phe His
225                 230                 235                 240

Leu Arg Arg Glu Gln Ile Phe Ala Arg His Phe Phe Asn Lys Ala Gly
                245                 250                 255

Thr Ile Gly Asp Pro Val Pro Val Ser Met Tyr Ile Lys Gly Ala Gly
            260                 265                 270

Gln Gly Arg Glu Pro Pro Thr Thr Ser Ile Tyr Ser Ala Thr Pro Ser
        275                 280                 285

Gly Ser Met Ile Thr Ser Asp Ser Gln Ile Phe Asn Lys Pro Tyr Trp
    290                 295                 300

Leu His Arg Ala Gln Gly His Asn Asn Gly Ile Cys Trp Asn Asn Gln
305                 310                 315                 320

Leu Phe Ile Thr Cys Val Asp Thr Thr Arg Ser Thr Asn Leu Thr Ile
                325                 330                 335

Ser Thr Ala Ser Ala Ala Ser Ala Ser Thr Pro Phe Lys Pro Ser Asp
            340                 345                 350

Phe Lys Gln Tyr Ile Arg His Gly Glu Glu Tyr Glu Leu Gln Phe Ile
        355                 360                 365

Phe Gln Leu Cys Lys Ile Thr Leu Thr Thr Glu Val Met Ala Tyr Leu
    370                 375                 380

His Thr Met Asp Pro Thr Ile Leu Glu Gln Trp Asn Phe Gly Leu Thr
385                 390                 395                 400
```

```
Leu Pro Pro Ser Ala Ser Leu Glu Asp Ala Tyr Arg Phe Val Arg Asn
                405                 410                 415

Ala Ala Thr Ser Cys Gln Lys Asp Thr Pro Pro Gln Ala Lys Pro Asp
            420                 425                 430

Pro Leu Ala Lys Tyr Lys Phe Trp Asp Val Asp Leu Lys Glu Arg Phe
        435                 440                 445

Ser Leu Asp Leu Asp Gln Phe Ala Leu Gly Arg Lys Phe Leu Leu Gln
    450                 455                 460

Val Gly Val Gln Arg Lys Pro Arg Pro Gly Leu Lys Arg Pro Ala Ser
465                 470                 475                 480

Ser Ala Ser Ser Ser Ser Ser Ser Ser Ala Lys Arg Lys Arg Val Lys
                485                 490                 495

Lys


<210> SEQ ID NO 48
<211> LENGTH: 1491
<212> TYPE: DNA
<213> ORGANISM: Artificial Sequence
<220> FEATURE:
<223> OTHER INFORMATION: The DNA sequence encoding H51N9-69T2-26S1

<400> SEQUENCE: 48

atgaaggtgt acctgccccc cgcccccgtg agcaggatcg tgaacaccga ggagtacatc      60

accaggaccg gcatctacta ctacgccggc agcagcaggc tgatcaccct gggccacccc     120

tacttctcta tcccgaaaac cggtcagaaa gctgaaatcc cgaaagtttc tgccttccag     180

tacagggtgt tcagggtgca gctccccgac cccaacaagt tcggcctgcc cgaccccaac     240

ctgtacaacc ccgacaccga caggctggtg tggggctgcg tgggcgtgga ggtgggtcgt     300

ggtcagccgc tgggtgtcgg tctgtctggt cacccgctgt tcaacaaact ggacgacacc     360

gaaaactctc acctggctac cgctaacgct gacaccgaca accgtgacaa cgtttgcgtt     420

gacaacaagc agacccagct gtgcatcatc ggctgcgccc cccccatcgg cgagcactgg     480

ggcatcggca ccacctgcaa gaacaccccc gtgccccccg gcgactgccc cccccctggag     540

ctggtgagca gcgtgatcca ggacggcgac atgatcgaca ccggcttcgg cgccatggac     600

ttcgccgccc tgcaggccac caagagcgac gtgcccctgg acatcagcca gagcgtgtgc     660

aagtaccccg actacctgaa gatgagcgcc gacacctacg gcaacagcat gttcttccac     720

ctgaggaggg agcagatctt cgccaggcac tactacaaca agctgggcag cgtgggcgag     780

gacatcccca ccgactacta catcaagggc agcggcaacg gcagggaccc catcgagagc     840

tacatctaca gcgccacccc cagcggcagc atgatcacca gcgacagcca gatcttcaac     900

aagccctact ggctgcacag ggcccagggc cacaacaacg gcatctgctg gaacaaccag     960

ctgttcatca cctgcgtgga caccaccagg agcaccaacc tgaccatcag caccgccacc    1020

gccgccgtga gccccacctt caccccccagc aacttcaagc agtacatcag gcacggcgag    1080

gagtacgagc tgcagttcat cttccagctg tgcaagatca ccctgaccac cgaggtgatg    1140

gcctacctgc acaccatgga ccccaccatc ctggagcagt ggaacttcgg cctgaccctg    1200

ccccccagcg ccagcctgga ggacgcctac aggttcgtga ggaacgccgc caccagctgc    1260

cagaaggaca cccccccccca ggccaagccc gacccccctgg ccaagtacaa gttctgggac    1320

gtggacctga aggagaggtt cagcctggac ctggaccagt tcgccctggg caggaagttc    1380

ctgctgcagg tgggcgtgca gaggaagccc aggcccggcc tgaagaggcc cgctagcagc    1440

gccagctcca gcagctccag cagcgccaag aggaagaggg tgaagaagta a             1491
```

<210> SEQ ID NO 49
<211> LENGTH: 1491
<212> TYPE: DNA
<213> ORGANISM: Artificial Sequence
<220> FEATURE:
<223> OTHER INFORMATION: The DNA sequence encoding H51N9-69T2-26S3

<400> SEQUENCE: 49
atgaaggtgt acctgccccc cgcccccgtg agcaggatcg tgaacaccga ggagtacatc 60
accaggaccg gcatctacta ctacgccggc agcagcaggc tgatcaccct gggccacccc 120
tacttccccc tgcccaagac cagcaccagg gccgccatcc ccaaggtgag cgccttccag 180
tacagggtgt tcagggtgca gctccccgac cccaacaagt tcggcctgcc cgaccccaac 240
ctgtacaacc ccgacaccga caggctggtg tggggctgcg tgggcgtgga ggtgggtcgt 300
ggtcagccgc tgggtgtcgg tctgtctggt cacccgctgt tcaacaaact ggacgacacc 360
gaaaactctc acctggctac cgctaacgct gacaccgaca accgtgacaa cgtttgcgtt 420
gacaacaagc agacccagct gtgcatcatc ggctgcgccc cccccatcgg cgagcactgg 480
ggtatcggta ccatctgcaa aaacacccag acccagcgtg gtgactgccc gccgctggag 540
ctggtgagca gcgtgatcca ggacggcgac atgatcgaca ccggcttcgg cgccatggac 600
ttcgccgccc tgcaggccac caagagcgac gtgcccctgg acatcagcca gagcgtgtgc 660
aagtaccccg actacctgaa gatgagcgcc gacacctacg gcaacagcat gttcttccac 720
ctgaggaggg agcagatctt cgccaggcac tactacaaca agctgggcag cgtgggcgag 780
gacatcccca ccgactacta catcaagggc agcggcaacg gcagggaccc catcgagagc 840
tacatctaca gcgccacccc cagcggcagc atgatcacca gcgacagcca gatcttcaac 900
aagccctact ggctgcacag ggcccagggc cacaacaacg gcatctgctg gaacaaccag 960
ctgttcatca cctgcgtgga caccaccagg agcaccaacc tgaccatcag caccgccacc 1020
gccgccgtga gccccacctt cacccccagc aacttcaagc agtacatcag gcacggcgag 1080
gagtacgagc tgcagttcat cttccagctg tgcaagatca ccctgaccac cgaggtgatg 1140
gcctacctgc acaccatgga ccccaccatc ctggagcagt ggaacttcgg cctgaccctg 1200
ccccccagcg ccagcctgga ggacgcctac aggttcgtga ggaacgccgc caccagctgc 1260
cagaaggaca ccccccccca ggccaagccc gacccccctgg ccaagtacaa gttctgggac 1320
gtggacctga aggagaggtt cagcctggac ctggaccagt tcgccctggg caggaagttc 1380
ctgctgcagg tgggcgtgca gaggaagccc aggcccggcc tgaagaggcc cgctagcagc 1440
gccagctcca gcagctccag cagcgccaag aggaagaggg tgaagaagta a 1491

<210> SEQ ID NO 50
<211> LENGTH: 1491
<212> TYPE: DNA
<213> ORGANISM: Artificial Sequence
<220> FEATURE:
<223> OTHER INFORMATION: The DNA sequence encoding H51N9-69T2-26S4

<400> SEQUENCE: 50
atgaaggtgt acctgccccc cgcccccgtg agcaggatcg tgaacaccga ggagtacatc 60
accaggaccg gcatctacta ctacgccggc agcagcaggc tgatcaccct gggccacccc 120
tacttccccc tgcccaagac cagcaccagg gccgccatcc ccaaggtgag cgccttccag 180
tacagggtgt tcagggtgca gctccccgac cccaacaagt tcggcctgcc cgaccccaac 240
ctgtacaacc ccgacaccga caggctggtg tggggctgcg tgggcgtgga ggtgggtcgt 300
ggtcagccgc tgggtgtcgg tctgtctggt cacccgctgt tcaacaaact ggacgacacc 360
gaaaactctc acctggctac cgctaacgct gacaccgaca accgtgacaa cgtttgcgtt 420
gacaacaagc agacccagct gtgcatcatc ggctgcgccc cccccatcgg cgagcactgg 480
ggcatcggca ccacctgcaa gaacaccccc gtgccccccg gcgactgccc ccccctggag 540
ctggtgagca gcgtgatcca ggacggcgac atgatcgaca ccggcttcgg cgccatggac 600
ttcgccgccc tgcaggccac caagagcgac gtgcccctgg acatcagcca gagcgtgtgc 660
aagtaccccg actacctgaa gatgagcgcc gacacctacg gcaacagcat gttcttccac 720
ctgaggaggg agcagatctt cgccaggcac ttctacaaca aagctggtgc tgttggtgac 780
gctatcccga ccaccctgta catcaaaggt gctgaatctg gtcgtgaacc gccgacctct 840
tctatctact ctgccacccc cagcggcagc atgatcacca gcgacagcca gatcttcaac 900
aagccctact ggctgcacag ggcccagggc cacaacaacg gcatctgctg gaacaaccag 960
ctgttcatca cctgcgtgga caccaccagg agcaccaacc tgaccatcag caccgccacc 1020
gccgccgtga gccccacctt cacccccagc aacttcaagc agtacatcag gcacggcgag 1080
gagtacgagc tgcagttcat cttccagctg tgcaagatca ccctgaccac cgaggtgatg 1140
gcctacctgc acaccatgga ccccaccatc ctggagcagt ggaacttcgg cctgaccctg 1200
ccccccagcg ccagcctgga ggacgcctac aggttcgtga ggaacgccgc caccagctgc 1260
cagaaggaca cccccccccca ggccaagccc gaccccctgg ccaagtacaa gttctgggac 1320
gtggacctga aggagaggtt cagcctggac ctggaccagt tcgccctggg caggaagttc 1380
ctgctgcagg tgggcgtgca gaggaagccc aggcccggcc tgaagaggcc cgctagcagc 1440
gccagctcca gcagctccag cagcgccaag aggaagaggg tgaagaagta a 1491

<210> SEQ ID NO 51
<211> LENGTH: 1494
<212> TYPE: DNA
<213> ORGANISM: Artificial Sequence
<220> FEATURE:
<223> OTHER INFORMATION: The DNA sequence encoding H51N9-69T2-26S5

<400> SEQUENCE: 51
atgaaggtgt acctgccccc cgcccccgtg agcaggatcg tgaacaccga ggagtacatc 60
accaggaccg gcatctacta ctacgccggc agcagcaggc tgatcaccct gggccacccc 120
tacttccccc tgcccaagac cagcaccagg gccgccatcc ccaaggtgag cgccttccag 180
tacagggtgt tcagggtgca gctccccgac cccaacaagt tcggcctgcc cgaccccaac 240
ctgtacaacc ccgacaccga caggctggtg tggggctgcg tgggcgtgga ggtgggtcgt 300
ggtcagccgc tgggtgtcgg tctgtctggt cacccgctgt tcaacaaact ggacgacacc 360
gaaaactctc acctggctac cgctaacgct gacaccgaca accgtgacaa cgtttgcgtt 420
gacaacaagc agacccagct gtgcatcatc ggctgcgccc cccccatcgg cgagcactgg 480
ggcatcggca ccacctgcaa gaacaccccc gtgccccccg gcgactgccc ccccctggag 540
ctggtgagca gcgtgatcca ggacggcgac atgatcgaca ccggcttcgg cgccatggac 600
ttcgccgccc tgcaggccac caagagcgac gtgcccctgg acatcagcca gagcgtgtgc 660
aagtaccccg actacctgaa gatgagcgcc gacacctacg gcaacagcat gttcttccac 720
ctgaggaggg agcagatctt cgccaggcac tactacaaca agctgggcag cgtgggcgag 780
gacatcccca ccgactacta catcaagggc agcggcaacg gcagggaccc catcgagagc 840
tacatctaca gcgccacccc cagcggcagc atgatcacca gcgacagcca gatcttcaac 900
aagccctact ggctgcacag ggcccagggc cacaacaacg gcatctgctg gaacaaccag 960
ctgttcatca cctgcgtgga caccaccagg agcaccaacc tgaccatcag caccgcctct 1020
gctgcttctg cttctacccc gttcaaaccg tctgacttca agcagtacat caggcacggc 1080
gaggagtacg agctgcagtt catcttccag ctgtgcaaga tcaccctgac caccgaggtg 1140
atggcctacc tgcacaccat ggaccccacc atcctggagc agtggaactt cggcctgacc 1200
ctgcccccca gcgccagcct ggaggacgcc tacaggttcg tgaggaacgc cgccaccagc 1260
tgccagaagg acaccccccc ccaggccaag cccgaccccc tggccaagta caagttctgg 1320
gacgtggacc tgaaggagag gttcagcctg gacctggacc agttcgccct gggcaggaag 1380
ttcctgctgc aggtgggcgt gcagaggaag cccaggcccg gcctgaagag gcccgctagc 1440
agcgccagct ccagcagctc cagcagcgcc aagaggaaga gggtgaagaa gtaa 1494

<210> SEQ ID NO 52
<211> LENGTH: 1491
<212> TYPE: DNA
<213> ORGANISM: Artificial Sequence
<220> FEATURE:
<223> OTHER INFORMATION: The DNA sequence encoding H51N9-69T4-26S1

<400> SEQUENCE: 52
atgaaggtgt acctgccccc cgcccccgtg agcaggatcg tgaacaccga ggagtacatc 60
accaggaccg gcatctacta ctacgccggc agcagcaggc tgatcaccct gggccacccc 120
tacttctcta tcccgaaaac cggtcagaaa gctgaaatcc cgaaagtttc tgccttccag 180
tacagggtgt tcagggtgca gctccccgac cccaacaagt tcggcctgcc cgaccccaac 240
ctgtacaacc ccgacaccga caggctggtg tggggctgcg tgggcgtgga ggtgggcagg 300
ggccagcccc tgggcgtggg cctgagcggc cacccccctgt tcaacaagta cgacgacacc 360
gagaacagca ggatcgccaa cggcaacgcc cagcaggacg tgagggacaa caccagcgtg 420
gacaacaagc agacccagct gtgcatcatc ggctgcgccc cccccatcgg cgagcactgg 480
ggcatcggca ccacctgcaa gaacaccccc gtgccccccg gcgactgccc ccccctggag 540
ctggtgagca gcgtgatcca ggacggcgac atgatcgaca ccggcttcgg cgccatggac 600
ttcgccgccc tgcaggccac caagagcgac gtgcccctgg acatcagcca gagcgtgtgc 660
aagtaccccg actacctgaa gatgagcgcc gacacctacg gcaacagcat gttcttccac 720
ctgaggaggg agcagatctt cgccaggcac ttcttcaaca aagctggtac catcggtgac 780
cctgttccgg tttctatgta catcaaaggt gctggtcagg gtcgtgaacc gccgaccaca 840
tccatctact ctgccacccc cagcggcagc atgatcacca gcgacagcca gatcttcaac 900
aagccctact ggctgcacag ggcccagggc cacaacaacg gcatctgctg gaacaaccag 960
ctgttcatca cctgcgtgga caccaccagg agcaccaacc tgaccatcag caccgccacc 1020
gccgccgtga gccccacctt cacccccagc aacttcaagc agtacatcag gcacggcgag 1080
gagtacgagc tgcagttcat cttccagctg tgcaagatca ccctgaccac cgaggtgatg 1140
gcctacctgc acaccatgga ccccaccatc ctggagcagt ggaacttcgg cctgaccctg 1200
ccccccagcg ccagcctgga ggacgcctac aggttcgtga ggaacgccgc caccagctgc 1260
cagaaggaca ccccccccca ggccaagccc gacccccctgg ccaagtacaa gttctgggac 1320
gtggacctga aggagaggtt cagcctggac ctggaccagt tcgccctggg caggaagttc 1380
ctgctgcagg tgggcgtgca gaggaagccc aggcccggcc tgaagaggcc cgctagcagc 1440
gccagctcca gcagctccag cagcgccaag aggaagaggg tgaagaagta a 1491

<210> SEQ ID NO 53
<211> LENGTH: 1491
<212> TYPE: DNA
<213> ORGANISM: Artificial Sequence
<220> FEATURE:
<223> OTHER INFORMATION: The DNA sequence encoding H51N9-69T4-26S2

<400> SEQUENCE: 53
atgaaggtgt acctgccccc cgcccccgtg agcaggatcg tgaacaccga ggagtacatc 60
accaggaccg gcatctacta ctacgccggc agcagcaggc tgatcaccct gggccacccc 120
tacttccccc tgcccaagac cagcaccagg gccgccatcc ccaaggtgag cgccttccag 180
tacagggtgt tcagggtgca gctccccgac cccaacaagt tcggcctgcc cgaccccaac 240
ctgtacaacc ccgacaccga caggctggtg tggggctgcg tgggcgtgga ggtgggtcgt 300
ggtcagccgc tgggtatcgg tctgtctggt cacccgctgt tcaacaaact ggacgacacc 360
gaaaactctc acctggctac cgttaacgct gacaccgaca accgtgacaa cgtttctgtt 420
gacaacaagc agacccagct gtgcatcatc ggctgcgccc cccccatcgg cgagcactgg 480
ggcatcggca ccacctgcaa gaacaccccc gtgccccccg gcgactgccc cccccctggag 540 ctggtgagca gcgtgatcca ggacggcgac atgatcgaca ccggcttcgg cgccatggac 600
ttcgccgccc tgcaggccac caagagcgac gtgcccctgg acatcagcca gagcgtgtgc 660
aagtaccccg actacctgaa gatgagcgcc gacacctacg gcaacagcat gttcttccac 720
ctgaggaggg agcagatctt cgccaggcac ttcttcaaca aagctggtac catcggtgac 780
cctgttccgg tttctatgta catcaaaggt gctggtcagg gtcgtgaacc gccgaccaca 840
tccatctact ctgccacccc cagcggcagc atgatcacca gcgacagcca gatcttcaac 900
aagccctact ggctgcacag ggcccagggc cacaacaacg gcatctgctg gaacaaccag 960
ctgttcatca cctgcgtgga caccaccagg agcaccaacc tgaccatcag caccgccacc 1020
gccgccgtga gccccacctt cacccccagc aacttcaagc agtacatcag gcacggcgag 1080
gagtacgagc tgcagttcat cttccagctg tgcaagatca ccctgaccac cgaggtgatg 1140
gcctacctgc acaccatgga ccccaccatc ctggagcagt ggaacttcgg cctgaccctg 1200
ccccccagcg ccagcctgga ggacgcctac aggttcgtga ggaacgccgc caccagctgc 1260
cagaaggaca cccccccccca ggccaagccc gacccccctgg ccaagtacaa gttctgggac 1320
gtggacctga aggagaggtt cagcctggac ctggaccagt tcgccctggg caggaagttc 1380
ctgctgcagg tgggcgtgca gaggaagccc aggcccggcc tgaagaggcc cgctagcagc 1440
gccagctcca gcagctccag cagcgccaag aggaagaggg tgaagaagta a 1491

<210> SEQ ID NO 54
<211> LENGTH: 1491
<212> TYPE: DNA
<213> ORGANISM: Artificial Sequence
<220> FEATURE:
<223> OTHER INFORMATION: The DNA sequence encoding H51N9-69T4-26S3

<400> SEQUENCE: 54
atgaaggtgt acctgccccc cgcccccgtg agcaggatcg tgaacaccga ggagtacatc 60
accaggaccg gcatctacta ctacgccggc agcagcaggc tgatcaccct gggccacccc 120
tacttccccc tgcccaagac cagcaccagg gccgccatcc ccaaggtgag cgccttccag 180
tacagggtgt tcagggtgca gctccccgac cccaacaagt tcggcctgcc cgaccccaac 240
ctgtacaacc ccgacaccga caggctggtg tggggctgcg tgggcgtgga ggtgggcagg 300
ggccagcccc tgggcgtggg cctgagcggc cacccccctgt tcaacaagta cgacgacacc 360
gagaacagca ggatcgccaa cggcaacgcc cagcaggacg tgagggacaa caccagcgtg 420
gacaacaagc agacccagct gtgcatcatc ggctgcgccc cccccatcgg cgagcactgg 480
ggtatcggta ccatctgcaa aaacacccag acccagcgtg gtgactgccc gccgctggag 540
ctggtgagca gcgtgatcca ggacggcgac atgatcgaca ccggcttcgg cgccatggac 600
ttcgccgccc tgcaggccac caagagcgac gtgcccctgg acatcagcca gagcgtgtgc 660
aagtaccccg actacctgaa gatgagcgcc gacacctacg gcaacagcat gttcttccac 720
ctgaggaggg agcagatctt cgccaggcac ttcttcaaca aagctggtac catcggtgac 780
cctgttccgg tttctatgta catcaaaggt gctggtcagg gtcgtgaacc gccgaccaca 840
tccatctact ctgccacccc cagcggcagc atgatcacca gcgacagcca gatcttcaac 900
aagccctact ggctgcacag ggcccagggc cacaacaacg gcatctgctg gaacaaccag 960
ctgttcatca cctgcgtgga caccaccagg agcaccaacc tgaccatcag caccgccacc 1020
gccgccgtga gccccacctt cacccccagc aacttcaagc agtacatcag gcacggcgag 1080
gagtacgagc tgcagttcat cttccagctg tgcaagatca ccctgaccac cgaggtgatg 1140
gcctacctgc acaccatgga ccccaccatc ctggagcagt ggaacttcgg cctgaccctg 1200
ccccccagcg ccagcctgga ggacgcctac aggttcgtga ggaacgccgc caccagctgc 1260
cagaaggaca cccccccccca ggccaagccc gaccccctgg ccaagtacaa gttctgggac 1320
gtggacctga aggagaggtt cagcctggac ctggaccagt tcgccctggg caggaagttc 1380
ctgctgcagg tgggcgtgca gaggaagccc aggcccggcc tgaagaggcc cgctagcagc 1440
gccagctcca gcagctccag cagcgccaag aggaagaggg tgaagaagta a 1491

<210> SEQ ID NO 55
<211> LENGTH: 1494
<212> TYPE: DNA
<213> ORGANISM: Artificial Sequence
<220> FEATURE:
<223> OTHER INFORMATION: The DNA sequence encoding H51N9-69T4-26S5

<400> SEQUENCE: 55
atgaaggtgt acctgccccc cgcccccgtg agcaggatcg tgaacaccga ggagtacatc 60
accaggaccg gcatctacta ctacgccggc agcagcaggc tgatcaccct gggccacccc 120
tacttccccc tgcccaagac cagcaccagg gccgccatcc ccaaggtgag cgccttccag 180
tacagggtgt tcagggtgca gctccccgac cccaacaagt tcggcctgcc cgaccccaac 240
ctgtacaacc ccgacaccga caggctggtg tggggctgcg tgggcgtgga ggtgggcagg 300
ggccagcccc tgggcgtggg cctgagcggc cacccccctgt tcaacaagta cgacgacacc 360
gagaacagca ggatcgccaa cggcaacgcc cagcaggacg tgagggacaa caccagcgtg 420
gacaacaagc agacccagct gtgcatcatc ggctgcgccc cccccatcgg cgagcactgg 480
ggcatcggca ccacctgcaa gaacaccccc gtgccccccg gcgactgccc cccccctggag 540 ctggtgagca gcgtgatcca ggacggcgac atgatcgaca ccggcttcgg cgccatggac 600
ttcgccgccc tgcaggccac caagagcgac gtgcccctgg acatcagcca gagcgtgtgc 660
aagtaccccg actacctgaa gatgagcgcc gacacctacg gcaacagcat gttcttccac 720

```
ctgaggaggg agcagatctt cgccaggcac ttcttcaaca aagctggtac catcggtgac    780

cctgttccgg tttctatgta catcaaaggt gctggtcagg gtcgtgaacc gccgaccaca    840

tccatctact ctgccacccc cagcggcagc atgatcacca gcgacagcca gatcttcaac    900

aagccctact ggctgcacag ggcccagggc cacaacaacg gcatctgctg gaacaaccag    960

ctgttcatca cctgcgtgga caccaccagg agcaccaacc tgaccatcag caccgcctct   1020

gctgcttctg cttctacccc gttcaaaccg tctgacttca agcagtacat caggcacggc   1080

gaggagtacg agctgcagtt catcttccag ctgtgcaaga tcaccctgac caccgaggtg   1140

atggcctacc tgcacaccat ggaccccacc atcctggagc agtggaactt cggcctgacc   1200

ctgcccccca gcgccagcct ggaggacgcc tacaggttcg tgaggaacgc cgccaccagc   1260

tgccagaagg acaccccccc ccaggccaag cccgaccccc tggccaagta caagttctgg   1320

gacgtggacc tgaaggagag gttcagcctg gacctggacc agttcgccct gggcaggaag   1380

ttcctgctgc aggtgggcgt gcagaggaag cccaggcccg gcctgaagag gcccgctagc   1440

agcgccagct ccagcagctc cagcagcgcc aagaggaaga gggtgaagaa gtaa         1494
```

```
<210> SEQ ID NO 56
<211> LENGTH: 10
<212> TYPE: PRT
<213> ORGANISM: Human papillomavirus type 26

<400> SEQUENCE: 56

Ser Ile Pro Lys Thr Gly Gln Lys Ala Glu
1               5                   10


<210> SEQ ID NO 57
<211> LENGTH: 33
<212> TYPE: PRT
<213> ORGANISM: Human papillomavirus type 26

<400> SEQUENCE: 57

Ile Gly Leu Ser Gly His Pro Leu Phe Asn Lys Leu Asp Asp Thr Glu
1               5                   10                  15

Asn Ser His Leu Ala Thr Val Asn Ala Asp Thr Asp Asn Arg Asp Asn
            20                  25                  30

Val


<210> SEQ ID NO 58
<211> LENGTH: 9
<212> TYPE: PRT
<213> ORGANISM: Human papillomavirus type 26

<400> SEQUENCE: 58

Ile Cys Lys Asn Thr Gln Thr Gln Arg
1               5


<210> SEQ ID NO 59
<211> LENGTH: 31
<212> TYPE: PRT
<213> ORGANISM: Human papillomavirus type 26

<400> SEQUENCE: 59

Phe Tyr Asn Lys Ala Gly Ala Val Gly Asp Ala Ile Pro Thr Thr Leu
1               5                   10                  15

Tyr Ile Lys Gly Ala Glu Ser Gly Arg Glu Pro Pro Thr Ser Ser
            20                  25                  30
```

```
<210> SEQ ID NO 60
<211> LENGTH: 13
<212> TYPE: PRT
<213> ORGANISM: Human papillomavirus type 26

<400> SEQUENCE: 60

Ser Ala Ala Ser Ala Ser Thr Pro Phe Lys Pro Ser Asp
1               5                   10


<210> SEQ ID NO 61
<211> LENGTH: 24
<212> TYPE: DNA
<213> ORGANISM: Artificial Sequence
<220> FEATURE:
<223> OTHER INFORMATION: Primer

<400> SEQUENCE: 61

gtaggggtgg cccagggtga tcag                                            24


<210> SEQ ID NO 62
<211> LENGTH: 24
<212> TYPE: DNA
<213> ORGANISM: Artificial Sequence
<220> FEATURE:
<223> OTHER INFORMATION: Primer

<400> SEQUENCE: 62

gccttccagt acagggtgtt cagg                                            24


<210> SEQ ID NO 63
<211> LENGTH: 24
<212> TYPE: DNA
<213> ORGANISM: Artificial Sequence
<220> FEATURE:
<223> OTHER INFORMATION: Primer

<400> SEQUENCE: 63

cacctccacg cccacgcagc ccca                                            24


<210> SEQ ID NO 64
<211> LENGTH: 24
<212> TYPE: DNA
<213> ORGANISM: Artificial Sequence
<220> FEATURE:
<223> OTHER INFORMATION: Primer

<400> SEQUENCE: 64

acaagcagac ccagctgtgc atca                                            24


<210> SEQ ID NO 65
<211> LENGTH: 39
<212> TYPE: DNA
<213> ORGANISM: Artificial Sequence
<220> FEATURE:
<223> OTHER INFORMATION: Primer

<400> SEQUENCE: 65

ctcgccgatg gggggggcgc agccgatgat gcacagctg                             39


<210> SEQ ID NO 66
<211> LENGTH: 39
<212> TYPE: DNA
<213> ORGANISM: Artificial Sequence
<220> FEATURE:
<223> OTHER INFORMATION: Primer

<400> SEQUENCE: 66
```

ccctggagct ggtgagcagc gtgatccagg acggcgaca 39

<210> SEQ ID NO 67
<211> LENGTH: 24
<212> TYPE: DNA
<213> ORGANISM: Artificial Sequence
<220> FEATURE:
<223> OTHER INFORMATION: Primer

<400> SEQUENCE: 67
gtgcctggcg aagatctgct ccct 24

<210> SEQ ID NO 68
<211> LENGTH: 24
<212> TYPE: DNA
<213> ORGANISM: Artificial Sequence
<220> FEATURE:
<223> OTHER INFORMATION: Primer

<400> SEQUENCE: 68
gccaccccca gcggcagcat gatc 24

<210> SEQ ID NO 69
<211> LENGTH: 24
<212> TYPE: DNA
<213> ORGANISM: Artificial Sequence
<220> FEATURE:
<223> OTHER INFORMATION: Primer

<400> SEQUENCE: 69
ggcggtgctg atggtcaggt tggt 24

<210> SEQ ID NO 70
<211> LENGTH: 24
<212> TYPE: DNA
<213> ORGANISM: Artificial Sequence
<220> FEATURE:
<223> OTHER INFORMATION: Primer

<400> SEQUENCE: 70
acttcaagca gtacatcagg cacg 24

<210> SEQ ID NO 71
<211> LENGTH: 45
<212> TYPE: DNA
<213> ORGANISM: Artificial Sequence
<220> FEATURE:
<223> OTHER INFORMATION: Primer

<400> SEQUENCE: 71
ctgatcaccc tgggccaccc ctacttcccg atcccgaaat ctggt 45

<210> SEQ ID NO 72
<211> LENGTH: 45
<212> TYPE: DNA
<213> ORGANISM: Artificial Sequence
<220> FEATURE:
<223> OTHER INFORMATION: Primer

<400> SEQUENCE: 72
cctgaacacc ctgtactgga aggcagagac cttcgggatt tcagc 45

<210> SEQ ID NO 73
<211> LENGTH: 42
<212> TYPE: DNA

<213> ORGANISM: Artificial Sequence
<220> FEATURE:
<223> OTHER INFORMATION: Primer

<400> SEQUENCE: 73
tggggctgcg tgggcgtgga ggtgggtcgt ggtcagccgc tg 42

<210> SEQ ID NO 74
<211> LENGTH: 45
<212> TYPE: DNA
<213> ORGANISM: Artificial Sequence
<220> FEATURE:
<223> OTHER INFORMATION: Primer

<400> SEQUENCE: 74
tgatgcacag ctgggtctgc ttgttgtcaa cgcaaacgtt gtcac 45

<210> SEQ ID NO 75
<211> LENGTH: 45
<212> TYPE: DNA
<213> ORGANISM: Artificial Sequence
<220> FEATURE:
<223> OTHER INFORMATION: Primer

<400> SEQUENCE: 75
ggctgcgccc cccccatcgg cgagcactgg ggtgtcggta ccgtt 45

<210> SEQ ID NO 76
<211> LENGTH: 45
<212> TYPE: DNA
<213> ORGANISM: Artificial Sequence
<220> FEATURE:
<223> OTHER INFORMATION: Primer

<400> SEQUENCE: 76
tcacgctgct caccagctcc aggggcgggc agtcaccacg ctgaa 45

<210> SEQ ID NO 77
<211> LENGTH: 45
<212> TYPE: DNA
<213> ORGANISM: Artificial Sequence
<220> FEATURE:
<223> OTHER INFORMATION: Primer

<400> SEQUENCE: 77
agggagcaga tcttcgccag gcacttcttc aacaaagctg gtacc 45

<210> SEQ ID NO 78
<211> LENGTH: 45
<212> TYPE: DNA
<213> ORGANISM: Artificial Sequence
<220> FEATURE:
<223> OTHER INFORMATION: Primer

<400> SEQUENCE: 78
gatcatgctg ccgctggggg tggcagagta gatggatgtg gtcgg 45

<210> SEQ ID NO 79
<211> LENGTH: 45
<212> TYPE: DNA
<213> ORGANISM: Artificial Sequence
<220> FEATURE:
<223> OTHER INFORMATION: Primer

<400> SEQUENCE: 79
accaacctga ccatcagcac cgcctctgct cagtctgctt ctgct 45

<210> SEQ ID NO 80
<211> LENGTH: 45
<212> TYPE: DNA
<213> ORGANISM: Artificial Sequence
<220> FEATURE:
<223> OTHER INFORMATION: Primer

<400> SEQUENCE: 80
cgtgcctgat gtactgcttg aagtcagacg gtttgaaggt agcag 45

<210> SEQ ID NO 81
<211> LENGTH: 45
<212> TYPE: DNA
<213> ORGANISM: Artificial Sequence
<220> FEATURE:
<223> OTHER INFORMATION: Primer

<400> SEQUENCE: 81
tggggctgcg tgggcgtgga ggtgggtcgt ggtcagccgc tgggt 45

<210> SEQ ID NO 82
<211> LENGTH: 45
<212> TYPE: DNA
<213> ORGANISM: Artificial Sequence
<220> FEATURE:
<223> OTHER INFORMATION: Primer

<400> SEQUENCE: 82
gggggcgcag ccgatgatgc acagctgggt ctgtttgttg tcaac 45

<210> SEQ ID NO 83
<211> LENGTH: 24
<212> TYPE: DNA
<213> ORGANISM: Artificial Sequence
<220> FEATURE:
<223> OTHER INFORMATION: Primer

<400> SEQUENCE: 83
cacctccacg cccacgcagc ccca 24

<210> SEQ ID NO 84
<211> LENGTH: 31
<212> TYPE: DNA
<213> ORGANISM: Artificial Sequence
<220> FEATURE:
<223> OTHER INFORMATION: Primer

<400> SEQUENCE: 84
ctgtgcatca tcggctgcgc tccccccatc g 31

<210> SEQ ID NO 85
<211> LENGTH: 45
<212> TYPE: DNA
<213> ORGANISM: Artificial Sequence
<220> FEATURE:
<223> OTHER INFORMATION: Primer

<400> SEQUENCE: 85
atcatcggct gcgccccccc catcggtgaa cactggggta tcggt 45

<210> SEQ ID NO 86
<211> LENGTH: 42
<212> TYPE: DNA
<213> ORGANISM: Artificial Sequence
<220> FEATURE:

<223> OTHER INFORMATION: Primer

<400> SEQUENCE: 86
gccgtcctgg atcacgctgc tcaccagttc cagcggcggg ca          42

<210> SEQ ID NO 87
<211> LENGTH: 24
<212> TYPE: DNA
<213> ORGANISM: Artificial Sequence
<220> FEATURE:
<223> OTHER INFORMATION: Primer

<400> SEQUENCE: 87
gatggggggg gcgcagccga tgat          24

<210> SEQ ID NO 88
<211> LENGTH: 24
<212> TYPE: DNA
<213> ORGANISM: Artificial Sequence
<220> FEATURE:
<223> OTHER INFORMATION: Primer

<400> SEQUENCE: 88
gtgagcagcg tgatccagga cggc          24

<210> SEQ ID NO 89
<211> LENGTH: 54
<212> TYPE: DNA
<213> ORGANISM: Artificial Sequence
<220> FEATURE:
<223> OTHER INFORMATION: Primer

<400> SEQUENCE: 89
tacggcaaca gcatgttctt ccacctgcgt cgtgaacaga tcttcgctcg tcac          54

<210> SEQ ID NO 90
<211> LENGTH: 45
<212> TYPE: DNA
<213> ORGANISM: Artificial Sequence
<220> FEATURE:
<223> OTHER INFORMATION: Primer

<400> SEQUENCE: 90
gctgtcgctg gtgatcatgc tgccagacgg ggtagcagag tagat          45

<210> SEQ ID NO 91
<211> LENGTH: 24
<212> TYPE: DNA
<213> ORGANISM: Artificial Sequence
<220> FEATURE:
<223> OTHER INFORMATION: Primer

<400> SEQUENCE: 91
gtggaagaac atgctgttgc cgta          24

<210> SEQ ID NO 92
<211> LENGTH: 24
<212> TYPE: DNA
<213> ORGANISM: Artificial Sequence
<220> FEATURE:
<223> OTHER INFORMATION: Primer

<400> SEQUENCE: 92
ggcagcatga tcaccagcga cagc          24

<210> SEQ ID NO 93
<211> LENGTH: 54
<212> TYPE: DNA
<213> ORGANISM: Artificial Sequence
<220> FEATURE:
<223> OTHER INFORMATION: Primer

<400> SEQUENCE: 93
ttcatcacct gcgtggacac cacccgttct accaacctga ccatctctac cgcg 54

<210> SEQ ID NO 94
<211> LENGTH: 57
<212> TYPE: DNA
<213> ORGANISM: Artificial Sequence
<220> FEATURE:
<223> OTHER INFORMATION: Primer

<400> SEQUENCE: 94
cagctggaag atgaactgca gctcgtattc ttcaccgtga cggatgtact gtttgaa 57

<210> SEQ ID NO 95
<211> LENGTH: 27
<212> TYPE: DNA
<213> ORGANISM: Artificial Sequence
<220> FEATURE:
<223> OTHER INFORMATION: Primer

<400> SEQUENCE: 95
ggtggtgtcc acgcaggtga tgaacag 27

<210> SEQ ID NO 96
<211> LENGTH: 24
<212> TYPE: DNA
<213> ORGANISM: Artificial Sequence
<220> FEATURE:
<223> OTHER INFORMATION: Primer

<400> SEQUENCE: 96
gagctgcagt tcatcttcca gctg 24

<210> SEQ ID NO 97
<211> LENGTH: 42
<212> TYPE: DNA
<213> ORGANISM: Artificial Sequence
<220> FEATURE:
<223> OTHER INFORMATION: Primer

<400> SEQUENCE: 97
tacgccggca gcagcaggct gatcaccctg ggtcacccgt ac 42

<210> SEQ ID NO 98
<211> LENGTH: 42
<212> TYPE: DNA
<213> ORGANISM: Artificial Sequence
<220> FEATURE:
<223> OTHER INFORMATION: Primer

<400> SEQUENCE: 98
caccctgaac accctgtact ggaaagcaga aactttcggg at 42

<210> SEQ ID NO 99
<211> LENGTH: 24
<212> TYPE: DNA
<213> ORGANISM: Artificial Sequence
<220> FEATURE:
<223> OTHER INFORMATION: Primer

<400> SEQUENCE: 99
gatcagcctg ctgctgccgg cgta 24

<210> SEQ ID NO 100
<211> LENGTH: 24
<212> TYPE: DNA
<213> ORGANISM: Artificial Sequence
<220> FEATURE:
<223> OTHER INFORMATION: Primer

<400> SEQUENCE: 100
ttccagtaca gggtgttcag ggtg 24

<210> SEQ ID NO 101
<211> LENGTH: 45
<212> TYPE: DNA
<213> ORGANISM: Artificial Sequence
<220> FEATURE:
<223> OTHER INFORMATION: Primer

<400> SEQUENCE: 101
tggggctgcg tgggcgtgga ggtgggtcgt ggtcagccgc tgggt 45

<210> SEQ ID NO 102
<211> LENGTH: 45
<212> TYPE: DNA
<213> ORGANISM: Artificial Sequence
<220> FEATURE:
<223> OTHER INFORMATION: Primer

<400> SEQUENCE: 102
gggggcgcag ccgatgatgc acagctgggt ctgtttgttg tcaac 45

<210> SEQ ID NO 103
<211> LENGTH: 24
<212> TYPE: DNA
<213> ORGANISM: Artificial Sequence
<220> FEATURE:
<223> OTHER INFORMATION: Primer

<400> SEQUENCE: 103
cacctccacg cccacgcagc ccca 24

<210> SEQ ID NO 104
<211> LENGTH: 31
<212> TYPE: DNA
<213> ORGANISM: Artificial Sequence
<220> FEATURE:
<223> OTHER INFORMATION: Primer

<400> SEQUENCE: 104
ctgtgcatca tcggctgcgc tccccccatc g 31

<210> SEQ ID NO 105
<211> LENGTH: 54
<212> TYPE: DNA
<213> ORGANISM: Artificial Sequence
<220> FEATURE:
<223> OTHER INFORMATION: Primer

<400> SEQUENCE: 105
tacggcaaca gcatgttctt ccacctgcgt cgtgaacaga tcttcgctcg tcac 54

<210> SEQ ID NO 106
<211> LENGTH: 45

<212> TYPE: DNA
<213> ORGANISM: Artificial Sequence
<220> FEATURE:
<223> OTHER INFORMATION: Primer

<400> SEQUENCE: 106
gctgtcgctg gtgatcatgc tgccagacgg ggtagcagag tagat 45

<210> SEQ ID NO 107
<211> LENGTH: 24
<212> TYPE: DNA
<213> ORGANISM: Artificial Sequence
<220> FEATURE:
<223> OTHER INFORMATION: Primer

<400> SEQUENCE: 107
gtggaagaac atgctgttgc cgta 24

<210> SEQ ID NO 108
<211> LENGTH: 24
<212> TYPE: DNA
<213> ORGANISM: Artificial Sequence
<220> FEATURE:
<223> OTHER INFORMATION: Primer

<400> SEQUENCE: 108
ggcagcatga tcaccagcga cagc 24

<210> SEQ ID NO 109
<211> LENGTH: 51
<212> TYPE: DNA
<213> ORGANISM: Artificial Sequence
<220> FEATURE:
<223> OTHER INFORMATION: Primer

<400> SEQUENCE: 109
ttcatcacct gcgtggacac cacccgttct accaacctga ccatctctac c 51

<210> SEQ ID NO 110
<211> LENGTH: 57
<212> TYPE: DNA
<213> ORGANISM: Artificial Sequence
<220> FEATURE:
<223> OTHER INFORMATION: Primer

<400> SEQUENCE: 110
cagctggaag atgaactgca gctcgtattc ttcaccgtga cggatgtact gtttgaa 57

<210> SEQ ID NO 111
<211> LENGTH: 27
<212> TYPE: DNA
<213> ORGANISM: Artificial Sequence
<220> FEATURE:
<223> OTHER INFORMATION: Primer

<400> SEQUENCE: 111
ggtggtgtcc acgcaggtga tgaacag 27

<210> SEQ ID NO 112
<211> LENGTH: 24
<212> TYPE: DNA
<213> ORGANISM: Artificial Sequence
<220> FEATURE:
<223> OTHER INFORMATION: Primer

<400> SEQUENCE: 112
gagctgcagt tcatcttcca gctg 24

<210> SEQ ID NO 113
<211> LENGTH: 42
<212> TYPE: DNA
<213> ORGANISM: Artificial Sequence
<220> FEATURE:
<223> OTHER INFORMATION: Primer

<400> SEQUENCE: 113
tacgccggca gcagcaggct gatcaccctg ggtcacccgt ac 42

<210> SEQ ID NO 114
<211> LENGTH: 42
<212> TYPE: DNA
<213> ORGANISM: Artificial Sequence
<220> FEATURE:
<223> OTHER INFORMATION: Primer

<400> SEQUENCE: 114
caccctgaac accctgtact ggaaagcaga aactttcggg at 42

<210> SEQ ID NO 115
<211> LENGTH: 24
<212> TYPE: DNA
<213> ORGANISM: Artificial Sequence
<220> FEATURE:
<223> OTHER INFORMATION: Primer

<400> SEQUENCE: 115
gatcagcctg ctgctgccgg cgta 24

<210> SEQ ID NO 116
<211> LENGTH: 24
<212> TYPE: DNA
<213> ORGANISM: Artificial Sequence
<220> FEATURE:
<223> OTHER INFORMATION: Primer

<400> SEQUENCE: 116
ttccagtaca gggtgttcag ggtg 24

<210> SEQ ID NO 117
<211> LENGTH: 45
<212> TYPE: DNA
<213> ORGANISM: Artificial Sequence
<220> FEATURE:
<223> OTHER INFORMATION: Primer

<400> SEQUENCE: 117
atcatcggct gcgccccccc catcggtgaa cactggggta tcggt 45

<210> SEQ ID NO 118
<211> LENGTH: 42
<212> TYPE: DNA
<213> ORGANISM: Artificial Sequence
<220> FEATURE:
<223> OTHER INFORMATION: Primer

<400> SEQUENCE: 118
gccgtcctgg atcacgctgc tcaccagttc cagcggcggg ca 42

<210> SEQ ID NO 119
<211> LENGTH: 24
<212> TYPE: DNA
<213> ORGANISM: Artificial Sequence
<220> FEATURE:
<223> OTHER INFORMATION: Primer

<400> SEQUENCE: 119
gatggggggg gcgcagccga tgat 24

<210> SEQ ID NO 120
<211> LENGTH: 24
<212> TYPE: DNA
<213> ORGANISM: Artificial Sequence
<220> FEATURE:
<223> OTHER INFORMATION: Primer

<400> SEQUENCE: 120
gtgagcagcg tgatccagga cggc 24

<210> SEQ ID NO 121
<211> LENGTH: 54
<212> TYPE: DNA
<213> ORGANISM: Artificial Sequence
<220> FEATURE:
<223> OTHER INFORMATION: Primer

<400> SEQUENCE: 121
tacggcaaca gcatgttctt ccacctgcgt cgtgaacaga tcttcgctcg tcac 54

<210> SEQ ID NO 122
<211> LENGTH: 45
<212> TYPE: DNA
<213> ORGANISM: Artificial Sequence
<220> FEATURE:
<223> OTHER INFORMATION: Primer

<400> SEQUENCE: 122
gctgtcgctg gtgatcatgc tgccagacgg ggtagcagag tagat 45

<210> SEQ ID NO 123
<211> LENGTH: 24
<212> TYPE: DNA
<213> ORGANISM: Artificial Sequence
<220> FEATURE:
<223> OTHER INFORMATION: Primer

<400> SEQUENCE: 123
gtggaagaac atgctgttgc cgta 24

<210> SEQ ID NO 124
<211> LENGTH: 24
<212> TYPE: DNA
<213> ORGANISM: Artificial Sequence
<220> FEATURE:
<223> OTHER INFORMATION: Primer

<400> SEQUENCE: 124
ggcagcatga tcaccagcga cagc 24

<210> SEQ ID NO 125
<211> LENGTH: 51
<212> TYPE: DNA
<213> ORGANISM: Artificial Sequence
<220> FEATURE:
<223> OTHER INFORMATION: Primer

<400> SEQUENCE: 125
ttcatcacct gcgtggacac cacccgttct accaacctga ccatctctac c 51

-continued

<210> SEQ ID NO 126
<211> LENGTH: 57
<212> TYPE: DNA
<213> ORGANISM: Artificial Sequence
<220> FEATURE:
<223> OTHER INFORMATION: Primer

<400> SEQUENCE: 126
cagctggaag atgaactgca gctcgtattc ttcaccgtga cggatgtact gtttgaa 57

<210> SEQ ID NO 127
<211> LENGTH: 27
<212> TYPE: DNA
<213> ORGANISM: Artificial Sequence
<220> FEATURE:
<223> OTHER INFORMATION: Primer

<400> SEQUENCE: 127
ggtggtgtcc acgcaggtga tgaacag 27

<210> SEQ ID NO 128
<211> LENGTH: 24
<212> TYPE: DNA
<213> ORGANISM: Artificial Sequence
<220> FEATURE:
<223> OTHER INFORMATION: Primer

<400> SEQUENCE: 128
gagctgcagt tcatcttcca gctg 24

<210> SEQ ID NO 129
<211> LENGTH: 42
<212> TYPE: DNA
<213> ORGANISM: Artificial Sequence
<220> FEATURE:
<223> OTHER INFORMATION: Primer

<400> SEQUENCE: 129
tacgccggca gcagcaggct gatcaccctg ggtcacccgt ac 42

<210> SEQ ID NO 130
<211> LENGTH: 42
<212> TYPE: DNA
<213> ORGANISM: Artificial Sequence
<220> FEATURE:
<223> OTHER INFORMATION: Primer

<400> SEQUENCE: 130
caccctgaac accctgtact ggaaagcaga aactttcggg at 42

<210> SEQ ID NO 131
<211> LENGTH: 24
<212> TYPE: DNA
<213> ORGANISM: Artificial Sequence
<220> FEATURE:
<223> OTHER INFORMATION: Primer

<400> SEQUENCE: 131
gatcagcctg ctgctgccgg cgta 24

<210> SEQ ID NO 132
<211> LENGTH: 24
<212> TYPE: DNA
<213> ORGANISM: Artificial Sequence
<220> FEATURE:
<223> OTHER INFORMATION: Primer

<400> SEQUENCE: 132
ttccagtaca gggtgttcag ggtg 24

<210> SEQ ID NO 133
<211> LENGTH: 45
<212> TYPE: DNA
<213> ORGANISM: Artificial Sequence
<220> FEATURE:
<223> OTHER INFORMATION: Primer

<400> SEQUENCE: 133
tggggctgcg tgggcgtgga ggtgggtcgt ggtcagccgc tgggt 45

<210> SEQ ID NO 134
<211> LENGTH: 45
<212> TYPE: DNA
<213> ORGANISM: Artificial Sequence
<220> FEATURE:
<223> OTHER INFORMATION: Primer

<400> SEQUENCE: 134
gggggcgcag ccgatgatgc acagctgggt ctgtttgttg tcaac 45

<210> SEQ ID NO 135
<211> LENGTH: 24
<212> TYPE: DNA
<213> ORGANISM: Artificial Sequence
<220> FEATURE:
<223> OTHER INFORMATION: Primer

<400> SEQUENCE: 135
cacctccacg cccacgcagc ccca 24

<210> SEQ ID NO 136
<211> LENGTH: 31
<212> TYPE: DNA
<213> ORGANISM: Artificial Sequence
<220> FEATURE:
<223> OTHER INFORMATION: Primer

<400> SEQUENCE: 136
ctgtgcatca tcggctgcgc tccccccatc g 31

<210> SEQ ID NO 137
<211> LENGTH: 45
<212> TYPE: DNA
<213> ORGANISM: Artificial Sequence
<220> FEATURE:
<223> OTHER INFORMATION: Primer

<400> SEQUENCE: 137
atcatcggct gcgccccccc catcggtgaa cactggggta tcggt 45

<210> SEQ ID NO 138
<211> LENGTH: 42
<212> TYPE: DNA
<213> ORGANISM: Artificial Sequence
<220> FEATURE:
<223> OTHER INFORMATION: Primer

<400> SEQUENCE: 138
gccgtcctgg atcacgctgc tcaccagttc cagcggcggg ca 42

<210> SEQ ID NO 139

```
<211> LENGTH: 24
<212> TYPE: DNA
<213> ORGANISM: Artificial Sequence
<220> FEATURE:
<223> OTHER INFORMATION: Primer

<400> SEQUENCE: 139

gatggggggg gcgcagccga tgat                                              24

<210> SEQ ID NO 140
<211> LENGTH: 24
<212> TYPE: DNA
<213> ORGANISM: Artificial Sequence
<220> FEATURE:
<223> OTHER INFORMATION: Primer

<400> SEQUENCE: 140

gtgagcagcg tgatccagga cggc                                              24

<210> SEQ ID NO 141
<211> LENGTH: 51
<212> TYPE: DNA
<213> ORGANISM: Artificial Sequence
<220> FEATURE:
<223> OTHER INFORMATION: Primer

<400> SEQUENCE: 141

ttcatcacct gcgtggacac cacccgttct accaacctga ccatctctac c                51

<210> SEQ ID NO 142
<211> LENGTH: 57
<212> TYPE: DNA
<213> ORGANISM: Artificial Sequence
<220> FEATURE:
<223> OTHER INFORMATION: Primer

<400> SEQUENCE: 142

cagctggaag atgaactgca gctcgtattc ttcaccgtga cggatgtact gtttgaa         57

<210> SEQ ID NO 143
<211> LENGTH: 27
<212> TYPE: DNA
<213> ORGANISM: Artificial Sequence
<220> FEATURE:
<223> OTHER INFORMATION: Primer

<400> SEQUENCE: 143

ggtggtgtcc acgcaggtga tgaacag                                           27

<210> SEQ ID NO 144
<211> LENGTH: 24
<212> TYPE: DNA
<213> ORGANISM: Artificial Sequence
<220> FEATURE:
<223> OTHER INFORMATION: Primer

<400> SEQUENCE: 144

gagctgcagt tcatcttcca gctg                                              24
```

HUMAN PAPILLOMA VIRUS TYPE 51 L1 PROTEIN MUTANTS

The application is based on and claims the benefit of priority from Chinese application No. 201811122822.1, filed on Sep. 26, 2018, the disclosures of which are incorporated herein by reference in its entirety.

TECHNICAL FIELD

The application relates to the field of molecular virology and immunology. In particular, the invention relates to a mutated HPV51 L1 protein (or a variant thereof), a sequence encoding the same, a method for preparing the same, and a virus-like particle comprising the same, wherein the protein (or a variant thereof) and the virus-like particle can induce the generation of neutralizing antibodies against at least two HPV types (e.g. HPV51 and HPV69, or HPV51, HPV69 and HPV26), and therefore can be used to prevent infection by said at least two HPV types, and a disease caused by said infection, such as cervical cancer and condyloma acuminatum. The invention further relates to the use of the protein and the virus-like particle in the manufacture of a pharmaceutical composition or a vaccine for preventing infection by said at least two HPV types, and a disease caused by said infection, such as cervical cancer and condyloma acuminatum.

BACKGROUND ART

Human Papillomavirus (HPV) mainly causes warts in skin and mucosa. HPV types are divided into high-risk types and low-risk types depending on their association with tumorigenesis. Among them, infection by high-risk HPV types has been demonstrated to be the leading cause of genital cancer including cervical cancer in women; and low-risk HPV types mainly cause condyloma acuminatum. The most effective way to prevent and control HPV infection is to vaccinate HPV vaccines, particularly vaccines against high-risk HPV types causing cervical cancer.

Major capsid protein L1 of HPV has the characteristic of self-assembling into hollow Virus-Like Particle (VLP). HPV VLP has a symmetrical icosahedral structure composed of 72 pentamers of major capsid protein L1 (Doorbar, J. and P. H. Gallimore. 1987. J Virol, 61(9): 2793-9). HPV VLP is highly similar to natural HPV in terms of structure, retains most of the neutralizing epitopes of natural virus, and can induce the generation of high-titer neutralizing antibodies (Kirnbauer, R., F. Booy, et al. 1992 Proc Natl Acad Sci USA 89(24): 12180-4).

The existing studies show that HPV VLPs mainly induce the generation of neutralizing antibodies against the same HPV type, produce the protective immunity against the same HPV type, and only have low cross-protective effect among a few highly homologous HPV types (Sara L. Bissett, Giada Mattiuzzo, et al. 2014 Vaccine. 32:6548-6555). Therefore, the existing HPV vaccines have a very limited protection range. In general, VLP of one HPV type can only be used to prevent infection by the same HPV type. In this case, if it needs to broaden the protection range of HPV vaccines, the only way is to add VLPs of more HPV types in vaccines. Currently, the commercially available HPV vaccines, including Gardasil® (which is a quadrivalent vaccine against HPV16, 18, 6 and 11) and Gardasil®9 (which is a 9-valent vaccine against HPV6, 11, 16, 18, 31, 33, 45, 52 and 58) from Merck, and Cervarix® (which is a bivalent vaccine against HPV16 and 18) from GSK, are prepared by combining VLPs of multiple HPV types. However, such a solution would greatly increase the production cost of HPV vaccines, and might cause safety problem due to an increase in immunizing dose.

Therefore, it is urgent in the art to develop HPV virus-like particles capable of inducing the generation of protective neutralizing antibodies against multiple HPV types, so as to prevent infection by multiple HPV types, and a disease caused by the infection, such as cervical cancer and condyloma acuminatum, more economically and effectively.

CONTENTS OF INVENTION

The application is at least partially based on the inventors' surprising discovery: after substitution of a specific segment of L1 protein of Human Papillomavirus (HPV) Type 51 with the corresponding segment of L1 protein of a second HPV type (such as HPV69), the mutated HPV51 L1 protein thus obtained can induce the generation of high-titer neutralizing antibodies against HPV51 and the second HPV type (such as HPV69) in organisms, and its protection effect is comparable to that of a mixture of HPV51 VLP and VLP of the second HPV type, its protection effect against HPV51 is comparable to that of HPV51 VLP alone, and its protection effect against the second HPV type (such as HPV69) is comparable to that of the VLP of the second HPV type alone.

In addition, on the basis of the substitution above, another specific segment of HPV51 L1 protein can be further substituted with the corresponding segment of L1 protein of a third HPV type (such as HPV26), and the mutated HPV51 L1 protein having double substitutions thus obtained can induce the generation of high-titer neutralizing antibodies against HPV51, the second HPV type (such as HPV69) and the third HPV type (such as HPV26), and its protection effect is comparable to that of a mixture of HPV51 VLP, VLP of the second HPV type and VLP of the third HPV type.

Therefore, in an aspect, the application provides a mutated HPV51 L1 protein or a variant thereof, wherein as compared with a wild type HPV51 L1 protein, the mutated HPV51 L1 protein has the following mutations:

(1) truncation of 0-15 amino acids, for example, 0, 1, 2, 3, 4, 5, 6, 7, 8, 9, 10, 11, 12, 13, 14 or 15 amino acids, at N-terminal of the wild type HPV51 L1 protein; and the mutation as defined in (2)(a), (2)(b), (2)(c) or (2)(d):

(2)(a) substitution of amino acid residues at positions 52-60 of the wild type HPV51 L1 protein with amino acid residues at the corresponding positions of a L1 protein of a second type of wild type HPV; (2)(b) substitution of amino acid residues at positions 125-147 of the wild type HPV51 L1 protein with amino acid residues at the corresponding positions of a L1 protein of a second type of wild type HPV;

(2)(c) substitution of amino acid residues at positions 170-181 of the wild type HPV51 L1 protein with amino acid residues at the corresponding positions of a L1 protein of a second type of wild type HPV;

(2)(d) substitution of amino acid residues at positions 259-289 of the wild type HPV51 L1 protein with amino acid residues at the corresponding positions of a L1 protein of a second type of wild type HPV, and, the variant differs from the mutated HPV51 L1 protein only by substitution (preferably conservative substitution), addition or deletion of one or more (e.g. 1, 2, 3, 4, 5, 6, 7, 8, 9, 10, 11, 12, 13, 14, 15, 16 or 17) amino acids, and retains the function of the mutated HPV51 L1 protein, i.e. capability of inducing generation of neutralizing antibodies against at least two HPV types (e.g. HPV51 and HPV69).

In some embodiments, the mutated HPV51 L1 protein has the mutation as defined in (1) and (2)(a), and optionally, further has a mutation as defined in (3)(b).

In some embodiments, the mutated HPV51 L1 protein has the mutation as defined in (1) and (2)(b), and optionally, further has a mutation as defined in (3)(c).

In some embodiments, the mutated HPV51 L1 protein has the mutation as defined in (1) and (2)(c), and optionally, further has a mutation as defined in (3)(a) or (3)(b).

In some embodiments, the mutated HPV51 L1 protein has the mutation as defined in (1) and (2)(d), and optionally, further has a mutation as defined in (3)(b).

The mutations as defined in (3)(a), (3)(b) or (3)(c) are as follows:

(3)(a) substitution of amino acid residues at positions 51-60 of the wild type HPV51 L1 protein with amino acid residues at the corresponding positions of a L1 protein of a third type of wild type HPV;

(3)(b) substitution of amino acid residues at positions 114-146 of the wild type HPV51 L1 protein with amino acid residues at the corresponding positions of a L1 protein of a third type of wild type HPV;

(3)(c) substitution of amino acid residues at positions 173-181 of the wild type HPV51 L1 protein with amino acid residues at the corresponding positions of a L1 protein of a third type of wild type HPV;

In some embodiments, the mutated HPV51 L1 protein has 9 amino acids truncated at N-terminal, as compared with the wild type HPV51 L1 protein.

In some embodiments, the second type of wild type HPV is HPV69. In some embodiments, the amino acid residues at the corresponding positions as described in (2)(a) are amino acid residues at positions 52-60 of a wild type HPV69 L1 protein. In some embodiments, the amino acid residues at the corresponding positions as described in (2)(b) are amino acid residues at positions 125-147 of a wild type HPV69 L1 protein. In some embodiments, the amino acid residues at the corresponding positions as described in (2)(c) are amino acid residues at positions 170-183 of a wild type HPV69 L1 protein. In some embodiments, the amino acid residues at the corresponding positions as described in (2)(d) are amino acid residues at positions 261-291 of a wild type HPV69 L1 protein.

In some embodiments, the third type of wild type HPV is HPV26. In some embodiments, the amino acid residues at the corresponding positions as described in (3)(a) are amino acid residues at positions 51-60 of a wild type HPV26 L1 protein. In some embodiments, the amino acid residues at the corresponding positions as described in (3)(b) are amino acid residues at positions 114-146 of a wild type HPV26 L1 protein. In some embodiments, the amino acid residues at the corresponding positions as described in (3)(c) are amino acid residues at positions 173-181 of a wild type HPV26 L1 protein.

In some embodiments, the wild type HPV51 L1 protein has an amino acid sequence as set forth in SEQ ID NO: 1.

In some embodiments, the wild type HPV69 L1 protein has an amino acid sequence as set forth in SEQ ID NO: 2.

In some embodiments, the wild type HPV26 L1 protein has an amino acid sequence as set forth in SEQ ID NO: 22.

In some embodiments, the amino acid residues at positions 52-60 of the wild type HPV69 L1 protein have a sequence as set forth in SEQ ID NO: 17.

In some embodiments, the amino acid residues at positions 125-147 of the wild type HPV69 L1 protein have a sequence as set forth in SEQ ID NO: 18.

In some embodiments, the amino acid residues at positions 170-183 of the wild type HPV69 L1 protein have a sequence as set forth in SEQ ID NO: 19.

In some embodiments, the amino acid residues at positions 261-291 of the wild type HPV69 L1 protein have a sequence as set forth in SEQ ID NO: 20.

In some embodiments, the amino acid residues at positions 350-362 of the wild type HPV69 L1 protein have a sequence as set forth in SEQ ID NO: 21.

In some embodiments, the amino acid residues at positions 51-60 of the wild type HPV26 L1 protein have a sequence as set forth in SEQ ID NO: 56.

In some embodiments, the amino acid residues at positions 114-146 of the wild type HPV26 L1 protein have a sequence as set forth in SEQ ID NO: 57.

In some embodiments, the amino acid residues at positions 173-181 of the wild type HPV26 L1 protein have a sequence as set forth in SEQ ID NO: 58.

In some embodiments, the amino acid residues at positions 259-289 of the wild type HPV26 L1 protein have a sequence as set forth in SEQ ID NO: 59.

In some embodiments, the amino acid residues at positions 348-360 of the wild type HPV26 L1 protein have a sequence as set forth in SEQ ID NO: 60.

In some embodiments, the mutated HPV51 L1 protein has an amino acid sequence as set forth in SEQ ID NO: 4, 5, 6 or 7.

In some embodiments, the mutated HPV51 L1 protein has an amino acid sequence as set forth in SEQ ID NO: 23, 27, 28, 41 or 45.

In another aspect, the application provides an isolated nucleic acid, encoding the mutated HPV51 L1 protein or a variant thereof as described above. In another aspect, the application provides a vector comprising the isolated nucleic acid. In some embodiments, the isolated nucleic acid according to the application has a nucleotide sequence as set forth in SEQ ID NO: 12, 13, 14 or 15.

In some embodiments, the isolated nucleic acid according to the application has a nucleotide sequence as set forth in SEQ ID NO: 32, 36, 37, 49 or 53.

Vectors useful for insertion of a polynucleotide of interest are well known in the art, including, but not limited to cloning vectors and expression vectors. In one embodiment, the vectors are, for example, plasmids, cosmids, phages, etc.

In another aspect, the application further relates to a host cell comprising the isolated nucleic acid or the vector as described above. The host cell includes, but is not limited to prokaryotic cells such as *E. coli* cells, and eukaryotic cells such as yeast cells, insect cells, plant cells and animal cells (such as mammalian cells, for example, mouse cells, human cells, etc.). The host cell according to the application may also be a cell line, such as 293T cell.

In another aspect, the application relates to a HPV virus-like particle, comprising or consisting of the mutated HPV51 L1 protein or a variant thereof according to the application.

In some preferred embodiments, the HPV virus-like particle according to the application comprises the mutated HPV51 L1 protein, which has truncation of 0-15 amino acids, for example, 0, 1, 2, 3, 4, 5, 6, 7, 8, 9, 10, 11, 12, 13, 14 or 15 amino acids, at N-terminal of the wild type HPV51 L1 protein, as compared to a wild type HPV51 L1 protein, and substitution of the amino acid residues at positions 52-60 of the wild type HPV51 L1 protein with the amino acid residues at positions 52-60 of a wild type HPV69 L1 protein.

In some preferred embodiments, the HPV virus-like particle according to the application comprises the mutated HPV51 L1 protein, which has truncation of 0-15 amino acids, for example, 0, 1, 2, 3, 4, 5, 6, 7, 8, 9, 10, 11, 12, 13, 14 or 15 amino acids, at N-terminal of the wild type HPV51 L1 protein, as compared to a wild type HPV51 L1 protein, and substitution of the amino acid residues at positions 125-147 of the wild type HPV51 L1 protein with the amino acid residues at positions 125-147 of a wild type HPV69 L1 protein.

In some preferred embodiments, the HPV virus-like particle according to the application comprises the mutated HPV51 L1 protein, which has truncation of 0-15 amino acids, for example, 0, 1, 2, 3, 4, 5, 6, 7, 8, 9, 10, 11, 12, 13, 14 or 15 amino acids, at N-terminal of the wild type HPV51 L1 protein, as compared to a wild type HPV51 L1 protein, and substitution of the amino acid residues at positions 170-181 of the wild type HPV51 L1 protein with the amino acid residues at positions 170-183 of a wild type HPV69 L1 protein.

In some preferred embodiments, the HPV virus-like particle according to the application comprises the mutated HPV51 L1 protein, which has truncation of 0-15 amino acids, for example, 0, 1, 2, 3, 4, 5, 6, 7, 8, 9, 10, 11, 12, 13, 14 or 15 amino acids, at N-terminal of the wild type HPV51 L1 protein, as compared to a wild type HPV51 L1 protein, and substitution of the amino acid residues at positions 259-289 of the wild type HPV51 L1 protein with the amino acid residues at positions 261-291 of a wild type HPV69 L1 protein.

In some embodiments, the HPV virus-like particle according to the application comprises the mutated HPV51 L1 protein, which has truncation of 0-15 amino acids, for example, 0, 1, 2, 3, 4, 5, 6, 7, 8, 9, 10, 11, 12, 13, 14 or 15 amino acids, at N-terminal of the wild type HPV51 L1 protein, as compared to a wild type HPV51 L1 protein, and substitution of the amino acid residues at positions 52-60 of the wild type HPV51 L1 protein with the amino acid residues at positions 52-60 of a wild type HPV69 L1 protein, and substitution of the amino acid residues at positions 114-146 of the wild type HPV51 L1 protein with the amino acid residues at positions 114-146 of a wild type HPV26 L1 protein.

In some embodiments, the HPV virus-like particle according to the application comprises the mutated HPV51 L1 protein, which has truncation of 0-15 amino acids, for example, 0, 1, 2, 3, 4, 5, 6, 7, 8, 9, 10, 11, 12, 13, 14 or 15 amino acids, at N-terminal of the wild type HPV51 L1 protein, as compared to a wild type HPV51 L1 protein, and substitution of the amino acid residues at positions 125-147 of the wild type HPV51 L1 protein with the amino acid residues at positions 125-147 of a wild type HPV69 L1 protein, and substitution of the amino acid residues at positions 173-181 of the wild type HPV51 L1 protein with the amino acid residues at positions 173-181 of a wild type HPV26 L1 protein.

In some embodiments, the HPV virus-like particle according to the application comprises the mutated HPV51 L1 protein, which has truncation of 0-15 amino acids, for example, 0, 1, 2, 3, 4, 5, 6, 7, 8, 9, 10, 11, 12, 13, 14 or 15 amino acids, at N-terminal of the wild type HPV51 L1 protein, as compared to a wild type HPV51 L1 protein, and substitution of the amino acid residues at positions 170-181 of the wild type HPV51 L1 protein with the amino acid residues at positions 170-183 of a wild type HPV69 L1 protein, and substitution of the amino acid residues at positions 51-60 of the wild type HPV51 L1 protein with the amino acid residues at positions 51-60 of a wild type HPV26 L1 protein.

In some embodiments, the HPV virus-like particle according to the application comprises the mutated HPV51 L1 protein, which has truncation of 0-15 amino acids, for example, 0, 1, 2, 3, 4, 5, 6, 7, 8, 9, 10, 11, 12, 13, 14 or 15 amino acids, at N-terminal of the wild type HPV51 L1 protein, as compared to a wild type HPV51 L1 protein, and substitution of the amino acid residues at positions 170-181 of the wild type HPV51 L1 protein with the amino acid residues at positions 170-183 of a wild type HPV69 L1 protein, and substitution of the amino acid residues at positions 114-146 of the wild type HPV51 L1 protein with the amino acid residues at positions 114-146 of a wild type HPV26 L1 protein.

In some embodiments, the HPV virus-like particle according to the application comprises the mutated HPV51 L1 protein, which has truncation of 0-15 amino acids, for example, 0, 1, 2, 3, 4, 5, 6, 7, 8, 9, 10, 11, 12, 13, 14 or 15 amino acids, at N-terminal of the wild type HPV51 L1 protein, as compared to a wild type HPV51 L1 protein, and substitution of the amino acid residues at positions 259-289 of the wild type HPV51 L1 protein with the amino acid residues at positions 261-291 of a wild type HPV69 L1 protein, and substitution of the amino acid residues at positions 114-146 of the wild type HPV51 L1 protein with the amino acid residues at positions 114-146 of a wild type HPV26 L1 protein.

In some embodiments, the HPV virus-like particle according to the application comprises the mutated HPV51 L1 protein, which has truncation of 9 amino acids at N-terminal of the wild type HPV51 L1 protein, as compared to a wild type HPV51 L1 protein, and substitution of the amino acid residues at positions 52-60 of the wild type HPV51 L1 protein with the amino acid residues at positions 52-60 of a wild type HPV69 L1 protein.

In some embodiments, the HPV virus-like particle according to the application comprises the mutated HPV51 L1 protein, which has truncation of 9 amino acids at N-terminal of the wild type HPV51 L1 protein, as compared to a wild type HPV51 L1 protein, and substitution of the amino acid residues at positions 125-147 of the wild type HPV51 L1 protein with the amino acid residues at positions 125-147 of a wild type HPV69 L1 protein.

In some embodiments, the HPV virus-like particle according to the application comprises the mutated HPV51 L1 protein, which has truncation of 9 amino acids at N-terminal of the wild type HPV51 L1 protein, as compared to a wild type HPV51 L1 protein, and substitution of the amino acid residues at positions 170-181 of the wild type HPV51 L1 protein with the amino acid residues at positions 170-183 of a wild type HPV69 L1 protein.

In some preferred embodiments, the HPV virus-like particle according to the application comprises the mutated HPV51 L1 protein, which has truncation of 9 amino acids at N-terminal of the wild type HPV51 L1 protein, as compared to a wild type HPV51 L1 protein, and substitution of the amino acid residues at positions 259-289 of the wild type HPV51 L1 protein with the amino acid residues at positions 261-291 of a wild type HPV69 L1 protein.

In some embodiments, the HPV virus-like particle according to the application comprises the mutated HPV51 L1 protein, which has truncation of 9 amino acids at N-terminal of the wild type HPV51 L1 protein, as compared to a wild type HPV51 L1 protein, and substitution of the amino acid residues at positions 52-60 of the wild type HPV51 L1 protein with the amino acid residues at positions 52-60 of a wild type HPV69 L1 protein, and substitution of the amino acid residues at positions 114-146 of the wild type HPV51 L1 protein with the amino acid residues at positions 114-146 of a wild type HPV26 L1 protein.

In some embodiments, the HPV virus-like particle according to the application comprises the mutated HPV51 L1 protein, which has truncation of 9 amino acid at N-terminal of the wild type HPV51 L1 protein, as compared to a wild type HPV51 L1 protein, and substitution of the amino acid residues at positions 125-147 of the wild type HPV51 L1 protein with the amino acid residues at positions 125-147 of a wild type HPV69 L1 protein, and substitution of the amino acid residues at positions 173-181 of the wild type HPV51 L1 protein with the amino acid residues at positions 173-181 of a wild type HPV26 L1 protein.

In some embodiments, the HPV virus-like particle according to the application comprises the mutated HPV51 L1 protein, which has truncation of 9 amino acids at N-terminal of the wild type HPV51 L1 protein, as compared to a wild type HPV51 L1 protein, and substitution of the amino acid residues at positions 170-181 of the wild type HPV51 L1 protein with the amino acid residues at positions 170-183 of a wild type HPV69 L1 protein, and substitution of the amino acid residues at positions 51-60 of the wild type HPV51 L1 protein with the amino acid residues at positions 51-60 of a wild type HPV26 L1 protein.

In some embodiments, the HPV virus-like particle according to the application comprises the mutated HPV51 L1 protein, which has truncation of 9 amino acids at N-terminal of the wild type HPV51 L1 protein, as compared to a wild type HPV51 L1 protein, and substitution of the amino acid residues at positions 170-181 of the wild type HPV51 L1 protein with the amino acid residues at positions 170-183 of a wild type HPV69 L1 protein, and substitution of the amino acid residues at positions 114-146 of the wild type HPV51 L1 protein with the amino acid residues at positions 114-146 of a wild type HPV26 L1 protein.

In some embodiments, the HPV virus-like particle according to the application comprises the mutated HPV51 L1 protein, which has truncation of 9 amino acids at N-terminal of the wild type HPV51 L1 protein, as compared to a wild type HPV51 L1 protein, and substitution of the amino acid residues at positions 259-289 of the wild type HPV51 L1 protein with the amino acid residues at positions 261-291 of a wild type HPV69 L1 protein, and substitution of the amino acid residues at positions 114-146 of the wild type HPV51 L1 protein with the amino acid residues at positions 114-146 of a wild type HPV26 L1 protein.

In some embodiments, the HPV virus-like particle according to the application comprises the mutated HPV51 L1 protein, which has a sequence as set forth in SEQ ID NO: 4, 5, 6 or 7.

In some embodiments, the HPV virus-like particle according to the application comprises the mutated HPV51 L1 protein, which has a sequence as set forth in SEQ ID NO: 23, 27, 28, 41 or 45.

In another aspect, the application further relates to a composition comprising the mutated HPV51 L1 protein or a variant thereof, the isolated nucleic acid, the vector, the host cell, or the HPV virus-like particle. In some preferred embodiments, the composition comprises the mutated HPV51 L1 protein or a variant thereof according to the application. In some preferred embodiments, the composition comprises the HPV virus-like particle according to the application.

In another aspect, the application further relates to a pharmaceutical composition or vaccine, comprising the HPV virus-like particle according to the application, and optionally a pharmaceutically acceptable carrier and/or excipient. The pharmaceutical composition or vaccine according to the application can be used for preventing HPV infection, or a disease caused by HPV infection, such as cervical cancer and condyloma acuminatum.

In some embodiments, the HPV virus-like particle is present in an amount effective for preventing HPV infection or a disease caused by HPV infection. In some embodiments, the HPV infection is infection by one or more HPV types (e.g. at least one infection selected from the group consisting of HPV51 infection, HPV69 infection and HPV26 infection). In some embodiments, the disease caused by HPV infection is selected from the group consisting of cervical cancer, condyloma acuminatum and any combination thereof.

The pharmaceutical composition or vaccine according to the application may be administrated by methods well known in the art, for example, but not limited to, orally or by injection. In the application, a particularly preferred administration route is injection.

In some preferred embodiments, the pharmaceutical composition or vaccine according to the application is administrated in a form of a unit dosage. For example, but not for limiting the application, each unit dosage contains 5 μg-80 μg, preferably 20 μg-40 μg of HPV virus-like particle.

In another aspect, the application relates to a method for preparing the mutated HPV51 L1 protein or a variant thereof as described above, comprising expressing the mutated HPV51 L1 protein or a variant thereof in a host cell, and then recovering the mutated HPV51 L1 protein or a variant thereof from a culture of the host cell.

In some preferred embodiments, the host cell is *E. coli.*

In some preferred embodiments, the method comprises the steps of: expressing the mutated HPV51 L1 protein or a variant thereof in *E. coli*, and then obtaining the mutated HPV51 L1 protein or a variant thereof by purifying a lysate supernatant of the *E. coli*. In some preferred embodiments, the mutated HPV51 L1 protein or a variant thereof is recovered from the lysate supernatant of the *E. coli* by chromatography (e.g. cation-exchange chromatography, hydroxyapatite chromatography and/or hydrophobic interaction chromatography).

In another aspect, the application relates to a method for preparing a vaccine, comprising combining the HPV virus-like particle according to the application with a pharmaceutically acceptable carrier and/or excipient.

In another aspect, the application relates to a method for preventing HPV infection or a disease caused by HPV infection, comprising administering to a subject a prophylactically effective amount of the HPV virus-like particle or the pharmaceutical composition or vaccine according to the application. In a preferred embodiment, the HPV infection is infection by one or more HPV types (e.g. HPV51 infection, HPV69 infection and/or HPV26 infection). In another preferred embodiment, the disease caused by HPV infection includes, but is not limited to cervical cancer and condyloma acuminatum. In another preferred embodiment, the subject is mammal, such as human.

In another aspect, the application further relates to use of the mutated HPV51 L1 protein or a variant thereof or the HPV virus-like particle according to the application in the manufacture of a pharmaceutical composition or vaccine for preventing HPV infection or a disease caused by HPV infection. In a preferred embodiment, the HPV infection is infection by one or more HPV types (e.g. HPV51 infection, HPV69 infection and/or HPV26 infection). In another preferred embodiment, the disease caused by HPV infection includes, but is not limited to, cervical cancer and condyloma acuminatum.

In another aspect, the application further relates to the mutated HPV51 L1 protein or a variant thereof or the HPV virus-like particle according to the application for the prevention of HPV infection or a disease caused by HPV infection. In a preferred embodiment, the HPV infection is infection by one or more HPV types (e.g. HPV51 infection, HPV69 infection and/or HPV26 infection). In another preferred embodiment, the disease caused by HPV infection includes, but is not limited to, cervical cancer and condyloma acuminatum.

Definitions of Terms in the Application

In the application, unless otherwise specified, the scientific and technical terms used herein have the meanings generally understood by a person skilled in the art. Moreover, the laboratory operations of cell culture, molecular genetics, nucleic acid chemistry, and immunology used herein are the routine operations widely used in the corresponding fields. Meanwhile, in order to better understand the application, the definitions and explanations of the relevant terms are provided as follows.

According to the application, the term "a second type of wild type HPV" refers to a wild type HPV type other than HPV51. In the application, a second type of wild type HPV is preferably wild type HPV69.

According to the application, the term "a third type of wild type HPV" refers to a wild type HPV type other than HPV51 and the second type of wild type HPV. In the application, a third type of wild type HPV is preferably wild type HPV26.

According to the application, the expression "corresponding positions" refers to the equivalent positions of the sequences being compared when the sequences are optimally aligned, i.e. the sequences are aligned to obtain a highest percentage of identity.

According to the application, the term "wild type HPV51 L1 protein" refers to the naturally-occurring major capsid protein L1 in Human Papillomavirus Type 51 (HPV51). The sequence of wild type HPV51 L1 protein is well known in the art, and can be found in public database (such as Accession No. ACV88631.1, ALJ32930.1, CRH69903.1 and AJS10540.1 in NCBI database).

In the application, when an amino acid sequence of wild type HPV51 L1 protein is mentioned, it is described by reference to the sequence as set forth in SEQ ID NO: 1. For example, the expression "amino acid residues at positions 52-60 of a wild type HPV51 L1 protein" refers to the amino acid residues at positions 52-60 of the polypeptide as set forth in SEQ ID NO: 1. However, a person skilled in the art understands that wild type HPV51 may include various isolates, and there might be difference in the amino acid sequence of L1 protein among various isolates. Furthermore, a person skilled in the art understands that although there might be difference in sequence, the amino acid sequences of L1 protein have a very high identity (generally higher than 95%, e.g. higher than 96%, higher than 97%, higher than 98%, or higher than 99%) among different HPV51 isolates, and have substantively the same biological function. Therefore, in the application, the term "wild type HPV51 L1 protein" includes not only the protein as set forth in SEQ ID NO: 1, but also L1 protein of various HPV51 isolates (such as HPV51 L1 protein as set forth in No. ACV88631.1, ALJ32930.1, CRH69903.1 and AJS10540.1). Moreover, when a sequence fragment of a wild type HPV51 L1 protein is described, it includes not only the sequence fragment of SEQ ID NO: 1, but also the corresponding sequence fragment of a L1 protein of various HPV51 isolates. For example, the expression "amino acid residues at positions 52-60 of a wild type HPV51 L1 protein" includes the amino acid residues at positions 52-60 of SEQ ID NO: 1, and the corresponding fragment of a L1 protein of various HPV51 isolates.

According to the application, the term "wild type HPV69 L1 protein" refers to the naturally-occurring major capsid protein L1 in Human Papillomavirus Type 69 (HPV69). The sequence of wild type HPV69 L1 protein is well known in the art, and can be found in public database (such as Accession No. AHV83654.1, ALJ32844.1 and ALJ32828.1 in NCBI database).

In the application, when an amino acid sequence of wild type HPV69 L1 protein is mentioned, it is described by reference to the sequence as set forth in SEQ ID NO: 2. For example, the expression "amino acid residues at positions 52-60 of a wild type HPV69 L1 protein" refers to the amino acid residues at positions 52-60 of the polypeptide as set forth in SEQ ID NO: 2; the expression "amino acid residues at positions 170-183 of a wild type HPV69 L1 protein" refers to the amino acid residues at positions 170-183 of the polypeptide as set forth in SEQ ID NO: 2. However, a person skilled in the art understands that wild type HPV69 may include various isolates, and there might be difference in the amino acid sequence of L1 protein among various isolates. Furthermore, a person skilled in the art understands that although there might be difference in sequence, the amino acid sequences of L1 protein have a very high identity (generally higher than 95%, e.g. higher than 96%, higher than 97%, higher than 98%, or higher than 99%) among different HPV69 isolates, and have substantively the same biological function. Therefore, in the application, the term "wild type HPV69 L1 protein" includes not only the protein as set forth in SEQ ID NO: 2, but also L1 protein of various HPV69 isolates (such as HPV69 L1 protein as set forth in AHV83654.1, ALJ32844.1 and ALJ32828.1). Moreover, when a sequence fragment of a wild type HPV69 L1 protein is described, it includes not only the sequence fragment of SEQ ID NO: 2, but also the corresponding sequence fragment of a L1 protein of various HPV69 isolates. For example, the expression "amino acid residues at positions 52-60 of a wild type HPV69 L1 protein" includes the amino acid residues at positions 52-60 of SEQ ID NO: 2, and the corresponding fragment of a L1 protein of various HPV69 isolates.

According to the application, the term "wild type HPV26 L1 protein" refers to the naturally-occurring major capsid protein L1 in Human Papillomavirus Type 26 (HPV26). The sequence of wild type HPV26 L1 protein is well known in the art, and can be found in public database (such as Accession No. NP041787.1, AHY96046.1 and AHY96053.1 in NCBI database).

In the application, when an amino acid sequence of wild type HPV26 L1 protein is mentioned, it is described by reference to the sequence as set forth in SEQ ID NO: 22. For example, the expression "amino acid residues at positions 51-60 of a wild type HPV26 L1 protein" refers to amino acid residues at positions 51-60 of the polypeptide as set forth in SEQ ID NO: 22; the expression "amino acid residues at positions 173-181 of a wild type HPV26 L1 protein" refers to amino acid residues at positions 173-181 of the polypeptide as set forth in SEQ ID NO: 22. However, a person skilled in the art understands that wild type HPV26 may include various isolates, and there might be difference in the amino acid sequence of L1 protein among various isolates. Furthermore, a person skilled in the art understands that although there might be difference in sequence, the amino acid sequences of L1 protein have a very high identity (generally higher than 95%, e.g. higher than 96%, higher than 97%, higher than 98%, or higher than 99%) among different HPV26 isolates, and have substantively the same biological function. Therefore, in the application, the term "wild type HPV26 L1 protein" includes not only the protein as set forth in SEQ ID NO: 22, but also L1 protein of various HPV26 isolates (such as HPV26 L1 protein as set forth in NP041787.1, AHY96046.1 and AHY96053.1). Moreover, when a sequence fragment of a wild type HPV26 L1 protein is described, it includes not only the sequence fragment of SEQ ID NO: 22, but also the corresponding sequence fragment of L1 protein of various HPV26 isolates. For example, the expression "amino acid residues at positions 51-60 of a wild type HPV26 L1 protein" includes the amino acid residues at positions 51-60 of SEQ ID NO: 22, and the corresponding fragment of L1 protein of various HPV26 isolates.

According to the application, the expression "corresponding sequence fragments" or "corresponding fragments" refers to the fragments that are located at equivalent positions of the sequences being compared when the sequences are optimally aligned, i.e. the sequences are aligned to obtain a highest percentage of identity.

According to the application, the expression "truncation of X amino acids at N-terminal" or "having X amino acids truncated at N-terminal" refers to substitution of the amino acid residues from positions 1 to X at the N-terminal of a protein with methionine residue encoded by an initiator codon (for initiating protein translation). For example, a HPV51 L1 protein having 9 amino acids truncated at N-terminal refers to a protein resulted from substituting the amino acid residues from positions 1 to 9 at the N-terminal of wild type HPV51 L1 protein with methionine residue encoded by an initiator codon.

According to the application, the term "variant" refers to a protein, whose amino acid sequence has substitution (preferably conservative substitution), addition or deletion of one or more (e.g. 1, 2, 3, 4, 5 or 6) amino acids, or has an identity of at least 90%, 95%, 96%, 97%, 98%, or 99%, as compared with the mutated HPV51 L1 protein according to the application (for example, the protein as set forth in SEQ ID NO: 5 or 6), and which retains a function of the mutated HPV51 L1 protein according to the application. In the application, the term "function of the mutated HPV51 L1 protein" refers to a capability of inducing generation of neutralizing antibodies against at least two HPV types (e.g. HPV51 and HPV69). The term "identity" refers to a measure of similarity between nucleotide sequences or amino acid sequences. Generally, sequences were aligned to obtain a maximum matching. "Identity" has well-known meanings in the art and can be calculated by published algorithm (such as BLAST).

According to the application, the term "identity" refers to the match degree between two polypeptides or between two nucleic acids. When two sequences for comparison have the same monomer sub-unit of base or amino acid at a certain site (e.g., each of two DNA molecules has an adenine at a certain site, or each of two polypeptides has a lysine at a certain site), the two molecules are identical at the site. The percent identity between two sequences is a function of the number of identical sites shared by the two sequences over the total number of sites for comparison×100. For example, if 6 of 10 sites of two sequences are matched, these two sequences have an identity of 60%. For example, DNA sequences: CTGACT and CAGGTT share an identity of 50% (3 of 6 sites are matched). Generally, the comparison of two sequences is conducted in a manner to produce maximum identity. Such alignment can be conducted by for example using a computer program such as Align program (DNAstar, Inc.) which is based on the method of Needleman, et al. (J. Mol. Biol. 48:443-453, 1970). The percent identity between two amino acid sequences can also be determined using the algorithm of E. Meyers and W. Miller (Comput. Appl. Biosci., 4:11-17 (1988)) which has been incorporated into the ALIGN program (version 2.0), using a PAM120 weight residue table, and with a gap length penalty of 12 and a gap penalty of 4. In addition, the percentage of identity between two amino acid sequences can be determined by the algorithm of Needleman and Wunsch (J. Mol. Biol. 48:444-453 (1970)) which has been incorporated into the GAP program in the GCG software package (available at http://www.gcg.com), using either a Blossum 62 matrix or a PAM250 matrix, and with a gap weight of 16, 14, 12, 10, 8, 6 or 4 and a length weight of 1, 2, 3, 4, 5 or 6.

As used herein, the term "conservative substitution" refers to amino acid substitutions which would not disadvantageously affect or change the essential properties of a protein/polypeptide comprising the amino acid sequence. For example, a conservative substitution may be introduced by standard techniques known in the art such as site-directed mutagenesis and PCR-mediated mutagenesis. Conservative amino acid substitutions include substitutions wherein an amino acid residue is substituted with another amino acid residue having a similar side chain, for example, a residue physically or functionally similar (such as, having similar size, shape, charge, chemical property including the capability of forming covalent bond or hydrogen bond, etc.) to the corresponding amino acid residue. The families of amino acid residues having similar side chains have been defined in the art. These families include amino acids having basic side chains (for example, lysine, arginine and histidine), amino acids having acidic side chains (for example, aspartic acid and glutamic acid), amino acids having uncharged polar side chains (for example, glycine, asparagine, glutamine, serine, threonine, tyrosine, cysteine, and tryptophan), amino acids having nonpolar side chains (for example, alanine, valine, leucine, isoleucine, proline, phenylalanine, and methionine), amino acids having β-branched side chains (such as threonine, valine, and isoleucine) and amino acids having aromatic side chains (for example, tyrosine, phenylalanine, tryptophan, and histidine). Therefore, generally a conservative substitution refers to a substitution of a corresponding amino acid residue with another amino acid residue from the same side-chain family. Methods for identifying amino acid conservative substitutions are well known in the art (see, for example, Brummell et al., Biochem. 32: 1180-1187 (1993); Kobayashi et al., Protein Eng. 12(10): 879-884 (1999); and Burks et al., Proc. Natl. Acad. Sci. USA 94: 412-417 (1997), which are incorporated herein by reference).

According to the application, the term "*E. coli* expression system" refers to an expression system consisting of *E. coli* (strain) and a vector, wherein the *E. coli* (strain) is derived from the commercially available strains, including, but not limited to: ER2566, BL21 (DE3), B834 (DE3), and BLR (DE3).

According to the application, the term "vector" refers to a nucleic acid carrier tool which can have a polynucleotide inserted therein. When the vector allows for the expression of the protein encoded by the polynucleotide inserted therein, the vector is called an expression vector. The vector can have the carried genetic material elements expressed in a host cell by transformation, transduction, or transfection into the host cell. Vectors are well known by a person skilled in the art, including, but not limited to plasmids, phages, cosmids, etc.

According to the application, the term "a pharmaceutically acceptable carrier and/or excipient" refers to a carrier and/or excipient that is pharmacologically and/or physiologically compatible to a subject and active ingredients, which is well known in the art (see, for example, Remington's Pharmaceutical Sciences. Edited by Gennaro A R, 19th ed. Pennsylvania: Mack Publishing Company, 1995), including, but not limited to: pH regulators, surfactants, adjuvants, and ionic strength enhancers. For example, pH regulators include, but are not limited to, phosphate buffers; surfactants include, but are not limited to: cation surfactants, anion surfactants, or non-ionic surfactants, e.g., Tween-80; adjuvants include, but are not limited to, aluminium adjuvant (e.g., aluminium hydroxide), and Freund's adjuvant (e.g., Freund's complete adjuvant); and ionic strength enhancers include, but are not limited to, NaCl.

According to the application, the term "an effective amount" refers to an amount that can effectively achieve the intended purpose. For example, an amount effective for preventing a disease (such as HPV infection) refers to an amount effective for preventing, suppressing, or delaying the occurrence of a disease (such as HPV infection). The determination of such an effective amount is within the ability of a person skilled in the art.

According to the application, the term "chromatography" includes, but is not limited to: ion exchange chromatography (such as cation-exchange chromatography), hydrophobic interaction chromatography, absorbent chromatography (such as hydroxyapatite chromatography), gel filtration chromatography (gel exclusion chromatography), and affinity chromatography.

According to the application, the term "lysate supernatant" refers to a solution produced by the following steps: host cells (such as *E. coli*) are disrupted in a lysis buffer, and the insoluble substances are then removed from the lysed solution containing the disrupted host cells. Various lysis buffers are well known in the art, including, but not limited to Tris buffers, phosphate buffers, HEPES buffers, MOPS buffers, etc. In addition, the disrupting of a host cell can be accomplished by methods well known by a person skilled in the art, including, but not limited to homogenizer disrupting, ultrasonic treatment, grinding, high pressure extrusion, lysozyme treatment, etc. Methods for removing insoluble substances are also well known by a person skilled in the art, including, but not limited to filtration and centrifugation.

Beneficial Effects of Application

Studies show that although there is certain cross-protection between HPV51 and other HPV type(s) (such as HPV69 and/or HPV26), such cross-protection is very low, generally lower than one percent, even one thousandth of the protection level of VLP of the same HPV type. Therefore, a subject vaccinated with HPV51 vaccine, still has a high risk of being infected by other HPV type(s) (such as HPV69 and/or HPV26).

The application provides a mutated HPV51 L1 protein and a HPV virus-like particle formed by the same. The HPV virus-like particle according to the application can provide significant cross-protection against HPV51 and other HPV type(s) (such as HPV69 and/or HPV26). Especially, at the same immunizing dose, the HPV virus-like particle according to the application can induce the generation of high-titer neutralizing antibodies against at least two HPV types (e.g. HPV51 and HPV69, or HPV51, HPV69 and HPV26) in organisms, and its effect is comparable to that of a mixture of VLPs of multiple HPV types (e.g. a mixture of HPV51 VLP and HPV69 VLP, or a mixture of HPV51 VLP, HPV69 VLP and HPV26 VLP). Therefore, the HPV virus-like particle according to the application can be used to prevent infection by at least two HPV types (e.g. HPV51 and HPV69, or HPV51, HPV69 and HPV26) at the same time as well as diseases associated with the infection, and has significantly beneficial technical effects. This has particularly significant advantages in terms of extending the protection range of HPV vaccines and reducing the production cost of HPV vaccines.

The embodiments of the application are further described in detail by reference to the drawings and examples. However, a person skilled in the art would understand that the following drawings and examples are intended for illustrating the application only, rather than defining the scope of the application. According to the detailed description of the following drawings and preferred embodiments, various purposes and advantages of the application are apparent for a person skilled in the art.

DESCRIPTION OF DRAWINGS

FIG. 10A: Aluminum adjuvant group 1 (at an immunizing dose of 5.0 μg, using aluminum adjuvant); FIG. 10B: Aluminum adjuvant group 2 (at an immunizing dose of 1 μg, using aluminum adjuvant). The result showed that H51N9-69T1 VLP, H51N9-69T2 VLP, H51N9-69T3 VLP and H51N9-69T4 VLP each could induce the generation of high-titer neutralizing antibodies against HPV51 in mice, and their protective effects were comparable to that of HPV51N9 VLP alone and that of the mixed HPV51/HPV69 VLP at the same dose, and were significantly higher than that of HPV69N0 VLP alone at the same dose. H51N9-69T1 VLP, H51N9-69T2 VLP, H51N9-69T3 VLP and H51N9-69T4 VLP each could also induce the generation of high-titer neutralizing antibodies against HPV69 in mice, and their protective effects were comparable to that of HPV69N0 VLP alone and that of the mixed HPV51/HPV69 VLP at the same dose, and were significantly higher than that of HPV51N9 VLP alone at the same dose. This showed that H51N9-69T1 VLP, H51N9-69T2 VLP, H51N9-69T3 VLP and H51N9-69T4 VLP had good cross-immunogenicity and cross-protection against HPV51 and HPV69.

FIG. 11A: Aluminum adjuvant group 1 (at an immunizing dose of 5.0 μg, using aluminum adjuvant); FIG. 11B: Aluminum adjuvant group 2 (at an immunizing dose of 1 gig, using aluminum adjuvant). The result showed that H51N9-69T1-26S2 VLP, H51N9-69T3-26S1 VLP and H51N9-69T3-26S2 VLP each could induce the generation of high-titer neutralizing antibodies against HPV51 in mice, and their protective effects were comparable to that of HPV51N9 VLP alone and that of the mixed HPV51/HPV69/HPV26 VLP at the same dose, and were significantly higher than that of HPV69N0 VLP alone and that of HPV26N0 VLP alone at the same dose. H51N9-69T1-26S2 VLP, H51N9-69T3-26S1 VLP and H51N9-69T3-26S2 VLP each could also induce the generation of high-titer neutralizing antibodies against HPV69 in mice, and their protective effects were comparable to that of HPV69N0 VLP alone and that of the mixed HPV51/HPV69/HPV26 VLP at the same dose, and were significantly higher than that of HPV51N9 VLP alone at the same dose. H51N9-69T1-26S2 VLP, H51N9-69T3-26S1 VLP and H51N9-69T3-26S2 VLP each could also induce the generation of high-titer neutralizing antibodies against HPV26 in mice, and their protective effects were comparable to that of HPV26N0 VLP alone and that of the mixed HPV51/HPV69/HPV26 VLP at the same dose, and were significantly higher than that of HPV51N9 VLP alone at the same dose. This showed that H51N9-69T1-26S2 VLP, H51N9-69T3-26S1 VLP and H51N9-69T3-26S2 VLP had good cross-immunogenicity and cross-protection against HPV51, HPV69 and HPV26.

FIG. 12A: Aluminum adjuvant group 1 (at an immunizing dose of 5.0 gig, using aluminum adjuvant); FIG. 12B: Aluminum adjuvant group 2 (at an immunizing dose of 1 gig, using aluminum adjuvant). The result showed that H51N9-69T2-26S3 VLP and H51N9-69T4-26S2 VLP each could induce the generation of high-titer neutralizing antibodies against HPV51 in mice, and their protective effects were comparable to that of HPV51N9 VLP alone and that of the mixed HPV51/HPV69/HPV26 VLP at the same dose, and were significantly higher than that of HPV69N0 VLP alone and that of HPV26N0 VLP alone at the same dose. H51N9-69T2-26S3 VLP and H51N9-69T4-26S2 VLP each could also induce the generation of high-titer neutralizing antibodies against HPV69 in mice, and their protective effects were comparable to that of HPV69N0 VLP alone and that of the mixed HPV51/HPV69/HPV26 VLP at the same dose, and were significantly higher than that of HPV51N9 VLP alone at the same dose. H51N9-69T2-26S3 VLP and H51N9-69T4-26S2 VLP each could also induce the generation of high-titer neutralizing antibodies against HPV26 in mice, and their protective effects were comparable to that of HPV26N0 VLP alone and that of the mixed HPV51/HPV69/HPV26 VLP at the same dose, and were significantly higher than that of HPV51N9 VLP alone at the same dose. This showed that H51N9-69T2-26S3 VLP and H51N9-69T4-26S2 VLP had good cross-immunogenicity and cross-protection against HPV51, HPV69 and HPV26.

SEQUENCE INFORMATION

Figure 1A:
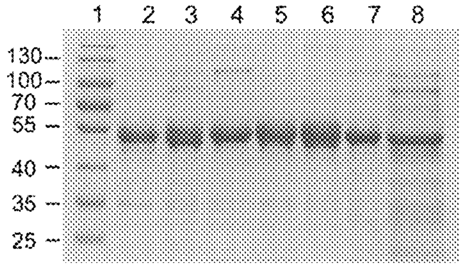
FIG. 1A shows the SDS-PAGE result of the purified mutated proteins in Example 1. Lane 1: protein molecular weight marker; Lane 2: HPV51N9 (HPV51 L1 protein having 9 amino acids truncated at N-terminal); Lane 3: HPV69N0 (full-length wild type HPV69 L1 protein); Lane 4: H51N9-69T1 (the mutated protein as set forth in SEQ ID NO: 4); Lane 5: H51N9-69T2 (the mutated protein as set forth in SEQ ID NO: 5); Lane 6: H51N9-69T3 (the mutated protein as set forth in SEQ ID NO: 6); Lane 7: H51N9-69T4 (the mutated protein as set forth in SEQ ID NO: 7); Lane 8: H51N9-69T5 (the mutated protein as set forth in SEQ ID NO: 8). The result showed that after chromatographic purification, the mutated proteins H51N9-69T1, H51N9-69T2, H51N9-69T3, H51N9-69T4 and H51N9-69T5 reached a purity of about 90%.
Figure 1B:
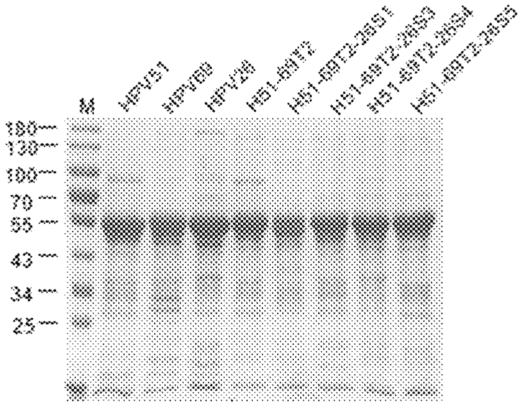
FIGS. 1B to 1D show the SDS-PAGE result of the purified mutated proteins H51N9-69T2-26S1, H51N9-69T2-26S3, H51N9-69T2-26S4, H51N9-69T2-26S5, H51N9-69T3-26S1, H51N9-69T3-26S2, H51N9-69T3-26S4, H51N9-69T3-26S5, H51N9-69T4-26S1, H51N9-69T4-26S2, H51N9-69T4-26S3 and H51N9-69T4-26S5 in Example 1. The SDS-PAGE results showed that after chromatographic purification, the mutated proteins reached a relatively high purity of about 80-90%.
Figure 1C:
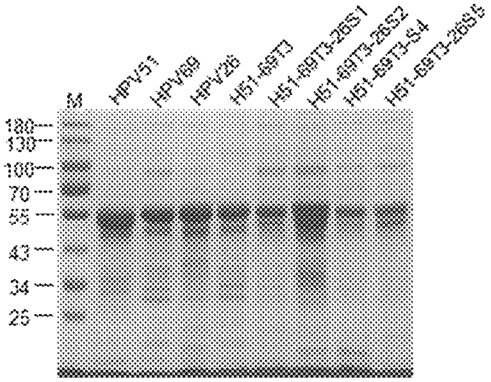
Figure 1D:
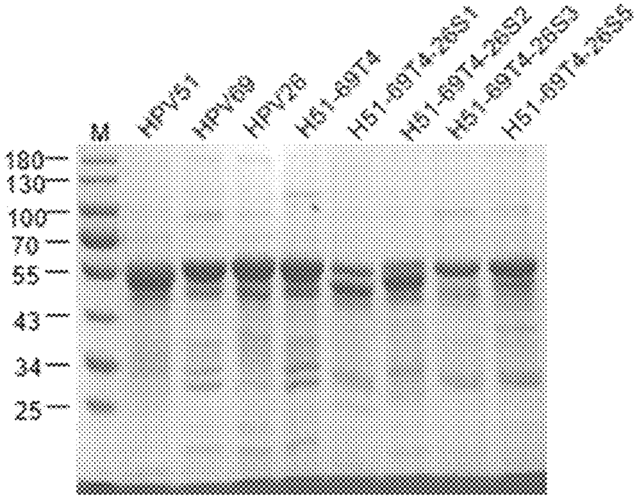
Figure 2A:
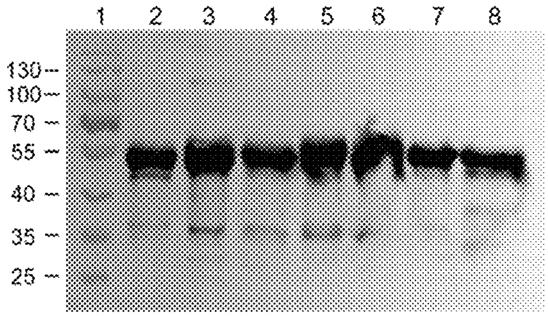
FIG. 2A shows the Western Blot result of the mutated proteins H51N9-69T1, H51N9-69T2, H51N9-69T3, H51N9-69T4 and H51N9-69T5 prepared in Example 1, as determined by using a broad-spectrum antibody 4B3 against HPV L1 protein. Lane 1: protein molecular weight marker; Lane 2: HPV51N9 (HPV51 L1 protein having 9 amino acids truncated at N-terminal); Lane 3: HPV69N0 (full-length wild type HPV69 L1 protein); Lane 4: H51N9-69T1; Lane 5: H51N9-69T2; Lane 6: H51N9-69T3; Lane 7: H51N9-69T4; Lane 8: H51N9-69T5. The result showed that the mutated proteins H51N9-69T1, H51N9-69T2, H51N9-69T3, H51N9-69T4 and H51N9-69T5 could be specifically recognized by the broad-spectrum antibody 4B3.
Figure 2B:
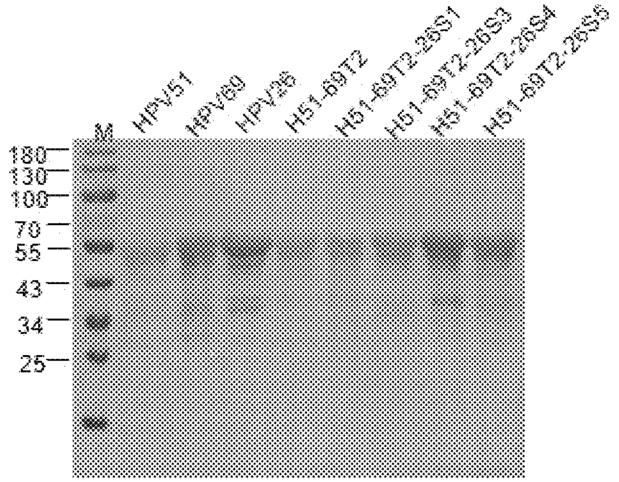
FIGS. 2B to 2D show the Western Blot result of the mutated proteins H51N9-69T2-26S1, H51N9-69T2-26S3, H51N9-69T2-26S4, H51N9-69T2-26S5, H51N9-69T3-26S1, H51N9-69T3-26S2, H51N9-69T3-26S4, H51N9-69T3-26S5, H51N9-69T4-26S1, H51N9-69T4-26S2, H51N9-69T4-26S3 and H51N9-69T4-26S5 prepared in Example 1, as determined by using a broad-spectrum antibody 4B3 against HPV L1 protein. The results showed that after chromatographic purification, the mutated proteins could be specifically recognized by the broad-spectrum antibody 4B3.
Figure 2C:
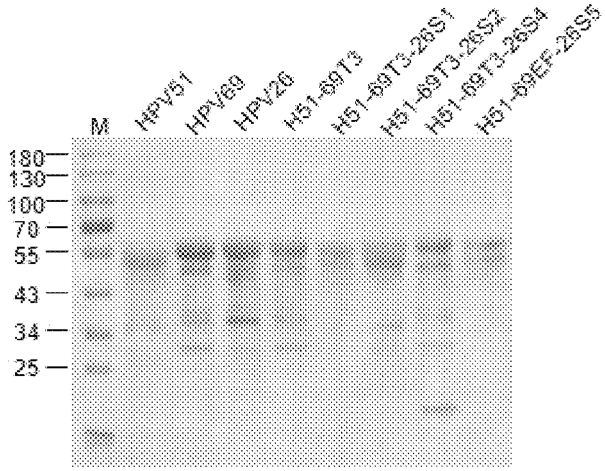
Figure 2D:
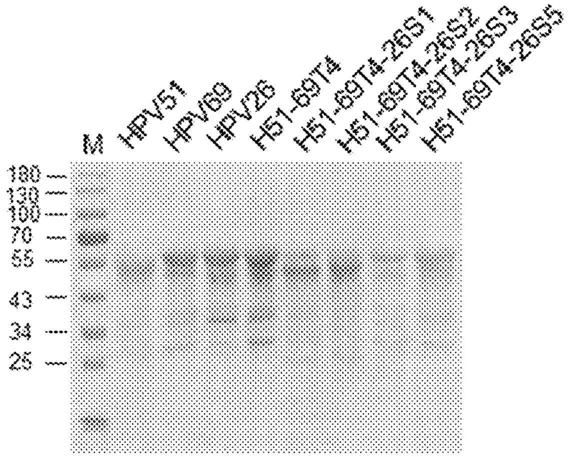

Some of the sequences involved in the application are provided in the following Table 1.

TABLE 1

| Description of Sequences | |
|---|---|
| SEQ ID NO: | Description |
| 1 | wild type HPV51 L1 protein, HPV51 L1 |
| 2 | wild type HPV69 L1 protein, HPV69L1, i.e., HPV69 NO |
| 3 | the HPV51 L1 protein having 9 amino acids truncated at N-terminal, HPV51N9 |
| 4 | the mutated HPV51 L1 protein having 9 amino acids truncated at N-terminal and comprising segment 1 of HPV69 L1 protein, H51N9-69T1 |
| 5 | the mutated HPV51 L1 protein having 9 amino acids truncated at N-terminal and comprising segment 2 of HPV69 L1 protein, H51N9-69T2 |
| 6 | the mutated HPV51 L1 protein having 9 amino acids truncated at N-terminal and comprising segment 3 of HPV69 L1 protein, H51N9-69T3 |
| 7 | the mutated HPV51 L1 protein having 9 amino acids truncated at N-terminal and comprising segment 4 of HPV69 L1 protein, H51N9-69T4 |

TABLE 1-continued

| Description of Sequences | |
|---|---|
| 8 | the mutated HPV51 L1 protein having 9 amino acids truncated at N-terminal and comprising segment 5 of HPV69 L1 protein, H51N9-69T5 |
| 9 | the DNA Sequence encoding SEQ ID NO: 1 |
| 10 | the DNA Sequence encoding SEQ ID NO: 2 |
| 11 | the DNA Sequence encoding SEQ ID NO: 3 |
| 12 | the DNA Sequence encoding SEQ ID NO: 4 |
| 13 | the DNA Sequence encoding SEQ ID NO: 5 |
| 14 | the DNA Sequence encoding SEQ ID NO: 6 |
| 15 | the DNA Sequence encoding SEQ ID NO: 7 |
| 16 | the DNA Sequence encoding SEQ ID NO: 8 |
| 17 | the Sequence of the amino acid residues at positions 52-60 of wild type HPV69 L1 protein, i.e., segment 1 of HPV69 L1 protein |
| 18 | the Sequence of the amino acid residues at positions 125-147 wild type HPV69 L1 protein, i.e., segment 2 of HPV69 L1 protein |
| 19 | the Sequence of the amino acid residues at positions 170-183 wild type HPV69 L1 protein, i.e., segment 3 of HPV69 L1 protein |
| 20 | the Sequence of the amino acid residues at positions 261-291 wild type HPV69 L1 protein, i.e., segment 4 of HPV69 L1 protein |
| 21 | the Sequence of the amino acid residues at positions 350-362 wild type HPV69 L1 protein, i.e., segment 5 of HPV69 L1 protein |
| 22 | wild type HPV26 L1 protein, HPV26 L1 |
| 23 | the mutated HPV51 L1 protein having 9 amino acids truncated at N-terminal and comprising segment 1 of HPV69 L1 protein and segment 2 of HPV26 L1 protein, H51N9-69T1-26S2 |
| 24 | the mutated HPV51 L1 protein having 9 amino acids truncated at N-terminal and comprising segment 1 of HPV69 L1 protein and segment 3 of HPV26 L1 protein, H51N9-69T1-26S3 |
| 25 | the mutated HPV51 L1 protein having 9 amino acids truncated at N-terminal and comprising segment 1 of HPV69 L1 protein and segment 4 of HPV26 L1 protein, H51N9-69T1-26S4 |
| 26 | the mutated HPV51 L1 protein having 9 amino acids truncated at N-terminal and comprising segment 1 of HPV69 L1 protein and segment 5 of HPV26 L1 protein, H51N9-69T1-26S5 |
| 27 | the mutated HPV51 L1 protein having 9 amino acids truncated at N-terminal and comprising segment 3 of HPV69 L1 protein and segment 1 of HPV26 L1 protein, H51N9-69T3-2651 |
| 28 | the mutated HPV51 L1 protein having 9 amino acids truncated at N-terminal and comprising segment 3 of HPV69 L1 protein and segment 2 of HPV26 L1 protein, H51N9-69T3-26S2 |
| 29 | the mutated HPV51 L1 protein having 9 amino acids truncated at N-terminal and comprising segment 3 of HPV69 L1 protein and segment 4 of HPV26 L1 protein, H51N9-69T3-26S4 |
| 30 | the mutated HPV51 L1 protein having 9 amino acids truncated at N-terminal and comprising segment 3 of HPV69 L1 protein and segment 5 of HPV26 L1 protein, H51N9-69T3-26S5 |
| 31 | the DNA Sequence encoding SEQ ID NO: 22 |
| 32 | the DNA Sequence encoding SEQ ID NO: 23 |

TABLE 1-continued

| Description of Sequences | |
|---|---|
| 33 | the DNA Sequence encoding SEQ ID NO: 24 |
| 34 | the DNA Sequence encoding SEQ ID NO: 25 |
| 35 | the DNA Sequence encoding SEQ ID NO: 26 |
| 36 | the DNA Sequence encoding SEQ ID NO: 27 |
| 37 | the DNA Sequence encoding SEQ ID NO: 28 |
| 38 | the DNA Sequence encoding SEQ ID NO: 29 |
| 39 | the DNA Sequence encoding SEQ ID NO: 30 |
| 40 | the mutated HPV51 L1 protein having 9 amino acids truncated at N-terminal and comprising segment 2 of HPV69 L1 protein and segment 1 of HPV26 L1 protein, H51N9-69T2-26S1 |
| 41 | the mutated HPV51 L1 protein having 9 amino acids truncated at N-terminal and comprising segment 2 of HPV69 L1 protein and segment 3 of HPV26 L1 protein, H51N9-69T2-26S3 |
| 42 | the mutated HPV51 L1 protein having 9 amino acids truncated at N-terminal and comprising segment 2 of HPV69 L1 protein and segment 4 of HPV26 L1 protein, H51N9-69T2-26S4 |
| 43 | the mutated HPV51 L1 protein having 9 amino acids truncated at N-terminal and comprising segment 2 of HPV69 L1 protein and segment 5 of HPV26 L1 protein, H51N9-69T2-26S5 |
| 44 | the mutated HPV51 L1 protein having 9 amino acids truncated at N-terminal and comprising segment 4 of HPV69 L1 protein and segment 1 of HPV26 L1 protein, H51N9-69T4-26S1 |
| 45 | the mutated HPV51 L1 protein having 9 amino acids truncated at N-terminal and comprising segment 4 of HPV69 L1 protein and segment 2 of HPV26 L1 protein, H51N9-69T4-26S2 |
| 46 | the mutated HPV51 L1 protein having 9 amino acids truncated at N-terminal and comprising segment 4 of HPV69 L1 protein and segment 3 of HPV26 L1 protein, H51N9-69T4-26S3 |
| 47 | the mutated HPV51 L1 protein having 9 amino acids truncated at N-terminal and comprising segment 4 of HPV69 L1 protein and segment 5 of HPV26 L1 protein, H51N9-69T4-26S5 |
| 48 | the DNA Sequence encoding SEQ ID NO: 40 |
| 49 | the DNA Sequence encoding SEQ ID NO: 41 |
| 50 | the DNA Sequence encoding SEQ ID NO: 42 |
| 51 | the DNA Sequence encoding SEQ ID NO: 43 |
| 52 | the DNA Sequence encoding SEQ ID NO: 44 |
| 53 | the DNA Sequence encoding SEQ ID NO: 45 |
| 54 | the DNA Sequence encoding SEQ ID NO: 46 |
| 55 | the DNA Sequence encoding SEQ ID NO: 47 |
| 56 | the Sequence of the amino acid residues at positions 51-60 of wild type HPV26 L1 protein, i.e., segment 1 of HPV26 L1 protein |
| 57 | the Sequence of the amino acid residues at positions 114-146 of wild type HPV26 L1 protein, i.e., segment 2 of HPV26 L1 protein |
| 58 | the Sequence of the amino acid residues at positions 173-181 of wild type HPV26 L1 protein, i.e., segment 3 of HPV26 L1 protein |
| 59 | the Sequence of the amino acid residues at positions 259-289 of wild type HPV26 L1 protein, i.e., segment 4 of HPV26 L1 protein |

TABLE 1-continued

| Description of Sequences | |
|---|---|
| 60 | the Sequence of the amino acid residues at positions 348-360 of wild type HPV26 L1 protein, i.e., segment 5 of HPV26 L1 protein |

Sequence 1 (SEQ ID NO: 1):
MALWRTNDSKVYLPPAPVSRIVNTEEYITRTGIYYYAGSSRLITLGHPYFPLPKTSTRAAIPKVSAF

QYRVFRVQLPDPNKFGLPDPNLYNPDTDRLVWGCVGVEVGRGQPLGVGLSGHPLFNKYDDTENSRIA

NGNAQQDVRDNTSVDNKQTQLCIIGCAPPIGEHWGIGTTCKNTPVPPGDCPPLELVSSVIQDGDMID

TGFGAMDFAALQATKSDVPLDISQSVCKYPDYLKMSADTYGNSMFFHLRREQIFARHYYNKLGSVGE

DIPTDYYIKGSGNGRDPIESYIYSATPSGSMITSDSQIFNKPYWLHRAQGHNNGICWNNQLFITCVD

TTRSTNLTISTATAAVSPTFTPSNFKQYIRHGEEYELQFIFQLCKITLTTEVMAYLHTMDPTILEQW

NFGLTLPPSASLEDAYRFVRNAATSCQKDTPPQAKPDPLAKYKFWDVDLKERFSLDLDQFALGRKFL

LQVGVQRKPRPGLKRPASSASSSSSSSAKRKRVKK.

Sequence 2 (SEQ ID NO: 2):
MALWRTSDSKVYLPPTPVSRVVSTDEYVTRTGIYYYAGSSRLLTLGHPYFPIPKSGSTAEIPKVSAY

QYRVFRVHLPDPNKFGLPDPQLYNPETERLVWACVGVEVGRGQPLGVGLSGHPLFNKLDDTENSHLA

TANADTDNRDNVCVDNKQTQLCIIGCTPPLGEHWGVGTVCKNAQSQVQRGDCPPLELISSVIEDGDM

IDTGFGAMDFTALQATKCDVPLDINQSICKYPDYLKMSADTYGNSMFFFLRREQLFARHFFNKAGTI

GDPVPVSMYIKGAGQGREPPTTSIYSATPSGSMVTSDAQLFNKPYWLQRAQGHNNGICWGNQLFVTC

VDTTRSTNLTISTVSAQSASATFKPSDYKQFIRHGEEYELQFIFQLCKITLTTDVMAYIHTMNSTIL

ENWNFGLTLPPTASLEDAYRFIKNSATTCQRDAPAQPKEDPFSKLKFWDVDLKEKFSIDLDQFPLGR

KFMLQAGIQRRPKLGTKRPASSLSASSSSTTRKKRKLTK.

Sequence 3 (SEQ ID NO: 3):
MKVYLPPAPVSRIVNTEEYITRTGIYYYAGSSRLITLGHPYFPLPKTSTRAAIPKVSAFQYRVFRVQ

LPDPNKFGLPDPNLYNPDTDRLVWGCVGVEVGRGQPLGVGLSGHPLFNKYDDTENSRIANGNAQQDV

RDNTSVDNKQTQLCIIGCAPPIGEHWGIGTTCKNTPVPPGDCPPLELVSSVIQDGDMIDTGFGAMDF

AALQATKSDVPLDISQSVCKYPDYLKMSADTYGNSMFFHLRREQIFARHYYNKLGSVGEDIPTDYYI

KGSGNGRDPIESYIYSATPSGSMITSDSQIFNKPYWLHRAQGHNNGICWNNQLFITCVDTTRSTNLT

ISTATAAVSPTFTPSNFKQYIRHGEEYELQFIFQLCKITLTTEVMAYLHTMDPTILEQWNFGLTLPP

SASLEDAYRFVRNAATSCQKDTPPQAKPDPLAKYKFWDVDLKERFSLDLDQFALGRKFLLQVGVQRK

PRPGLKRPASSASSSSSSSAKRKRVKK

Sequence 4 (SEQ ID NO: 4):
MKVYLPPAPVSRIVNTEEYITRTGIYYYAGSSRLITLGHPYFPIPKSGSTAEIPKVSAFQYRVFRVQ

LPDPNKFGLPDPNLYNPDTDRLVWGCVGVEVGRGQPLGVGLSGHPLFNKYDDTENSRIANGNAQQDV

RDNTSVDNKQTQLCIIGCAPPIGEHWGIGTTCKNTPVPPGDCPPLELVSSVIQDGDMIDTGFGAMDF

AALQATKSDVPLDISQSVCKYPDYLKMSADTYGNSMFFHLRREQIFARHYYNKLGSVGEDIPTDYYI

KGSGNGRDPIESYIYSATPSGSMITSDSQIFNKPYWLHRAQGHNNGICWNNQLFITCVDTTRSTNLT

ISTATAAVSPTFTPSNFKQYIRHGEEYELQFIFQLCKITLTTEVMAYLHTMDPTILEQWNFGLTLPP

SASLEDAYRFVRNAATSCQKDTPPQAKPDPLAKYKFWDVDLKERFSLDLDQFALGRKFLLQVGVQRK

PRPGLKRPASSASSSSSSSAKRKRVKK

Sequence 5 (SEQ ID NO: 5):
MKVYLPPAPVSRIVNTEEYITRTGIYYYAGSSRLITLGHPYFPLPKTSTRAAIPKVSAFQYRVFRVQ

LPDPNKFGLPDPNLYNPDTDRLVWGCVGVEVGRGQPLGVGLSGHPLFNKLDDTENSHLATANADTDN

RDNVCVDNKQTQLCIIGCAPPIGEHWGIGTTCKNTPVPPGDCPPLELVSSVIQDGDMIDTGFGAMDF

TABLE 1-continued

| Description of Sequences |
|---|
| AALQATKSDVPLDISQSVCKYPDYLKMSADTYGNSMFFHLRREQIFARHYYNKLGSVGEDIPTDYYI<br>KGSGNGRDPIESYIYSATPSGSMITSDSQIFNKPYWLHRAQGHNNGICWNNQLFITCVDTTRSTNLT<br>ISTATAAVSPTFTPSNFKQYIRHGEEYELQFIFQLCKITLTTEVMAYLHTMDPTILEQWNFGLTLPP<br>SASLEDAYRFVRNAATSCQKDTPPQAKPDPLAKYKFWDVDLKERFSLDLDQFALGRKFLLQVGVQRK<br>PRPGLKRPASSASSSSSSSAKRKRVKK |
| Sequence 6 (SEQ ID NO: 6):<br>MKVYLPPAPVSRIVNTEEYITRTGIYYYAGSSRLITLGHPYFPLPKTSTRAAIPKVSAFQYRVFRVQ<br>LPDPNKFGLPDPNLYNPDTDRLVWGCVGVEVGRGQPLGVGLSGHPLFNKYDDTENSRIANGNAQQDV<br>RDNTSVDNKQTQLCIIGCAPPIGEHWGVGTVCKNAQSQVQRGDCPPLELVSSVIQDGDMIDTGFGAM<br>DFAALQATKSDVPLDISQSVCKYPDYLKMSADTYGNSMFFHLRREQIFARHYYNKLGSVGEDIPTDY<br>YIKGSGNGRDPIESYIYSATPSGSMITSDSQIFNKPYWLHRAQGHNNGICWNNQLFITCVDTTRSTN<br>LTISTATAAVSPTFTPSNFKQYIRHGEEYELQFIFQLCKITLTTEVMAYLHTMDPTILEQWNFGLTL<br>PPSASLEDAYRFVRNAATSCQKDTPPQAKPDPLAKYKFWDVDLKERFSLDLDQFALGRKFLLQVGVQ<br>RKPRPGLKRPASSASSSSSSSAKRKRVKK. |
| Sequence 7 (SEQ ID NO: 7):<br>MKVYLPPAPVSRIVNTEEYITRTGIYYYAGSSRLITLGHPYFPLPKTSTRAAIPKVSAFQYRVFRVQ<br>LPDPNKFGLPDPNLYNPDTDRLVWGCVGVEVGRGQPLGVGLSGHPLFNKYDDTENSRIANGNAQQDV<br>RDNTSVDNKQTQLCIIGCAPPIGEHWGIGTTCKNTPVPPGDCPPLELVSSVIQDGDMIDTGFGAMDF<br>AALQATKSDVPLDISQSVCKYPDYLKMSADTYGNSMFFHLRREQIFARHFFNKAGTIGDPVPVSMYI<br>KGAGQGREPPTTSIYSATPSGSMITSDSQIFNKPYWLHRAQGHNNGICWNNQLFITCVDTTRSTNLT<br>ISTATAAVSPTFTPSNFKQYIRHGEEYELQFIFQLCKITLTTEVMAYLHTMDPTILEQWNFGLTLPP<br>SASLEDAYRFVRNAATSCQKDTPPQAKPDPLAKYKFWDVDLKERFSLDLDQFALGRKFLLQVGVQRK<br>PRPGLKRPASSASSSSSSSAKRKRVKK |
| Sequence 8 (SEQ ID NO: 8):<br>MKVYLPPAPVSRIVNTEEYITRTGIYYYAGSSRLITLGHPYFPLPKTSTRAAIPKVSAFQYRVFRVQ<br>LPDPNKFGLPDPNLYNPDTDRLVWGCVGVEVGRGQPLGVGLSGHPLFNKYDDTENSRIANGNAQQDV<br>RDNTSVDNKQTQLCIIGCAPPIGEHWGIGTTCKNTPVPPGDCPPLELVSSVIQDGDMIDTGFGAMDF<br>AALQATKSDVPLDISQSVCKYPDYLKMSADTYGNSMFFHLRREQIFARHYYNKLGSVGEDIPTDYYI<br>KGSGNGRDPIESYIYSATPSGSMITSDSQIFNKPYWLHRAQGHNNGICWNNQLFITCVDTTRSTNLT<br>ISTASAQSASATFKPSDFKQYIRHGEEYELQFIFQLCKITLTTEVMAYLHTMDPTILEQWNFGLTLP<br>PSASLEDAYRFVRNAATSCQKDTPPQAKPDPLAKYKFWDVDLKERFSLDLDQFALGRKFLLQVGVQR<br>KPRPGLKRPASSASSSSSSSAKRKRVKK. |
| Sequence 9 (SEQ ID NO: 9):<br>ATGGCCCTGTGGAGGACCAACGACAGCAAGGTGTACCTGCCCCCCGCCCCCGTGAGCAGGATCGTGA<br>ACACCGAGGAGTACATCACCAGGACCGGCATCTACTACTACGCCGGCAGCAGCAGGCTGATCACCCT<br>GGGCCACCCCTACTTCCCCCTGCCCAAGACCAGCACCAGGGCCGCCATCCCCAAGGTGAGCGCCTTC<br>CAGTACAGGGTGTTCAGGGTGCAGCTCCCCGACCCCAACAAGTTCGGCCTGCCCGACCCCAACCTGT<br>ACAACCCCGACACCGACAGGCTGGTGTGGGGCTGCGTGGGCGTGGAGGTGGGCAGGGGCCAGCCCCT<br>GGGCGTGGGCCTGAGCGGCCACCCCCTGTTCAACAAGTACGACGACACCGAGAACAGCAGGATCGCC<br>AACGGCAACGCCCAGCAGGACGTGAGGGACAACACCAGCGTGGACAACAAGCAGACCCAGCTGTGCA<br>TCATCGGCTGCGCCCCCCCCATCGGCGAGCACTGGGGCATCGGCACCACCTGCAAGAACACCCCCGT |

TABLE 1-continued

| Description of Sequences |
|---|
| GCCCCCCGGCGACTGCCCCCCCCTGGAGCTGGTGAGCAGCGTGATCCAGGACGGCGACATGATCGAC |
| ACCGGCTTCGGCGCCATGGACTTCGCCGCCCTGCAGGCCACCAAGAGCGACGTGCCCCTGGACATCA |
| GCCAGAGCGTGTGCAAGTACCCCGACTACCTGAAGATGAGCGCCGACACCTACGGCAACAGCATGTT |
| CTTCCACCTGAGGAGGGAGCAGATCTTCGCCAGGCACTACTACAACAAGCTGGGCAGCGTGGGCGAG |
| GACATCCCCACCGACTACTACATCAAGGGCAGCGGCAACGGCAGGGACCCCATCGAGAGCTACATCT |
| ACAGCGCCACCCCCAGCGGCAGCATGATCACCAGCGACAGCCAGATCTTCAACAAGCCCTACTGGCT |
| GCACAGGGCCCAGGGCCACAACAACGGCATCTGCTGGAACAACCAGCTGTTCATCACCTGCGTGGAC |
| ACCACCAGGAGCACCAACCTGACCATCAGCACCGCCACCGCCGCCGTGAGCCCCACCTTCACCCCCA |
| GCAACTTCAAGCAGTACATCAGGCACGGCGAGGAGTACGAGCTGCAGTTCATCTTCCAGCTGTGCAA |
| GATCACCCTGACCACCGAGGTGATGGCCTACCTGCACACCATGGACCCCACCATCCTGGAGCAGTGG |
| AACTTCGGCCTGACCCTGCCCCCCAGCGCCAGCCTGGAGGACGCCTACAGGTTCGTGAGGAACGCCG |
| CCACCAGCTGCCAGAAGGACACCCCCCCCCAGGCCAAGCCCGACCCCCTGGCCAAGTACAAGTTCTG |
| GGACGTGGACCTGAAGGAGAGGTTCAGCCTGGACCTGGACCAGTTCGCCCTGGGCAGGAAGTTCCTG |
| CTGCAGGTGGGCGTGCAGAGGAAGCCCAGGCCCGGCCTGAAGAGGCCCGCTAGCAGCGCCAGCTCCA |
| GCAGCTCCAGCAGCGCCAAGAGGAAGAGGGTGAAGAAGTAA |
| Sequence 10 (SEQ ID NO: 10):<br>ATGGCTCTGTGGCGTACCTCTGACTCTAAAGTTTACCTGCCGCCGACCCCGGTTTCTCGTGTTGTTT |
| CTACCGACGAATACGTTACCCGTACCGGTATCTACTACTACGCTGGTTCTTCTCGTCTGCTGACCCT |
| GGGTCACCCGTACTTCCCGATCCCGAAATCTGGTTCTACCGCTGAAATCCCGAAGGTCTCTGCTTAC |
| CAGTACCGGGTATTCCGTGTCCACCTGCCGGACCCGAACAAATTCGGTCTGCCGGACCCGCAGCTGT |
| ACAATCCAGAAACCGAACGTCTGGTTTGGGCTTGCGTTGGTGTCGAGGTCGGTCGTGGTCAGCCGCT |
| GGGTGTCGGTCTGTCTGGTCACCCGCTGTTCAACAAACTGGACGACACCGAAAACTCTCACCTGGCT |
| ACCGCTAACGCTGACACCGACAACCGTGACAACGTTTGCGTTGACAACAAACAGACCCAGCTGTGCA |
| TCATCGGTTGCACCCCGCCGCTGGGTGAACACTGGGGTGTCGGTACCGTTTGCAAAAACGCTCAGTC |
| TCAGGTTCAGCGTGGTGACTGCCCGCCGCTGGAACTGATCTCTTCTGTTATCGAAGACGGTGACATG |
| ATCGACACCGGTTTCGGTGCTATGGACTTCACCGCTCTGCAGGCTACCAAATGCGACGTTCCGCTGG |
| ACATCAACCAGTCTATCTGCAAATACCCCGACTACCTGAAAATGTCTGCTGACACCTACGGTAACTC |
| TATGTTCTTCTTCCTGCGTCGTGAACAGCTGTTCGCTCGTCACTTCTTCAACAAAGCTGGTACCATC |
| GGTGACCCTGTTCCGGTTTCTATGTACATCAAAGGTGCTGGTCAGGGTCGTGAACCGCCGACCACAT |
| CCATCTACTCTGCTACCCCGTCTGGTTCTATGGTTACATCCGACGCTCAGCTGTTCAACAAACCGTA |
| CTGGCTGCAGCGTGCTCAGGGTCACAACAACGGTATCTGCTGGGGTAACCAGCTGTTCGTTACCTGC |
| GTTGACACCACCCGTTCTACCAACCTGACCATCTCTACCGTTTCTGCTCAGTCTGCTTCTGCTACCT |
| TCAAACCGTCTGACTACAAACAATTTATCCGTCACGGTGAAGAATACGAACTGCAGTTCATCTTCCA |
| GCTGTGCAAAATCACCCTGACCACCGACGTTATGGCTTACATCCACACCATGAACTCTACCATCCTG |
| GAAAACTGGAACTTCGGTCTGACCCTGCCGCCGACCGCTTCTCTGGAAGACGCTTACCGTTTCATCA |
| AAAACTCTGCTACCACCTGCCAGCGTGACGCTCCGGCTCAGCCGAAAGAAGACCCGTTCTCTAAACT |
| GAAATTCTGGGACGTTGACCTGAAAGAAAAATTCTCTATCGACCTGGACCAGTTCCCGCTGGGTCGT |
| AAATTCATGCTGCAGGCTGGTATCCAGCGTCGTCCGAAACTGGGTACCAAACGTCCGGCTTCTTCTC |
| TGTCTGCTTCTTCTTCTTCTACCACCCGTAAAAAACGTAAACTGACCAAATAA |

TABLE 1-continued

| Description of Sequences |
| --- |
| Sequence 11 (SEQ ID NO: 11):<br>ATGAAGGTGTACCTGCCCCCCGCCCCCGTGAGCAGGATCGTGAACACCGAGGAGTACATCACCAGGA<br>CCGGCATCTACTACTACGCCGGCAGCAGCAGGCTGATCACCCTGGGCCACCCCTACTTCCCCCTGCC<br>CAAGACCAGCACCAGGGCCGCCATCCCCAAGGTGAGCGCCTTCCAGTACAGGGTGTTCAGGGTGCAG<br>CTCCCCGACCCCAACAAGTTCGGCCTGCCCGACCCCAACCTGTACAACCCCGACACCGACAGGCTGG<br>TGTGGGGCTGCGTGGGCGTGGAGGTGGGCAGGGGCCAGCCCCTGGGCGTGGGCCTGAGCGGCCACCC<br>CCTGTTCAACAAGTACGACGACACCGAGAACAGCAGGATCGCCAACGGCAACGCCCAGCAGGACGTG<br>AGGGACAACACCAGCGTGGACAACAAGCAGACCCAGCTGTGCATCATCGGCTGCGCCCCCCCCATCG<br>GCGAGCACTGGGGCATCGGCACCACCTGCAAGAACACCCCCGTGCCCCCCGGCGACTGCCCCCCCCT<br>GGAGCTGGTGAGCAGCGTGATCCAGGACGGCGACATGATCGACACCGGCTTCGGCGCCATGGACTTC<br>GCCGCCCTGCAGGCCACCAAGAGCGACGTGCCCCTGGACATCAGCCAGAGCGTGTGCAAGTACCCCG<br>ACTACCTGAAGATGAGCGCCGACACCTACGGCAACAGCATGTTCTTCCACCTGAGGAGGGAGCAGAT<br>CTTCGCCAGGCACTACTACAACAAGCTGGGCAGCGTGGGCGAGGACATCCCCACCGACTACTACATC<br>AAGGGCAGCGGCAACGGCAGGGACCCCATCGAGAGCTACATCTACAGCGCCACCCCCAGCGGCAGCA<br>TGATCACCAGCGACAGCCAGATCTTCAACAAGCCCTACTGGCTGCACAGGGCCCAGGGCCACAACAA<br>CGGCATCTGCTGGAACAACCAGCTGTTCATCACCTGCGTGGACACCACCAGGAGCACCAACCTGACC<br>ATCAGCACCGCCACCGCCGCCGTGAGCCCCACCTTCACCCCCAGCAACTTCAAGCAGTACATCAGGC<br>ACGGCGAGGAGTACGAGCTGCAGTTCATCTTCCAGCTGTGCAAGATCACCCTGACCACCGAGGTGAT<br>GGCCTACCTGCACACCATGGACCCCACCATCCTGGAGCAGTGGAACTTCGGCCTGACCCTGCCCCCC<br>AGCGCCAGCCTGGAGGACGCCTACAGGTTCGTGAGGAACGCCGCCACCAGCTGCCAGAAGGACACCC<br>CCCCCCAGGCCAAGCCCGACCCCCTGGCCAAGTACAAGTTCTGGGACGTGGACCTGAAGGAGAGGTT<br>CAGCCTGGACCTGGACCAGTTCGCCCTGGGCAGGAAGTTCCTGCTGCAGGTGGGCGTGCAGAGGAAG<br>CCCAGGCCCGGCCTGAAGAGGCCCGCTAGCAGCGCCAGCTCCAGCAGCTCCAGCAGCGCCAAGAGGA<br>AGAGGGTGAAGAAGTAA |
| Sequence 12 (SEQ ID NO: 12):<br>ATGAAGGTGTACCTGCCCCCCGCCCCCGTGAGCAGGATCGTGAACACCGAGGAGTACATCACCAGGA<br>CCGGCATCTACTACTACGCCGGCAGCAGCAGGCTGATCACCCTGGGCCACCCCTACTTCCCGATCCC<br>GAAATCTGGTTCTACCGCTGAAATCCCGAAGGTCTCTGCCTTCCAGTACAGGGTGTTCAGGGTGCAG<br>CTCCCCGACCCCAACAAGTTCGGCCTGCCCGACCCCAACCTGTACAACCCCGACACCGACAGGCTGG<br>TGTGGGGCTGCGTGGGCGTGGAGGTGGGCAGGGGCCAGCCCCTGGGCGTGGGCCTGAGCGGCCACCC<br>CCTGTTCAACAAGTACGACGACACCGAGAACAGCAGGATCGCCAACGGCAACGCCCAGCAGGACGTG<br>AGGGACAACACCAGCGTGGACAACAAGCAGACCCAGCTGTGCATCATCGGCTGCGCCCCCCCCATCG<br>GCGAGCACTGGGGCATCGGCACCACCTGCAAGAACACCCCCGTGCCCCCCGGCGACTGCCCCCCCCT<br>GGAGCTGGTGAGCAGCGTGATCCAGGACGGCGACATGATCGACACCGGCTTCGGCGCCATGGACTTC<br>GCCGCCCTGCAGGCCACCAAGAGCGACGTGCCCCTGGACATCAGCCAGAGCGTGTGCAAGTACCCCG<br>ACTACCTGAAGATGAGCGCCGACACCTACGGCAACAGCATGTTCTTCCACCTGAGGAGGGAGCAGAT<br>CTTCGCCAGGCACTACTACAACAAGCTGGGCAGCGTGGGCGAGGACATCCCCACCGACTACTACATC<br>AAGGGCAGCGGCAACGGCAGGGACCCCATCGAGAGCTACATCTACAGCGCCACCCCCAGCGGCAGCA<br>TGATCACCAGCGACAGCCAGATCTTCAACAAGCCCTACTGGCTGCACAGGGCCCAGGGCCACAACAA<br>CGGCATCTGCTGGAACAACCAGCTGTTCATCACCTGCGTGGACACCACCAGGAGCACCAACCTGACC |

TABLE 1-continued

| Description of Sequences |
|---|
| ATCAGCACCGCCACCGCCGCCGTGAGCCCCACCTTCACCCCCAGCAACTTCAAGCAGTACATCAGGC |
| ACGGCGAGGAGTACGAGCTGCAGTTCATCTTCCAGCTGTGCAAGATCACCCTGACCACCGAGGTGAT |
| GGCCTACCTGCACACCATGGACCCCACCATCCTGGAGCAGTGGAACTTCGGCCTGACCCTGCCCCCC |
| AGCGCCAGCCTGGAGGACGCCTACAGGTTCGTGAGGAACGCCGCCACCAGCTGCCAGAAGGACACCC |
| CCCCCCAGGCCAAGCCCGACCCCCTGGCCAAGTACAAGTTCTGGGACGTGGACCTGAAGGAGAGGTT |
| CAGCCTGGACCTGGACCAGTTCGCCCTGGGCAGGAAGTTCCTGCTGCAGGTGGGCGTGCAGAGGAAG |
| CCCAGGCCCGGCCTGAAGAGGCCCGCTAGCAGCGCCAGCTCCAGCAGCTCCAGCAGCGCCAAGAGGA |
| AGAGGGTGAAGAAGTAA |
| Sequence 13 (SEQ ID NO: 13):<br>ATGAAGGTGTACCTGCCCCCCGCCCCCGTGAGCAGGATCGTGAACACCGAGGAGTACATCACCAGGA |
| CCGGCATCTACTACTACGCCGGCAGCAGCAGGCTGATCACCCTGGGCCACCCCTACTTCCCCCTGCC |
| CAAGACCAGCACCAGGGCCGCCATCCCCAAGGTGAGCGCCTTCCAGTACAGGGTGTTCAGGGTGCAG |
| CTCCCCGACCCCAACAAGTTCGGCCTGCCCGACCCCAACCTGTACAACCCCGACACCGACAGGCTGG |
| TGTGGGGCTGCGTGGGCGTGGAGGTGGGTCGTGGTCAGCCGCTGGGTGTCGGTCTGTCTGGTCACCC |
| GCTGTTCAACAAACTGGACGACACCGAAAACTCTCACCTGGCTACCGCTAACGCTGACACCGACAAC |
| CGTGACAACGTTTGCGTTGACAACAAGCAGACCCAGCTGTGCATCATCGGCTGCGCCCCCCCCATCG |
| GCGAGCACTGGGGCATCGGCACCACCTGCAAGAACACCCCCGTGCCCCCCGGCGACTGCCCCCCCCT |
| GGAGCTGGTGAGCAGCGTGATCCAGGACGGCGACATGATCGACACCGGCTTCGGCGCCATGGACTTC |
| GCCGCCCTGCAGGCCACCAAGAGCGACGTGCCCCTGGACATCAGCCAGAGCGTGTGCAAGTACCCCG |
| ACTACCTGAAGATGAGCGCCGACACCTACGGCAACAGCATGTTCTTCCACCTGAGGAGGGAGCAGAT |
| CTTCGCCAGGCACTACTACAACAAGCTGGGCAGCGTGGGCGAGGACATCCCCACCGACTACTACATC |
| AAGGGCAGCGGCAACGGCAGGGACCCCATCGAGAGCTACATCTACAGCGCCACCCCCAGCGGCAGCA |
| TGATCACCAGCGACAGCCAGATCTTCAACAAGCCCTACTGGCTGCACAGGGCCCAGGGCCACAACAA |
| CGGCATCTGCTGGAACAACCAGCTGTTCATCACCTGCGTGGACACCACCAGGAGCACCAACCTGACC |
| ATCAGCACCGCCACCGCCGCCGTGAGCCCCACCTTCACCCCCAGCAACTTCAAGCAGTACATCAGGC |
| ACGGCGAGGAGTACGAGCTGCAGTTCATCTTCCAGCTGTGCAAGATCACCCTGACCACCGAGGTGAT |
| GGCCTACCTGCACACCATGGACCCCACCATCCTGGAGCAGTGGAACTTCGGCCTGACCCTGCCCCCC |
| AGCGCCAGCCTGGAGGACGCCTACAGGTTCGTGAGGAACGCCGCCACCAGCTGCCAGAAGGACACCC |
| CCCCCCAGGCCAAGCCCGACCCCCTGGCCAAGTACAAGTTCTGGGACGTGGACCTGAAGGAGAGGTT |
| CAGCCTGGACCTGGACCAGTTCGCCCTGGGCAGGAAGTTCCTGCTGCAGGTGGGCGTGCAGAGGAAG |
| CCCAGGCCCGGCCTGAAGAGGCCCGCTAGCAGCGCCAGCTCCAGCAGCTCCAGCAGCGCCAAGAGGA |
| AGAGGGTGAAGAAGTAA |
| Sequence 14 (SEQ ID NO: 14):<br>ATGAAGGTGTACCTGCCCCCCGCCCCCGTGAGCAGGATCGTGAACACCGAGGAGTACATCACCAGGA |
| CCGGCATCTACTACTACGCCGGCAGCAGCAGGCTGATCACCCTGGGCCACCCCTACTTCCCCCTGCC |
| CAAGACCAGCACCAGGGCCGCCATCCCCAAGGTGAGCGCCTTCCAGTACAGGGTGTTCAGGGTGCAG |
| CTCCCCGACCCCAACAAGTTCGGCCTGCCCGACCCCAACCTGTACAACCCCGACACCGACAGGCTGG |
| TGTGGGGCTGCGTGGGCGTGGAGGTGGGCAGGGGCCAGCCCCTGGGCGTGGGCCTGAGCGGCCACCC |
| CCTGTTCAACAAGTACGACGACACCGAGAACAGCAGGATCGCCAACGGCAACGCCCAGCAGGACGTG |
| AGGGACAACACCAGCGTGGACAACAAGCAGACCCAGCTGTGCATCATCGGCTGCGCCCCCCCCATCG |

TABLE 1-continued

| Description of Sequences |
|---|
| GCGAGCACTGGGGTGTCGGTACCGTTTGCAAAAACGCTCAGTCTCAGGTTCAGCGTGGTGACTGCCC |
| GCCGCTGGAGCTGGTGAGCAGCGTGATCCAGGACGGCGACATGATCGACACCGGCTTCGGCGCCATG |
| GACTTCGCCGCCCTGCAGGCCACCAAGAGCGACGTGCCCCTGGACATCAGCCAGAGCGTGTGCAAGT |
| ACCCCGACTACCTGAAGATGAGCGCCGACACCTACGGCAACAGCATGTTCTTCCACCTGAGGAGGGA |
| GCAGATCTTCGCCAGGCACTACTACAACAAGCTGGGCAGCGTGGGCGAGGACATCCCCACCGACTAC |
| TACATCAAGGGCAGCGGCAACGGCAGGGACCCCATCGAGAGCTACATCTACAGCGCCACCCCCAGCG |
| GCAGCATGATCACCAGCGACAGCCAGATCTTCAACAAGCCCTACTGGCTGCACAGGGCCCAGGGCCA |
| CAACAACGGCATCTGCTGGAACAACCAGCTGTTCATCACCTGCGTGGACACCACCAGGAGCACCAAC |
| CTGACCATCAGCACCGCCACCGCCGCCGTGAGCCCCACCTTCACCCCCAGCAACTTCAAGCAGTACA |
| TCAGGCACGGCGAGGAGTACGAGCTGCAGTTCATCTTCCAGCTGTGCAAGATCACCCTGACCACCGA |
| GGTGATGGCCTACCTGCACACCATGGACCCCACCATCCTGGAGCAGTGGAACTTCGGCCTGACCCTG |
| CCCCCCAGCGCCAGCCTGGAGGACGCCTACAGGTTCGTGAGGAACGCCGCCACCAGCTGCCAGAAGG |
| ACACCCCCCCCCAGGCCAAGCCCGACCCCCTGGCCAAGTACAAGTTCTGGGACGTGGACCTGAAGGA |
| GAGGTTCAGCCTGGACCTGGACCAGTTCGCCCTGGGCAGGAAGTTCCTGCTGCAGGTGGGCGTGCAG |
| AGGAAGCCCAGGCCCGGCCTGAAGAGGCCCGCTAGCAGCGCCAGCTCCAGCAGCTCCAGCAGCGCCA |
| AGAGGAAGAGGGTGAAGAAGTAA |
| Sequence 15 (SEQ ID NO: 15):<br>ATGAAGGTGTACCTGCCCCCCGCCCCCGTGAGCAGGATCGTGAACACCGAGGAGTACATCACCAGGA |
| CCGGCATCTACTACTACGCCGGCAGCAGCAGGCTGATCACCCTGGGCCACCCCTACTTCCCCCTGCC |
| CAAGACCAGCACCAGGGCCGCCATCCCCAAGGTGAGCGCCTTCCAGTACAGGGTGTTCAGGGTGCAG |
| CTCCCCGACCCCAACAAGTTCGGCCTGCCCGACCCCAACCTGTACAACCCCGACACCGACAGGCTGG |
| TGTGGGGCTGCGTGGGCGTGGAGGTGGGCAGGGGCCAGCCCCTGGGCGTGGGCCTGAGCGGCCACCC |
| CCTGTTCAACAAGTACGACGACACCGAGAACAGCAGGATCGCCAACGGCAACGCCCAGCAGGACGTG |
| AGGGACAACACCAGCGTGGACAACAAGCAGACCCAGCTGTGCATCATCGGCTGCGCCCCCCCCATCG |
| GCGAGCACTGGGGCATCGGCACCACCTGCAAGAACACCCCCGTGCCCCCCGGCGACTGCCCCCCCCT |
| GGAGCTGGTGAGCAGCGTGATCCAGGACGGCGACATGATCGACACCGGCTTCGGCGCCATGGACTTC |
| GCCGCCCTGCAGGCCACCAAGAGCGACGTGCCCCTGGACATCAGCCAGAGCGTGTGCAAGTACCCCG |
| ACTACCTGAAGATGAGCGCCGACACCTACGGCAACAGCATGTTCTTCCACCTGAGGAGGGAGCAGAT |
| CTTCGCCAGGCACTTCTTCAACAAAGCTGGTACCATCGGTGACCCTGTTCCGGTTTCTATGTACATC |
| AAAGGTGCTGGTCAGGGTCGTGAACCGCCGACCACATCCATCTACTCTGCCACCCCCAGCGGCAGCA |
| TGATCACCAGCGACAGCCAGATCTTCAACAAGCCCTACTGGCTGCACAGGGCCCAGGGCCACAACAA |
| CGGCATCTGCTGGAACAACCAGCTGTTCATCACCTGCGTGGACACCACCAGGAGCACCAACCTGACC |
| ATCAGCACCGCCACCGCCGCCGTGAGCCCCACCTTCACCCCCAGCAACTTCAAGCAGTACATCAGGC |
| ACGGCGAGGAGTACGAGCTGCAGTTCATCTTCCAGCTGTGCAAGATCACCCTGACCACCGAGGTGAT |
| GGCCTACCTGCACACCATGGACCCCACCATCCTGGAGCAGTGGAACTTCGGCCTGACCCTGCCCCCC |
| AGCGCCAGCCTGGAGGACGCCTACAGGTTCGTGAGGAACGCCGCCACCAGCTGCCAGAAGGACACCC |
| CCCCCCAGGCCAAGCCCGACCCCCTGGCCAAGTACAAGTTCTGGGACGTGGACCTGAAGGAGAGGTT |
| CAGCCTGGACCTGGACCAGTTCGCCCTGGGCAGGAAGTTCCTGCTGCAGGTGGGCGTGCAGAGGAAG |
| CCCAGGCCCGGCCTGAAGAGGCCCGCTAGCAGCGCCAGCTCCAGCAGCTCCAGCAGCGCCAAGAGGA |
| AGAGGGTGAAGAAGTAA |

TABLE 1-continued

| Description of Sequences |
|---|
| Sequence 16 (SEQ ID NO: 16):<br>ATGAAGGTGTACCTGCCCCCCGCCCCCGTGAGCAGGATCGTGAACACCGAGGAGTACATCACCAGGA<br>CCGGCATCTACTACTACGCCGGCAGCAGCAGGCTGATCACCCTGGGCCACCCCTACTTCCCCCTGCC<br>CAAGACCAGCACCAGGGCCGCCATCCCCAAGGTGAGCGCCTTCCAGTACAGGGTGTTCAGGGTGCAG<br>CTCCCCGACCCCAACAAGTTCGGCCTGCCCGACCCCAACCTGTACAACCCCGACACCGACAGGCTGG<br>TGTGGGGCTGCGTGGGCGTGGAGGTGGGCAGGGGCCAGCCCCTGGGCGTGGGCCTGAGCGGCCACCC<br>CCTGTTCAACAAGTACGACGACACCGAGAACAGCAGGATCGCCAACGGCAACGCCCAGCAGGACGTG<br>AGGGACAACACCAGCGTGGACAACAAGCAGACCCAGCTGTGCATCATCGGCTGCGCCCCCCCCATCG<br>GCGAGCACTGGGGCATCGGCACCACCTGCAAGAACACCCCCGTGCCCCCCGGCGACTGCCCCCCCCT<br>GGAGCTGGTGAGCAGCGTGATCCAGGACGGCGACATGATCGACACCGGCTTCGGCGCCATGGACTTC<br>GCCGCCCTGCAGGCCACCAAGAGCGACGTGCCCCTGGACATCAGCCAGAGCGTGTGCAAGTACCCCG<br>ACTACCTGAAGATGAGCGCCGACACCTACGGCAACAGCATGTTCTTCCACCTGAGGAGGGAGCAGAT<br>CTTCGCCAGGCACTACTACAACAAGCTGGGCAGCGTGGGCGAGGACATCCCCACCGACTACTACATC<br>AAGGGCAGCGGCAACGGCAGGGACCCCATCGAGAGCTACATCTACAGCGCCACCCCCAGCGGCAGCA<br>TGATCACCAGCGACAGCCAGATCTTCAACAAGCCCTACTGGCTGCACAGGGCCCAGGGCCACAACAA<br>CGGCATCTGCTGGAACAACCAGCTGTTCATCACCTGCGTGGACACCACCAGGAGCACCAACCTGACC<br>ATCAGCACCGCCTCTGCTCAGTCTGCTTCTGCTACCTTCAAACCGTCTGACTTCAAGCAGTACATCA<br>GGCACGGCGAGGAGTACGAGCTGCAGTTCATCTTCCAGCTGTGCAAGATCACCCTGACCACCGAGGT<br>GATGGCCTACCTGCACACCATGGACCCCACCATCCTGGAGCAGTGGAACTTCGGCCTGACCCTGCCC<br>CCCAGCGCCAGCCTGGAGGACGCCTACAGGTTCGTGAGGAACGCCGCCACCAGCTGCCAGAAGGACA<br>CCCCCCCCCAGGCCAAGCCCGACCCCCTGGCCAAGTACAAGTTCTGGGACGTGGACCTGAAGGAGAG<br>GTTCAGCCTGGACCTGGACCAGTTCGCCCTGGGCAGGAAGTTCCTGCTGCAGGTGGGCGTGCAGAGG<br>AAGCCCAGGCCCGGCCTGAAGAGGCCCGCTAGCAGCGCCAGCTCCAGCAGCTCCAGCAGCGCCAAGA<br>GGAAGAGGGTGAAGAAGTAA |
| Sequence 17 (SEQ ID NO: 17):<br>IPKSGSTAE |
| Sequence 18 (SEQ ID NO: 18):<br>LDDTENSHLATANADTDNRDNVC |
| Sequence 19 (SEQ ID NO: 19):<br>VGTVCKNAQSQVQR |
| Sequence 20 (SEQ ID NO: 20):<br>FFNKAGTIGDPVPVSMYIKGAGQGREPPTTS |
| Sequence 21 (SEQ ID NO: 21):<br>SAQSASATFKPSD |
| Sequence 22 (SEQ ID NO: 22):<br>MALWRTSDSKVYLPPTPVSRVVNTDEYVTRTGIYYYAGSSRLLTLGHPYFSIPKTGQKAEIPKVSAY<br>QYRVFRVHLPDPNKFGLPDPQLYNPDTERLVWACVGVEVGRGQPLGIGLSGHPLFNKLDDTENSHLA<br>TVNADTDNRDNVSVDNKQTQLCIIGCTPPLGEHWGIGTICKNTQTQRGDCPPLELISSIIEDGDMID<br>TGFGAMDFTALQATKSDVPIDISQSTCKYPDYLKMSADTYGNSMFFFLRREQLFARHFYNKAGAVGD<br>AIPTTLYIKGAESGREPPTSSIYSATPSGSMVTSDAQLFNKPYWLQRAQGHNNGICWGNQLFVTCVD |

TABLE 1-continued

Description of Sequences

TTRSTNLTISTLSAASASTPFKPSDYKQFIRHGEEYELQFIFQLCKITLTTDVMAYIHLMNASILED

WNFGLTLPPTASLEDAYRFIKNSATTCQRNAPPVPKEDPFQKFKFWDVDLKEKFSIDLDQFPLGRKF

MLQAGIQRRPKLGTKRPLSSTSSSTKRKKRKLTK.

Sequence 23 (SEQ ID NO: 23):
MKVYLPPAPVSRIVNTEEYITRTGIYYYAGSSRLITLGHPYFPIPKSGSTAEIPKVSAFQYRVFRVQ

LPDPNKFGLPDPNLYNPDTDRLVWGCVGVEVGRGQPLGIGLSGHPLFNKLDDTENSHLATVNADTDN

RDNVSVDNKQTQLCIIGCAPPIGEHWGIGTTCKNTPVPPGDCPPLELVSSVIQDGDMIDTGFGAMDF

AALQATKSDVPLDISQSVCKYPDYLKMSADTYGNSMFFHLRREQIFARHYYNKLGSVGEDIPTDYYI

KGSGNGRDPIESYIYSATPSGSMITSDSQIFNKPYWLHRAQGHNNGICWNNQLFITCVDTTRSTNLT

ISTATAAVSPTFTPSNFKQYIRHGEEYELQFIFQLCKITLTTEVMAYLHTMDPTILEQWNFGLTLPP

SASLEDAYRFVRNAATSCQKDTPPQAKPDPLAKYKFWDVDLKERFSLDLDQFALGRKFLLQVGVQRK

PRPGLKRPASSASSSSSSSAKRKRVKK

Sequence 24 (SEQ ID NO: 24):
MKVYLPPAPVSRIVNTEEYITRTGIYYYAGSSRLITLGHPYFPIPKSGSTAEIPKVSAFQYRVFRVQ

LPDPNKFGLPDPNLYNPDTDRLVWGCVGVEVGRGQPLGVGLSGHPLFNKYDDTENSRIANGNAQQDV

RDNTSVDNKQTQLCIIGCAPPIGEHWGIGTICKNTQTQRGDCPPLELVSSVIQDGDMIDTGFGAMDF

AALQATKSDVPLDISQSVCKYPDYLKMSADTYGNSMFFHLRREQIFARHYYNKLGSVGEDIPTDYYI

KGSGNGRDPIESYIYSATPSGSMITSDSQIFNKPYWLHRAQGHNNGICWNNQLFITCVDTTRSTNLT

ISTATAAVSPTFTPSNFKQYIRHGEEYELQFIFQLCKITLTTEVMAYLHTMDPTILEQWNFGLTLPP

SASLEDAYRFVRNAATSCQKDTPPQAKPDPLAKYKFWDVDLKERFSLDLDQFALGRKFLLQVGVQRK

PRPGLKRPASSASSSSSSSAKRKRVKK

Sequence 25 (SEQ ID NO: 25):
MKVYLPPAPVSRIVNTEEYITRTGIYYYAGSSRLITLGHPYFPIPKSGSTAEIPKVSAFQYRVFRVQ

LPDPNKFGLPDPNLYNPDTDRLVWGCVGVEVGRGQPLGVGLSGHPLFNKYDDTENSRIANGNAQQDV

RDNTSVDNKQTQLCIIGCAPPIGEHWGIGTTCKNTPVPPGDCPPLELVSSVIQDGDMIDTGFGAMDF

AALQATKSDVPLDISQSVCKYPDYLKMSADTYGNSMFFHLRREQIFARHFYNKAGAVGDAIPTTLYI

KGAESGREPPTSSIYSATPSGSMITSDSQIFNKPYWLHRAQGHNNGICWNNQLFITCVDTTRSTNLT

ISTATAAVSPTFTPSNFKQYIRHGEEYELQFIFQLCKITLTTEVMAYLHTMDPTILEQWNFGLTLPP

SASLEDAYRFVRNAATSCQKDTPPQAKPDPLAKYKFWDVDLKERFSLDLDQFALGRKFLLQVGVQRK

PRPGLKRPASSASSSSSSSAKRKRVKK

Sequence 26 (SEQ ID NO: 26):
MKVYLPPAPVSRIVNTEEYITRTGIYYYAGSSRLITLGHPYFPIPKSGSTAEIPKVSAFQYRVFRVQ

LPDPNKFGLPDPNLYNPDTDRLVWGCVGVEVGRGQPLGVGLSGHPLFNKYDDTENSRIANGNAQQDV

RDNTSVDNKQTQLCIIGCAPPIGEHWGIGTTCKNTPVPPGDCPPLELVSSVIQDGDMIDTGFGAMDF

AALQATKSDVPLDISQSVCKYPDYLKMSADTYGNSMFFHLRREQIFARHYYNKLGSVGEDIPTDYYI

KGSGNGRDPIESYIYSATPSGSMITSDSQIFNKPYWLHRAQGHNNGICWNNQLFITCVDTTRSTNLT

ISTASAASASTPFKPSDFKQYIRHGEEYELQFIFQLCKITLTTEVMAYLHTMDPTILEQWNFGLTLP

PSASLEDAYRFVRNAATSCQKDTPPQAKPDPLAKYKFWDVDLKERFSLDLDQFALGRKFLLQVGVQR

KPRPGLKRPASSASSSSSSSAKRKRVKK

TABLE 1-continued

| Description of Sequences |
|---|
| Sequence 27 (SEQ ID NO: 27):<br>MKVYLPPAPVSRIVNTEEYITRTGIYYYAGSSRLITLGHPYFSIPKTGQKAEIPKVSAFQYRVFRVQ<br>LPDPNKFGLPDPNLYNPDTDRLVWGCVGVEVGRGQPLGVGLSGHPLFNKYDDTENSRIANGNAQQDV<br>RDNTSVDNKQTQLCIIGCAPPIGEHWGVGTVCKNAQSQVQRGDCPPLELVSSVIQDGDMIDTGFGAM<br>DFAALQATKSDVPLDISQSVCKYPDYLKMSADTYGNSMFFHLRREQIFARHYYNKLGSVGEDIPTDY<br>YIKGSGNGRDPIESYIYSATPSGSMITSDSQIFNKPYWLHRAQGHNNGICWNNQLFITCVDTTRSTN<br>LTISTATAAVSPTFTPSNFKQYIRHGEEYELQFIFQLCKITLTTEVMAYLHTMDPTILEQWNFGLTL<br>PPSASLEDAYRFVRNAATSCQKDTPPQAKPDPLAKYKFWDVDLKERFSLDLDQFALGRKFLLQVGVQ<br>RKPRPGLKRPASSASSSSSSSAKRKRVKK |
| Sequence 28 (SEQ ID NO: 28):<br>MKVYLPPAPVSRIVNTEEYITRTGIYYYAGSSRLITLGHPYFPLPKTSTRAAIPKVSAFQYRVFRVQ<br>LPDPNKFGLPDPNLYNPDTDRLVWGCVGVEVGRGQPLGIGLSGHPLFNKLDDTENSHLATVNADTDN<br>RDNVSVDNKQTQLCIIGCAPPIGEHWGVGTVCKNAQSQVQRGDCPPLELVSSVIQDGDMIDTGFGAM<br>DFAALQATKSDVPLDISQSVCKYPDYLKMSADTYGNSMFFHLRREQIFARHYYNKLGSVGEDIPTDY<br>YIKGSGNGRDPIESYIYSATPSGSMITSDSQIFNKPYWLHRAQGHNNGICWNNQLFITCVDTTRSTN<br>LTISTATAAVSPTFTPSNFKQYIRHGEEYELQFIFQLCKITLTTEVMAYLHTMDPTILEQWNFGLTL<br>PPSASLEDAYRFVRNAATSCQKDTPPQAKPDPLAKYKFWDVDLKERFSLDLDQFALGRKFLLQVGVQ<br>RKPRPGLKRPASSASSSSSSSAKRKRVKK |
| Sequence 29 (SEQ ID NO: 29):<br>MKVYLPPAPVSRIVNTEEYITRTGIYYYAGSSRLITLGHPYFPLPKTSTRAAIPKVSAFQYRVFRVQ<br>LPDPNKFGLPDPNLYNPDTDRLVWGCVGVEVGRGQPLGVGLSGHPLFNKYDDTENSRIANGNAQQDV<br>RDNTSVDNKQTQLCIIGCAPPIGEHWGVGTVCKNAQSQVQRGDCPPLELVSSVIQDGDMIDTGFGAM<br>DFAALQATKSDVPLDISQSVCKYPDYLKMSADTYGNSMFFHLRREQIFARHFYNKAGAVGDAIPTTL<br>YIKGAESGREPPTSSIYSATPSGSMITSDSQIFNKPYWLHRAQGHNNGICWNNQLFITCVDTTRSTN<br>LTISTATAAVSPTFTPSNFKQYIRHGEEYELQFIFQLCKITLTTEVMAYLHTMDPTILEQWNFGLTL<br>PPSASLEDAYRFVRNAATSCQKDTPPQAKPDPLAKYKFWDVDLKERFSLDLDQFALGRKFLLQVGVQ<br>RKPRPGLKRPASSASSSSSSSAKRKRVKK |
| Sequence 30 (SEQ ID NO: 30):<br>MKVYLPPAPVSRIVNTEEYITRTGIYYYAGSSRLITLGHPYFPLPKTSTRAAIPKVSAFQYRVFRVQ<br>LPDPNKFGLPDPNLYNPDTDRLVWGCVGVEVGRGQPLGVGLSGHPLFNKYDDTENSRIANGNAQQDV<br>RDNTSVDNKQTQLCIIGCAPPIGEHWGVGTVCKNAQSQVQRGDCPPLELVSSVIQDGDMIDTGFGAM<br>DFAALQATKSDVPLDISQSVCKYPDYLKMSADTYGNSMFFHLRREQIFARHYYNKLGSVGEDIPTDY<br>YIKGSGNGRDPIESYIYSATPSGSMITSDSQIFNKPYWLHRAQGHNNGICWNNQLFITCVDTTRSTN<br>LTISTASAASASTPFKPSDFKQYIRHGEEYELQFIFQLCKITLTTEVMAYLHTMDPTILEQWNFGLT<br>LPPSASLEDAYRFVRNAATSCQKDTPPQAKPDPLAKYKFWDVDLKERFSLDLDQFALGRKFLLQVGV<br>QRKPRPGLKRPASSASSSSSSSAKRKRVKK |
| Sequence 31 (SEQ ID NO: 31):<br>The DNA Sequence encoding SEQ ID NO: 22<br>ATGGCTCTGTGGCGTACCTCTGACTCTAAAGTTTACCTGCCGCCGACCCCGGTTTCTCGTGTTGTTA<br>ACACCGACGAATACGTTACCCGTACCGGTATCTACTACTACGCTGGTTCTTCTCGTCTGCTGACCCT<br>GGGTCACCCGTACTTCTCTATCCCGAAAACCGGTCAGAAAGCTGAAATCCCGAAAGTTTCTGCTTAC<br>CAGTACCGTGTTTTCCGTGTTCACCTGCCGGACCCGAACAAATTCGGTCTGCCGGACCCGCAGCTGT |

TABLE 1-continued

| Description of Sequences |
|---|
| ACAACCCGGACACCGAACGTCTGGTTTGGGCTTGCGTTGGTGTTGAAGTTGGTCGTGGTCAGCCGCT<br>GGGTATCGGTCTGTCTGGTCACCCGCTGTTCAACAAACTGGACGACACCGAAAACTCTCACCTGGCT<br>ACCGTTAACGCTGACACCGACAACCGTGACAACGTTTCTGTTGACAACAAACAGACCCAGCTGTGCA<br>TCATCGGTTGCACCCCGCCGCTGGGTGAACACTGGGGTATCGGTACCATCTGCAAAAACACCCAGAC<br>CCAGCGTGGTGACTGCCCGCCGCTGGAACTGATCTCTTCTATCATCGAAGACGGTGACATGATCGAC<br>ACCGGTTTCGGTGCTATGGACTTCACCGCTCTGCAGGCTACCAAATCTGACGTTCCGATCGACATCT<br>CTCAGTCTACCTGCAAATACCCGGACTACCTGAAAATGTCTGCTGACACCTACGGTAACTCTATGTT<br>CTTCTTCCTGCGTCGTGAACAGCTGTTCGCTCGTCACTTCTACAACAAAGCTGGTGCTGTTGGTGAC<br>GCTATCCCGACCACCCTGTACATCAAAGGTGCTGAATCTGGTCGTGAACCGCCGACCTCTTCTATCT<br>ACTCTGCTACCCCGTCTGGTTCTATGGTTACCTCTGACGCTCAGCTGTTCAACAAACCGTACTGGCT<br>GCAGCGTGCTCAGGGTCACAACAACGGTATCTGCTGGGGTAACCAGCTGTTCGTTACCTGCGTTGAC<br>ACCACCCGTTCTACCAACCTGACCATCTCTACCCTGTCTGCTGCTTCTGCTTCTACCCCGTTCAAAC<br>CGTCTGACTACAAACAGTTCATCCGTCACGGTGAAGAATACGAACTGCAGTTCATCTTCCAGCTGTG<br>CAAAATCACCCTGACCACCGACGTTATGGCTTACATCCACCTGATGAACGCTTCTATCCTGGAAGAC<br>TGGAACTTCGGTCTGACCCTGCCGCCGACCGCTTCTCTGGAAGACGCTTACCGTTTCATCAAAAACT<br>CTGCTACCACCTGCCAGCGTAACGCTCCGCCGGTTCCGAAAGAAGACCCGTTCCAGAAATTCAAATT<br>CTGGGACGTTGACCTGAAAGAAAAATTCTCTATCGACCTGGACCAGTTCCCGCTGGGTCGTAAATTC<br>ATGCTGCAGGCTGGTATCCAGCGTCGTCCGAAACTGGGTACCAAACGTCCGCTGTCTTCTACCTCTT<br>CTTCTACCAAACGTAAAAAACGTAAACTGACCAAATAA |
| Sequence 32 (SEQ ID NO: 32):<br>The DNA Sequence encoding SEQ ID NO: 23<br>ATGAAGGTGTACCTGCCCCCCGCCCCCGTGAGCAGGATCGTGAACACCGAGGAGTACATCACCAGGA<br>CCGGCATCTACTACTACGCCGGCAGCAGCAGGCTGATCACCCTGGGCCACCCCTACTTCCCGATCCC<br>GAAATCTGGTTCTACCGCTGAAATCCCGAAGGTCTCTGCCTTCCAGTACAGGGTGTTCAGGGTGCAG<br>CTCCCCGACCCCAACAAGTTCGGCCTGCCCGACCCCAACCTGTACAACCCCGACACCGACAGGCTGG<br>TGTGGGGCTGCGTGGGCGTGGAGGTGGGTCGTGGTCAGCCGCTGGGTATCGGTCTGTCTGGTCACCC<br>GCTGTTCAACAAACTGGACGACACCGAAAACTCTCACCTGGCTACCGTTAACGCTGACACCGACAAC<br>CGTGACAACGTTTCTGTTGACAACAAGCAGACCCAGCTGTGCATCATCGGCTGCGCCCCCCCCATCG<br>GCGAGCACTGGGGCATCGGCACCACCTGCAAGAACACCCCCGTGCCCCCCGGCGACTGCCCCCCCCT<br>GGAGCTGGTGAGCAGCGTGATCCAGGACGGCGACATGATCGACACCGGCTTCGGCGCCATGGACTTC<br>GCCGCCCTGCAGGCCACCAAGAGCGACGTGCCCCTGGACATCAGCCAGAGCGTGTGCAAGTACCCCG<br>ACTACCTGAAGATGAGCGCCGACACCTACGGCAACAGCATGTTCTTCCACCTGAGGAGGGAGCAGAT<br>CTTCGCCAGGCACTACTACAACAAGCTGGGCAGCGTGGGCGAGGACATCCCCACCGACTACTACATC<br>AAGGGCAGCGGCAACGGCAGGGACCCCATCGAGAGCTACATCTACAGCGCCACCCCCAGCGGCAGCA<br>TGATCACCAGCGACAGCCAGATCTTCAACAAGCCCTACTGGCTGCACAGGGCCCAGGGCCACAACAA<br>CGGCATCTGCTGGAACAACCAGCTGTTCATCACCTGCGTGGACACCACCAGGAGCACCAACCTGACC<br>ATCAGCACCGCCACCGCCGCCGTGAGCCCCACCTTCACCCCCAGCAACTTCAAGCAGTACATCAGGC<br>ACGGCGAGGAGTACGAGCTGCAGTTCATCTTCCAGCTGTGCAAGATCACCCTGACCACCGAGGTGAT<br>GGCCTACCTGCACACCATGGACCCCACCATCCTGGAGCAGTGGAACTTCGGCCTGACCCTGCCCCCC<br>AGCGCCAGCCTGGAGGACGCCTACAGGTTCGTGAGGAACGCCGCCACCAGCTGCCAGAAGGACACCC |

TABLE 1-continued

| Description of Sequences |
|---|
| CCCCCCAGGCCAAGCCCGACCCCCTGGCCAAGTACAAGTTCTGGGACGTGGACCTGAAGGAGAGGTT |
| CAGCCTGGACCTGGACCAGTTCGCCCTGGGCAGGAAGTTCCTGCTGCAGGTGGGCGTGCAGAGGAAG |
| CCCAGGCCCGGCCTGAAGAGGCCCGCTAGCAGCGCCAGCTCCAGCAGCTCCAGCAGCGCCAAGAGGA |
| AGAGGGTGAAGAAGTAA |
| Sequence 33 (SEQ ID NO: 33):<br>The DNA Sequence encoding SEQ ID NO: 24<br>ATGAAGGTGTACCTGCCCCCCGCCCCCGTGAGCAGGATCGTGAACACCGAGGAGTACATCACCAGGA |
| CCGGCATCTACTACTACGCCGGCAGCAGCAGGCTGATCACCCTGGGCCACCCCTACTTCCCGATCCC |
| GAAATCTGGTTCTACCGCTGAAATCCCGAAGGTCTCTGCCTTCCAGTACAGGGTGTTCAGGGTGCAG |
| CTCCCCGACCCCAACAAGTTCGGCCTGCCCGACCCCAACCTGTACAACCCCGACACCGACAGGCTGG |
| TGTGGGGCTGCGTGGGCGTGGAGGTGGGCAGGGGCCAGCCCCTGGGCGTGGGCCTGAGCGGCCACCC |
| CCTGTTCAACAAGTACGACGACACCGAGAACAGCAGGATCGCCAACGGCAACGCCCAGCAGGACGTG |
| AGGGACAACACCAGCGTGGACAACAAGCAGACCCAGCTGTGCATCATCGGCTGCGCCCCCCCCATCG |
| GCGAGCACTGGGGTATCGGTACCATCTGCAAAAACACCCAGACCCAGCGTGGTGACTGCCCGCCGCT |
| GGAGCTGGTGAGCAGCGTGATCCAGGACGGCGACATGATCGACACCGGCTTCGGCGCCATGGACTTC |
| GCCGCCCTGCAGGCCACCAAGAGCGACGTGCCCCTGGACATCAGCCAGAGCGTGTGCAAGTACCCCG |
| ACTACCTGAAGATGAGCGCCGACACCTACGGCAACAGCATGTTCTTCCACCTGAGGAGGGAGCAGAT |
| CTTCGCCAGGCACTACTACAACAAGCTGGGCAGCGTGGGCGAGGACATCCCCACCGACTACTACATC |
| AAGGGCAGCGGCAACGGCAGGGACCCCATCGAGAGCTACATCTACAGCGCCACCCCCAGCGGCAGCA |
| TGATCACCAGCGACAGCCAGATCTTCAACAAGCCCTACTGGCTGCACAGGGCCCAGGGCCACAACAA |
| CGGCATCTGCTGGAACAACCAGCTGTTCATCACCTGCGTGGACACCACCAGGAGCACCAACCTGACC |
| ATCAGCACCGCCACCGCCGCCGTGAGCCCCACCTTCACCCCCAGCAACTTCAAGCAGTACATCAGGC |
| ACGGCGAGGAGTACGAGCTGCAGTTCATCTTCCAGCTGTGCAAGATCACCCTGACCACCGAGGTGAT |
| GGCCTACCTGCACACCATGGACCCCACCATCCTGGAGCAGTGGAACTTCGGCCTGACCCTGCCCCCC |
| AGCGCCAGCCTGGAGGACGCCTACAGGTTCGTGAGGAACGCCGCCACCAGCTGCCAGAAGGACACCC |
| CCCCCCAGGCCAAGCCCGACCCCCTGGCCAAGTACAAGTTCTGGGACGTGGACCTGAAGGAGAGGTT |
| CAGCCTGGACCTGGACCAGTTCGCCCTGGGCAGGAAGTTCCTGCTGCAGGTGGGCGTGCAGAGGAAG |
| CCCAGGCCCGGCCTGAAGAGGCCCGCTAGCAGCGCCAGCTCCAGCAGCTCCAGCAGCGCCAAGAGGA |
| AGAGGGTGAAGAAGTAA |
| Sequence 34 (SEQ ID NO: 34):<br>The DNA Sequence encoding SEQ ID NO: 25<br>ATGAAGGTGTACCTGCCCCCCGCCCCCGTGAGCAGGATCGTGAACACCGAGGAGTACATCACCAGGA |
| CCGGCATCTACTACTACGCCGGCAGCAGCAGGCTGATCACCCTGGGCCACCCCTACTTCCCGATCCC |
| GAAATCTGGTTCTACCGCTGAAATCCCGAAGGTCTCTGCCTTCCAGTACAGGGTGTTCAGGGTGCAG |
| CTCCCCGACCCCAACAAGTTCGGCCTGCCCGACCCCAACCTGTACAACCCCGACACCGACAGGCTGG |
| TGTGGGGCTGCGTGGGCGTGGAGGTGGGCAGGGGCCAGCCCCTGGGCGTGGGCCTGAGCGGCCACCC |
| CCTGTTCAACAAGTACGACGACACCGAGAACAGCAGGATCGCCAACGGCAACGCCCAGCAGGACGTG |
| AGGGACAACACCAGCGTGGACAACAAGCAGACCCAGCTGTGCATCATCGGCTGCGCCCCCCCCATCG |
| GCGAGCACTGGGGCATCGGCACCACCTGCAAGAACACCCCCGTGCCCCCCGGCGACTGCCCCCCCCT |
| GGAGCTGGTGAGCAGCGTGATCCAGGACGGCGACATGATCGACACCGGCTTCGGCGCCATGGACTTC |
| GCCGCCCTGCAGGCCACCAAGAGCGACGTGCCCCTGGACATCAGCCAGAGCGTGTGCAAGTACCCCG |

TABLE 1-continued

Description of Sequences

ACTACCTGAAGATGAGCGCCGACACCTACGGCAACAGCATGTTCTTCCACCTGAGGAGGGAGCAGAT

CTTCGCCAGGCACTTCTACAACAAAGCTGGTGCTGTTGGTGACGCTATCCCGACCACCCTGTACATC

AAAGGTGCTGAATCTGGTCGTGAACCGCCGACCTCTTCTATCTACTCTGCCACCCCCAGCGGCAGCA

TGATCACCAGCGACAGCCAGATCTTCAACAAGCCCTACTGGCTGCACAGGGCCCAGGGCCACAACAA

CGGCATCTGCTGGAACAACCAGCTGTTCATCACCTGCGTGGACACCACCAGGAGCACCAACCTGACC

ATCAGCACCGCCACCGCCGCCGTGAGCCCCACCTTCACCCCCAGCAACTTCAAGCAGTACATCAGGC

ACGGCGAGGAGTACGAGCTGCAGTTCATCTTCCAGCTGTGCAAGATCACCCTGACCACCGAGGTGAT

GGCCTACCTGCACACCATGGACCCCACCATCCTGGAGCAGTGGAACTTCGGCCTGACCCTGCCCCCC

AGCGCCAGCCTGGAGGACGCCTACAGGTTCGTGAGGAACGCCGCCACCAGCTGCCAGAAGGACACCC

CCCCCCAGGCCAAGCCCGACCCCCTGGCCAAGTACAAGTTCTGGGACGTGGACCTGAAGGAGAGGTT

CAGCCTGGACCTGGACCAGTTCGCCCTGGGCAGGAAGTTCCTGCTGCAGGTGGGCGTGCAGAGGAAG

CCCAGGCCCGGCCTGAAGAGGCCCGCTAGCAGCGCCAGCTCCAGCAGCTCCAGCAGCGCCAAGAGGA

AGAGGGTGAAGAAGTAA

Sequence 35 (SEQ ID NO: 35):
The DNA Sequence encoding SEQ ID NO: 26
ATGAAGGTGTACCTGCCCCCCGCCCCCGTGAGCAGGATCGTGAACACCGAGGAGTACATCACCAGGA

CCGGCATCTACTACTACGCCGGCAGCAGCAGGCTGATCACCCTGGGCCACCCCTACTTCCCGATCCC

GAAATCTGGTTCTACCGCTGAAATCCCGAAGGTCTCTGCCTTCCAGTACAGGGTGTTCAGGGTGCAG

CTCCCCGACCCCAACAAGTTCGGCCTGCCCGACCCCAACCTGTACAACCCCGACACCGACAGGCTGG

TGTGGGGCTGCGTGGGCGTGGAGGTGGGCAGGGGCCAGCCCCTGGGCGTGGGCCTGAGCGGCCACCC

CCTGTTCAACAAGTACGACGACACCGAGAACAGCAGGATCGCCAACGGCAACGCCCAGCAGGACGTG

AGGGACAACACCAGCGTGGACAACAAGCAGACCCAGCTGTGCATCATCGGCTGCGCCCCCCCCATCG

GCGAGCACTGGGGCATCGGCACCACCTGCAAGAACACCCCCGTGCCCCCCGGCGACTGCCCCCCCCT

GGAGCTGGTGAGCAGCGTGATCCAGGACGGCGACATGATCGACACCGGCTTCGGCGCCATGGACTTC

GCCGCCCTGCAGGCCACCAAGAGCGACGTGCCCCTGGACATCAGCCAGAGCGTGTGCAAGTACCCCG

ACTACCTGAAGATGAGCGCCGACACCTACGGCAACAGCATGTTCTTCCACCTGAGGAGGGAGCAGAT

CTTCGCCAGGCACTACTACAACAAGCTGGGCAGCGTGGGCGAGGACATCCCCACCGACTACTACATC

AAGGGCAGCGGCAACGGCAGGGACCCCATCGAGAGCTACATCTACAGCGCCACCCCCAGCGGCAGCA

TGATCACCAGCGACAGCCAGATCTTCAACAAGCCCTACTGGCTGCACAGGGCCCAGGGCCACAACAA

CGGCATCTGCTGGAACAACCAGCTGTTCATCACCTGCGTGGACACCACCAGGAGCACCAACCTGACC

ATCAGCACCGCCTCTGCTGCTTCTGCTTCTACCCCGTTCAAACCGTCTGACTTCAAGCAGTACATCA

GGCACGGCGAGGAGTACGAGCTGCAGTTCATCTTCCAGCTGTGCAAGATCACCCTGACCACCGAGGT

GATGGCCTACCTGCACACCATGGACCCCACCATCCTGGAGCAGTGGAACTTCGGCCTGACCCTGCCC

CCCAGCGCCAGCCTGGAGGACGCCTACAGGTTCGTGAGGAACGCCGCCACCAGCTGCCAGAAGGACA

CCCCCCCCCAGGCCAAGCCCGACCCCCTGGCCAAGTACAAGTTCTGGGACGTGGACCTGAAGGAGAG

GTTCAGCCTGGACCTGGACCAGTTCGCCCTGGGCAGGAAGTTCCTGCTGCAGGTGGGCGTGCAGAGG

AAGCCCAGGCCCGGCCTGAAGAGGCCCGCTAGCAGCGCCAGCTCCAGCAGCTCCAGCAGCGCCAAGA

GGAAGAGGGTGAAGAAGTAA

TABLE 1-continued

| Description of Sequences |
|---|

Sequence 36 (SEQ ID NO: 36):
The DNA Sequence encoding SEQ ID NO: 27
ATGAAGGTGTACCTGCCCCCCGCCCCCGTGAGCAGGATCGTGAACACCGAGGAGTACATCACCAGGA

CCGGCATCTACTACTACGCCGGCAGCAGCAGGCTGATCACCCTGGGCCACCCCTACTTCTCTATCCC

GAAAACCGGTCAGAAAGCTGAAATCCCGAAAGTTTCTGCCTTCCAGTACAGGGTGTTCAGGGTGCAG

CTCCCCGACCCCAACAAGTTCGGCCTGCCCGACCCCAACCTGTACAACCCCGACACCGACAGGCTGG

TGTGGGGCTGCGTGGGCGTGGAGGTGGGCAGGGGCCAGCCCCTGGGCGTGGGCCTGAGCGGCCACCC

CCTGTTCAACAAGTACGACGACACCGAGAACAGCAGGATCGCCAACGGCAACGCCCAGCAGGACGTG

AGGGACAACACCAGCGTGGACAACAAGCAGACCCAGCTGTGCATCATCGGCTGCGCCCCCCCCATCG

GCGAGCACTGGGGTGTCGGTACCGTTTGCAAAAACGCTCAGTCTCAGGTTCAGCGTGGTGACTGCCC

GCCGCTGGAGCTGGTGAGCAGCGTGATCCAGGACGGCGACATGATCGACACCGGCTTCGGCGCCATG

GACTTCGCCGCCCTGCAGGCCACCAAGAGCGACGTGCCCCTGGACATCAGCCAGAGCGTGTGCAAGT

ACCCCGACTACCTGAAGATGAGCGCCGACACCTACGGCAACAGCATGTTCTTCCACCTGAGGAGGGA

GCAGATCTTCGCCAGGCACTACTACAACAAGCTGGGCAGCGTGGGCGAGGACATCCCCACCGACTAC

TACATCAAGGGCAGCGGCAACGGCAGGGACCCCATCGAGAGCTACATCTACAGCGCCACCCCCAGCG

GCAGCATGATCACCAGCGACAGCCAGATCTTCAACAAGCCCTACTGGCTGCACAGGGCCCAGGGCCA

CAACAACGGCATCTGCTGGAACAACCAGCTGTTCATCACCTGCGTGGACACCACCAGGAGCACCAAC

CTGACCATCAGCACCGCCACCGCCGCCGTGAGCCCCACCTTCACCCCCAGCAACTTCAAGCAGTACA

TCAGGCACGGCGAGGAGTACGAGCTGCAGTTCATCTTCCAGCTGTGCAAGATCACCCTGACCACCGA

GGTGATGGCCTACCTGCACACCATGGACCCCACCATCCTGGAGCAGTGGAACTTCGGCCTGACCCTG

CCCCCCAGCGCCAGCCTGGAGGACGCCTACAGGTTCGTGAGGAACGCCGCCACCAGCTGCCAGAAGG

ACACCCCCCCCCAGGCCAAGCCCGACCCCCTGGCCAAGTACAAGTTCTGGGACGTGGACCTGAAGGA

GAGGTTCAGCCTGGACCTGGACCAGTTCGCCCTGGGCAGGAAGTTCCTGCTGCAGGTGGGCGTGCAG

AGGAAGCCCAGGCCCGGCCTGAAGAGGCCCGCTAGCAGCGCCAGCTCCAGCAGCTCCAGCAGCGCCA

AGAGGAAGAGGGTGAAGAAGTAA

Sequence 37 (SEQ ID NO: 37):
The DNA Sequence encoding SEQ ID NO: 28
ATGAAGGTGTACCTGCCCCCCGCCCCCGTGAGCAGGATCGTGAACACCGAGGAGTACATCACCAGGA

CCGGCATCTACTACTACGCCGGCAGCAGCAGGCTGATCACCCTGGGCCACCCCTACTTCCCCCTGCC

CAAGACCAGCACCAGGGCCGCCATCCCCAAGGTGAGCGCCTTCCAGTACAGGGTGTTCAGGGTGCAG

CTCCCCGACCCCAACAAGTTCGGCCTGCCCGACCCCAACCTGTACAACCCCGACACCGACAGGCTGG

TGTGGGGCTGCGTGGGCGTGGAGGTGGGTCGTGGTCAGCCGCTGGGTATCGGTCTGTCTGGTCACCC

GCTGTTCAACAAACTGGACGACACCGAAAACTCTCACCTGGCTACCGTTAACGCTGACACCGACAAC

CGTGACAACGTTTCTGTTGACAACAAGCAGACCCAGCTGTGCATCATCGGCTGCGCCCCCCCCATCG

GCGAGCACTGGGGTGTCGGTACCGTTTGCAAAAACGCTCAGTCTCAGGTTCAGCGTGGTGACTGCCC

GCCGCTGGAGCTGGTGAGCAGCGTGATCCAGGACGGCGACATGATCGACACCGGCTTCGGCGCCATG

GACTTCGCCGCCCTGCAGGCCACCAAGAGCGACGTGCCCCTGGACATCAGCCAGAGCGTGTGCAAGT

ACCCCGACTACCTGAAGATGAGCGCCGACACCTACGGCAACAGCATGTTCTTCCACCTGAGGAGGGA

GCAGATCTTCGCCAGGCACTACTACAACAAGCTGGGCAGCGTGGGCGAGGACATCCCCACCGACTAC

TACATCAAGGGCAGCGGCAACGGCAGGGACCCCATCGAGAGCTACATCTACAGCGCCACCCCCAGCG

GCAGCATGATCACCAGCGACAGCCAGATCTTCAACAAGCCCTACTGGCTGCACAGGGCCCAGGGCCA

TABLE 1-continued

| Description of Sequences |
| --- |
| CAACAACGGCATCTGCTGGAACAACCAGCTGTTCATCACCTGCGTGGACACCACCAGGAGCACCAAC<br>CTGACCATCAGCACCGCCACCGCCGCCGTGAGCCCCACCTTCACCCCCAGCAACTTCAAGCAGTACA<br>TCAGGCACGGCGAGGAGTACGAGCTGCAGTTCATCTTCCAGCTGTGCAAGATCACCCTGACCACCGA<br>GGTGATGGCCTACCTGCACACCATGGACCCCACCATCCTGGAGCAGTGGAACTTCGGCCTGACCCTG<br>CCCCCCAGCGCCAGCCTGGAGGACGCCTACAGGTTCGTGAGGAACGCCGCCACCAGCTGCCAGAAGG<br>ACACCCCCCCCCAGGCCAAGCCCGACCCCCTGGCCAAGTACAAGTTCTGGGACGTGGACCTGAAGGA<br>GAGGTTCAGCCTGGACCTGGACCAGTTCGCCCTGGGCAGGAAGTTCCTGCTGCAGGTGGGCGTGCAG<br>AGGAAGCCCAGGCCCGGCCTGAAGAGGCCCGCTAGCAGCGCCAGCTCCAGCAGCTCCAGCAGCGCCA<br>AGAGGAAGAGGGTGAAGAAGTAA |
| Sequence 38 (SEQ ID NO: 38):<br>The DNA Sequence encoding SEQ ID NO: 29<br>ATGAAGGTGTACCTGCCCCCCGCCCCCGTGAGCAGGATCGTGAACACCGAGGAGTACATCACCAGGA<br>CCGGCATCTACTACTACGCCGGCAGCAGCAGGCTGATCACCCTGGGCCACCCCTACTTCCCCCTGCC<br>CAAGACCAGCACCAGGGCCGCCATCCCCAAGGTGAGCGCCTTCCAGTACAGGGTGTTCAGGGTGCAG<br>CTCCCCGACCCCAACAAGTTCGGCCTGCCCGACCCCAACCTGTACAACCCCGACACCGACAGGCTGG<br>TGTGGGGCTGCGTGGGCGTGGAGGTGGGCAGGGGCCAGCCCCTGGGCGTGGGCCTGAGCGGCCACCC<br>CCTGTTCAACAAGTACGACGACACCGAGAACAGCAGGATCGCCAACGGCAACGCCCAGCAGGACGTG<br>AGGGACAACACCAGCGTGGACAACAAGCAGACCCAGCTGTGCATCATCGGCTGCGCCCCCCCCATCG<br>GCGAGCACTGGGGTGTCGGTACCGTTTGCAAAAACGCTCAGTCTCAGGTTCAGCGTGGTGACTGCCC<br>GCCGCTGGAGCTGGTGAGCAGCGTGATCCAGGACGGCGACATGATCGACACCGGCTTCGGCGCCATG<br>GACTTCGCCGCCCTGCAGGCCACCAAGAGCGACGTGCCCCTGGACATCAGCCAGAGCGTGTGCAAGT<br>ACCCCGACTACCTGAAGATGAGCGCCGACACCTACGGCAACAGCATGTTCTTCCACCTGAGGAGGGA<br>GCAGATCTTCGCCAGGCACTTCTACAACAAAGCTGGTGCTGTTGGTGACGCTATCCCGACCACCCTG<br>TACATCAAAGGTGCTGAATCTGGTCGTGAACCGCCGACCTCTTCTATCTACTCTGCCACCCCCAGCG<br>GCAGCATGATCACCAGCGACAGCCAGATCTTCAACAAGCCCTACTGGCTGCACAGGGCCCAGGGCCA<br>CAACAACGGCATCTGCTGGAACAACCAGCTGTTCATCACCTGCGTGGACACCACCAGGAGCACCAAC<br>CTGACCATCAGCACCGCCACCGCCGCCGTGAGCCCCACCTTCACCCCCAGCAACTTCAAGCAGTACA<br>TCAGGCACGGCGAGGAGTACGAGCTGCAGTTCATCTTCCAGCTGTGCAAGATCACCCTGACCACCGA<br>GGTGATGGCCTACCTGCACACCATGGACCCCACCATCCTGGAGCAGTGGAACTTCGGCCTGACCCTG<br>CCCCCCAGCGCCAGCCTGGAGGACGCCTACAGGTTCGTGAGGAACGCCGCCACCAGCTGCCAGAAGG<br>ACACCCCCCCCCAGGCCAAGCCCGACCCCCTGGCCAAGTACAAGTTCTGGGACGTGGACCTGAAGGA<br>GAGGTTCAGCCTGGACCTGGACCAGTTCGCCCTGGGCAGGAAGTTCCTGCTGCAGGTGGGCGTGCAG<br>AGGAAGCCCAGGCCCGGCCTGAAGAGGCCCGCTAGCAGCGCCAGCTCCAGCAGCTCCAGCAGCGCCA<br>AGAGGAAGAGGGTGAAGAAGTAA |
| Sequence 39 (SEQ ID NO: 39):<br>The DNA Sequence encoding SEQ ID NO: 30<br>ATGAAGGTGTACCTGCCCCCCGCCCCCGTGAGCAGGATCGTGAACACCGAGGAGTACATCACCAGGA<br>CCGGCATCTACTACTACGCCGGCAGCAGCAGGCTGATCACCCTGGGCCACCCCTACTTCCCCCTGCC<br>CAAGACCAGCACCAGGGCCGCCATCCCCAAGGTGAGCGCCTTCCAGTACAGGGTGTTCAGGGTGCAG<br>CTCCCCGACCCCAACAAGTTCGGCCTGCCCGACCCCAACCTGTACAACCCCGACACCGACAGGCTGG<br>TGTGGGGCTGCGTGGGCGTGGAGGTGGGCAGGGGCCAGCCCCTGGGCGTGGGCCTGAGCGGCCACCC |

TABLE 1-continued

| Description of Sequences |
|---|
| CCTGTTCAACAAGTACGACGACACCGAGAACAGCAGGATCGCCAACGGCAACGCCCAGCAGGACGTG |
| AGGGACAACACCAGCGTGGACAACAAGCAGACCCAGCTGTGCATCATCGGCTGCGCCCCCCCCATCG |
| GCGAGCACTGGGGTGTCGGTACCGTTTGCAAAAACGCTCAGTCTCAGGTTCAGCGTGGTGACTGCCC |
| GCCGCTGGAGCTGGTGAGCAGCGTGATCCAGGACGGCGACATGATCGACACCGGCTTCGGCGCCATG |
| GACTTCGCCGCCCTGCAGGCCACCAAGAGCGACGTGCCCCTGGACATCAGCCAGAGCGTGTGCAAGT |
| ACCCCGACTACCTGAAGATGAGCGCCGACACCTACGGCAACAGCATGTTCTTCCACCTGAGGAGGGA |
| GCAGATCTTCGCCAGGCACTACTACAACAAGCTGGGCAGCGTGGGCGAGGACATCCCCACCGACTAC |
| TACATCAAGGGCAGCGGCAACGGCAGGGACCCCATCGAGAGCTACATCTACAGCGCCACCCCCAGCG |
| GCAGCATGATCACCAGCGACAGCCAGATCTTCAACAAGCCCTACTGGCTGCACAGGGCCCAGGGCCA |
| CAACAACGGCATCTGCTGGAACAACCAGCTGTTCATCACCTGCGTGGACACCACCAGGAGCACCAAC |
| CTGACCATCAGCACCGCCTCTGCTGCTTCTGCTTCTACCCCGTTCAAACCGTCTGACTTCAAGCAGT |
| ACATCAGGCACGGCGAGGAGTACGAGCTGCAGTTCATCTTCCAGCTGTGCAAGATCACCCTGACCAC |
| CGAGGTGATGGCCTACCTGCACACCATGGACCCCACCATCCTGGAGCAGTGGAACTTCGGCCTGACC |
| CTGCCCCCCAGCGCCAGCCTGGAGGACGCCTACAGGTTCGTGAGGAACGCCGCCACCAGCTGCCAGA |
| AGGACACCCCCCCCCAGGCCAAGCCCGACCCCCTGGCCAAGTACAAGTTCTGGGACGTGGACCTGAA |
| GGAGAGGTTCAGCCTGGACCTGGACCAGTTCGCCCTGGGCAGGAAGTTCCTGCTGCAGGTGGGCGTG |
| CAGAGGAAGCCCAGGCCCGGCCTGAAGAGGCCCGCTAGCAGCGCCAGCTCCAGCAGCTCCAGCAGCG |
| CCAAGAGGAAGAGGGTGAAGAAGTAA |
| Sequence 40 (SEQ ID NO: 40):<br>MKVYLPPAPVSRIVNTEEYITRTGIYYYAGSSRLITLGHPYFSIPKTGQKAEIPKVSAFQYRVFRVQ |
| LPDPNKFGLPDPNLYNPDTDRLVWGCVGVEVGRGQPLGVGLSGHPLFNKLDDTENSHLATANADTDN |
| RDNVCVDNKQTQLCIIGCAPPIGEHWGIGTTCKNTPVPPGDCPPLELVSSVIQDGDMIDTGFGAMDF |
| AALQATKSDVPLDISQSVCKYPDYLKMSADTYGNSMFFHLRREQIFARHYYNKLGSVGEDIPTDYYI |
| KGSGNGRDPIESYIYSATPSGSMITSDSQIFNKPYWLHRAQGHNNGICWNNQLFITCVDTTRSTNLT |
| ISTATAAVSPTFTPSNFKQYIRHGEEYELQFIFQLCKITLTTEVMAYLHTMDPTILEQWNFGLTLPP |
| SASLEDAYRFVRNAATSCQKDTPPQAKPDPLAKYKFWDVDLKERFSLDLDQFALGRKFLLQVGVQRK |
| PRPGLKRPASSASSSSSSSAKRKRVKK |
| Sequence 41 (SEQ ID NO: 41):<br>MKVYLPPAPVSRIVNTEEYITRTGIYYYAGSSRLITLGHPYFPLPKTSTRAAIPKVSAFQYRVFRVQ |
| LPDPNKFGLPDPNLYNPDTDRLVWGCVGVEVGRGQPLGVGLSGHPLFNKLDDTENSHLATANADTDN |
| RDNVCVDNKQTQLCIIGCAPPIGEHWGIGTICKNTQTQRGDCPPLELVSSVIQDGDMIDTGFGAMDF |
| AALQATKSDVPLDISQSVCKYPDYLKMSADTYGNSMFFHLRREQIFARHYYNKLGSVGEDIPTDYYI |
| KGSGNGRDPIESYIYSATPSGSMITSDSQIFNKPYWLHRAQGHNNGICWNNQLFITCVDTTRSTNLT |
| ISTATAAVSPTFTPSNFKQYIRHGEEYELQFIFQLCKITLTTEVMAYLHTMDPTILEQWNFGLTLPP |
| SASLEDAYRFVRNAATSCQKDTPPQAKPDPLAKYKFWDVDLKERFSLDLDQFALGRKFLLQVGVQRK |
| PRPGLKRPASSASSSSSSSAKRKRVKK |
| Sequence 42 (SEQ ID NO: 42):<br>MKVYLPPAPVSRIVNTEEYITRTGIYYYAGSSRLITLGHPYFPLPKTSTRAAIPKVSAFQYRVFRVQ |
| LPDPNKFGLPDPNLYNPDTDRLVWGCVGVEVGRGQPLGVGLSGHPLFNKLDDTENSHLATANADTDN |
| RDNVCVDNKQTQLCIIGCAPPIGEHWGIGTTCKNTPVPPGDCPPLELVSSVIQDGDMIDTGFGAMDF |

TABLE 1-continued

| Description of Sequences |
|---|
| AALQATKSDVPLDISQSVCKYPDYLKMSADTYGNSMFFHLRREQIFARHFYNKAGAVGDAIPTTLYI |
| KGAESGREPPTSSIYSATPSGSMITSDSQIFNKPYWLHRAQGHNNGICWNNQLFITCVDTTRSTNLT |
| ISTATAAVSPTFTPSNFKQYIRHGEEYELQFIFQLCKITLTTEVMAYLHTMDPTILEQWNFGLTLPP |
| SASLEDAYRFVRNAATSCQKDTPPQAKPDPLAKYKFWDVDLKERFSLDLDQFALGRKFLLQVGVQRK |
| PRPGLKRPASSASSSSSSSAKRKRVKK |
| Sequence 43 (SEQ ID NO: 43): MKVYLPPAPVSRIVNTEEYITRTGIYYYAGSSRLITLGHPYFPLPKTSTRAAIPKVSAFQYRVFRVQ |
| LPDPNKFGLPDPNLYNPDTDRLVWGCVGVEVGRGQPLGVGLSGHPLFNKLDDTENSHLATANADTDN |
| RDNVCVDNKQTQLCIIGCAPPIGEHWGIGTTCKNTPVPPGDCPPLELVSSVIQDGDMIDTGFGAMDF |
| AALQATKSDVPLDISQSVCKYPDYLKMSADTYGNSMFFHLRREQIFARHYYNKLGSVGEDIPTDYYI |
| KGSGNGRDPIESYIYSATPSGSMITSDSQIFNKPYWLHRAQGHNNGICWNNQLFITCVDTTRSTNLT |
| ISTASAASASTPFKPSDFKQYIRHGEEYELQFIFQLCKITLTTEVMAYLHTMDPTILEQWNFGLTLP |
| PSASLEDAYRFVRNAATSCQKDTPPQAKPDPLAKYKFWDVDLKERFSLDLDQFALGRKFLLQVGVQR |
| KPRPGLKRPASSASSSSSSSAKRKRVKK |
| Sequence 44 (SEQ ID NO: 44): MKVYLPPAPVSRIVNTEEYITRTGIYYYAGSSRLITLGHPYFSIPKTGQKAEIPKVSAFQYRVFRVQ |
| LPDPNKFGLPDPNLYNPDTDRLVWGCVGVEVGRGQPLGVGLSGHPLFNKYDDTENSRIANGNAQQDV |
| RDNTSVDNKQTQLCIIGCAPPIGEHWGIGTTCKNTPVPPGDCPPLELVSSVIQDGDMIDTGFGAMDF |
| AALQATKSDVPLDISQSVCKYPDYLKMSADTYGNSMFFHLRREQIFARHFFNKAGTIGDPVPVSMYI |
| KGAGQGREPPTTSIYSATPSGSMITSDSQIFNKPYWLHRAQGHNNGICWNNQLFITCVDTTRSTNLT |
| ISTATAAVSPTFTPSNFKQYIRHGEEYELQFIFQLCKITLTTEVMAYLHTMDPTILEQWNFGLTLPP |
| SASLEDAYRFVRNAATSCQKDTPPQAKPDPLAKYKFWDVDLKERFSLDLDQFALGRKFLLQVGVQRK |
| PRPGLKRPASSASSSSSSSAKRKRVKK |
| Sequence 45 (SEQ ID NO: 45): MKVYLPPAPVSRIVNTEEYITRTGIYYYAGSSRLITLGHPYFPLPKTSTRAAIPKVSAFQYRVFRVQ |
| LPDPNKFGLPDPNLYNPDTDRLVWGCVGVEVGRGQPLGIGLSGHPLFNKLDDTENSHLATVNADTDN |
| RDNVSVDNKQTQLCIIGCAPPIGEHWGIGTTCKNTPVPPGDCPPLELVSSVIQDGDMIDTGFGAMDF |
| AALQATKSDVPLDISQSVCKYPDYLKMSADTYGNSMFFHLRREQIFARHFFNKAGTIGDPVPVSMYI |
| KGAGQGREPPTTSIYSATPSGSMITSDSQIFNKPYWLHRAQGHNNGICWNNQLFITCVDTTRSTNLT |
| ISTATAAVSPTFTPSNFKQYIRHGEEYELQFIFQLCKITLTTEVMAYLHTMDPTILEQWNFGLTLPP |
| SASLEDAYRFVRNAATSCQKDTPPQAKPDPLAKYKFWDVDLKERFSLDLDQFALGRKFLLQVGVQRK |
| PRPGLKRPASSASSSSSSSAKRKRVKK |
| Sequence 46 (SEQ ID NO: 46): MKVYLPPAPVSRIVNTEEYITRTGIYYYAGSSRLITLGHPYFPLPKTSTRAAIPKVSAFQYRVFRVQ |
| LPDPNKFGLPDPNLYNPDTDRLVWGCVGVEVGRGQPLGVGLSGHPLFNKYDDTENSRIANGNAQQDV |
| RDNTSVDNKQTQLCIIGCAPPIGEHWGIGTICKNTQTQRGDCPPLELVSSVIQDGDMIDTGFGAMDF |
| AALQATKSDVPLDISQSVCKYPDYLKMSADTYGNSMFFHLRREQIFARHFFNKAGTIGDPVPVSMYI |
| KGAGQGREPPTTSIYSATPSGSMITSDSQIFNKPYWLHRAQGHNNGICWNNQLFITCVDTTRSTNLT |
| ISTATAAVSPTFTPSNFKQYIRHGEEYELQFIFQLCKITLTTEVMAYLHTMDPTILEQWNFGLTLPP |
| SASLEDAYRFVRNAATSCQKDTPPQAKPDPLAKYKFWDVDLKERFSLDLDQFALGRKFLLQVGVQRK |
| PRPGLKRPASSASSSSSSSAKRKRVKK |

TABLE 1-continued

| Description of Sequences |
|---|
| Sequence 47 (SEQ ID NO: 47):<br>MKVYLPPAPVSRIVNTEEYITRTGIYYYAGSSRLITLGHPYFPLPKTSTRAAIPKVSAFQYRVFRVQ<br>LPDPNKFGLPDPNLYNPDTDRLVWGCVGVEVGRGQPLGVGLSGHPLFNKYDDTENSRIANGNAQQDV<br>RDNTSVDNKQTQLCIIGCAPPIGEHWGIGTTCKNTPVPPGDCPPLELVSSVIQDGDMIDTGFGAMDF<br>AALQATKSDVPLDISQSVCKYPDYLKMSADTYGNSMFFHLRREQIFARHFFNKAGTIGDPVPVSMYI<br>KGAGQGREPPTTSIYSATPSGSMITSDSQIFNKPYWLHRAQGHNNGICWNNQLFITCVDTTRSTNLT<br>ISTASAASASTPFKPSDFKQYIRHGEEYELQFIFQLCKITLTTEVMAYLHTMDPTILEQWNFGLTLP<br>PSASLEDAYRFVRNAATSCQKDTPPQAKPDPLAKYKFWDVDLKERFSLDLDQFALGRKFLLQVGVQR<br>KPRPGLKRPASSASSSSSSSAKRKRVKK |
| Sequence 48 (SEQ ID NO: 48):<br>The DNA Sequence encoding SEQ ID NO: 40<br>ATGAAGGTGTACCTGCCCCCCGCCCCCGTGAGCAGGATCGTGAACACCGAGGAGTACATCACCAGGA<br>CCGGCATCTACTACTACGCCGGCAGCAGCAGGCTGATCACCCTGGGCCACCCCTACTTCTCTATCCC<br>GAAAACCGGTCAGAAAGCTGAAATCCCGAAAGTTTCTGCCTTCCAGTACAGGGTGTTCAGGGTGCAG<br>CTCCCCGACCCCAACAAGTTCGGCCTGCCCGACCCCAACCTGTACAACCCCGACACCGACAGGCTGG<br>TGTGGGGCTGCGTGGGCGTGGAGGTGGGTCGTGGTCAGCCGCTGGGTGTCGGTCTGTCTGGTCACCC<br>GCTGTTCAACAAACTGGACGACACCGAAAACTCTCACCTGGCTACCGCTAACGCTGACACCGACAAC<br>CGTGACAACGTTTGCGTTGACAACAAGCAGACCCAGCTGTGCATCATCGGCTGCGCCCCCCCCATCG<br>GCGAGCACTGGGGCATCGGCACCACCTGCAAGAACACCCCCGTGCCCCCCGGCGACTGCCCCCCCCT<br>GGAGCTGGTGAGCAGCGTGATCCAGGACGGCGACATGATCGACACCGGCTTCGGCGCCATGGACTTC<br>GCCGCCCTGCAGGCCACCAAGAGCGACGTGCCCCTGGACATCAGCCAGAGCGTGTGCAAGTACCCCG<br>ACTACCTGAAGATGAGCGCCGACACCTACGGCAACAGCATGTTCTTCCACCTGAGGAGGGAGCAGAT<br>CTTCGCCAGGCACTACTACAACAAGCTGGGCAGCGTGGGCGAGGACATCCCCACCGACTACTACATC<br>AAGGGCAGCGGCAACGGCAGGGACCCCATCGAGAGCTACATCTACAGCGCCACCCCCAGCGGCAGCA<br>TGATCACCAGCGACAGCCAGATCTTCAACAAGCCCTACTGGCTGCACAGGGCCCAGGGCCACAACAA<br>CGGCATCTGCTGGAACAACCAGCTGTTCATCACCTGCGTGGACACCACCAGGAGCACCAACCTGACC<br>ATCAGCACCGCCACCGCCGCCGTGAGCCCCACCTTCACCCCCAGCAACTTCAAGCAGTACATCAGGC<br>ACGGCGAGGAGTACGAGCTGCAGTTCATCTTCCAGCTGTGCAAGATCACCCTGACCACCGAGGTGAT<br>GGCCTACCTGCACACCATGGACCCCACCATCCTGGAGCAGTGGAACTTCGGCCTGACCCTGCCCCCC<br>AGCGCCAGCCTGGAGGACGCCTACAGGTTCGTGAGGAACGCCGCCACCAGCTGCCAGAAGGACACCC<br>CCCCCCAGGCCAAGCCCGACCCCCTGGCCAAGTACAAGTTCTGGGACGTGGACCTGAAGGAGAGGTT<br>CAGCCTGGACCTGGACCAGTTCGCCCTGGGCAGGAAGTTCCTGCTGCAGGTGGGCGTGCAGAGGAAG<br>CCCAGGCCCGGCCTGAAGAGGCCCGCTAGCAGCGCCAGCTCCAGCAGCTCCAGCAGCGCCAAGAGGA<br>AGAGGGTGAAGAAGTAA |
| Sequence 49 (SEQ ID NO: 49):<br>The DNA Sequence encoding SEQ ID NO: 41<br>ATGAAGGTGTACCTGCCCCCCGCCCCCGTGAGCAGGATCGTGAACACCGAGGAGTACATCACCAGGA<br>CCGGCATCTACTACTACGCCGGCAGCAGCAGGCTGATCACCCTGGGCCACCCCTACTTCCCCCTGCC<br>CAAGACCAGCACCAGGGCCGCCATCCCCAAGGTGAGCGCCTTCCAGTACAGGGTGTTCAGGGTGCAG<br>CTCCCCGACCCCAACAAGTTCGGCCTGCCCGACCCCAACCTGTACAACCCCGACACCGACAGGCTGG<br>TGTGGGGCTGCGTGGGCGTGGAGGTGGGTCGTGGTCAGCCGCTGGGTGTCGGTCTGTCTGGTCACCC<br>GCTGTTCAACAAACTGGACGACACCGAAAACTCTCACCTGGCTACCGCTAACGCTGACACCGACAAC |

TABLE 1-continued

| Description of Sequences |
|---|

CGTGACAACGTTTGCGTTGACAACAAGCAGACCCAGCTGTGCATCATCGGCTGCGCCCCCCCCATCG

GCGAGCACTGGGGTATCGGTACCATCTGCAAAAACACCCAGACCCAGCGTGGTGACTGCCCGCCGCT

GGAGCTGGTGAGCAGCGTGATCCAGGACGGCGACATGATCGACACCGGCTTCGGCGCCATGGACTTC

GCCGCCCTGCAGGCCACCAAGAGCGACGTGCCCCTGGACATCAGCCAGAGCGTGTGCAAGTACCCCG

ACTACCTGAAGATGAGCGCCGACACCTACGGCAACAGCATGTTCTTCCACCTGAGGAGGGAGCAGAT

CTTCGCCAGGCACTACTACAACAAGCTGGGCAGCGTGGGCGAGGACATCCCCACCGACTACTACATC

AAGGGCAGCGGCAACGGCAGGGACCCCATCGAGAGCTACATCTACAGCGCCACCCCCAGCGGCAGCA

TGATCACCAGCGACAGCCAGATCTTCAACAAGCCCTACTGGCTGCACAGGGCCCAGGGCCACAACAA

CGGCATCTGCTGGAACAACCAGCTGTTCATCACCTGCGTGGACACCACCAGGAGCACCAACCTGACC

ATCAGCACCGCCACCGCCGCCGTGAGCCCCACCTTCACCCCCAGCAACTTCAAGCAGTACATCAGGC

ACGGCGAGGAGTACGAGCTGCAGTTCATCTTCCAGCTGTGCAAGATCACCCTGACCACCGAGGTGAT

GGCCTACCTGCACACCATGGACCCCACCATCCTGGAGCAGTGGAACTTCGGCCTGACCCTGCCCCCC

AGCGCCAGCCTGGAGGACGCCTACAGGTTCGTGAGGAACGCCGCCACCAGCTGCCAGAAGGACACCC

CCCCCCAGGCCAAGCCCGACCCCCTGGCCAAGTACAAGTTCTGGGACGTGGACCTGAAGGAGAGGTT

CAGCCTGGACCTGGACCAGTTCGCCCTGGGCAGGAAGTTCCTGCTGCAGGTGGGCGTGCAGAGGAAG

CCCAGGCCCGGCCTGAAGAGGCCCGCTAGCAGCGCCAGCTCCAGCAGCTCCAGCAGCGCCAAGAGGA

AGAGGGTGAAGAAGTAA

Sequence 50 (SEQ ID NO: 50):
The DNA Sequence encoding SEQ ID NO: 42
ATGAAGGTGTACCTGCCCCCCGCCCCCGTGAGCAGGATCGTGAACACCGAGGAGTACATCACCAGGA

CCGGCATCTACTACTACGCCGGCAGCAGCAGGCTGATCACCCTGGGCCACCCCTACTTCCCCCTGCC

CAAGACCAGCACCAGGGCCGCCATCCCCAAGGTGAGCGCCTTCCAGTACAGGGTGTTCAGGGTGCAG

CTCCCCGACCCCAACAAGTTCGGCCTGCCCGACCCCAACCTGTACAACCCCGACACCGACAGGCTGG

TGTGGGGCTGCGTGGGCGTGGAGGTGGGTCGTGGTCAGCCGCTGGGTGTCGGTCTGTCTGGTCACCC

GCTGTTCAACAAACTGGACGACACCGAAAACTCTCACCTGGCTACCGCTAACGCTGACACCGACAAC

CGTGACAACGTTTGCGTTGACAACAAGCAGACCCAGCTGTGCATCATCGGCTGCGCCCCCCCCATCG

GCGAGCACTGGGGCATCGGCACCACCTGCAAGAACACCCCCGTGCCCCCCGGCGACTGCCCCCCCCT

GGAGCTGGTGAGCAGCGTGATCCAGGACGGCGACATGATCGACACCGGCTTCGGCGCCATGGACTTC

GCCGCCCTGCAGGCCACCAAGAGCGACGTGCCCCTGGACATCAGCCAGAGCGTGTGCAAGTACCCCG

ACTACCTGAAGATGAGCGCCGACACCTACGGCAACAGCATGTTCTTCCACCTGAGGAGGGAGCAGAT

CTTCGCCAGGCACTTCTACAACAAAGCTGGTGCTGTTGGTGACGCTATCCCGACCACCCTGTACATC

AAAGGTGCTGAATCTGGTCGTGAACCGCCGACCTCTTCTATCTACTCTGCCACCCCCAGCGGCAGCA

TGATCACCAGCGACAGCCAGATCTTCAACAAGCCCTACTGGCTGCACAGGGCCCAGGGCCACAACAA

CGGCATCTGCTGGAACAACCAGCTGTTCATCACCTGCGTGGACACCACCAGGAGCACCAACCTGACC

ATCAGCACCGCCACCGCCGCCGTGAGCCCCACCTTCACCCCCAGCAACTTCAAGCAGTACATCAGGC

ACGGCGAGGAGTACGAGCTGCAGTTCATCTTCCAGCTGTGCAAGATCACCCTGACCACCGAGGTGAT

GGCCTACCTGCACACCATGGACCCCACCATCCTGGAGCAGTGGAACTTCGGCCTGACCCTGCCCCCC

AGCGCCAGCCTGGAGGACGCCTACAGGTTCGTGAGGAACGCCGCCACCAGCTGCCAGAAGGACACCC

CCCCCCAGGCCAAGCCCGACCCCCTGGCCAAGTACAAGTTCTGGGACGTGGACCTGAAGGAGAGGTT

CAGCCTGGACCTGGACCAGTTCGCCCTGGGCAGGAAGTTCCTGCTGCAGGTGGGCGTGCAGAGGAAG

TABLE 1-continued

| Description of Sequences |
| --- |
| CCCAGGCCCGGCCTGAAGAGGCCCGCTAGCAGCGCCAGCTCCAGCAGCTCCAGCAGCGCCAAGAGGA<br><br>AGAGGGTGAAGAAGTAA |
| Sequence 51 (SEQ ID NO: 51):<br>The DNA Sequence encoding SEQ ID NO: 43<br>ATGAAGGTGTACCTGCCCCCCGCCCCCGTGAGCAGGATCGTGAACACCGAGGAGTACATCACCAGGA<br><br>CCGGCATCTACTACTACGCCGGCAGCAGCAGGCTGATCACCCTGGGCCACCCCTACTTCCCCCTGCC<br><br>CAAGACCAGCACCAGGGCCGCCATCCCCAAGGTGAGCGCCTTCCAGTACAGGGTGTTCAGGGTGCAG<br><br>CTCCCCGACCCCAACAAGTTCGGCCTGCCCGACCCCAACCTGTACAACCCCGACACCGACAGGCTGG<br><br>TGTGGGGCTGCGTGGGCGTGGAGGTGGGTCGTGGTCAGCCGCTGGGTGTCGGTCTGTCTGGTCACCC<br><br>GCTGTTCAACAAACTGGACGACACCGAAAACTCTCACCTGGCTACCGCTAACGCTGACACCGACAAC<br><br>CGTGACAACGTTTGCGTTGACAACAAGCAGACCCAGCTGTGCATCATCGGCTGCGCCCCCCCCATCG<br><br>GCGAGCACTGGGGCATCGGCACCACCTGCAAGAACACCCCCGTGCCCCCCGGCGACTGCCCCCCCCT<br><br>GGAGCTGGTGAGCAGCGTGATCCAGGACGGCGACATGATCGACACCGGCTTCGGCGCCATGGACTTC<br><br>GCCGCCCTGCAGGCCACCAAGAGCGACGTGCCCCTGGACATCAGCCAGAGCGTGTGCAAGTACCCCG<br><br>ACTACCTGAAGATGAGCGCCGACACCTACGGCAACAGCATGTTCTTCCACCTGAGGAGGGAGCAGAT<br><br>CTTCGCCAGGCACTACTACAACAAGCTGGGCAGCGTGGGCGAGGACATCCCCACCGACTACTACATC<br><br>AAGGGCAGCGGCAACGGCAGGGACCCCATCGAGAGCTACATCTACAGCGCCACCCCCAGCGGCAGCA<br><br>TGATCACCAGCGACAGCCAGATCTTCAACAAGCCCTACTGGCTGCACAGGGCCCAGGGCCACAACAA<br><br>CGGCATCTGCTGGAACAACCAGCTGTTCATCACCTGCGTGGACACCACCAGGAGCACCAACCTGACC<br><br>ATCAGCACCGCCTCTGCTGCTTCTGCTTCTACCCCGTTCAAACCGTCTGACTTCAAGCAGTACATCA<br><br>GGCACGGCGAGGAGTACGAGCTGCAGTTCATCTTCCAGCTGTGCAAGATCACCCTGACCACCGAGGT<br><br>GATGGCCTACCTGCACACCATGGACCCCACCATCCTGGAGCAGTGGAACTTCGGCCTGACCCTGCCC<br><br>CCCAGCGCCAGCCTGGAGGACGCCTACAGGTTCGTGAGGAACGCCGCCACCAGCTGCCAGAAGGACA<br><br>CCCCCCCCCAGGCCAAGCCCGACCCCCTGGCCAAGTACAAGTTCTGGGACGTGGACCTGAAGGAGAG<br><br>GTTCAGCCTGGACCTGGACCAGTTCGCCCTGGGCAGGAAGTTCCTGCTGCAGGTGGGCGTGCAGAGG<br><br>AAGCCCAGGCCCGGCCTGAAGAGGCCCGCTAGCAGCGCCAGCTCCAGCAGCTCCAGCAGCGCCAAGA<br><br>GGAAGAGGGTGAAGAAGTAA |
| Sequence 52 (SEQ ID NO: 52):<br>The DNA Sequence encoding SEQ ID NO: 44<br>ATGAAGGTGTACCTGCCCCCCGCCCCCGTGAGCAGGATCGTGAACACCGAGGAGTACATCACCAGGA<br><br>CCGGCATCTACTACTACGCCGGCAGCAGCAGGCTGATCACCCTGGGCCACCCCTACTTCTCTATCCC<br><br>GAAAACCGGTCAGAAAGCTGAAATCCCGAAAGTTTCTGCCTTCCAGTACAGGGTGTTCAGGGTGCAG<br><br>CTCCCCGACCCCAACAAGTTCGGCCTGCCCGACCCCAACCTGTACAACCCCGACACCGACAGGCTGG<br><br>TGTGGGGCTGCGTGGGCGTGGAGGTGGGCAGGGGCCAGCCCCTGGGCGTGGGCCTGAGCGGCCACCC<br><br>CCTGTTCAACAAGTACGACGACACCGAGAACAGCAGGATCGCCAACGGCAACGCCCAGCAGGACGTG<br><br>AGGGACAACACCAGCGTGGACAACAAGCAGACCCAGCTGTGCATCATCGGCTGCGCCCCCCCCATCG<br><br>GCGAGCACTGGGGCATCGGCACCACCTGCAAGAACACCCCCGTGCCCCCCGGCGACTGCCCCCCCCT<br><br>GGAGCTGGTGAGCAGCGTGATCCAGGACGGCGACATGATCGACACCGGCTTCGGCGCCATGGACTTC<br><br>GCCGCCCTGCAGGCCACCAAGAGCGACGTGCCCCTGGACATCAGCCAGAGCGTGTGCAAGTACCCCG<br><br>ACTACCTGAAGATGAGCGCCGACACCTACGGCAACAGCATGTTCTTCCACCTGAGGAGGGAGCAGAT<br><br>CTTCGCCAGGCACTTCTTCAACAAAGCTGGTACCATCGGTGACCCTGTTCCGGTTTCTATGTACATC |

TABLE 1-continued

| Description of Sequences |
|---|
| AAAGGTGCTGGTCAGGGTCGTGAACCGCCGACCACATCCATCTACTCTGCCACCCCCAGCGGCAGCA<br>TGATCACCAGCGACAGCCAGATCTTCAACAAGCCCTACTGGCTGCACAGGGCCCAGGGCCACAACAA<br>CGGCATCTGCTGGAACAACCAGCTGTTCATCACCTGCGTGGACACCACCAGGAGCACCAACCTGACC<br>ATCAGCACCGCCACCGCCGCCGTGAGCCCCACCTTCACCCCCAGCAACTTCAAGCAGTACATCAGGC<br>ACGGCGAGGAGTACGAGCTGCAGTTCATCTTCCAGCTGTGCAAGATCACCCTGACCACCGAGGTGAT<br>GGCCTACCTGCACACCATGGACCCCACCATCCTGGAGCAGTGGAACTTCGGCCTGACCCTGCCCCCC<br>AGCGCCAGCCTGGAGGACGCCTACAGGTTCGTGAGGAACGCCGCCACCAGCTGCCAGAAGGACACCC<br>CCCCCCAGGCCAAGCCCGACCCCCTGGCCAAGTACAAGTTCTGGGACGTGGACCTGAAGGAGAGGTT<br>CAGCCTGGACCTGGACCAGTTCGCCCTGGGCAGGAAGTTCCTGCTGCAGGTGGGCGTGCAGAGGAAG<br>CCCAGGCCCGGCCTGAAGAGGCCCGCTAGCAGCGCCAGCTCCAGCAGCTCCAGCAGCGCCAAGAGGA<br>AGAGGGTGAAGAAGTAA |
| Sequence 53 (SEQ ID NO: 53):<br>The DNA Sequence encoding SEQ ID NO: 45<br>ATGAAGGTGTACCTGCCCCCCGCCCCCGTGAGCAGGATCGTGAACACCGAGGAGTACATCACCAGGA<br>CCGGCATCTACTACTACGCCGGCAGCAGCAGGCTGATCACCCTGGGCCACCCCTACTTCCCCCTGCC<br>CAAGACCAGCACCAGGGCCGCCATCCCCAAGGTGAGCGCCTTCCAGTACAGGGTGTTCAGGGTGCAG<br>CTCCCCGACCCCAACAAGTTCGGCCTGCCCGACCCCAACCTGTACAACCCCGACACCGACAGGCTGG<br>TGTGGGGCTGCGTGGGCGTGGAGGTGGGTCGTGGTCAGCCGCTGGGTATCGGTCTGTCTGGTCACCC<br>GCTGTTCAACAAACTGGACGACACCGAAAACTCTCACCTGGCTACCGTTAACGCTGACACCGACAAC<br>CGTGACAACGTTTCTGTTGACAACAAGCAGACCCAGCTGTGCATCATCGGCTGCGCCCCCCCCATCG<br>GCGAGCACTGGGGCATCGGCACCACCTGCAAGAACACCCCCGTGCCCCCCGGCGACTGCCCCCCCCT<br>GGAGCTGGTGAGCAGCGTGATCCAGGACGGCGACATGATCGACACCGGCTTCGGCGCCATGGACTTC<br>GCCGCCCTGCAGGCCACCAAGAGCGACGTGCCCCTGGACATCAGCCAGAGCGTGTGCAAGTACCCCG<br>ACTACCTGAAGATGAGCGCCGACACCTACGGCAACAGCATGTTCTTCCACCTGAGGAGGGAGCAGAT<br>CTTCGCCAGGCACTTCTTCAACAAAGCTGGTACCATCGGTGACCCTGTTCCGGTTTCTATGTACATC<br>AAAGGTGCTGGTCAGGGTCGTGAACCGCCGACCACATCCATCTACTCTGCCACCCCCAGCGGCAGCA<br>TGATCACCAGCGACAGCCAGATCTTCAACAAGCCCTACTGGCTGCACAGGGCCCAGGGCCACAACAA<br>CGGCATCTGCTGGAACAACCAGCTGTTCATCACCTGCGTGGACACCACCAGGAGCACCAACCTGACC<br>ATCAGCACCGCCACCGCCGCCGTGAGCCCCACCTTCACCCCCAGCAACTTCAAGCAGTACATCAGGC<br>ACGGCGAGGAGTACGAGCTGCAGTTCATCTTCCAGCTGTGCAAGATCACCCTGACCACCGAGGTGAT<br>GGCCTACCTGCACACCATGGACCCCACCATCCTGGAGCAGTGGAACTTCGGCCTGACCCTGCCCCCC<br>AGCGCCAGCCTGGAGGACGCCTACAGGTTCGTGAGGAACGCCGCCACCAGCTGCCAGAAGGACACCC<br>CCCCCCAGGCCAAGCCCGACCCCCTGGCCAAGTACAAGTTCTGGGACGTGGACCTGAAGGAGAGGTT<br>CAGCCTGGACCTGGACCAGTTCGCCCTGGGCAGGAAGTTCCTGCTGCAGGTGGGCGTGCAGAGGAAG<br>CCCAGGCCCGGCCTGAAGAGGCCCGCTAGCAGCGCCAGCTCCAGCAGCTCCAGCAGCGCCAAGAGGA<br>AGAGGGTGAAGAAGTAA |
| Sequence 54 (SEQ ID NO: 54):<br>The DNA Sequence encoding SEQ ID NO: 46<br>ATGAAGGTGTACCTGCCCCCCGCCCCCGTGAGCAGGATCGTGAACACCGAGGAGTACATCACCAGGA<br>CCGGCATCTACTACTACGCCGGCAGCAGCAGGCTGATCACCCTGGGCCACCCCTACTTCCCCCTGCC<br>CAAGACCAGCACCAGGGCCGCCATCCCCAAGGTGAGCGCCTTCCAGTACAGGGTGTTCAGGGTGCAG |

TABLE 1-continued

| Description of Sequences |
|---|
| CTCCCCGACCCCAACAAGTTCGGCCTGCCCGACCCCAACCTGTACAACCCCGACACCGACAGGCTGG |
| TGTGGGGCTGCGTGGGCGTGGAGGTGGGCAGGGGCCAGCCCCTGGGCGTGGGCCTGAGCGGCCACCC |
| CCTGTTCAACAAGTACGACGACACCGAGAACAGCAGGATCGCCAACGGCAACGCCCAGCAGGACGTG |
| AGGGACAACACCAGCGTGGACAACAAGCAGACCCAGCTGTGCATCATCGGCTGCGCCCCCCCCATCG |
| GCGAGCACTGGGGTATCGGTACCATCTGCAAAAACACCCAGACCCAGCGTGGTGACTGCCCGCCGCT |
| GGAGCTGGTGAGCAGCGTGATCCAGGACGGCGACATGATCGACACCGGCTTCGGCGCCATGGACTTC |
| GCCGCCCTGCAGGCCACCAAGAGCGACGTGCCCCTGGACATCAGCCAGAGCGTGTGCAAGTACCCCG |
| ACTACCTGAAGATGAGCGCCGACACCTACGGCAACAGCATGTTCTTCCACCTGAGGAGGGAGCAGAT |
| CTTCGCCAGGCACTTCTTCAACAAAGCTGGTACCATCGGTGACCCTGTTCCGGTTTCTATGTACATC |
| AAAGGTGCTGGTCAGGGTCGTGAACCGCCGACCACATCCATCTACTCTGCCACCCCCAGCGGCAGCA |
| TGATCACCAGCGACAGCCAGATCTTCAACAAGCCCTACTGGCTGCACAGGGCCCAGGGCCACAACAA |
| CGGCATCTGCTGGAACAACCAGCTGTTCATCACCTGCGTGGACACCACCAGGAGCACCAACCTGACC |
| ATCAGCACCGCCACCGCCGCCGTGAGCCCCACCTTCACCCCCAGCAACTTCAAGCAGTACATCAGGC |
| ACGGCGAGGAGTACGAGCTGCAGTTCATCTTCCAGCTGTGCAAGATCACCCTGACCACCGAGGTGAT |
| GGCCTACCTGCACACCATGGACCCCACCATCCTGGAGCAGTGGAACTTCGGCCTGACCCTGCCCCCC |
| AGCGCCAGCCTGGAGGACGCCTACAGGTTCGTGAGGAACGCCGCCACCAGCTGCCAGAAGGACACCC |
| CCCCCCAGGCCAAGCCCGACCCCCTGGCCAAGTACAAGTTCTGGGACGTGGACCTGAAGGAGAGGTT |
| CAGCCTGGACCTGGACCAGTTCGCCCTGGGCAGGAAGTTCCTGCTGCAGGTGGGCGTGCAGAGGAAG |
| CCCAGGCCCGGCCTGAAGAGGCCCGCTAGCAGCGCCAGCTCCAGCAGCTCCAGCAGCGCCAAGAGGA |
| AGAGGGTGAAGAAGTAA |
| Sequence 55 (SEQ ID NO: 55):<br>The DNA Sequence encoding SEQ ID NO: 47<br>ATGAAGGTGTACCTGCCCCCCGCCCCCGTGAGCAGGATCGTGAACACCGAGGAGTACATCACCAGGA |
| CCGGCATCTACTACTACGCCGGCAGCAGCAGGCTGATCACCCTGGGCCACCCCTACTTCCCCCTGCC |
| CAAGACCAGCACCAGGGCCGCCATCCCCAAGGTGAGCGCCTTCCAGTACAGGGTGTTCAGGGTGCAG |
| CTCCCCGACCCCAACAAGTTCGGCCTGCCCGACCCCAACCTGTACAACCCCGACACCGACAGGCTGG |
| TGTGGGGCTGCGTGGGCGTGGAGGTGGGCAGGGGCCAGCCCCTGGGCGTGGGCCTGAGCGGCCACCC |
| CCTGTTCAACAAGTACGACGACACCGAGAACAGCAGGATCGCCAACGGCAACGCCCAGCAGGACGTG |
| AGGGACAACACCAGCGTGGACAACAAGCAGACCCAGCTGTGCATCATCGGCTGCGCCCCCCCCATCG |
| GCGAGCACTGGGGCATCGGCACCACCTGCAAGAACACCCCCGTGCCCCCCGGCGACTGCCCCCCCCT |
| GGAGCTGGTGAGCAGCGTGATCCAGGACGGCGACATGATCGACACCGGCTTCGGCGCCATGGACTTC |
| GCCGCCCTGCAGGCCACCAAGAGCGACGTGCCCCTGGACATCAGCCAGAGCGTGTGCAAGTACCCCG |
| ACTACCTGAAGATGAGCGCCGACACCTACGGCAACAGCATGTTCTTCCACCTGAGGAGGGAGCAGAT |
| CTTCGCCAGGCACTTCTTCAACAAAGCTGGTACCATCGGTGACCCTGTTCCGGTTTCTATGTACATC |
| AAAGGTGCTGGTCAGGGTCGTGAACCGCCGACCACATCCATCTACTCTGCCACCCCCAGCGGCAGCA |
| TGATCACCAGCGACAGCCAGATCTTCAACAAGCCCTACTGGCTGCACAGGGCCCAGGGCCACAACAA |
| CGGCATCTGCTGGAACAACCAGCTGTTCATCACCTGCGTGGACACCACCAGGAGCACCAACCTGACC |
| ATCAGCACCGCCTCTGCTGCTTCTGCTTCTACCCCGTTCAAACCGTCTGACTTCAAGCAGTACATCA |
| GGCACGGCGAGGAGTACGAGCTGCAGTTCATCTTCCAGCTGTGCAAGATCACCCTGACCACCGAGGT |
| GATGGCCTACCTGCACACCATGGACCCCACCATCCTGGAGCAGTGGAACTTCGGCCTGACCCTGCCC |

TABLE 1-continued

| Description of Sequences |
|---|
| CCCAGCGCCAGCCTGGAGGACGCCTACAGGTTCGTGAGGAACGCCGCCACCAGCTGCCAGAAGGACA |
| CCCCCCCCCAGGCCAAGCCCGACCCCCTGGCCAAGTACAAGTTCTGGGACGTGGACCTGAAGGAGAG |
| GTTCAGCCTGGACCTGGACCAGTTCGCCCTGGGCAGGAAGTTCCTGCTGCAGGTGGGCGTGCAGAGG |
| AAGCCCAGGCCCGGCCTGAAGAGGCCCGCTAGCAGCGCCAGCTCCAGCAGCTCCAGCAGCGCCAAGA |
| GGAAGAGGGTGAAGAAGTAA |
| Sequence 56 (SEQ ID NO: 56): SIPKTGQKAE |
| Sequence 57 (SEQ ID NO: 57): IGLSGHPLFNKLDDTENSHLATVNADTDNRDNV |
| Sequence 58 (SEQ ID NO: 58): ICKNTQTQR |
| Sequence 59 (SEQ ID NO: 59): FYNKAGAVGDAIPTTLYIKGAESGREPPTSS |
| Sequence 60 (SEQ ID NO: 60): SAASASTPFKPSD |

SPECIFIC MODES FOR CARRYING OUT THE APPLICATION

The present application is further described by reference to the examples as follows, wherein the examples are used only for the purpose of illustrating the present application, rather than limiting the present application.

Unless indicated otherwise, the molecular biological experimental methods and immunological assays used in the present application are carried out substantially in accordance with the methods as described in Sambrook J et al., Molecular Cloning: A Laboratory Manual (Second Edition), Cold Spring Harbor Laboratory Press, 1989, and F. M. Ausubel et al., Short Protocols in Molecular Biology, 3rd Edition, John Wiley & Sons, Inc., 1995; and restriction enzymes are used under the conditions recommended by the manufacturers. Those skilled in the art understand that the examples are used for illustrating the present application, but not intended to limit the protection scope of the present application.

Example 1. Expression and Purification of the Mutated HPV51 L1 Proteins

Construction of Expression Vectors

Gibson assembly (Gibson D G, Young L, Chuang R Y, Venter J C, Hutchison C A, Smith H O. Enzymatic assembly of DNA molecules up to several hundred kilobases. Nat Methods. 2009; 6:343-5. doi: 10.1038/nmeth.1318) was used to construct the expression vector encoding the mutated HPV51 L1 protein comprising a specific segment from HPV69 L1 protein and/or a specific segment from HPV26 L1 protein. In brief, a short fragment comprising mutations and a long fragment comprising no mutation were first obtained by PCR, and Gibson assembly system was then used to ligate the two fragments to form a ring.

The initial template used comprised the plasmid pTO-T7-HPV51N9C (encoding the HPV51 L1 protein having 9 amino acids truncated at N-terminal, abbreviated as 51L1N9 in Table 2), the plasmid pTO-T7-HPV69N0C (encoding the full-length HPV69 L1 protein, abbreviated as 69L1N0 in Table 2), and the plasmid pTO-T7-HPV26N0C (encoding the full-length HPV26 L1 protein; abbreviated as 26L1N0 in Table 2). The templates and primers for each PCR were shown in Table 2, and the amplification conditions for PCR for amplifying the short fragment were as followed: denaturation at 94° C. for 10 min; 25 cycles (denaturation at 94° C. for 50 sec, annealing at a given temperature for a certain period of time, and extension at 72° C. for 1 min); and final extension at 72° C. for 10 min. The amplification conditions for PCR for amplifying the long fragment were as followed: denaturation at 94° C. for 10 min; 25 cycles (denaturation at 94° C. for 50 sec, annealing at a given temperature for a certain period of time, and extension at 72° C. for 7.5 min); and final extension at 72° C. for 10 min. The temperature and time of annealing were listed in Table 2. The sequences of the PCR primers used were listed in Table 3. The amplification product was subjected to electrophoresis, the fragment of interest was then recovered by using DNA Extraction Kit (BEYOTIME, Cat. No. D0033), and its concentration was determined. The short fragment and long fragment obtained by amplification were mixed at a molar ratio of 2:1 (a total volume of 3 μL), and 3 μL of 2× Gibson Assembly Master Mix (purchased from NEB, containing T5 exonuclease, Phusion DNA polymerase, Taq DNA ligase) was then added, and reacted at 50° C. for 1 h.

The assembled product (6 μL) was used to transform 40 μL competent *E. coli* ER2566 (purchased from New England Biolabs) prepared by the Calcium chloride method. The transformed *E. coli* were spread onto solid LB medium (components of LB medium: 10 g/L peptone, 5 g/L yeast powder, 10 g/L NaCl, the same hereinafter) containing kanamycin (at a final concentration of 25 μg/mL, the same hereinafter), and were subjected to static culture at 37° C. for 10-12 h until single colonies could be observed clearly. Single colony was picked and inoculated into a tube containing 4 mL liquid LB medium (containing kanamycin), and cultured with shaking at 220 rpm for 10 h at 37° C., and then 1 ml bacterial solution was taken and stored at −70° C. Plasmids were extracted from *E. coli*, and T7 primer was used to sequence the nucleotide sequences of the fragments of interest inserted into the plasmids. The sequencing result showed that the nucleotide sequences of the fragments of interest inserted into the constructed plasmids (expression vectors) were SEQ ID NO: 12, 13, 14, 15, 16, 32, 33, 34, 35, 36, 37, 38, 39, 48, 49, 50, 51, 52, 53, 54 and 55, respectively, and their encoded amino acid sequences were SEQ ID NO: 4, 5, 6, 7, 8, 23, 24, 25, 26, 27, 28, 29, 30, 40, 41, 42, 43, 44, 45, 46 and 47, respectively (the corresponding proteins were designated as H51N9-69T1, H51N9-69T2, H51N9-69T3, H51N9-69T4, H51N9-69T5, H51N9-69T1-26S2, H51N9-69T1-26S3, H51N9-69T1-26S4, H51N9-69T1-26S5, H51N9-69T3-26S1, H51N9-69T3-26S2, H51N9-69T3-26S4, H51N9-69T3-26S5, H51N9-69T2-26S1, H51N9-69T2-26S3, H51N9-69T2-26S4, H51N9-69T2-26S5, H51N9-69T4-26S1, H51N9-69T4-26S2, H51N9-69T4-26S3 and H51N9-69T4-26S5, respectively).

The mutated protein H51N9-69T1 differs from HPV51N9 by: substitution of the amino acid residues at positions 52-60 of the wild type HPV51 L1 protein with the amino acid residues at positions 52-60 of a wild type HPV69 L1 protein. The mutated protein H51N9-69T2 differs from HPV51N9 by: substitution of the amino acid residues at positions 125-147 of the wild type HPV51 L1 protein with the amino acid residues at positions 125-147 of a wild type HPV69 L1 protein. The mutated protein H51N9-69T3 differs from HPV51N9 by: substitution of the amino acid residues at positions 170-181 of the wild type HPV51 L1 protein with the amino acid residues at positions 170-183 of a wild type HPV69 L1 protein. The mutated protein H51N9-69T4 differs from HPV51N9 by: substitution of the amino acid residues at positions 259-289 of the wild type HPV51 L1 protein with the amino acid residues at positions 261-291 of a wild type HPV69 L1 protein. The mutated protein H51N9-69T5 differs from HPV51N9 by: substitution of the amino acid residues at positions 348-359 of the wild type HPV51 L1 protein with the amino acid residues at positions 350-362 of a wild type HPV69 L1 protein.

The mutated protein H51N9-69T1-26S2 differs from HPV51N9 by: substitution of the amino acid residues at positions 52-60 of the wild type HPV51 L1 protein with the amino acid residues at positions 52-60 of a wild type HPV69 L1 protein, and substitution of the amino acid residues at positions 114-146 of the wild type HPV51 L1 protein with the amino acid residues at positions 114-146 of a wild type HPV26 L1 protein.

The mutated protein H51N9-69T1-26S3 differs from HPV51N9 by: substitution of the amino acid residues at positions 52-60 of the wild type HPV51 L1 protein with the amino acid residues at positions 52-60 of a wild type HPV69 L1 protein, and substitution of the amino acid residues at positions 173-181 of the wild type HPV51 L1 protein with the amino acid residues at positions 173-181 of a wild type HPV26 L1 protein.

The mutated protein H51N9-69T1-26S4 differs from HPV51N9 by: substitution of the amino acid residues at positions 52-60 of the wild type HPV51 L1 protein with the amino acid residues at positions 52-60 of a wild type HPV69 L1 protein, and substitution of the amino acid residues at positions 259-289 of the wild type HPV51 L1 protein with the amino acid residues at positions 259-289 of a wild type HPV26 L1 protein.

The mutated protein H51N9-69T1-26S5 differs from HPV51N9 by: substitution of the amino acid residues at positions 52-60 of the wild type HPV51 L1 protein with the amino acid residues at positions 52-60 of a wild type HPV69 L1 protein, and substitution of the amino acid residues at positions 348-359 of the wild type HPV51 L1 protein with the amino acid residues at positions 348-360 of a wild type HPV26 L1 protein.

The mutated protein H51N9-69T3-26S1 differs from HPV51N9 by: substitution of the amino acid residues at positions 170-181 of the wild type HPV51 L1 protein with the amino acid residues at positions 170-183 of a wild type HPV69 L1 protein, and substitution of the amino acid residues at positions 51-60 of the wild type HPV51 L1 protein with the amino acid residues at positions 51-60 of a wild type HPV26 L1 protein.

The mutated protein H51N9-69T3-26S2 differs from HPV51N9 by: substitution of the amino acid residues at positions 170-181 of the wild type HPV51 L1 protein with the amino acid residues at positions 170-183 of a wild type HPV69 L1 protein, and substitution of the amino acid residues at positions 114-146 of the wild type HPV51 L1 protein with the amino acid residues at positions 114-146 of a wild type HPV26 L1 protein.

The mutated protein H51N9-69T3-26S4 differs from HPV51N9 by: substitution of the amino acid residues at positions 170-181 of the wild type HPV51 L1 protein with the amino acid residues at positions 170-183 of a wild type HPV69 L1 protein, and substitution of the amino acid residues at positions 259-289 of the wild type HPV51 L1 protein with the amino acid residues at positions 259-289 of a wild type HPV26 L1 protein.

The mutated protein H51N9-69T3-26S5 differs from HPV51N9 by: substitution of the amino acid residues at positions 170-181 of the wild type HPV51 L1 protein with the amino acid residues at positions 170-183 of a wild type HPV69 L1 protein, and substitution of the amino acid residues at positions 348-359 of the wild type HPV51 L1 protein with the amino acid residues at positions 348-360 of a wild type HPV26 L1 protein.

The mutated protein H51N9-69T2-26S1 differs from HPV51N9 by: substitution of the amino acid residues at positions 125-147 of the wild type HPV51 L1 protein with the amino acid residues at positions 125-147 of a wild type HPV69 L1 protein, and substitution of the amino acid residues at positions 51-60 of the wild type HPV51 L1 protein with the amino acid residues at positions 51-60 of a wild type HPV26 L1 protein.

The mutated protein H51N9-69T2-26S3 differs from HPV51N9 by: substitution of the amino acid residues at positions 125-147 of the wild type HPV51 L1 protein with the amino acid residues at positions 125-147 of a wild type HPV69 L1 protein, and substitution of the amino acid residues at positions 173-181 of the wild type HPV51 L1 protein with the amino acid residues at positions 173-181 of a wild type HPV26 L1 protein.

The mutated protein H51N9-69T2-26S4 differs from HPV51N9 by: substitution of the amino acid residues at positions 125-147 of the wild type HPV51 L1 protein with the amino acid residues at positions 125-147 of a wild type HPV69 L1 protein, and substitution of the amino acid residues at positions 259-289 of the wild type HPV51 L1 protein with the amino acid residues at positions 259-289 of a wild type HPV26 L1 protein.

The mutated protein H51N9-69T2-26S5 differs from HPV51N9 by: substitution of the amino acid residues at positions 125-147 of the wild type HPV51 L1 protein with the amino acid residues at positions 125-147 of a wild type HPV69 L1 protein, and substitution of the amino acid residues at positions 348-359 of the wild type HPV51 L1 protein with the amino acid residues at positions 348-360 of a wild type HPV26 L1 protein.

The mutated protein H51N9-69T4-26S1 differs from HPV51N9 by: substitution of the amino acid residues at positions 259-289 of the wild type HPV51 L1 protein with the amino acid residues at positions 261-291 of a wild type HPV69 L1 protein, and substitution of the amino acid residues at positions 51-60 of the wild type HPV51 L1 protein with the amino acid residues at positions 51-60 of a wild type HPV26 L1 protein.

The mutated protein H51N9-69T4-26S2 differs from HPV51N9 by: substitution of the amino acid residues at positions 259-289 of the wild type HPV51 L1 protein with the amino acid residues at positions 261-291 of a wild type HPV69 L1 protein, and substitution of the amino acid residues at positions 114-146 of the wild type HPV51 L1 protein with the amino acid residues at positions 114-146 of a wild type HPV26 L1 protein.

The mutated protein H51N9-69T4-26S3 differs from HPV51N9 by: substitution of the amino acid residues at positions 259-289 of the wild type HPV51 L1 protein with the amino acid residues at positions 261-291 of a wild type HPV69 L1 protein, and substitution of the amino acid residues at positions 173-181 of the wild type HPV51 L1 protein with the amino acid residues at positions 173-181 of a wild type HPV26 L1 protein.

The mutated protein H51N9-69T4-26S5 differs from HPV51N9 by: substitution of the amino acid residues at positions 259-289 of the wild type HPV51 L1 protein with the amino acid residues at positions 261-291 of a wild type HPV69 L1 protein, and substitution of the amino acid residues at positions 348-359 of the wild type HPV51 L1 protein with the amino acid residues at positions 348-360 of a wild type HPV26 L1 protein.

TABLE 2

PCR templates and primers for constructing expression vectors

| Template | Upstream primer | Downstream primer | Product | Temperature/ Time of annealing |
|---|---|---|---|---|
| 51L1N9 | G-V- H51N9-69T1-F | G-V- H51N9-69T1-R | H51N9-69T1 long fragment | 56° C./50 s |
| 51L1N9 | G-V- H51N9-69T2-F | G-V- H51N9-69T2-R | H51N9-69T2 long fragment | 56° C./50 s |
| 51L1N9 | G-V- H51N9-69T3-F | G-V- H51N9-69T3-R | H51N9-69T3 long fragment | 56° C./50 s |
| 51L1N9 | G-V- H51N9-69T4-F | G-V- H51N9-69T4-R | H51N9-69T4 long fragment | 56° C./50 s |
| 51L1N9 | G-V- H51N9-69T5-F | G-V- H51N9-69T5-R | H51N9-69T5 long fragment | 56° C./50 s |
| 69L1N0 | G- H51N9-69T1-F | G- H51N9-69T1-R | H51N9-69T1 short fragment | 56° C./30 s |
| 69L1N0 | G- H51N9-69T2-F | G- H51N9-69T3-R | H51N9-69T3 short fragment | 56° C./30 s |
| 69L1N0 | G- H51N9-69T3-F | G- H51N9-69T3-R | H51N9-69T3 short fragment | 56° C./30 s |
| 69L1N0 | G- H51N9-69T4-F | G- H51N9-69T4-R | H51N9-69T4 short fragment | 56° C./30 s |
| 69L1N0 | G- H51N9-69T5-F | G- H51N9-69T5-R | H51N9-69T5 short fragment | 56° C./30 s |
| 26L1N0 | Frag-H51-69T1-26S2-F | Frag-H51-69T1-26S2-R | H51-69T1-26S2 short fragment | 56° C./30 s |
| H51-69T1 | Vector-H51-69T1-26S2-R | Vector-H51-69T1-26S2-F | H51-69T1-26S2 long fragment | 56° C./50 s |
| 26L1N0 | Frag-H51-69T1-26S3-F | Frag-H51-69T1-26S3-R | H51-69T1-26S3 short fragment | 56° C./30 s |
| H51-69T1 | Vector-H51-69T1-26S3-R | Vector-H51-69T1-26S3-F | H51-69T1-26S3 long fragment | 56° C./50 s |
| 26L1N0 | Frag-H51-69T1-26S4-F | Frag-H51-69T1-26S4-R | H51-69T1-26S4 short fragment | 56° C./30 s |
| H51-69T1 | Vector-H51-69T1-26S4-R | Vector-H51-69T1-26S4-F | H51-69T1-26S4 long fragment | 56° C./50 s |
| 26L1N0 | Frag-H51-69T1-26S5-F | Frag-H51-69T1-26S5-R | H51-69T1-26S5 short fragment | 56° C./30 s |
| H51-69T1 | Vector-H51-69T1-26S5-R | Vector-H51-69T1-26S5-F | H51-69T1-26S5 long fragment | 56° C./50 s |
| 26L1N0 | Frag-H51-69T3-26S1-F | Frag-H51-69T3-26S1-R | H51-69T3-26S1 short fragment | 56° C./30 s |
| H51-69T3 | Vector-H51-69T3-26S1-R | Vector-H51-69T3-26S1-F | H51-69T3-26S1 long fragment | 56° C./50 s |
| 26L1N0 | Frag-H51-69T3-26S2-F | Frag-H51-69T3-26S2-R | H51-69T3-26S2 short fragment | 56° C./30 s |
| H51-69T3 | Vector-H51-69T3-26S2-R | Vector-H51-69T3-26S2-F | H51-69T3-26S2 long fragment | 56° C./50 s |
| 26L1N0 | Frag-H51-69T3-26S4-F | Frag-H51-69T3-26S4-R | H51-69T3-26S4 short fragment | 56° C./30 s |
| H51-69T3 | Vector-H51-69T3-26S4-R | Vector-H51-69T3-26S4-F | H51-69T3-26S4 long fragment | 56° C./50 s |
| 26L1N0 | Frag-H51-69T3-26S5-F | Frag-H51-69T3-26S5-R | H51-69T3-26S5 short fragment | 56° C./30 s |
| H51-69T3 | Vector-H51-69T3-26S5-R | Vector-H51-69T3-26S5-F | H51-69T3-26S5 long fragment | 56° C./50 s |
| 26L1N0 | Frag-H51-69T2-26S1-F | Frag-H51-69T2-26S1-R | H51-69T2-26S1 short fragment | 56° C./30 s |
| H51-69T2 | Vector-H51-69T2-26S1-R | Vector-H51-69T2-26S1-F | H51-69T2-26S1 long fragment | 56° C./50 s |
| 26L1N0 | Frag-H51-69T2-26S3-F | Frag-H51-69T2-26S3-R | H51-69T2-26S3 short fragment | 56° C./30 s |
| H51-69T2 | Vector-H51-69T2-26S3-R | Vector-H51-69T2-26S3-F | H51-69T2-26S3 long fragment | 56° C./50 s |
| 26L1N0 | Frag-H51-69T2-26S4-F | Frag-H51-69T2-26S4-R | H51-69T2-26S4 short fragment | 56° C./30 s |
| H51-69T2 | Vector-H51-69T2-26S4-R | Vector-H51-69T2-26S4-F | H51-69T2-26S4 long fragment | 56° C./50 s |
| 26L1N0 | Frag-H51-69T2-26S5-F | Frag-H51-69T2-26S5-R | H51-69T2-26S5 short fragment | 56° C./30 s |
| H51-69T2 | Vector-H51-69T2-26S5-R | Vector-H51-69T2-26S5-F | H51-69T2-26S5 long fragment | 56° C./50 s |
| 26L1N0 | Frag-H51-69T4-26S1-F | Frag-H51-69T4-26S1-R | H51-69T4-26S1 short fragment | 56° C./30 s |
| H51-69T4 | Vector-H51-69T4-26S1-R | Vector-H51-69T4-26S1-F | H51-69T4-26S1 long fragment | 56° C./50 s |
| 26L1N0 | Frag-H51-69T4-26S2-F | Frag-H51-69T4-26S2-R | H51-69T4-26S2 short fragment | 56° C./30 s |
| H51-69T4 | Vector-H51-69T4-26S2-R | Vector-H51-69T4-26S2-F | H51-69T4-26S2 long fragment | 56° C./50 s |
| 26L1N0 | Frag-H51-69T4-26S3-F | Frag-H51-69T4-26S3-R | H51-69T4-26S3 short fragment | 56° C./30 s |
| H51-69T4 | Vector-H51-69T4-26S3-R | Vector-H51-69T4-26S3-F | H51-69T4-26S3 long fragment | 56° C./50 s |
| 26L1N0 | Frag-H51-69T4-26S5-F | Frag-H51-69T4-26S5-R | H51-69T4-26S5 short fragment | 56° C./30 s |
| H51-69T4 | Vector-H51-69T4-26S5-R | Vector-H51-69T4-26S5-F | H51-69T4-26S5 long fragment | 56° C./50 s |

TABLE 3

Sequences of the primers used (SEQ ID NO: 61-144)

| SEQ ID NO: | Primer name | Primer Sequence (5'-3') |
|---|---|---|
| 61 | G-V-H51N9-69T1-F | GTAGGGGTGGCCCAGGGTGATCAG |
| 62 | G-V-H51N9-69T1-R | GCCTTCCAGTACAGGGTGTTCAGG |
| 63 | G-V-H51N9-69T2-F | CACCTCCACGCCCACGCAGCCCCA |
| 64 | G-V-H51N9-69T2-R | ACAAGCAGACCCAGCTGTGCATCA |
| 65 | G-V-H51N9-69T3-F | CTCGCCGATGGGGGGGGCGCAGCCGATGATGCACAGCTG |
| 66 | G-V-H51N9-69T3-R | CCCTGGAGCTGGTGAGCAGCGTGATCCAGGACGGCGACA |
| 67 | G-V-H51N9-69T4-F | GTGCCTGGCGAAGATCTGCTCCCT |
| 68 | G-V-H51N9-69T4-R | GCCACCCCCAGCGGCAGCATGATC |
| 69 | G-V-H51N9-69T5-F | GGCGGTGCTGATGGTCAGGTTGGT |
| 70 | G-V-H51N9-69T5-R | ACTTCAAGCAGTACATCAGGCACG |
| 71 | G-H51N9-69T1-F | CTGATCACCCTGGGCCACCCCTACTTCCCGATCCCGAAATC TGGT |
| 72 | G-H51N9-69T1-R | CCTGAACACCCTGTACTGGAAGGCAGAGACCTTCGGGATTT CAGC |
| 73 | G-H51N9-69T2-F | TGGGGCTGCGTGGGCGTGGAGGTGGGTCGTGGTCAGCCGCT G |
| 74 | G-H51N9-69T2-R | TGATGCACAGCTGGGTCTGCTTGTTGTCAACGCAAACGTTG TCAC |
| 75 | G-H51N9-69T3-F | GGCTGCGCCCCCCCCATCGGCGAGCACTGGGGTGTCGGTAC CGTT |
| 76 | G-H51N9-69T3-R | TCACGCTGCTCACCAGCTCCAGGGGCGGGCAGTCACCACGC TGAA |
| 77 | G-H51N9-69T4-F | AGGGAGCAGATCTTCGCCAGGCACTTCTTCAACAAAGCTGG TACC |
| 78 | G-H51N9-69T4-R | GATCATGCTGCCGCTGGGGGTGGCAGAGTAGATGGATGTGG TCGG |
| 79 | G-H51N9-69T5-F | ACCAACCTGACCATCAGCACCGCCTCTGCTCAGTCTGCTTC TGCT |
| 80 | G-H51N9-69T5-R | CGTGCCTGATGTACTGCTTGAAGTCAGACGGTTTGAAGGTA GCAG |
| 81 | Frag-H51-69T1-26S2-F | TGGGGCTGCGTGGGCGTGGAGGTGGGTCGTGGTCAGCCGCT GGGT |
| 82 | Frag-H51-69T1-26S2-R | GGGGGCGCAGCCGATGATGCACAGCTGGGTCTGTTTGTTGT CAAC |
| 83 | Vector-H51-69T1-26S2-R | CACCTCCACGCCCACGCAGCCCCA |
| 84 | Vector-H51-69T1-26S2-F | CTGTGCATCATCGGCTGCGCTCCCCCCATCG |
| 85 | Frag-H51-69T1-26S3-F | ATCATCGGCTGCGCCCCCCCCATCGGTGAACACTGGGGTAT CGGT |
| 86 | Frag-H51-69T1-26S3-R | GCCGTCCTGGATCACGCTGCTCACCAGTTCCAGCGGCGGGC A |
| 87 | Vector-H51-69T1-26S3-R | GATGGGGGGGGCGCAGCCGATGAT |
| 88 | Vector-H51-69T1-26S3-F | GTGAGCAGCGTGATCCAGGACGGC |
| 89 | Frag-H51-69T1-26S4-F | TACGGCAACAGCATGTTCTTCCACCTGCGTCGTGAACAGAT CTTCGCTCGTCAC |

TABLE 3-continued

| Sequences of the primers used (SEQ ID NO: 61-144) | | |
|---|---|---|
| SEQ ID NO: | Primer name | Primer Sequence (5'-3') |
| 90 | Frag-H51-69T1-26S4-R | GCTGTCGCTGGTGATCATGCTGCCAGACGGGGTAGCAGAGTAGAT |
| 91 | Vector-H51-69T1-26S4-R | GTGGAAGAACATGCTGTTGCCGTA |
| 92 | Vector-H51-69T1-26S4-F | GGCAGCATGATCACCAGCGACAGC |
| 93 | Frag-H51-69T1-26S5-F | TTCATCACCTGCGTGGACACCACCCGTTCTACCAACCTGACCATCTCTACCGCG |
| 94 | Frag-H51-69T1-26S5-R | CAGCTGGAAGATGAACTGCAGCTCGTATTCTTCACCGTGACGGATGTACTGTTTGAA |
| 95 | Vector-H51-69T1-26S5-R | GGTGGTGTCCACGCAGGTGATGAACAG |
| 96 | Vector-H51-69T1-26S5-F | GAGCTGCAGTTCATCTTCCAGCTG |
| 97 | Frag-H51-69T3-26S1-F | TACGCCGGCAGCAGCAGGCTGATCACCCTGGGTCACCCGTAC |
| 98 | Frag-H51-69T3-26S1-R | CACCCTGAACACCCTGTACTGGAAAGCAGAAACTTTCGGGAT |
| 99 | Vector-H51-69T3-26S1-R | GATCAGCCTGCTGCTGCCGGCGTA |
| 100 | Vector-H51-69T3-26S1-F | TTCCAGTACAGGGTGTTCAGGGTG |
| 101 | Frag-H51-69T3-26S2-F | TGGGGCTGCGTGGGCGTGGAGGTGGGTCGTGGTCAGCCGCTGGGT |
| 102 | Frag-H51-69T3-26S2-R | GGGGGCGCAGCCGATGATGCACAGCTGGGTCTGTTTGTTGTCAAC |
| 103 | Vector-H51-69T3-26S2-R | CACCTCCACGCCCACGCAGCCCCA |
| 104 | Vector-H51-69T3-26S2-F | CTGTGCATCATCGGCTGCGCTCCCCCCATCG |
| 105 | Frag-H51-69T3-26S4-F | TACGGCAACAGCATGTTCTTCCACCTGCGTCGTGAACAGATCTTCGCTCGTCAC |
| 106 | Frag-H51-69T3-26S4-R | GCTGTCGCTGGTGATCATGCTGCCAGACGGGGTAGCAGAGTAGAT |
| 107 | Vector-H51-69T3-26S4-R | GTGGAAGAACATGCTGTTGCCGTA |
| 108 | Vector-H51-69T3-26S4-F | GGCAGCATGATCACCAGCGACAGC |
| 109 | Frag-H51-69T3-26S5-F | TTCATCACCTGCGTGGACACCACCCGTTCTACCAACCTGACCATCTCTACC |
| 110 | Frag-H51-69T3-26S5-R | CAGCTGGAAGATGAACTGCAGCTCGTATTCTTCACCGTGACGGATGTACTGTTTGAA |
| 111 | Vector-H51-69T3-26S5-R | GGTGGTGTCCACGCAGGTGATGAACAG |
| 112 | Vector-H51-69T3-26S5-F | GAGCTGCAGTTCATCTTCCAGCTG |
| 113 | Frag-H51-69T2-26S1-F | TACGCCGGCAGCAGCAGGCTGATCACCCTGGGTCACCCGTAC |
| 114 | Frag-H51-69T2-26S1-R | CACCCTGAACACCCTGTACTGGAAAGCAGAAACTTTCGGGAT |
| 115 | Vector-H51-69T2-26S1-R | GATCAGCCTGCTGCTGCCGGCGTA |
| 116 | Vector-H51-69T2-26Sl-F | TTCCAGTACAGGGTGTTCAGGGTG |
| 117 | Frag-H51-69T2-26S3-F | ATCATCGGCTGCGCCCCCCCCATCGGTGAACACTGGGGTATCGGT |
| 118 | Frag-H51-69T2-26S3-R | GCCGTCCTGGATCACGCTGCTCACCAGTTCCAGCGGCGGGCA |
| 119 | Vector-H51-69T2-26S3-R | GATGGGGGGGGCGCAGCCGATGAT |

TABLE 3-continued

Sequences of the primers used (SEQ ID NO: 61-144)

| SEQ ID NO: | Primer name | Primer Sequence (5'-3') |
|---|---|---|
| 120 | Vector-H51-69T2-26S3-F | GTGAGCAGCGTGATCCAGGACGGC |
| 121 | Frag-H51-69T2-26S4-F | TACGGCAACAGCATGTTCTTCCACCTGCGTCGTGAACAGAT CTTCGCTCGTCAC |
| 122 | Frag-H51-69T2-26S4-R | GCTGTCGCTGGTGATCATGCTGCCAGACGGGGTAGCAGAGT AGAT |
| 123 | Vector-H51-69T2-26S4-R | GTGGAAGAACATGCTGTTGCCGTA |
| 124 | Vector-H51-69T2-26S4-F | GGCAGCATGATCACCAGCGACAGC |
| 125 | Frag-H51-69T2-26S5-F | TTCATCACCTGCGTGGACACCACCCGTTCTACCAACCTGAC CATCTCTACC |
| 126 | Frag-H51-69T2-26S5-R | CAGCTGGAAGATGAACTGCAGCTCGTATTCTTCACCGTGAC GGATGTACTGTTTGAA |
| 127 | Vector-H51-69T2-26S5-R | GGTGGTGTCCACGCAGGTGATGAACAG |
| 128 | Vector-H51-69T2-26S5-F | GAGCTGCAGTTCATCTTCCAGCTG |
| 129 | Frag-H51-69T4-26S1-F | TACGCCGGCAGCAGCAGGCTGATCACCCTGGGTCACCCGTA C |
| 130 | Frag-H51-69T4-26S1-R | CACCCTGAACACCCTGTACTGGAAAGCAGAAACTTTCGGGA T |
| 131 | Vector-H51-69T4-26S1-R | GATCAGCCTGCTGCTGCCGGCGTA |
| 132 | Vector-H51-69T4-26S1-F | TTCCAGTACAGGGTGTTCAGGGTG |
| 133 | Frag-H51-69T4-26S2-F | TGGGGCTGCGTGGGCGTGGAGGTGGGTCGTGGTCAGCCGCT GGGT |
| 135 | Frag-H51-69T4-26S2-R | GGGGGCGCAGCCGATGATGCACAGCTGGGTCTGTTTGTTGT CAAC |
| 135 | Vector-H51-69T4-26S2-R | CACCTCCACGCCCACGCAGCCCCA |
| 136 | Vector-H51-69T4-26S2-F | CTGTGCATCATCGGCTGCGCTCCCCCCATCG |
| 137 | Frag-H51-69T4-26S3-F | ATCATCGGCTGCGCCCCCCCCATCGGTGAACACTGGGGTAT CGGT |
| 138 | Frag-H51-69T4-26S3-R | GCCGTCCTGGATCACGCTGCTCACCAGTTCCAGCGGCGGGC A |
| 139 | Vector-H51-69T4-26S3-R | GATGGGGGGGGCGCAGCCGATGAT |
| 140 | Vector-H51-69T4-26S3-F | GTGAGCAGCGTGATCCAGGACGGC |
| 141 | Frag-H51-69T4-26S5-F | TTCATCACCTGCGTGGACACCACCCGTTCTACCAACCTGAC CATCTCTACC |
| 142 | Frag-H51-69T4-26S5-R | CAGCTGGAAGATGAACTGCAGCTCGTATTCTTCACCGTGAC GGATGTACTGTTTGAA |
| 143 | Vector-H51-69T4-26S5-R | GGTGGTGTCCACGCAGGTGATGAACAG |
| 144 | Vector-H51-69T4-26S5-F | GAGCTGCAGTTCATCTTCCAGCTG |

Expression of the Mutated Proteins on a Large Scale

The *E. coli* solutions comprising the recombinant plasmid pTO-T7-H51N9-69T1, pTO-T7-H51N9-69T2, pTO-T7-H51N9-69T3, pTO-T7-H51N9-69T4, pTO-T7-H51N9-69T5, H51N9-69T1-26S2, H51N9-69T1-26S3, H51N9-69T1-26S4, H51N9-69T1-26S5, H51N9-69T2-26S1, H51N9-69T2-26S3, H51N9-69T2-26S4, H51N9-69T2-26S5, H51N9-69T3-26S1, H51N9-69T3-26S2, H51N9-69T3-26S4, H51N9-69T3-26S5, H51N9-69T4-26S1, H51N9-69T4-26S2, H51N9-69T4-26S3 and H51N9-69T4-26S5, respectively, were taken from −70° C. refrigerator, were inoculated in 100 mL LB liquid medium containing kanamycin, and incubated at 200 rpm and 37° C. for about 8 h. Then, the culture was transferred to 500 mL LB medium containing kanamycin (1 ml bacterial solution was transferred), and was further incubated. When the bacterial concentration reached an $OD_{600}$ of about 0.6, the culturing temperature was lowered to 25° C. and 500 μL IPTG was added to each culture bottle. The incubation was further performed for 8 h. After the incubation was finished, the bacteria were collected by centrifugation. The bacteria expressing H51N9-69T1, H51N9-69T2, H51N9-69T3, H51N9-69T4, H51N9-69T5, H51N9-69T1-26S2, H51N9-69T1-26S3, H51N9-69T1-26S4, H51N9-69T1-26S5, H51N9-69T2-26S1, H51N9-69T2-26S3, H51N9-69T2-26S4, H51N9-69T2-26S5, H51N9-69T3-26S1, H51N9-69T3-26S2, H51N9-69T3-26S4, H51N9-69T3-26S5, H51N9-69T4-26S1, H51N9-69T4-26S2, H51N9-69T4-26S3 and H51N9-69T4-26S5 protein were obtained, respectively.

Disruption of Bacteria Expressing the Mutated Proteins

The bacteria obtained above were re-suspended at a ratio of 1 g bacteria to 10 mL lysis buffer (20 mM Tris buffer, pH7.2, 300 mM NaCl). The bacteria were disrupted by using an ultrasonic apparatus for 30 min. The lysis solution containing the disrupted bacteria were centrifuged at 13500 rpm (30000 g) for 15 min, and the supernatant (i.e. the supernatant of disrupted bacteria) was obtained.

Chromatographic Purification of the Mutated Protein

Equipment: AKTA Explorer 100 preparative liquid chromatography system produced by GE Healthcare (i.e. the original Amershan Pharmacia Co.)

Chromatographic media: SP Sepharose 4 Fast Flow (GE Healthcare Co.), CHT-II (purchased from Bio-RAD) and Butyl Sepharose 4 Fast Flow (GE Healthcare Co.)

The buffers containing different concentrations of NaCl used in the following elution protocol were prepared by mixing Buffer A and Buffer B at a certain ratio.

Buffer: Buffer A (20 mM phosphate buffer, pH8.0, 20 mM DTT); and Buffer B (20 mM phosphate buffer, pH8.0, 20 mM DTT, 2M NaCl).

Sample: the supernatants of disrupted bacteria containing H51N9-69T1 and H51N9-69T3, respectively, as obtained above.

Elution Protocol:

(1) Cation exchange purification of the supernatant of disrupted bacteria by SP Sepharose 4 Fast Flow: the sample was loaded on the column, undesired proteins were then eluted with a buffer containing 400 mM NaCl (80% Buffer A+20% Buffer B), followed by the elution of the protein of interest with a buffer containing 800 mM NaCl (60% Buffer A+40% Buffer B), and the fraction eluted with the buffer containing 800 mM NaCl was collected;

(2) Chromatographic purification of the elution fraction obtained in the step (1) by CHTII (hydroxyapatite chromatography): the elution fraction obtained in the step (1) was diluted so that the NaCl concentration was decreased to 0.5 M; the sample was loaded on the column, undesired proteins were then eluted with a buffer containing 500 mM NaCl (75% Buffer A+25% Buffer B), followed by the elution of the protein of interest with a buffer containing 1000 mM NaCl (50% Buffer A+50% Buffer B), and the fraction eluted with the buffer containing 1000 mM NaCl was collected;

(3) Chromatographic purification of the elution fraction obtained in the step (2) by HIC (hydrophobic interaction chromatography): the sample was loaded on the column, undesired proteins were then eluted with a buffer containing 1000 mM NaCl, followed by the elution of the protein of interest with a buffer containing 200 mM NaCl (90% Buffer A+10% Buffer B), and the fraction eluted with the buffer containing 200 mM NaCl was collected.

150 μL of elution fraction obtained in the step (3) was added to 30 μL of 6× Loading Buffer (1 L of which contained 300 ml of 1M TB 6.8, 600 ml of 100% glycerol, 120 g of SDS, 6 g of bromophenol blue, and 50 ml of β-mercapto-ethanol). The resultant solution was mixed well and incubated in 80° C. water bath for 10 min. 10 μl of the resultant sample was then subjected to 10% SDS-PAGE at 120V for 120 min; and the electrophoretic bands were stained by Coomassie brilliant blue. The electrophoretic result was shown in FIGS. 1A, 1B, 1C and 1D. The result showed that after above purification steps, H51N9-69T1, H51N9-69T2, H51N9-69T3, H51N9-69T4, H51N9-69T5, H51N9-69T1-26S2, H51N9-69T1-26S3, H51N9-69T1-26S4, H51N9-69T1-26S5, H51N9-69T2-26S1, H51N9-69T2-26S3, H51N9-69T2-26S4, H51N9-69T2-26S5, H51N9-69T3-26S1, H51N9-69T3-26S2, H51N9-69T3-26S4, H51N9-69T3-26S5, H51N9-69T4-26S1, H51N9-69T4-26S2, H51N9-69T4-26S3 and H51N9-69T4-26S5 protein had a purity of about 90%.

By similar methods, HPV51N9 protein was prepared and purified by using *E. coli* and the plasmid pTO-T7-HPV51N9C; HPV69N0 protein was prepared and purified by using *E. coli* and the plasmid pTO-T7-HPV69L1N0C; and HPV26N0 protein was prepared and purified by using *E. coli* and the plasmid pTO-T7-HPV26L1N0C.

Western Blot Assay of the Mutated Proteins

The H51N9-69T1, H51N9-69T2, H51N9-69T3, H51N9-69T4, H51N9-69T5, H51N9-69T1-26S2, H51N9-69T1-26S3, H51N9-69T1-26S4, H51N9-69T1-26S5, H51N9-69T2-26S1, H51N9-69T2-26S3, H51N9-69T2-26S4, H51N9-69T2-26S5, H51N9-69T3-26S1, H51N9-69T3-26S2, H51N9-69T3-26S4, H51N9-69T3-26S5, H51N9-69T4-26S1, H51N9-69T4-26S2, H51N9-69T4-26S3 and H51N9-69T4-26S5 protein purified by the method above were subjected to electrophoresis. After electrophoresis, Western Blot assay was carried out by using a broad-spectrum antibody 4B3 against HPV L1 protein, and the result was shown in FIGS. 2A, 2B, 2C and 2D. The result showed that the mutated proteins H51N9-69T1, H51N9-69T2, H51N9-69T3, H51N9-69T4, H51N9-69T5, H51N9-69T1-26S2, H51N9-69T1-26S3, H51N9-69T1-26S4, H51N9-69T1-26S5, H51N9-69T2-26S1, H51N9-69T2-26S3, H51N9-69T2-26S4, H51N9-69T2-26S5, H51N9-69T3-26S1, H51N9-69T3-26S2, H51N9-69T3-26S4, H51N9-69T3-26S5, H51N9-69T4-26S1, H51N9-69T4-26S2, H51N9-69T4-26S3 and H51N9-69T4-26S5 could be specifically recognized by the broad-spectrum antibody 4B3.

Example 2: Assembly of HPV Virus-Like Particles and Morphological Detection of Particles Assembly of HPV Virus-Like Particles A given volume (about 2 ml) of the protein H51N9-69T1, H51N9-69T2, H51N9-69T3, H51N9-69T4, H51N9-69T5, H51N9-69T1-26S2, H51N9-69T1-26S3, H51N9-69T1-26S4, H51N9-69T1-26S5, H51N9-69T2-26S1, H51N9-69T2-26S3, H51N9-69T2-26S4, H51N9-69T2-26S5, H51N9-69T3-26S1, H51N9-69T3-26S2, H51N9-69T3-26S4, H51N9-69T3-26S5, H51N9-69T4-26S1, H51N9-69T4-26S2, H51N9-69T4-26S3 and H51N9-69T4-26S5, was dialyzed to (1) 2 L storage buffer (20 mM sodium phosphate buffer pH 6.5, 0.5 M NaCl); (2) 2 L renaturation buffer (50 mM sodium phosphate buffer pH 6.0, 2 mM $CaCl_2$, 2 mM $MgCl_2$, 0.5 M NaCl); and (3) 20 mM sodium phosphate buffer pH 7.0, 0.5 M NaCl, successively. The dialysis was performed in each of the three buffers for 12h.

By similar methods, the HPV51N9, HPV69N0 and HPV26N0 protein were assembled into HPV51N9 VLP, HPV69N0 VLP and HPV26N0 VLP, respectively.

Molecular Sieve Chromatographic Analysis

Figure 3:
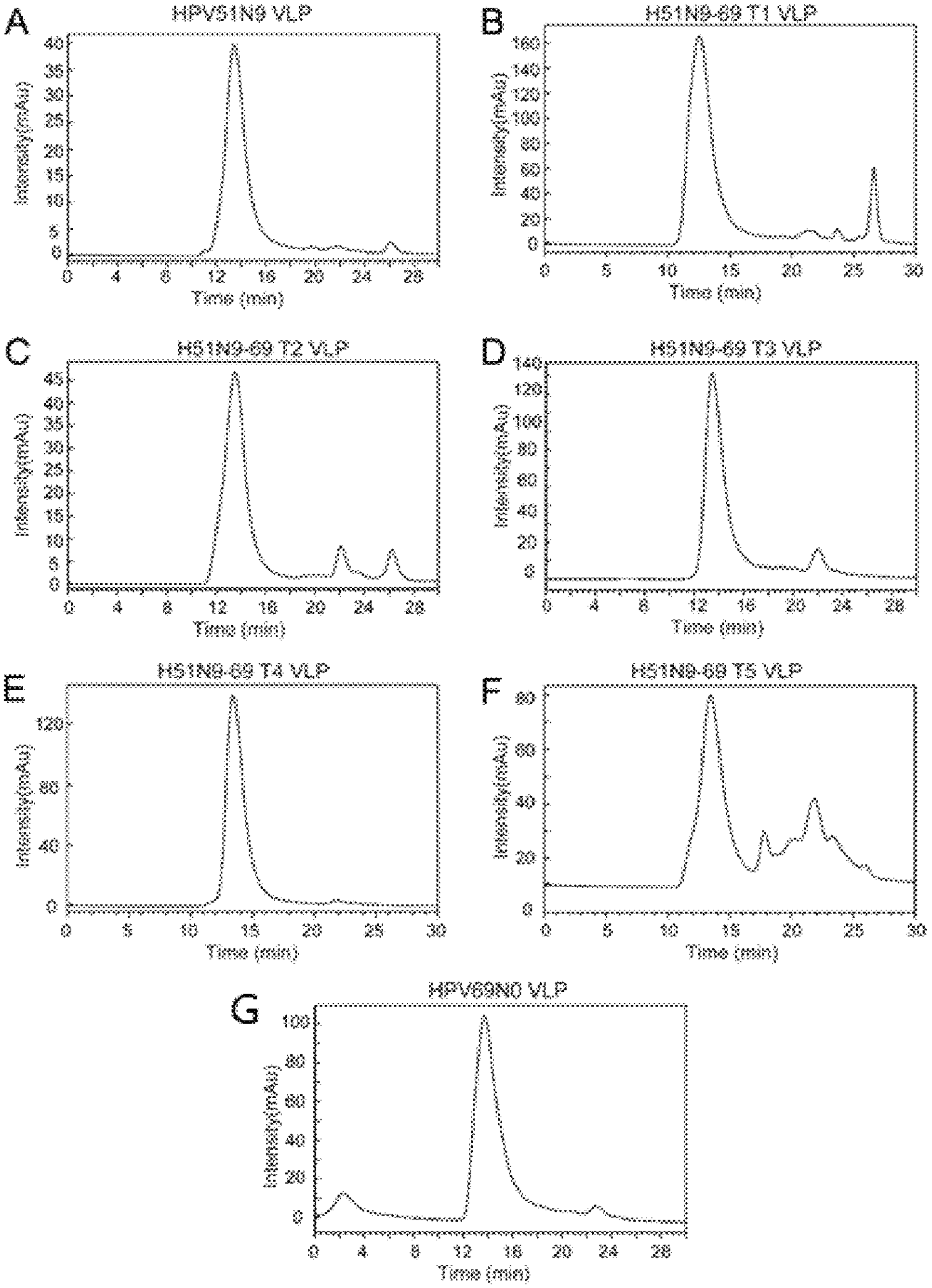
FIG. 3 shows the results of the samples comprising the mutated protein H51N9-69T1, H51N9-69T2, H51N9-69T3, H51N9-69T4 or H51N9-69T5, as analyzed by molecular sieve chromatography. The results showed that the first protein peak of the samples comprising the mutated protein H51N9-69T1, H51N9-69T2, H51N9-69T3, H51N9-69T4 or H51N9-69T5 appeared at about 13-14 min, which was comparable to that of HPV51N9 VLP. This showed that the mutated proteins H51N9-69T1, H51N9-69T2, H51N9-69T3, H51N9-69T4 and H51N9-69T5 were all able to assemble into VLPs with a uniform size.
Figure 4:
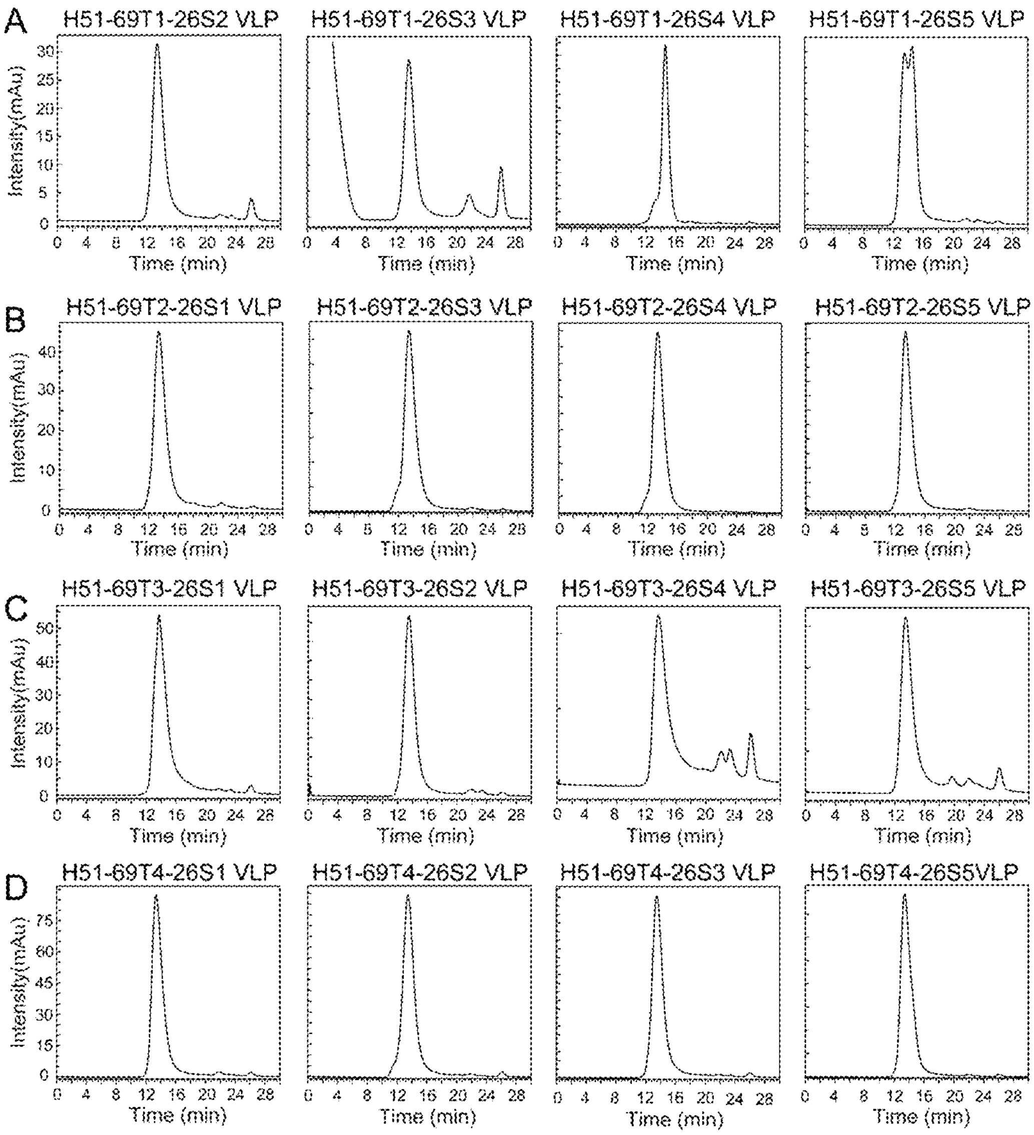
FIG. 4 shows the results of the samples comprising the mutated protein H51N9-69T1-26S2, H51N9-69T1-26S3, H51N9-69T1-26S4, H51N9-69T1-26S5, H51N9-69T2-26S1, H51N9-69T2-26S3, H51N9-69T2-26S4, H51N9-69T2-26S5, H51N9-69T3-26S1, H51N9-69T3-26S2, H51N9-69T3-26S4, H51N9-69T3-26S5, H51N9-69T4-26S1, H51N9-69T4-26S2, H51N9-69T4-26S3 or H51N9-69T4-26S5, as analyzed by molecular sieve chromatography. The results showed that the first protein peak of these mutated VLPs appeared at about 13-14 min, which was comparable to that of HPV51N9 VLP. This showed that these mutated proteins H51N9-69T1-26S2, H51N9-69T1-26S3, H51N9-69T2-26S1, H51N9-69T2-26S3, H51N9-69T2-26S4, H51N9-69T2-26S5, H51N9-69T3-26S1, H51N9-69T3-26S2, H51N9-69T3-26S4, H51N9-69T3-26S5, H51N9-69T4-26S1, H51N9-69T4-26S2, H51N9-69T4-26S3 and H51N9-69T4-26S5 were all able to assemble into VLPs with a uniform size. VLPs formed by the mutated protein H51N9-69T1-26S4 or H51N9-69T1-26S5 had a non-uniform size.
Figure 9:
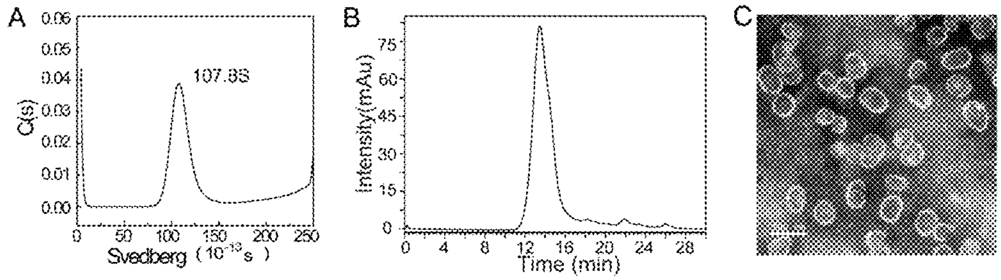
FIG. 9 shows the identification results of HPV26N0 VLP, wherein A shows the result of HPV26N0 VLP as analyzed by molecular sieve chromatography; B shows the results of sedimentation velocity analysis of HPV26N0 VLP; C shows the TEM photograph of HPV26N0 VLP.

The dialyzed sample was subjected to molecular sieve chromatographic analysis by 1120 Compact LC High Performance Liquid Chromatographic System (Agilent Technologies), wherein the analytical column used was TSK Gel PW5000×17.8×300 mm. The analysis result of HPV26N0 VLP was shown in FIG. 9, the analysis results of other samples were shown in FIGS. 3 and 4. The results showed that the first protein peak of the samples comprising the protein H51N9-69T1, H51N9-69T2, H51N9-69T3, H51N9-69T4, H51N9-69T5, H51N9-69T1-26S2, H51N9-69T1-26S3, H51N9-69T1-26S4, H51N9-69T1-26S5, H51N9-69T2-26S1, H51N9-69T2-26S3, H51N9-69T2-26S4, H51N9-69T2-26S5, H51N9-69T3-26S1, H51N9-69T3-26S2, H51N9-69T3-26S4, H51N9-69T3-26S5, H51N9-69T4-26S1, H51N9-69T4-26S2, H51N9-69T4-26S3 and H51N9-69T4-26S5 appeared at about 13-14 min, which was comparable to that of HPV51N9 VLP. This showed that except for the mutated proteins H51N9-69T1-26S4 and H51N9-69T1-26S5, the other mutated proteins H51N9-69T1, H51N9-69T2, H51N9-69T3, H51N9-69T4, H51N9-69T5, H51N9-69T1-26S2, H51N9-69T1-26S3, H51N9-69T2-26S1, H51N9-69T2-26S3, H51N9-69T2-26S4, H51N9-69T2-26S5, H51N9-69T3-26S1, H51N9-69T3-26S2, H51N9-69T3-26S4, H51N9-69T3-26S5, H51N9-69T4-26S1, H51N9-69T4-26S2, H51N9-69T4-26S3 and H51N9-69T4-26S5 were all able to assemble into VLPs with a uniform size. VLPs formed by the mutated protein H51N9-69T1-26S4 or H51N9-69T1-26S5 had a non-uniform size.

Sedimentation Velocity Analysis

Figure 5:
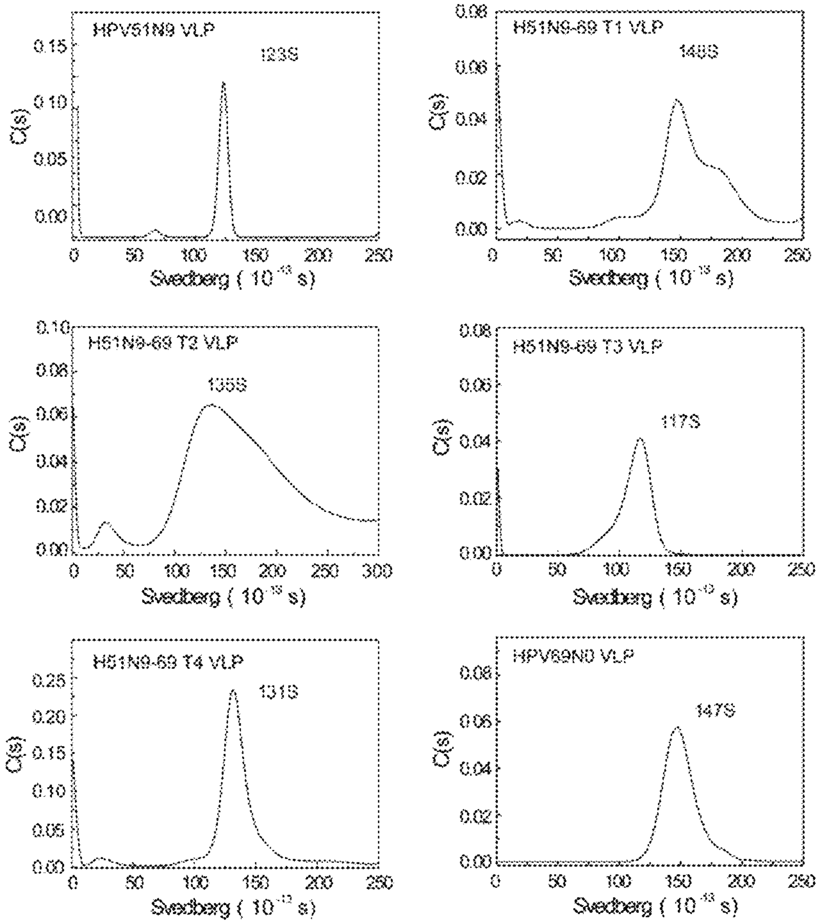
FIG. 5 shows the results of sedimentation velocity analysis of H51N9-69T1 VLP, H51N9-69T2 VLP, H51N9-69T3 VLP and H51N9-69T4 VLP. The results showed that the sedimentation coefficients of H51N9-69T1 VLP, H51N9-69T2 VLP, H51N9-69T3 VLP and H51N9-69T4 VLP were 148S, 135S, 117S and 131S, respectively. This showed that the mutated proteins H51N9-69T1, H51N9-69T2, H51N9-69T3 and H51N9-69T4 were all able to assemble into virus-like particles that were similar to wild type VLP (HPV51N9 VLP, 123S) in terms of size and morphology.
Figure 6:
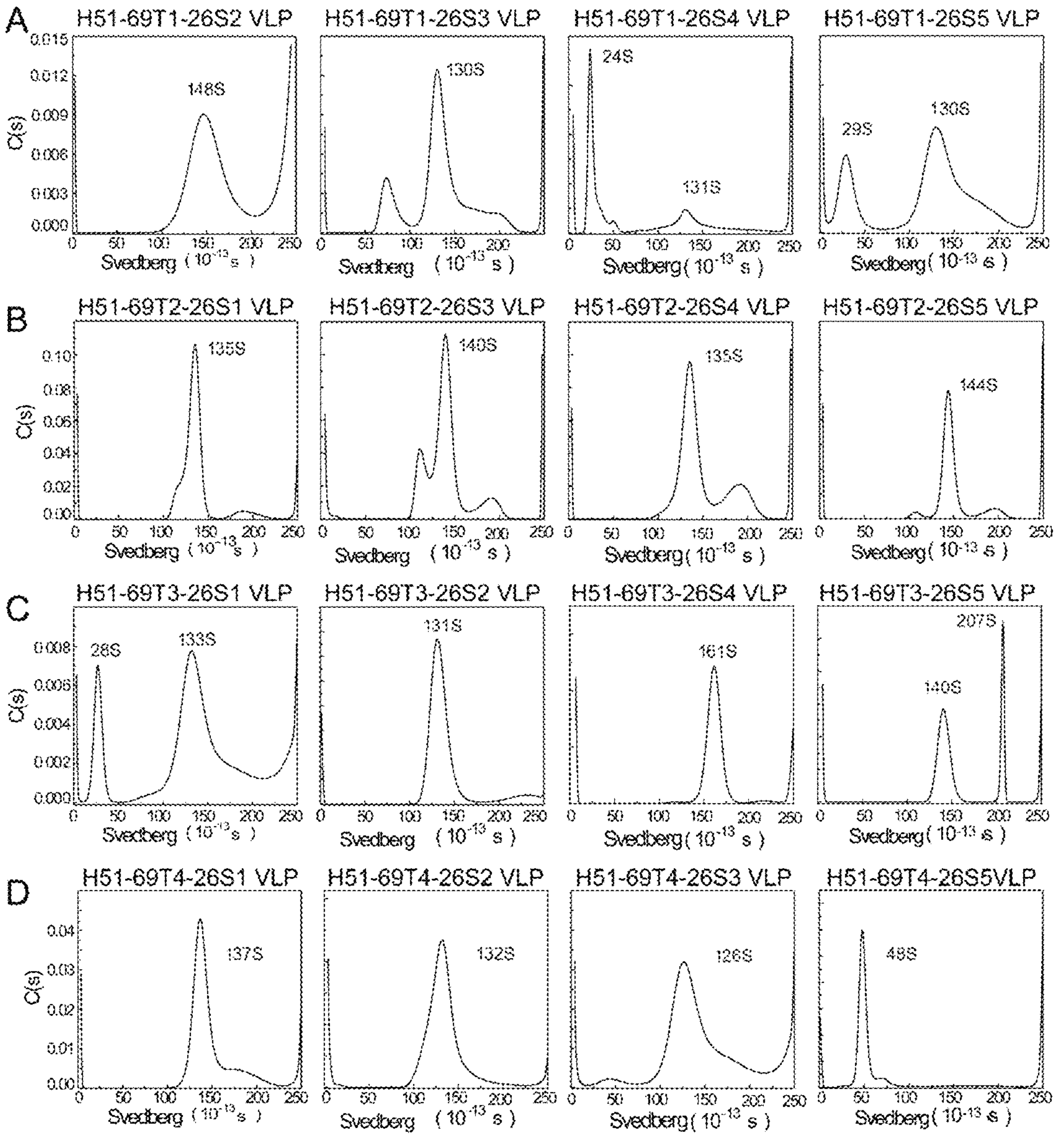
FIG. 6 shows the results of sedimentation velocity analysis of the mutated H51N9-69T1-26S2 VLP, H51N9-69T1-26S3 VLP, H51N9-69T1-26S4 VLP, H51N9-69T1-26S5VLP, H51N9-69T2-26S1 VLP, H51N9-69T2-26S3 VLP, H51N9-69T2-26S4 VLP, H51N9-69T2-26S5 VLP, H51N9-69T3-26S1 VLP, H51N9-69T3-26S2 VLP, H51N9-69T3-26S4 VLP, H51N9-69T3-26S5 VLP, H51N9-69T4-26S1 VLP, H51N9-69T4-26S2 VLP, H51N9-69T4-26S3 VLP and H51N9-69T4-26S5 VLP. The results showed that the sedimentation coefficients of H51N9-69T1-26S2 VLP, H51N9-69T1-26S3 VLP, H51N9-69T1-26S4 VLP, H51N9-69T1-26S5VLP, H51N9-69T2-26S1 VLP, H51N9-69T2-26S3 VLP, H51N9-69T2-26S4 VLP, H51N9-69T2-26S5 VLP, H51N9-69T3-26S1 VLP, H51N9-69T3-26S2 VLP, H51N9-69T3-26S4 VLP, H51N9-69T3-26S5 VLP, H51N9-69T4-26S1 VLP, H51N9-69T4-26S2 VLP, H51N9-69T4-26S3 VLP and H51N9-69T4-26S5 VLP were 148S, 130S, 131S, 130S, 135S, 140S, 135S, 144S, 133S, 131S, 161S, 140S, 137S, 132S, 126S and 48S, respectively, wherein H51N9-69T1-26S3 VLP, H51N9-69T1-26S4 VLP, H51N9-69T1-26S5VLP, H51N9-69T2-26S3 VLP, H51N9-69T3-26S1 VLP and H51N9-69T3-26S5 VLP had poor uniformity, and had two different sizes.

The apparatus for sedimentation velocity analysis was Beckman XL-A Analytical Ultracentrifuge, equipped with optical inspection system and An-50Ti and An-60Ti rotor. The sedimentation coefficients of HPV51N9 VLP, HPV69N0 VLP, H51N9-69T1 VLP, H51N9-69T2 VLP, H51N9-69T3 VLP, H51N9-69T4 VLP, H51N9-69T1-26S2 VLP, H51N9-69T1-26S3 VLP, H51N9-69T1-26S4 VLP, H51N9-69T1-26S5VLP, H51N9-69T2-26S1 VLP, H51N9-69T2-26S3 VLP, H51N9-69T2-26S4 VLP, H51N9-69T2-26S5 VLP, H51N9-69T3-26S1 VLP, H51N9-69T3-26S2 VLP, H51N9-69T3-26S4 VLP, H51N9-69T3-26S5 VLP, H51N9-69T4-26S1 VLP, H51N9-69T4-26S2 VLP, H51N9-69T4-26S3 VLP and H51N9-69T4-26S5 VLP were analyzed by sedimentation velocity method. The analysis result of HPV26N0 VLP was shown in FIG. 9, the analysis results of other samples were shown in FIGS. 5 and 6. The results showed that the sedimentation coefficients of H51N9-69T1 VLP, H51N9-69T2 VLP, H51N9-69T3 VLP, H51N9-69T4 VLP, H51N9-69T1-26S2 VLP, H51N9-69T1-26S3 VLP, H51N9-69T1-26S4 VLP, H51N9-69T1-26S5VLP, H51N9-69T2-26S1 VLP, H51N9-69T2-26S3 VLP, H51N9-69T2-26S4 VLP, H51N9-69T2-26S5 VLP, H51N9-69T3-26S1 VLP, H51N9-69T3-26S2 VLP, H51N9-69T3-26S4 VLP, H51N9-69T3-26S5 VLP, H51N9-69T4-26S1 VLP, H51N9-69T4-26S2 VLP, H51N9-69T4-26S3 VLP and H51N9-69T4-26S5 VLP were 148S, 135S, 117S, 131S, 148S, 130S, 131S, 130S, 135S, 140S, 135S, 144S, 133S, 131S, 161S, 140S, 137S, 132S, 126S and 48S, respectively, wherein H51N9-69T1-26S3 VLP, H51N9-69T1-26S4 VLP, H51N9-69T1-26S5VLP, H51N9-69T2-26S3 VLP, H51N9-69T3-26S1 VLP and H51N9-69T3-26S5 VLP had poor uniformity, and had two different sizes.

Morphological Test of Virus-Like Particles

Figure 7:
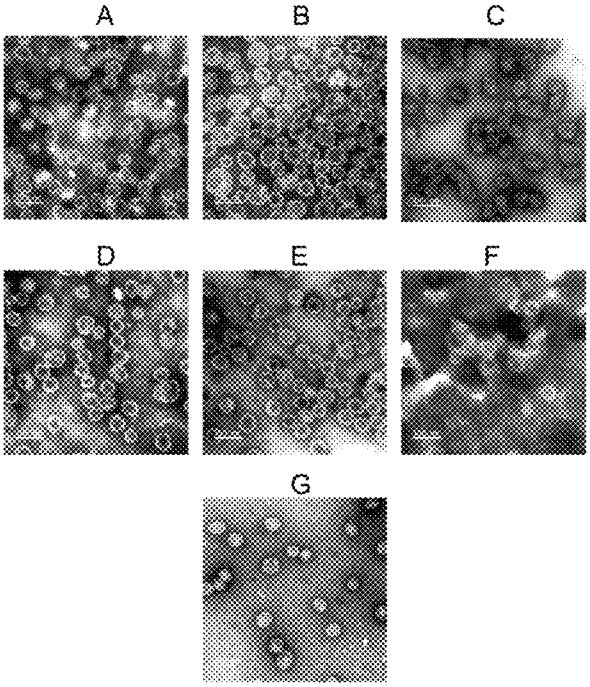
FIG. 7 shows the transmission electron microscopy (TEM) photographs (taken at 100,000× magnification, Bar=0.1 μm) of various VLP samples, wherein A shows the TEM photograph of HPV51N9 VLP; B shows the TEM photograph of H51N9-69T1 VLP; C shows the TEM photograph of H51N9-69T2 VLP; D shows the TEM photograph of H51N9-69T3 VLP; E shows the TEM photograph of H51N9-69T4 VLP; F shows the TEM photograph of H51N9-69T5 VLP; G shows the TEM photograph of HPV69N0 VLP. The results showed that H51N9-69T1 VLP, H51N9-69T2 VLP, H51N9-69T3 VLP and H51N9-69T4 VLP and H51N9-69T5 VLP were similar to HPV51N9 VLP, these mutated proteins were able to assemble into VLPs with a radius of about 25 nm.
Figure 8:
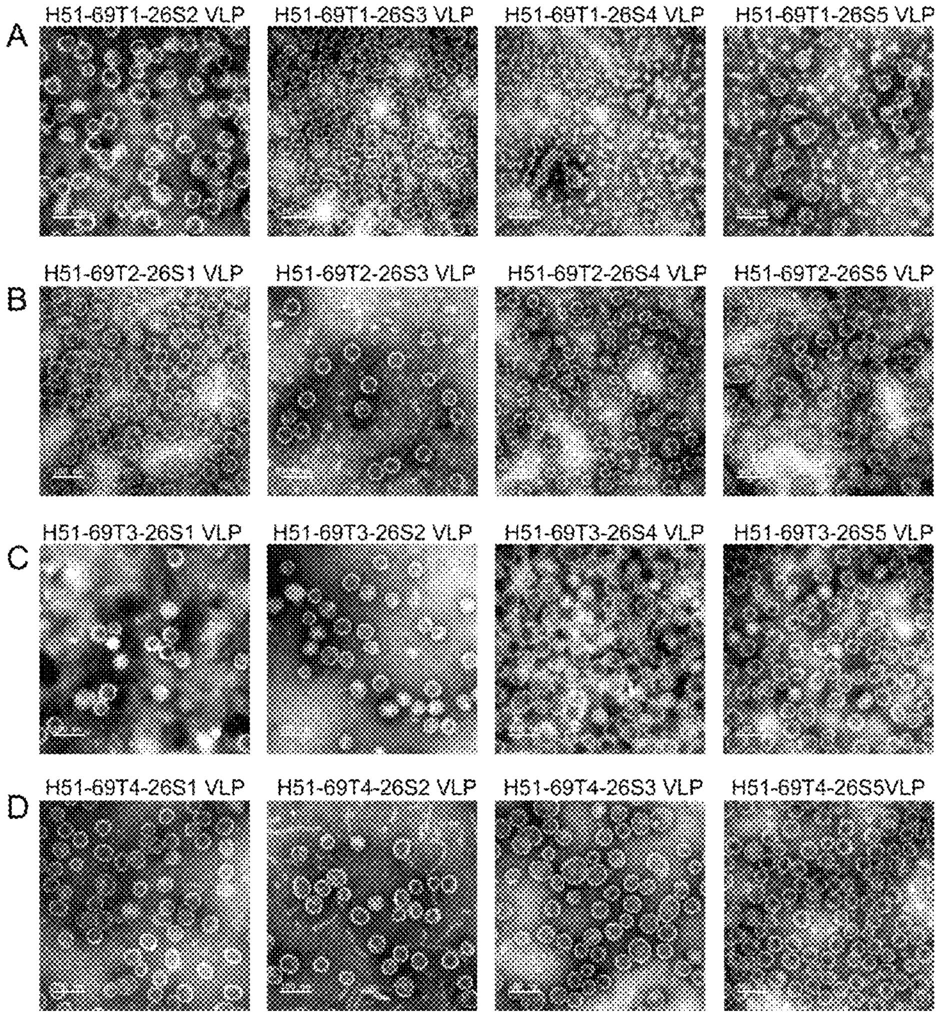
FIG. 8 shows the transmission electron microscopy (TEM) photographs (taken at 100,000× magnification, Bar=0.1 μm) of various VLP samples, wherein A shows the TEM photographs of H51N9-69T1-26S2 VLP, H51N9-69T1-26S3 VLP, H51N9-69T1-26S4 VLP and H51N9-69T1-26S5VLP; B shows the TEM photographs of H51N9-69T2-26S1 VLP, H51N9-69T2-26S3 VLP, H51N9-69T2-26S4 VLP and H51N9-69T2-26S5 VLP; C shows the TEM photographs of H51N9-69T3-26S1 VLP, H51N9-69T3-26S2 VLP, H51N9-69T3-26S4 VLP and H51N9-69T3-26S5 VLP; D shows the TEM photographs of H51N9-69T4-26S1 VLP, H51N9-69T4-26S2 VLP, H51N9-69T4-26S3 VLP and H51N9-69T4-26S5 VLP. The results showed that except for the mutated protein H51N9-69T1-26S4, the other mutated proteins were able to assemble into VLPs with a radius of about 25 nm.

A 100 μL sample comprising VLP was observed by transmission electron microscope (TEM). The apparatus used was a 100 kV Transmission Electron Microscope supplied by JEOL Ltd. (100,000× magnification). In brief, a 13.5 μL of sample was negatively stained with 2% phosphotungstic acid (pH 7.0), fixed on a carbon-coated copper grid, and then observed by TEM. The TEM photographs of HPV26N0 VLP was shown in FIG. 9, and the TEM photographs of other samples were shown in FIGS. 7 and 8. The results showed that except for H51N9-69T1-26S4 VLP, the other VLPs H51N9-69T1 VLP, H51N9-69T2 VLP, H51N9-69T3 VLP, H51N9-69T4 VLP, H51N9-69T5 VLP, H51N9-69T1-26S2 VLP, H51N9-69T1-26S3 VLP, H51N9-69T1-26S5VLP, H51N9-69T2-26S1 VLP, H51N9-69T2-26S3 VLP, H51N9-69T2-26S4 VLP, H51N9-69T2-26S5 VLP, H51N9-69T3-26S1 VLP, H51N9-69T3-26S2 VLP, H51N9-69T3-26S4 VLP, H51N9-69T3-26S5 VLP, H51N9-69T4-26S1 VLP, H51N9-69T4-26S2 VLP, H51N9-69T4-26S3 VLP and H51N9-69T4-26S5 VLP were similar to HPV51N9 VLP, and had a radius of about 25 nm.

Example 3: Evaluation 1 of Neutralizing Antibody Titer in Serum of Mice Vaccinated with Virus-Like Particles In this experiment, virus-like particles used were H51N9-69T1 VLP, H51N9-69T2 VLP, H51N9-69T3 VLP, H51N9-69T4 VLP and H51N9-69T5 VLP.

In this experiment, vaccination schedule was shown in Table 4. All the mice (6-week old BalB/c female mice) were divided into 2 groups: Aluminum adjuvant group 1 (at an immunizing dose of 5 μg, using aluminum adjuvant), Aluminum adjuvant group 2 (at an immunizing dose of 1 μg, using aluminum adjuvant). Each group was further divided into 8 subgroups. The Control subgroups 1 and 2 were vaccinated with HPV51N9 VLP alone and HPV69N0 VLP alone, respectively, the Control subgroup 3 was vaccinated with the mixed HPV51/HPV69 VLP (i.e. a mixture of HPV51N9 VLP and HPV69N0 VLP, at a given immunizing dose for each VLP). The Experimental subgroups 1, 2, 3, 4 and 5 were vaccinated with H51N9-69T1 VLP, H51N9-69T2 VLP, H51N9-69T3 VLP, H51N9-69T4 VLP and H51N9-69T5 VLP, respectively.

Figure 10A:
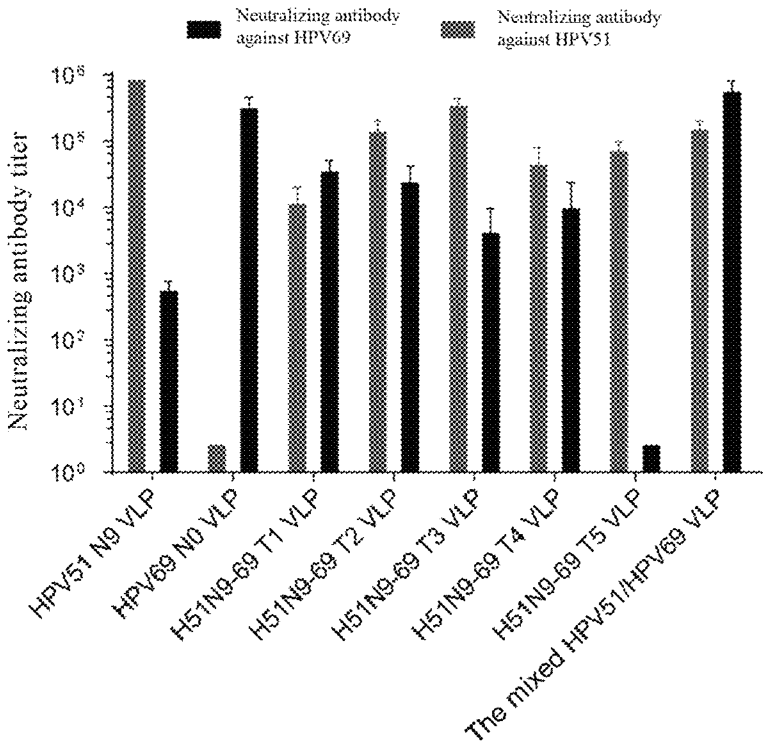
FIGS. 10A and 10B show the results of neutralizing antibody titer in mouse serum after vaccination of mice with H51N9-69T1 VLP, H51N9-69T2 VLP, H51N9-69T3 VLP, H51N9-69T4 VLP and H51N9-69T5 VLP.
Figure 10B:
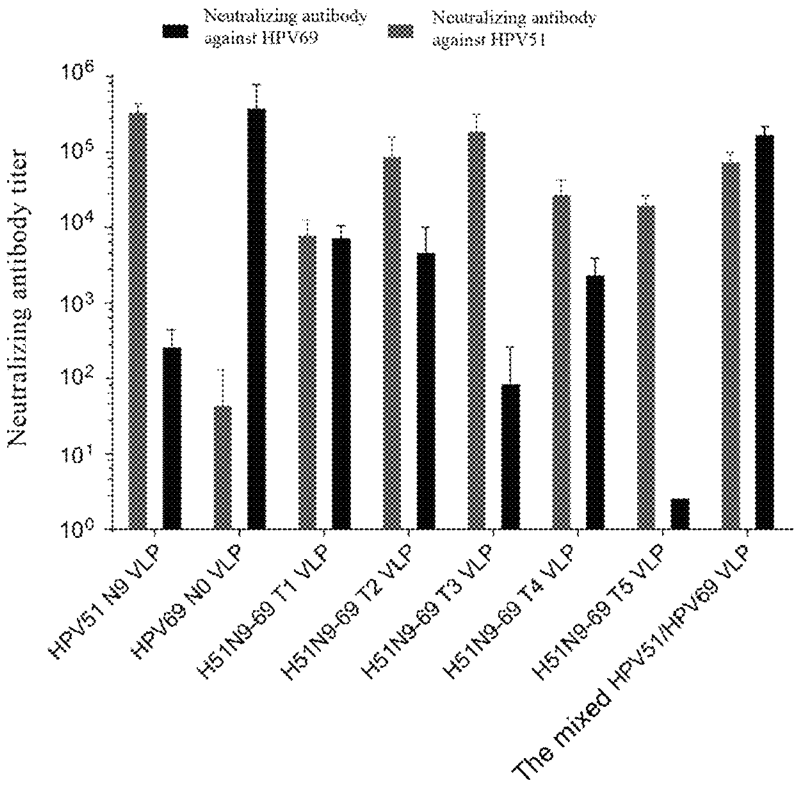

In Aluminum adjuvant groups 1-2, 5 mice/subgroup were vaccinated by intraperitoneal injection, at an immunizing dose 5 μg and 1 μg, respectively, and an injection volume of 1 mL. All the mice were subjected to the first vaccination at Week 0, and then subjected to the booster vaccination at Weeks 2 and 4, respectively. At Week 8, blood sample was collected via orbital bleeding, and the titers of antibodies against HPV51 and HPV69 in serum were analyzed. The analysis results were shown in FIGS. 10A and 10B. The result showed that H51N9-69T1 VLP, H51N9-69T2 VLP, H51N9-69T3 VLP and H51N9-69T4 VLP each could induce the generation of high-titer neutralizing antibodies against HPV51 in mice, and their protective effects were comparable to that of HPV51N9 VLP alone and that of the mixed HPV51/HPV69 VLP at the same dose, and were significantly higher than that of HPV69N0 VLP alone at the same dose. H51N9-69T1 VLP, H51N9-69T2 VLP, H51N9-69T3 VLP and H51N9-69T4 VLP each could also induce the generation of high-titer neutralizing antibodies against HPV69 in mice, and their protective effects were comparable to that of HPV69N0 VLP alone and that of the mixed HPV51/HPV69 VLP at the same dose, and were significantly higher than that of HPV51N9 VLP alone at the same dose.

This showed that H51N9-69T1 VLP, H51N9-69T2 VLP, H51N9-69T3 VLP and H51N9-69T4 VLP had good cross-immunogenicity and cross-protection against HPV51 and HPV69.

TABLE 4

Vaccination schedule

| Group | Antigen for vaccination | Adjuvant | Immunizing dose | Number | Vaccination procedure (week) |
|---|---|---|---|---|---|
| Aluminum adjuvant group 1 | HPV51N9 VLP | aluminum adjuvant | 5 μg | 5 | 0, 2, 4 |
| | HPV69N0 VLP | aluminum adjuvant | 5 μg | 5 | 0, 2, 4 |
| | HPV51/HPV69 VLP | aluminum adjuvant | 5 μg for each VLP | 5 | 0, 2, 4 |
| | H51N9-69T1 VLP | aluminum adjuvant | 5 μg | 5 | 0, 2, 4 |
| | H51N9-69T2 VLP | aluminum adjuvant | 5 μg | 5 | 0, 2, 4 |
| | H51N9-69T3 VLP | aluminum adjuvant | 5 μg | 5 | 0, 2, 4 |
| | H51N9-69T4 VLP | aluminum adjuvant | 5 μg | 5 | 0, 2, 4 |
| | H51N9-69T5 VLP | aluminum adjuvant | 5 μg | 5 | 0, 2, 4 |
| Aluminum adjuvant group 2 | HPV51N9 VLP | aluminum adjuvant | 1 μg | 5 | 0, 2, 4 |
| | HPV69N0 VLP | aluminum adjuvant | 1 μg | 5 | 0, 2, 4 |
| | HPV51/HPV69 VLP | aluminum adjuvant | 1 μg for each VLP | 5 | 0, 2, 4 |
| | H51N9-69T1 VLP | aluminum adjuvant | 1 μg | 5 | 0, 2, 4 |
| | H51N9-69T2 VLP | aluminum adjuvant | 1 μg | 5 | 0, 2, 4 |
| | H51N9-69T3 VLP | aluminum adjuvant | 1 μg | 5 | 0, 2, 4 |
| | H51N9-69T4 VLP | aluminum adjuvant | 1 μg | 5 | 0, 2, 4 |
| | H51N9-69T5 VLP | aluminum adjuvant | 1 μg | 5 | 0, 2, 4 |

Example 4: Evaluation 2 of Neutralizing Antibody Titer in Serum of Mice Vaccinated with Virus-Like Particles In this experiment, virus-like particles used were H51N9-69T1-26S2 VLP, H51N9-69T1-26S3 VLP, H51N9-69T1-26S4 VLP, H51N9-69T1-26S5VLP, H51N9-69T3-26S1 VLP, H51N9-69T3-26S2 VLP, H51N9-69T3-26S4 VLP and H51N9-69T3-26S5 VLP.

In this experiment, vaccination schedule was shown in Table 5. All the mice (6-week old BalB/c female mice) were divided into 2 groups: Aluminum adjuvant group 1 (at an immunizing dose of 5 μg, using aluminum adjuvant), Aluminum adjuvant group 2 (at an immunizing dose of 1 μg, using aluminum adjuvant). Each group was further divided into 12 subgroups. The Control subgroups 1, 2 and 3 were vaccinated with HPV51N9 VLP alone, HPV69N0 VLP alone and HPV26N0 VLP alone, respectively, the Control subgroup 4 was vaccinated with the mixed HPV51/HPV69/HPV26 VLP (i.e. a mixture of HPV51N9 VLP, HPV69N0 VLP and HPV26N0 VLP, at a given immunizing dose for each VLP). The Experimental subgroups 1, 2, 3, 4, 5, 6, 7 and 8 were vaccinated with H51N9-69T1-26S2 VLP, H51N9-69T1-26S3 VLP, H51N9-69T1-26S4 VLP, H51N9-69T1-26S5VLP, H51N9-69T3-26S1 VLP, H51N9-69T3-26S2 VLP, H51N9-69T3-26S4 VLP and H51N9-69T3-26S5 VLP, respectively.

Figure 11A:
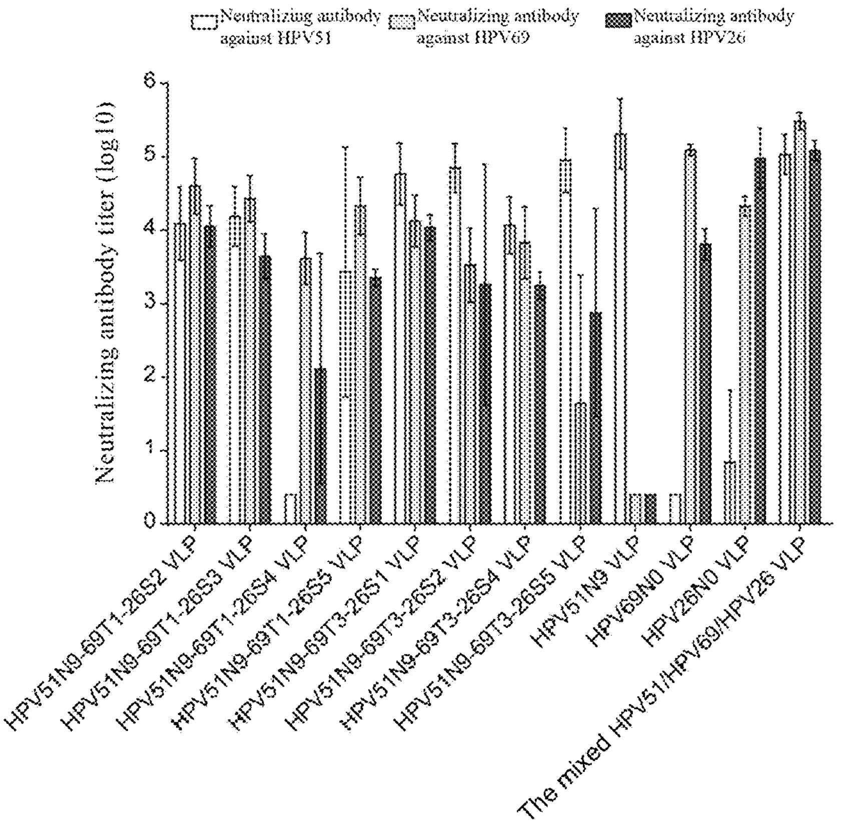
FIGS. 11A and 11B show the results of neutralizing antibody titer in mouse serum after vaccination of mice with H51N9-69T1-26S2 VLP, H51N9-69T1-26S3 VLP, H51N9-69T1-26S4 VLP, H51N9-69T1-26S5VLP, H51N9-69T3-26S1 VLP, H51N9-69T3-26S2 VLP, H51N9-69T3-26S4 VLP and H51N9-69T3-26S5 VLP.
Figure 11B:
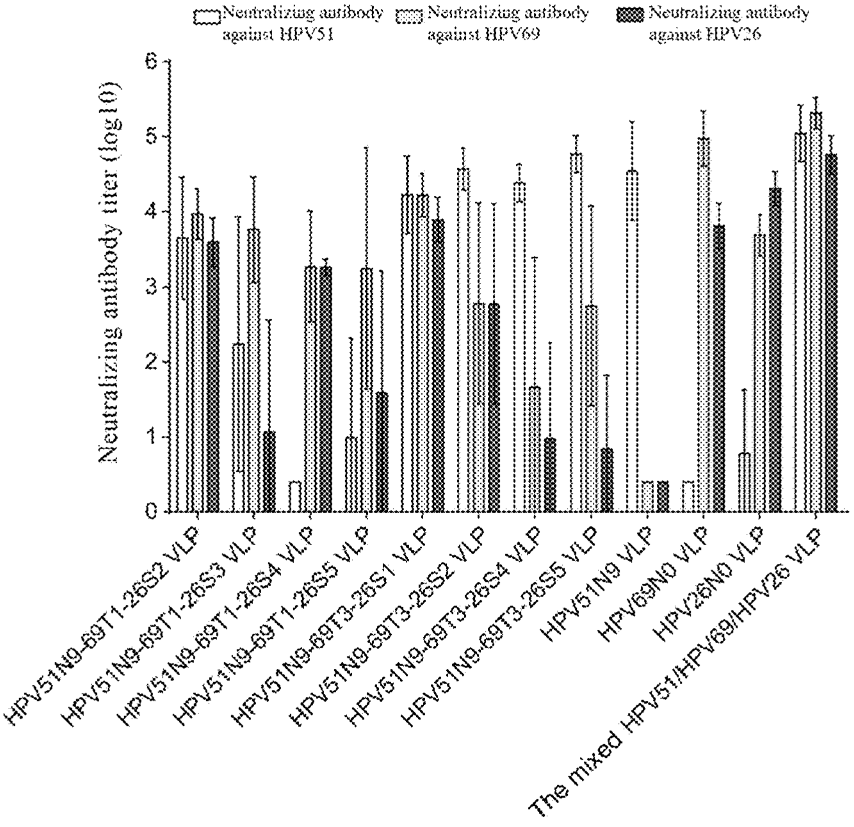

In Aluminum adjuvant groups 1-2, 5 mice/subgroup were vaccinated by intraperitoneal injection, at an immunizing dose 5 μg and 1 μg, respectively, and an injection volume of 1 mL. All the mice were subjected to the first vaccination at Week 0, and then subjected to the booster vaccination at Weeks 2 and 4, respectively. At Week 8, blood sample was collected via orbital bleeding, and the titers of antibodies against HPV51, HPV69 and HPV26 in serum were analyzed. The analysis results were shown in FIGS. 11A and 11B. The result showed that H51N9-69T1-26S2 VLP, H51N9-69T3-26S1 VLP and H51N9-69T3-26S2 VLP each could induce the generation of high-titer neutralizing antibodies against HPV51 in mice, and their protective effects were comparable to that of HPV51N9 VLP alone and that of the mixed HPV51/HPV69/HPV26 VLP at the same dose, and were significantly higher than that of HPV69N0 VLP alone and that of HPV26N0 VLP alone at the same dose. H51N9-69T1-26S2 VLP, H51N9-69T3-26S1 VLP and H51N9-69T3-26S2 VLP each could also induce the generation of high-titer neutralizing antibodies against HPV69 in mice, and their protective effects were comparable to that of HPV69N0 VLP alone and that of the mixed HPV51/HPV69/HPV26 VLP at the same dose, and were significantly higher than that of HPV51N9 VLP alone at the same dose. H51N9-69T1-26S2 VLP, H51N9-69T3-26S1 VLP and H51N9-69T3-26S2 VLP each could also induce the generation of high-titer neutralizing antibodies against HPV26 in mice, and their protective effects were comparable to that of HPV26N0 VLP alone and that of the mixed HPV51/HPV69/HPV26 VLP at the same dose, and were significantly higher than that of HPV51N9 VLP alone at the same dose. This showed that H51N9-69T1-26S2 VLP, H51N9-69T3-26S1 VLP and H51N9-69T3-26S2 VLP had good cross-immunogenicity and cross-protection against HPV51, HPV69 and HPV26.

TABLE 5

Vaccination schedule

| Group | Antigen for vaccination | Adjuvant | Immunizing dose | Number | Vaccination procedure (week) |
|---|---|---|---|---|---|
| Aluminum adjuvant group 1 | HPV51N9 VLP | aluminum adjuvant | 1 μg | 5 | 0, 2, 4 |
| | HPV69N0 VLP | aluminum adjuvant | 5 μg | 5 | 0, 2, 4 |
| | HPV26N0 VLP | aluminum adjuvant | 5 μg | 5 | 0, 2, 4 |
| | HPV51/HPV69/HPV26 VLP | aluminum adjuvant | 5 μg for each VLP | 5 | 0, 2, 4 |
| | H51N9-69T1-26S2 VLP | aluminum adjuvant | 5 μg | 5 | 0, 2, 4 |
| | H51N9-69T1-26S3 VLP | aluminum adjuvant | 5 μg | 5 | 0, 2, 4 |
| | H51N9-69T1-26S4 VLP | aluminum adjuvant | 5 μg | 5 | 0, 2, 4 |
| | H51N9-69T1-26S5 VLP | aluminum adjuvant | 5 μg | 5 | 0, 2, 4 |
| | H51N9-69T3-26S1 VLP | aluminum adjuvant | 5 μg | 5 | 0, 2, 4 |
| | H51N9-69T3-26S2 VLP | aluminum adjuvant | 5 μg | 5 | 0, 2, 4 |
| | H51N9-69T3-26S4 VLP | aluminum adjuvant | 5 μg | 5 | 0, 2, 4 |
| | H51N9-69T3-26S5 VLP | aluminum adjuvant | 5 μg | 5 | 0, 2, 4 |

TABLE 5-continued

| Vaccination schedule | | | | | |
|---|---|---|---|---|---|
| Group | Antigen for vaccination | Adjuvant | Immunizing dose | Number | Vaccination procedure (week) |
| Aluminum adjuvant group 2 | HPV51N9 VLP | aluminum adjuvant | 1 μg | 5 | 0, 2, 4 |
| | HPV69N0 VLP | aluminum adjuvant | 1 μg | 5 | 0, 2, 4 |
| | HPV26N0 VLP | aluminum adjuvant | 1 μg | 5 | 0, 2, 4 |
| | HPV51/HPV69/HPV26 VLP | aluminum adjuvant | 1 μg for each VLP | 5 | 0, 2, 4 |
| | H51N9-69T1-26S2 VLP | aluminum adjuvant | 1 μg | 5 | 0, 2, 4 |
| | H51N9-69T1-26S3 VLP | aluminum adjuvant | 1 μg | 5 | 0, 2, 4 |
| | H51N9-69T1-26S4 VLP | aluminum adjuvant | 1 μg | 5 | 0, 2, 4 |
| | H51N9-69T1-26S5 VLP | aluminum adjuvant | 1 μg | 5 | 0, 2, 4 |
| | H51N9-69T3-26S1 VLP | aluminum adjuvant | 1 μg | 5 | 0, 2, 4 |
| | H51N9-69T3-26S2 VLP | aluminum adjuvant | 1 μg | 5 | 0, 2, 4 |
| | H51N9-69T3-26S4 VLP | aluminum adjuvant | 1 μg | 5 | 0, 2, 4 |
| | H51N9-69T3-26S5 VLP | aluminum adjuvant | 1 μg | 5 | 0, 2, 4 |

Example 5: Evaluation 3 of Neutralizing Antibody Titer in Serum of Mice Vaccinated with Virus-Like Particles In this experiment, virus-like particles used were H51N9-69T2-26S1 VLP, H51N9-69T2-26S3 VLP, H51N9-69T2-26S4 VLP, H51N9-69T2-26S5 VLP, H51N9-69T4-26S1 VLP, H51N9-69T4-26S2 VLP, H51N9-69T4-26S3 VLP and H51N9-69T4-26S5 VLP.

In this experiment, vaccination schedule was shown in Table 6. All the mice (6-week old BalB/c female mice) were divided into 2 groups: Aluminum adjuvant group 1 (at an immunizing dose of 5 μg, using aluminum adjuvant), Aluminum adjuvant group 2 (at an immunizing dose of 1 μg, using aluminum adjuvant). Each group was further divided into 12 subgroups. The Control subgroups 1, 2 and 3 were vaccinated with HPV51N9 VLP alone, HPV69N0 VLP alone and HPV26N0 VLP alone, respectively, the Control subgroup 4 was vaccinated with the mixed HPV51/HPV69/HPV26 VLP (i.e. a mixture of HPV51N9 VLP, HPV69N0 VLP and HPV26N0 VLP, at a given immunizing dose for each VLP). The Experimental subgroups 1, 2, 3, 4, 5, 6, 7 and 8 were vaccinated with H51N9-69T2-26S1 VLP, H51N9-69T2-26S3 VLP, H51N9-69T2-26S4 VLP, H51N9-69T2-26S5VLP, H51N9-69T4-26S1 VLP, H51N9-69T4-26S2 VLP, H51N9-69T4-26S3 VLP and H51N9-69T4-26S5 VLP, respectively.

Figure 12A:
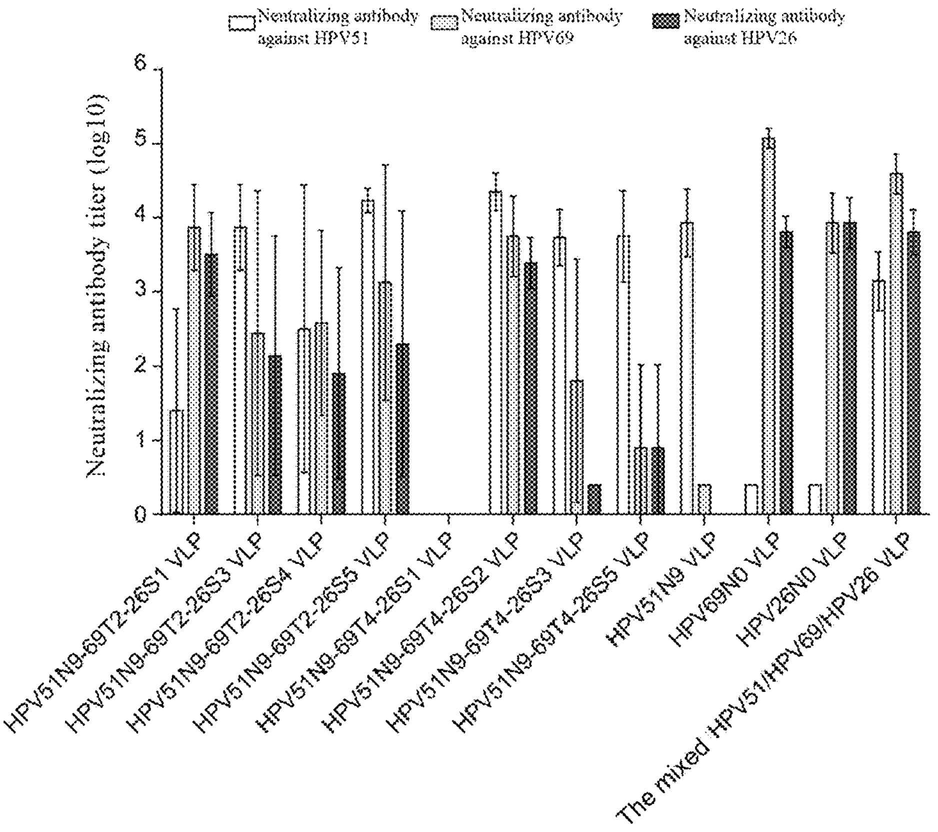
FIGS. 12A and 12B show the results of neutralizing antibody titer in mouse serum after vaccination of mice with H51N9-69T2-26S1 VLP, H51N9-69T2-26S3 VLP, H51N9-69T2-26S4 VLP, H51N9-69T2-26S5 VLP, H51N9-69T4-26S1 VLP, H51N9-69T4-26S2 VLP, H51N9-69T4-26S3 VLP and H51N9-69T4-26S5 VLP.
Figure 12B:
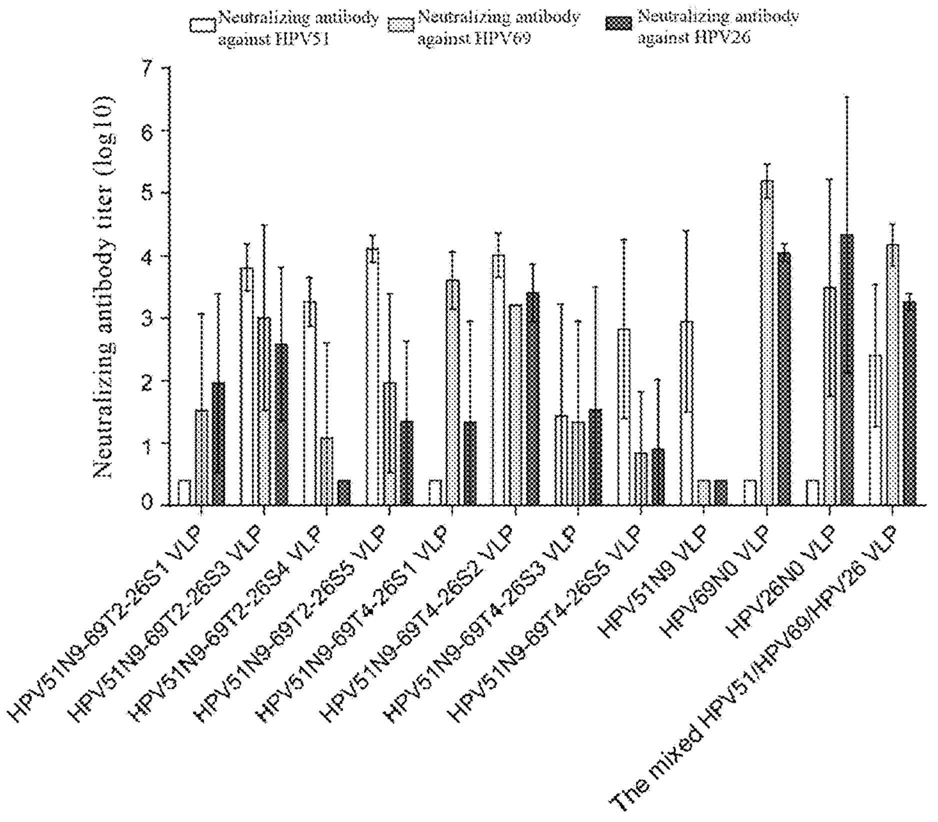

In Aluminum adjuvant groups 1-2, 5 mice/subgroup were vaccinated by intraperitoneal injection, at an immunizing dose 5 μg and 1 μg, respectively, and an injection volume of 1 mL. All the mice were subjected to the first vaccination at Week 0, and then subjected to the booster vaccination at Weeks 2 and 4, respectively. At Week 8, blood sample was collected via orbital bleeding, and the titers of antibodies against HPV51, HPV69 and HPV26 in serum were analyzed. The analysis results were shown in FIGS. 12A and 12B. The result showed that H51N9-69T2-26S3 VLP and H51N9-69T4-26S2 VLP each could induce the generation of high-titer neutralizing antibodies against HPV51 in mice, and their protective effects were comparable to that of HPV51N9 VLP alone and that of the mixed HPV51/HPV69/HPV26 VLP at the same dose, and were significantly higher than that of HPV69N0 VLP alone and that of HPV26N0 VLP alone at the same dose. H51N9-69T2-26S3 VLP and H51N9-69T4-26S2 VLP each could also induce the generation of high-titer neutralizing antibodies against HPV69 in mice, and their protective effects were comparable to that of HPV69N0 VLP alone and that of the mixed HPV51/HPV69/HPV26 VLP at the same dose, and were significantly higher than that of HPV51N9 VLP alone at the same dose. H51N9-69T2-26S3 VLP and H51N9-69T4-26S2 VLP each could also induce the generation of high-titer neutralizing antibodies against HPV26 in mice, and their protective effects were comparable to that of HPV26N0 VLP alone and that of the mixed HPV51/HPV69/HPV26 VLP at the same dose, and were significantly higher than that of HPV51N9 VLP alone at the same dose. This showed that H51N9-69T2-26S3 VLP and H51N9-69T4-26S2 VLP had good cross-immunogenicity and cross-protection against HPV51, HPV69 and HPV26.

TABLE 6

| Vaccination schedule | | | | | |
|---|---|---|---|---|---|
| Group | Antigen for vaccination | Adjuvant | Immunizing dose | Number | Vaccination procedure (week) |
| Aluminum adjuvant group 1 | HPV51N9 VLP | aluminum adjuvant | 1 μg | 5 | 0, 2, 4 |
| | HPV69N0 VLP | aluminum adjuvant | 5 μg | 5 | 0, 2, 4 |
| | HPV26N0 VLP | aluminum adjuvant | 5 μg | 5 | 0, 2, 4 |
| | HPV51/HPV69/HPV26 VLP | aluminum adjuvant | 5 μg for each VLP | 5 | 0, 2, 4 |
| | H51N9-69T2-6S1 VLP | aluminum adjuvant | 5 μg | 5 | 0, 2, 4 |
| | H51N9-69T2-6S3 VLP | aluminum adjuvant | 5 μg | 5 | 0, 2, 4 |
| | H51N9-69T2-6S4 VLP | aluminum adjuvant | 5 μg | 5 | 0, 2, 4 |
| | H51N9-69T2-6S5 VLP | aluminum adjuvant | 5 μg | 5 | 0, 2, 4 |
| | H51N9-69T4-26S1 VLP | aluminum adjuvant | 5 μg | 5 | 0, 2, 4 |
| | H51N9-69T4-26S2 VLP | aluminum adjuvant | 5 μg | 5 | 0, 2, 4 |
| | H51N9-69T4-26S4 VLP | aluminum adjuvant | 5 μg | 5 | 0, 2, 4 |
| | H51N9-69T4-26S5 VLP | aluminum adjuvant | 5 μg | 5 | 0, 2, 4 |
| Aluminum adjuvant group 2 | HPV51N9 VLP | aluminum adjuvant | 1 μg | 5 | 0, 2, 4 |
| | HPV69N0 VLP | aluminum adjuvant | 1 μg | 5 | 0, 2, 4 |
| | HPV26N0 VLP | aluminum adjuvant | 1 μg | 5 | 0, 2, 4 |
| | HPV51/HPV69/HPV26 VLP | aluminum adjuvant | 1 μg for each VLP | 5 | 0, 2, 4 |
| | H51N9-69T2-26S1 VLP | aluminum adjuvant | 1 μg | 5 | 0, 2, 4 |
| | H51N9-69T2-26S3 VLP | aluminum adjuvant | 1 μg | 5 | 0, 2, 4 |
| | H51N9-69T2-26S4 VLP | aluminum adjuvant | 1 μg | 5 | 0, 2, 4 |
| | H51N9-69T2-26S5 VLP | aluminum adjuvant | 1 μg | 5 | 0, 2, 4 |

TABLE 6-continued

| Vaccination schedule | | | | | |
|---|---|---|---|---|---|
| Group | Antigen for vaccination | Adjuvant | Immunizing dose | Number | Vaccination procedure (week) |
| | H51N9-69T4-26S1 VLP | aluminum adjuvant | 1 μg | 5 | 0, 2, 4 |
| | H51N9-69T4-26S2 VLP | aluminum adjuvant | 1 μg | 5 | 0, 2, 4 |
| | H51N9-69T4-26S3 VLP | aluminum adjuvant | 1 μg | 5 | 0, 2, 4 |
| | H51N9-69T4-26S5 VLP | aluminum adjuvant | 1 μg | 5 | 0, 2, 4 |

Example 6: Evaluation of $ED_{50}$ of Virus-Like Particles for Inducing Seroconversion In this experiment, the virus-like particles used were H51N9-69T1-26S2 VLP, H51N9-69T2-26S3 VLP, H51N9-69T3-26S1 VLP and H51N9-69T4-26S2 VLP.

6-Week old BalB/c female mice (8 mice) were vaccinated with aluminum adjuvant by single intraperitoneal injection, wherein H51N9-69T1-26S2 VLP, H51N9-69T2-26S3 VLP, H51N9-69T3-26S1 VLP or H51N9-69T4-26S2 VLP (at an immunizing dose of 0.900 μg, 0.300 μg, 0.100 μg, 0.033 μg and 0.011 μg) was used in the Experimental groups, and HPV51N9 VLP alone, HPV69N0 VLP alone, HPV26N0 VLP alone (at an immunizing dose of 0.900 μg, 0.300 μg, 0.100 μg, 0.033 μg and 0.011 μg), or the mixed HPV51/HPV69/HPV26 VLP (i.e. a mixture of HPV51N9 VLP, HPV69N0 VLP and HPV26N10 VLP, at an immunizing dose of 0.900 μg, 0.300 μg, 0.100 μg, 0.033 μg and 0.011 μg for each VLP); the immunizing volume was 1 mL. In addition, the diluent used to dilute the vaccine was used as a blank control. 8 Mice were vaccinated in each group, and at Week 5 after vaccination, venous blood was collected from eyeball. Antibodies against HPV in the serum were detected, and by Reed-Muench method (Reed L J M H. A simple method of estimating fifty percent endpoints. Am J Hyg. 1938; 27:493-7), $ED_{50}$ for inducing seroconversion (i.e. inducing the generation of antibodies in mice) was calculated for each sample. The results were shown in Table 7.

TABLE 7

$ED_{50}$ of H51N9-69T1-26S2 VLP, H51N9-69T2-26S3 VLP, H51N9-69T3-26S1 VLP and H51N9-69T4-26S2 VLP for inducing the generation of antibodies against HPV51, HPV69 and HPV26 (seroconversion) in mice

| HPV VLP (ug) | $ED_{50}$ against HPV51PsV (ug) | $ED_{50}$ against HPV69PsV (ug) | $ED_{50}$ against HPV26PsV (ug) |
|---|---|---|---|
| HPV51N9 | 0.058 | >0.9 | >0.9 |
| HPV69N0 | >0.9 | 0.029 | 0.019 |
| HPV26N0 | >0.9 | 0.008 | 0.057 |
| HPV51N9-69T1-26S2 | >0.9 | 0.178 | >0.9 |
| HPV51N9-69T3-26S1 | 0.066 | 0.048 | 0.176 |
| HPV51N9-69T2-26S3 | 0.170 | 0.180 | 0.120 |
| HPV51N9-69T4-26S2 | 0.010 | 0.007 | 0.058 |
| HPV51/69/26 | 0.066 | 0.010 | 0.007 |

The results showed that 5 weeks after vaccination of mice, $ED_{50}$ of H51N9-69T2-26S3 VLP, H51N9-69T3-26S1 VLP and H51N9-69T4-26S2 VLP for inducing the generation of antibodies against HPV51 in mice was comparable to that of HPV51N9 VLP alone and that of the mixed HPV51/HPV69/HPV26 VLP, and was significantly superior to that of HPV69N0 VLP alone and HPV26N0 VLP alone; and their $ED_{50}$ for inducing the generation of antibodies against HPV69 was comparable to that of HPV69N0 VLP alone and that of the mixed HPV51/HPV69/HPV26 VLP, and was significantly superior to that of HPV51N9 VLP alone; and their $ED_{50}$ for inducing the generation of antibodies against HPV26 was comparable to that of HPV26N0 VLP alone and that of the mixed HPV51/HPV69/HPV26 VLP, and was significantly superior to that of HPV51N9 VLP alone. This showed that H51N9-69T2-26S3 VLP, H51N9-69T3-26S1 VLP and H51N9-69T4-26S2 VLP had good cross-immunogenicity and cross-protection against HPV51, HPV69 and HPV26.

Although the specific embodiments of the present application have been described in details, those skilled in the art would understand that, according to the teachings disclosed in the specification, various modifications and changes can be made thereto, and that such modifications and changes are within the scope of the present application. The scope of the present application is given by the appended claims and any equivalents thereof.

What is claimed is:

1. A mutated HPV51 L1 protein, wherein as compared with a wild type HPV51 L1 protein, (I) the mutated HPV51 L1 protein has the following mutations:

(1) truncation of 1-15 amino acids at N-terminal of the wild type HPV51 L1 protein; and the mutation as defined in (2)(a), (2)(b), (2)(c) or (2)(d):

(2)(a) substitution of amino acid residues at positions of the wild type HPV51 L1 protein which correspond to positions 52-60 of SEQ ID NO: 1 with amino acid residues at the corresponding positions of a L1 protein of a second type of wild type HPV;

(2)(b) substitution of amino acid residues at positions of the wild type HPV51 L1 protein which correspond to positions 125-147 of SEQ ID NO: 1 with amino acid residues at the corresponding positions of a L1 protein of a second type of wild type HPV;

(2)(c) substitution of amino acid residues at positions of the wild type HPV51 L1 protein which correspond to positions 170-181 of SEQ ID NO: 1 with amino acid residues at the corresponding positions of a L1 protein of a second type of wild type HPV;

(2)(d) substitution of amino acid residues at positions of the wild type HPV51 L1 protein which correspond to positions 259-289 of SEQ ID NO: 1 with amino acid residues at the corresponding positions of a L1 protein of a second type of wild type HPV, or, (II) the mutated HPV51 L1 protein has the mutation as defined in (1) and (2)(a), and further has a mutation as defined in (3)(b);

or, (III) the mutated HPV51 L1 protein has the mutation as defined in (1) and (2)(b), and further has a mutation as defined in (3)(c);

or, (IV) the mutated HPV51 L1 protein has the mutation as defined in (1) and (2)(c), and further has a mutation as defined in (3)(a) or (3)(b);

or, (V) the mutated HPV51 L1 protein has the mutation as defined in (1) and (2)(d), and further has a mutation as defined in (3)(b);

or, (VI) the mutated HPV51 L1 protein has the mutation as defined in (2)(a), (2)(b), (2)(c) or (2)(d);

wherein the mutations as defined in (3)(a), (3)(b) or (3)(c) are as follows:

(3)(a) substitution of amino acid residues at positions of the wild type HPV51 L1 protein which correspond to positions 51-60 of SEQ ID NO: 1 with amino acid residues at the corresponding positions of a L1 protein of a third type of wild type HPV;

(3)(b) substitution of amino acid residues at positions of the wild type HPV51 L1 protein which correspond to positions 114-146 of SEQ ID NO: 1 with amino acid residues at the corresponding positions of a L1 protein of a third type of wild type HPV;

(3)(c) substitution of amino acid residues at positions of the wild type HPV51 L1 protein which correspond to positions 173-181 of SEQ ID NO: 1 with amino acid residues at the corresponding positions of a L1 protein of a third type of wild type HPV; wherein said corresponding positions are determined by optimal alignment of the sequences being compared.

2. An isolated nucleic acid, encoding the mutated HPV51 L1 protein or a variant thereof according to claim 1.

3. A vector comprising the isolated nucleic acid according to claim 2.

4. A host cell comprising the isolated nucleic acid according to claim 2 and/or a vector comprising the isolated nucleic acid according to claim 2.

5. An HPV virus-like particle, comprising or consisting of the mutated HPV51 L1 protein according to claim 1.

6. A composition comprising:

(i) a mutated HPV51 L1 protein according to claim 1

(ii) an isolated nucleic acid encoding the mutated HPV51 L1 protein as described in (i), or (iii) a vector comprising an isolated nucleic acid encoding the mutated HPV51 L1 protein as described in (i), or (iv) a host cell comprising the isolated nucleic acid encoding the mutated HPV51 L1 protein as described in (i) and/or a vector comprising an isolated nucleic acid encoding the mutated HPV51 L1 protein as described in (i), or (v) an HPV virus-like particle comprising or consisting of the mutated HPV51 L1 protein as described in (i).

7. A pharmaceutical composition or vaccine, comprising the HPV virus-like particle according to claim 5, and optionally a pharmaceutically acceptable carrier and/or excipient.

8. A method for preparing the mutated HPV51 L1 protein according to claim 1, comprising expressing the mutated HPV51 L1 protein in a host cell, and then recovering the mutated HPV51 L1 protein from a culture of the host cell.

9. A method for preparing a vaccine, comprising combining the HPV virus-like particle according to claim 5 with a pharmaceutically acceptable carrier and/or excipient.

10. A method for preventing HPV infection or a disease caused by HPV infection, comprising administering to a subject a prophylactically effective amount of the HPV virus-like particle according to claim 5 or a pharmaceutical composition or vaccine comprising the HPV virus-like particle according to claim 5 and optionally a pharmaceutically acceptable carrier and/or excipient.

11. The mutated HPV51 L1 protein according to claim 1, wherein:

(i) the mutated HPV51 L1 protein has 1, 2, 3, 4, 5, 6, 7, 8, 9, 10, 11, 12, 13, 14 or 15 amino acids truncated at N-terminal of the wild type HPV51 L1 protein, as compared with the wild type HPV51 L1 protein, (ii) the second type of wild type HPV is HPV69;

(iii) the third type of wild type HPV is HPV26.

12. The mutated HPV51 L1 protein according to claim 1, wherein the mutated HPV51 L1 protein has an amino acid sequence as set forth in SEQ ID NO: 4, 5, 6, 7, 23, 27, 28, 41 or 45.

13. The isolated nucleic acid according to claim 2, wherein the isolated nucleic acid has a nucleotide sequence as set forth in SEQ ID NO: 12, 13, 14, 15, 32, 36, 37, 49 or 53.

14. The pharmaceutical composition or vaccine according to claim 7, wherein the HPV virus-like particle is present in an amount effective for preventing HPV infection or a disease caused by HPV infection.

15. The pharmaceutical composition or vaccine according to claim 14, wherein the HPV infection is infection by one or more HPV types, and/or, the disease caused by HPV infection is selected from the group consisting of cervical cancer, condyloma acuminatum and any combination thereof.

16. The pharmaceutical composition or vaccine according to claim 15, wherein the HPV infection is selected from the group consisting of: HPV51 infection, HPV69 infection, HPV26 infection and any combination thereof.

17. The method according to claim 8, wherein the host cell is *E. coli*.

18. The method according to claim 17, wherein the method comprises the steps of: expressing the mutated HPV51 L1 protein in *E. coli*, and then obtaining the mutated HPV51 L1 protein by purifying a lysate supernatant of the *E. coli*.

19. The method according to claim 10, wherein the HPV infection is infection by one or more HPV types, and/or, the disease caused by HPV infection is selected from the group consisting of cervical cancer, condyloma *acuminatum* and any combination thereof.

20. The method according to claim 19, wherein the HPV infection is selected from the group consisting of: HPV51 infection, HPV69 infection, HPV26 infection and any combination thereof.

21. The mutated HPV51 L1 protein according to claim 11, wherein (iv) the amino acid residues at the corresponding positions as described in (2)(a) are amino acid residues at positions 52-60 of a wild type HPV69 L1 protein;

(v) the amino acid residues at the corresponding positions as described in (2)(b) are amino acid residues at positions 125-147 of a wild type HPV69 L1 protein;

(vi) the amino acid residues at the corresponding positions as described in (2)(c) are amino acid residues at positions 170-183 of a wild type HPV69 L1 protein;

(vii) the amino acid residues at the corresponding positions as described in (2)(d) are amino acid residues at positions 261-291 of a wild type HPV69 L1 protein;

(viii) the amino acid residues at the corresponding positions as described in (3)(a) are amino acid residues at positions 51-60 of a wild type HPV26 L1 protein;

(ix) the amino acid residues at the corresponding positions as described in (3)(b) are amino acid residues at positions 114-146 of a wild type HPV26 L1 protein;

(x) the amino acid residues at the corresponding positions as described in (3)(c) are amino acid residues at positions 173-181 of a wild type HPV26 L1 protein;

(xi) the wild type HPV51 L1 protein has an amino acid sequence as set forth in SEQ ID NO: 1;

(xii) the L1 protein of the second type of wild type HPV has an amino acid sequence as set forth in SEQ ID NO: 2; and (xiii) the L1 protein of the third type of wild type HPV has an amino acid sequence as set forth in SEQ ID NO: 22.

* * * * *